United States Patent
Conner et al.

(10) Patent No.: US 7,598,266 B2
(45) Date of Patent: Oct. 6, 2009

(54) FUSED HETEROCYCLIC DERIVATIVES AS PPAR MODULATORS

(75) Inventors: Scott Eugene Conner, Indianapolis, IN (US); Nathan Bryan Mantlo, Brownsburg, IN (US); Guoxin Zhu, Noblesville, IN (US)

(73) Assignee: Eli Lilly and Company, Indianapolis, IN (US)

( * ) Notice: Subject to any disclaimer, the term of this patent is extended or adjusted under 35 U.S.C. 154(b) by 0 days.

(21) Appl. No.: 12/099,929

(22) Filed: Apr. 9, 2008

(65) Prior Publication Data

US 2009/0054479 A1    Feb. 26, 2009

Related U.S. Application Data

(62) Division of application No. 10/539,477, filed as application No. PCT/US03/39120 on Dec. 31, 2003, now Pat. No. 7,384,965.

(60) Provisional application No. 60/438,540, filed on Jan. 6, 2003.

(51) Int. Cl.
*A61K 31/437* (2006.01)
*A61K 31/4353* (2006.01)
*C07D 471/04* (2006.01)

(52) U.S. Cl. ............... 514/303; 514/300; 546/118; 546/113

(58) Field of Classification Search ............... 546/118; 514/303
See application file for complete search history.

(56) References Cited

U.S. PATENT DOCUMENTS

| 5,859,051 A | 1/1999 | Adams |
| 7,384,965 B2 * | 6/2008 | Conner et al. ............... 514/367 |

FOREIGN PATENT DOCUMENTS

| EP | 1 167 357 A | 2/2002 |
| WO | WO 00/64876 A | 11/2000 |
| WO | WO 01/00603 A | 1/2001 |
| WO | WO 03/066574 A1 | 8/2003 |

OTHER PUBLICATIONS

Byrn et al. Solid-State Chemistry of Drugs, 2d, Chapter 11 Hydrates and Solvates, 233-247, 233.*
Rami, H.K., et al, "Synthetic ligands for PPAR gamma—review of patent literature 1994-1999", Expert Opinion Ther. Patents, 2000, 10(5):623-634.

* cited by examiner

*Primary Examiner*—Rebecca L Anderson
*Assistant Examiner*—Jason Nolan
(74) *Attorney, Agent, or Firm*—MaCharri Vorndran-Jones

(57) ABSTRACT

The present invention is directed to compounds represented by the following structural formula, Formula I:

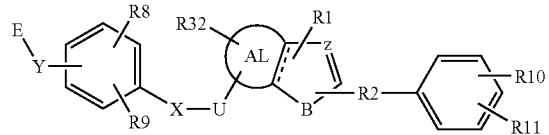

wherein:
(a) X is selected from the group consisting of a single bond, O, S, S(O)$_2$ and N;
(b) U is an aliphatic linker;
(c) Y is selected from the group consisting of C, O, S, NH and a single bond;
(d) E is C(R3)(R4)A or A and wherein
  (i) A is selected from the group consisting of carboxyl, tetrazole, C$_1$-C$_6$ alkylnitrile, carboxamide, sulfonamide and acylsulfonamide;
(e) B is selected from the group consisting of S, O, C, and N;
(f) Z is selected from the group consisting of N and C; with the proviso that when B is C then Z is N.

24 Claims, No Drawings

FUSED HETEROCYCLIC DERIVATIVES AS PPAR MODULATORS

This application is a divisional application of allowed U.S. patent application Ser. No. 10/539,477, filed Jun. 21, 2005 now U.S. Pat No. 7,384,965, filed as a national phase entry, pursuant to 35 U.S.C. 371, of PCT/US2003/039120, filed on Dec. 31, 2003, which claims the benefit of U.S. Provisional Application No. 60/438,540, filed Jan. 6, 2003, the entire teachings of which are incorporated herein by reference.

BACKGROUND OF THE INVENTION

Peroxisome Proliferator Activated Receptors (PPARs) are members of the nuclear hormone receptor superfamily, a large and diverse group of proteins that mediate ligand-dependent transcriptional activation and repression. Three subtypes of PPARs have been isolated: PPARα, PPARγ and PPARδ.

The expression profile of each isoform differs significantly from the others, whereby PPARα is expressed primarily, but not exclusively in liver; PPARγ is expressed primarily in adipose tissue; and PPARδ is expressed ubiquitously. Studies of the individual PPAR isoforms and ligands have revealed their regulation of processes involved in insulin resistance and diabetes, as well as lipid disorders, such as hyperlipidemia and dyslipidemia. PPARγ agonists, such as pioglitazone, can be useful in the treatment of non-insulin dependent diabetes mellitus. Such PPARγ agonists are associated with insulin sensitization.

PPARα agonists, such as fenofibrate, can be useful in the treatment of hyperlipidemia. Although clinical evidence is not available to reveal the utility of PPARδ agonists in humans, several preclinical studies suggest that PPARδ agonists can be useful in the treatment of diabetes and lipid disorders.

The prevalence of the conditions that comprise Metabolic Syndrome (obesity, insulin resistance, hyperlipidemia, hypertension and atherosclerosis) continues to increase. New pharmaceutical agents are needed to address the unmet clinical needs of patients.

PPARδ agonists have been suggested as a potential treatment for use in regulating many of the parameters associated with Metabolic Syndrome and Atherosclerosis. For example, in obese, non-diabetic rhesus monkeys, a PPARδ agonist reduced circulating triglycerides and LDL, decreased basal insulin levels and increased HDL (Oliver, W. R. et al. Proc Natl Acad Sci 98:5306-5311; 2001). The insulin sensitization observed with the use of a PPARδ agonist is thought to be in part due to decreased myocellular lipids (Dressel, U. et al. Mol Endocrinol 17:2477-2493; 2003).

Further, atherosclerosis is considered to be a disease consequence of dyslipidemia and may be associated with inflammatory disease. C-reactive protein (CRP) production is part of the acute-phase response to most forms of inflammation, infection and tissue damage. It is measured diagnostically as a marker of low-grade inflammation. Plasma CRP levels of greater than 3 mg/L have been considered predictive of high risk for coronary artery disease (J. Clin. Invest 111: 1085-1812, 2003).

PPARδ agonists are believed to mediate anti-inflammatory effects. Indeed, treatment of LPS-stimulated macrophages with a PPARδ agonist has been observed to reduce the expression of iNOS, IL12, and IL-6 (Welch, J. S. et al. Proc Natl Acad Sci 100:6712-67172003).

It may be especially desirable when the active pharmaceutical agent selectively modulates a PPAR receptor subtype to provide an especially desirable pharmacological profile. In some instances, it can be desirable when the active pharmacological agent selectively modulates more than one PPAR receptor subtype to provide a desired pharmacological profile.

SUMMARY OF THE INVENTION

The present invention is directed to compounds represented by the following structural Formula I':

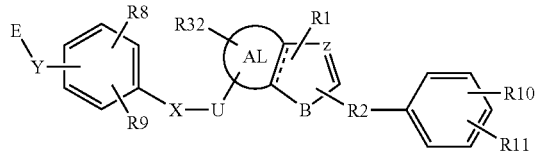

and stereoisomers, pharmaceutically acceptable salts, solvates and hydrates thereof, wherein:

(a) R1 is selected from the group consisting of hydrogen, $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and, wherein $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, $C_3$-$C_6$ cycloalkylaryl-$C_{0-2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;

(c) R2 is selected from the group consisting of $C_0$-$C_8$ alkyl and $C_{1-4}$-heteroalkyl;

(d) X is selected from the group consisting of a single bond, O, S, S(O)$_2$ and N;

(e) U is an aliphatic linker wherein one carbon atom of the aliphatic linker is optionally replaced with O, NH or S, and wherein such aliphatic linker is optionally substituted with from one to four substituents each independently selected from R30;

(f) Y is selected from the group consisting of C, NH, and a single bond;

(g) E is C(R3)(R4)A or A and wherein (i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from R$^7$;

(ii) each R$^7$ is independently selected from the group consisting of hydrogen, $C_1$-$C_6$ haloalkyl, aryl $C_0$-$C_4$ alkyl and $C_1$-$C_6$ alkyl;

(iii) R3 is selected from the group consisting of hydrogen, $C_1$-$C_5$ alkyl, and $C_1$-$C_5$ alkoxy; and (iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with one to three substituents each independently selected from R26;

(h) B is selected from the group consisting of S, O, C, and N;

(i) Z is selected from the group consisting of N and C, with the proviso that when B is C then Z is N;

(j) R8 is selected from the group consisting of hydrogen, $C_1-C_4$ alkyl, $C_1-C_4$ alkylenyl, and halo;

(k) R9 is selected from the group consisting of hydrogen, $C_1-C_4$ alkyl, $C_1-C_4$ alkylenyl, halo, aryl-$C_0-C_4$ alkyl, heteroaryl, $C_1-C_6$ alkyl, SR29, and OR29, and wherein aryl-$C_0-C_4$ alkyl, heteroaryl are each optionally substituted with from one to three independently selected from R27; R29 is selected from the group consisting of hydrogen, $C_1-C_4$ alkylenyl, and $C_1-C_4$ alkyl; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;

(l) R10, R11 are each independently selected from the group consisting of hydrogen, hydroxy, cyano, nitro, halo, oxo, $C_1-C_6$ alkyl, $C_1-C_6$ alkyl-COOR12", $C_0-C_6$ alkoxy, $C_1-C_6$ haloalkyl, $C_1-C_6$ haloalkyloxy, $C_3-C_7$ cycloalkyl, aryl-$C_{0-4}$-alkyl, aryl-$C_{1-4}$-heteroalkyl, heteroaryl-$C_{0-4}$-alkyl, $C_3-C_6$ cycloalkylaryl-$C_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents independently selected from R28;

(m) R12', R12", R13', R14', R15', R16', R17', R18', R19', R20', R21', R22', R23', R24', and R25' are each independently selected from the group consisting of hydrogen, $C_1-C_6$ alkyl and aryl;

(n) R30 is selected from the group consisting of $C_1-C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1-C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31;

(o) R32 is selected from the group consisting of a bond, hydrogen, halo, $C_1-C_6$ alkyl, $C_1-C_6$ haloalkyl, and $C_1-C_6$ alkyloxo;

(p) AL is selected from the group consisting of a fused $C_3-C_8$ carbocyclic, a fused pyridinyl, a fused pyrimidinyl, and a fused phenyl; and (q) ---- is optionally a bond to form a double bond at the indicated position.

Another embodiment of the present invention is compounds of the structural Formula I":

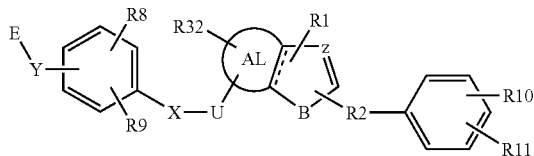

and stereoisomers, pharmaceutically acceptable salts, solvates and hydrates thereof, wherein:

(a) R1 is selected from the group consisting of hydrogen, $C_1-C_8$ alkyl, $C_1-C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and, wherein $C_1-C_8$ alkyl, $C_1-C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, $C_1-C_6$ alkyl, $C_1-C_6$ alkyl-COOR12, $C_1-C_6$ alkoxy, $C_1-C_6$ haloalkyl, $C_1-C_6$ haloalkyloxy, $C_3-C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1-C_6$ alkyl and aryl;

(c) R2 is selected from the group consisting of $C_0-C_8$ alkyl and $C_{1-4}$-heteroalkyl;

(d) X is selected from the group consisting of a single bond, O, S, S(O)$_2$ and N;

(a) U is an aliphatic linker wherein one carbon atom of the aliphatic linker is optionally replaced with O, NH or S, and wherein such aliphatic linker is substituted with from one to four substituents each independently selected from R30;

(e) Y is selected from the group consisting of C, O, S, NH and a single bond;

(f) E is C(R3)(R4)A or A and wherein (i) A is selected from the group consisting of carboxyl, tetrazole, $C_1-C_6$ alkylnitrile, carboxamide, sulfonamide and acylsulfonamide; wherein sulfonamide, acylsulfonamide and tetrazole are each optionally substituted with from one to two groups independently selected from $R^7$;

(ii) each $R^7$ is independently selected from the group consisting of hydrogen, $C_1-C_6$ haloalkyl, aryl $C_0-C_4$ alkyl and $C_1-C_6$ alkyl;

(iii) R3 is selected from the group consisting of hydrogen, $C_1-C_5$ alkyl, and $C_1-C_8$ alkoxy; and (iv) R4 is selected from the group consisting of H, $C_1-C_5$ alkyl, $C_1-C_5$ alkoxy, aryloxy, $C_3-C_6$ cycloalkyl, and aryl $C_0-C_4$ alkyl, and R3 and R4 are optionally combined to form a $C_3-C_4$ cycloalkyl, and wherein alkyl, alkoxy, aryloxy, cycloalkyl and aryl-alkyl are each optionally substituted with one to three substituents each independently selected from R26;

(g) B is selected from the group consisting of S, O, C, and N;

(h) Z is selected from the group consisting of N and C, with the proviso that when B is C then Z is N;

(i) R8 is selected from the group consisting of hydrogen, $C_1-C_4$ alkyl, $C_1-C_4$ alkylenyl, and halo;

(j) R9 is selected from the group consisting of hydrogen, $C_1-C_4$ alkyl, $C_1-C_4$ alkylenyl, halo, aryl-$C_0-C_4$ alkyl, heteroaryl, $C_1-C_6$ alkyl, SR29, and OR29, and wherein aryl-$C_0-C_4$ alkyl, heteroaryl are each optionally substituted with from one to three independently selected from R27; R29 is selected from the group consisting of hydrogen, $C_1-C_4$ alkylenyl, and $C_1-C_4$ alkyl; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;

(k) R10, R11 are each independently selected from the group consisting of hydrogen, hydroxy, cyano, nitro, halo, oxo, $C_1-C_6$ alkyl, $C_1-C_6$ alkyl-COOR12", $C_0-C_6$ alkoxy, $C_1-C_6$ haloalkyl, $C_1-C_6$ haloalkyloxy, $C_3-C_7$ cycloalkyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, aryloxy, C(O)R13', COOR14', OC(O)R15', OS(O)$_2$ R16', N(R17')$_2$, NR18'C(O)R19', NR20'SO$_2$R21', SR22', S(O)R23', S(O)$_2$R24', and S(O)$_2$N(R25')$_2$; and wherein aryl-C$_{0-4}$-alkyl, aryl-C$_{1-4}$-heteroalkyl, heteroaryl-C$_{0-4}$-alkyl, and C3-C6 cycloalkylaryl-C$_{0-2}$-alkyl are each optionally substituted with from one to three substituents independently selected from R28;

(l) R12', R12'', R13', R14', R15', R16', R17', R18', R19', R20', R21', R22', R23', R24', and R25' are each independently selected from the group consisting of hydrogen, C$_1$-C$_6$ alkyl and aryl;

(m) R30 is selected from the group consisting of C$_1$-C$_6$ alkyl, aryl-C$_{0-4}$-alkyl, aryl-C$_{1-4}$-heteroalkyl, heteroaryl-C$_{0-4}$-alkyl, and C3-C6 cycloalkylaryl-C$_{0-2}$-alkyl, and wherein C$_1$-C$_6$ alkyl, aryl-C$_{0-4}$-alkyl, aryl-C$_{1-4}$-heteroalkyl, heteroaryl-(C$_{0-4}$-alkyl, and C3-C6 cycloalkylaryl-C$_{0-2}$-alkyl are each optionally substituted with from one to three substituents each independently selected from R31;

(n) R32 is selected from the group consisting of a bond, hydrogen, halo, C$_1$-C$_6$ alkyl, C$_1$-C$_6$ haloalkyl, and C$_1$-C$_6$ alkyloxo;

(o) AL is selected from the group consisting of a fused C$_3$-C$_8$ carbocyclic, a fused pyridinyl, a fused pyrimidinyl, and a fused phenyl; and (p) ---- is optionally a bond to form a double bond at the indicated position.

A further embodiment of the present invention is compounds of the structural Formula I''':

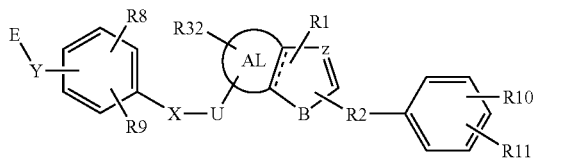

and stereoisomers, pharmaceutically acceptable salts, solvates and hydrates thereof, wherein:

(a) R1 is selected from the group consisting of hydrogen, C$_1$-C$_8$ alkyl, C$_1$-C$_8$ alkenyl, aryl-C$_{0-4}$-alkyl, aryl-C$_{1-4}$-heteroalkyl, heteroaryl-C$_{0-4}$-alkyl, C3-C6 cycloalkylaryl-C$_{0-2}$-alkyl, and, wherein C$_1$-C$_8$ alkyl, C$_1$-C$_8$ alkenyl, aryl-C$_{0-4}$-alkyl, aryl-C$_{1-4}$-heteroalkyl, heteroaryl-C$_{0-4}$-alkyl, C3-C6 cycloalkylaryl-C$_{0-2}$-alkyl are each optionally substituted with from one to three substituents independently selected from R1';

(b) R1', R26, R27, R28 and R31 are each independently selected from the group consisting of hydrogen, hydroxy, cyano, nitro, halo, oxo, C$_1$-C$_6$ alkyl, C$_1$-C$_6$ alkyl-COOR12, C$_1$-C$_6$ alkoxy, C$_1$-C$_6$ haloalkyl, C$_1$-C$_6$ haloalkyloxy, C$_3$-C$_7$ cycloalkyl, aryloxy, aryl-C$_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, C$_1$-C$_6$ alkyl and aryl;

(c) R2 is selected from the group consisting of C$_0$-C$_8$ alkyl and C$_{1-4}$-heteroalkyl;

(d) X is selected from the group consisting of a single bond, O, S, S(O)$_2$ and N;

(e) U is an aliphatic linker wherein one carbon atom of the aliphatic linker is optionally replaced with O, NH or S, and wherein such aliphatic linker is optionally substituted with from one to four substituents each independently selected from R30;

(f) Y is selected from the group consisting of C, O, S, NH and a single bond;

(g) E is C(R3)(R4)A or A and wherein
  (i) A is selected from the group consisting of carboxyl, tetrazole, C$_1$-C$_6$ alkylnitrile, carboxamide, sulfonamide and acylsulfonamide; wherein sulfonamide, acylsulfonamide and tetrazole are each optionally substituted with from one to two groups independently selected from R$^7$;
  (ii) each R$^7$ is independently selected from the group consisting of hydrogen, C$_1$-C$_6$haloalkyl, aryl C$_0$-C$_4$ alkyl and C$_1$-C$_6$ alkyl;
  (iii) R3 is selected from the group consisting of hydrogen, C$_1$-C$_5$ alkyl, and C$_1$-C$_5$ alkoxy; and
  (iv) R4 is selected from the group consisting of H, C$_1$-C$_5$ alkyl, C$_1$-C$_5$ alkoxy, aryloxy, C$_3$-C$_6$ cycloalkyl, and aryl C$_0$-C$_4$ alkyl, and R3 and R4 are optionally combined to form a C$_3$-C$_4$ cycloalkyl, and wherein alkyl, alkoxy, aryloxy, cycloalkyl and aryl-alkyl are each optionally substituted with one to three substituents each independently selected from R26;
  with the proviso that when Y is O then R4 is selected from the group consisting of C$_1$-C$_5$ alkyl, C$_1$-C$_5$ alkoxy, aryloxy, C$_3$-C$_6$ cycloalkyl, and aryl C$_0$-C$_4$ alkyl, and R3 and R4 are optionally combined to form a C$_3$-C$_4$ cycloalkyl, and wherein alkyl, alkoxy, cycloalkyl and aryl-alkyl are each optionally substituted with one to three each independently selected from R26;

(r) B is selected from the group consisting of S, O, C, and N;

(h) Z is selected from the group consisting of N and C, with the proviso that when B is C then Z is N;

(i) R8 is selected from the group consisting of hydrogen, C$_1$-C$_4$ alkyl, C$_1$-C$_4$ alkylenyl, and halo;

(j) R9 is selected from the group consisting of hydrogen, C$_1$-C$_4$ alkyl, C$_1$-C$_4$ alkylenyl, halo, aryl-C$_0$-C$_4$ alkyl, heteroaryl, C$_1$-C$_6$ alkyl, SR29, and OR29, and wherein aryl-C$_0$-C$_4$ alkyl, heteroaryl are each optionally substituted with from one to three independently selected from R27; R29 is selected from the group consisting of hydrogen, C$_1$-C$_4$ alkylenyl, and C$_1$-C$_4$ alkyl; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;

(k) R10, R11 are each independently selected from the group consisting of hydrogen, hydroxy, cyano, nitro, halo, oxo, C$_1$-C$_6$ alkyl, C$_1$-C$_6$ alkyl-COOR12'', C$_0$-C$_6$ alkoxy, C$_1$-C$_6$ haloalkyl, C$_1$-C$_6$ haloalkyloxy, C$_3$-C$_7$ cycloalkyl, aryl-C$_{0-4}$-alkyl, aryl-C$_{1-4}$-heteroalkyl, heteroaryl-C$_{0-4}$-alkyl, C$_3$-C$_6$ cycloalkylaryl-C$_{0-2}$-alkyl, aryloxy, C(O)R13', COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-C$_{0-4}$-alkyl, aryl-C$_{1-4}$-heteroalkyl, heteroaryl-C$_{0-4}$-alkyl, and C3-C6 cycloalkylaryl-C$_{0-2}$-alkyl are each optionally substituted with from one t three substituents independently selected from R28;

(l) R12', R12'', R13', R14', R15', R16', R17', R18', R19', R20', R21', R22', R23', R24', and R25' are each independently selected from the group consisting of hydrogen, C$_1$-C$_6$ alkyl and aryl;

(m) R30 is selected from the group consisting of C$_1$-C$_6$ alkyl, aryl-C$_{0-4}$-alkyl, aryl-C$_{1-4}$-heteroaryl, heteroaryl-C$_{0-4}$-alkyl, and C3-C6 cycloalkylaryl-C$_{0-2}$-alkyl, and wherein C$_1$-C$_6$ alkyl, aryl-C$_{0-4}$-alkyl, aryl-C$_{1-4}$-heteroalkyl, heteroaryl-C$_{0-4}$-alkyl, and C3-C6 cycloalkylaryl-$C_{0-2}$-alkyl are each optionally substituted with from one to three substituents each independently selected from R31;
(n) R32 is selected from the group consisting of a bond, hydrogen, halo, $C_1$-$C_6$ alkyl, $C_1$-$C_6$ haloalkyl, and $C_1$-$C_6$ alkyloxo;
(o) AL is selected from the group consisting of a fused $C_3$-$C_8$ carbocyclic, a fused pyridinyl, a fused pyrimidinyl, and a fused phenyl; and
(p) ---- is optionally a bond to form a double bond at the indicated position.

One embodiment of the present invention is compounds of the structural Formula I:

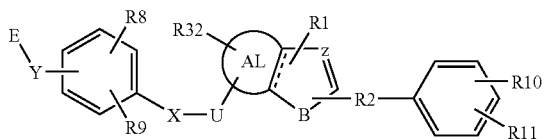

and stereoisomers, pharmaceutically acceptable salts, solvates and hydrates thereof, wherein:
(a) R1 is selected from the group consisting of hydrogen, $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl, and, wherein $C_1$-$C_8$ alkyl, $C_1$-$C_8$ alkenyl, aryl-$C_{0-4}$-alkyl, aryl-$C_{1-4}$-heteroalkyl, heteroaryl-$C_{0-4}$-alkyl, C3-C6 cycloalkylaryl-$C_{0-2}$-alkyl are each optionally substituted with from one to three substituents independently selected from R1';
(b) R1', R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18O(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;
(c) R2 is selected from the group consisting of $C_0$-$C_8$ alkyl and $C_{1-4}$-heteroalkyl;
(d) X is selected from the group consisting of a single bond, O, S, S(O)$_2$ and N;
(e) U is an aliphatic linker wherein one carbon atom of the aliphatic linker may be replaced with O, NH or S, and wherein such aliphatic linker is optionally substituted with R30;
(f) Y is selected from the group consisting of C, O, S, NH and a single bond;
(g) E is C(R3)(R4)A or A and wherein
(i) A is selected from the group consisting of carboxyl, tetrazole, $C_1$-$C_6$ alkylnitrile, carboxamide, sulfonamide and acylsulfonamide; wherein sulfonamide, acylsulfonamide and tetrazole are each optionally substituted with from one to two groups independently selected from R$^7$;
(ii) each R$^7$ is independently selected from the group consisting of hydrogen, $C_1$-$C_6$haloalkyl, aryl $C_0$-$C_4$ alkyl and $C_1$-$C_6$ alkyl;
(iii) R3 is selected from the group consisting of hydrogen, $C_1$-$C_5$ alkyl, and $C_1$-$C_5$ alkoxy; and
(iv) R4 is selected from the group consisting of H, $C_1$-$C_5$ alkyl, $C_1$-$C_5$ alkoxy, aryloxy, $C_3$-$C_6$ cycloalkyl, and aryl $C_0$-$C_4$ alkyl, and R3 and R4 are optionally combined to form a $C_3$-$C_4$ cycloalkyl, and wherein alkyl, alkoxy, aryloxy, cycloalkyl and aryl-alkyl are each optionally substituted with one to three substituents each independently selected from R26;
(h) B is selected from the group consisting of S, O, C, and N, with the proviso that when B is N then Z is C;
(i) Z is selected from the group consisting of N and C, with the proviso that when B is C then Z is N;
(j) R8 is selected from the group consisting of hydrogen, $C_1$-$C_4$ alkyl, $C_1$-$C_4$ alkylenyl, and halo;
(k) R9 is selected from the group consisting of hydrogen, $C_1$-$C_4$ alkyl, $C_1$-$C_4$ alkylenyl, halo, aryl-$C_0$-$C_4$ alkyl, heteroaryl, $C_1$-$C_6$ alkyl, and OR29, and wherein aryl-$C_0$-$C_4$ alkyl, heteroaryl are each optionally substituted with from one to three independently selected from R27; R29 is selected from the group consisting of hydrogen and $C_1$-$C_4$ alkyl;
(l) R10, R11 are each independently selected from the group consisting of hydrogen, hydroxy, cyano, nitro, halo, oxo, $C_1$-$C_6$ alkyl, $C_1$-$C_6$ alkyl-COOR12", $C_0$-$C_6$ alkoxy, $C_1$-$C_6$haloalkyl, $C_1$-$C_6$ haloalkyloxy, $C_3$-$C_7$ cycloalkyl, aryl-$C_{0-4}$-alkyl, aryl-$C_{1-4}$-heteroalkyl, heteroaryl-$C_{0-4}$-alkyl, $C_3$-$C_6$ cycloalkylaryl-$C_{0-2}$-alkyl, aryloxy, C(O)R13, COOR14', OC(O)R15', OS(O)$_2$R16', N(R17')$_2$, NR18'C(O)R19', NR20'SO$_2$R21', SR22', S(O)R23', S(O)$_2$R24', and S(O)$_2$N(R25')$_2$; and wherein aryl-$C_{0-4}$-alkyl, aryl-$C_{1-4}$-heteroalkyl, heteroaryl-$C_{0-4}$-alkyl, and $C_3$-$C_6$ cycloalkylaryl-$C_{0-2}$-alkyl are each optionally substituted with from one to three substituents independently selected from R28;
(m) R12', R12", R13', R14', R15', R16', R17', R18', R19', R20', R21', R12', R23', R24', and R25' are each independently selected from the group consisting of hydrogen, $C_1$-$C_6$ alkyl and aryl;
(n) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and $C_3$-$C_6$ cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and $C_3$-$C_6$ cycloalkylaryl-$C_{0-2}$-alkyl are each optionally substituted with from one to three substituents each independently selected from R31;
(o) R32 is selected from the group consisting of a bond, hydrogen, halo, $C_1$-$C_6$ alkyl, $C_1$-$C_6$ haloalkyl, and $C_1$-$C_6$ alkyloxo;
(p) AL is selected from the group consisting of a fused $C_3$-$C_8$ carbocyclic and a fused phenyl; and
(q) ---- is optionally a bond to form a double bond at the indicated position.

It can be preferred that the compound of this invention is of the structural Formula II:

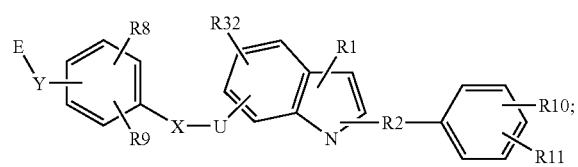

wherein the E, Y, R8, R9, X, U, R1, R32, R2, R10, and R11 are as defined herein above.

It can be preferred that the compound of this invention is of the structural Formula III:

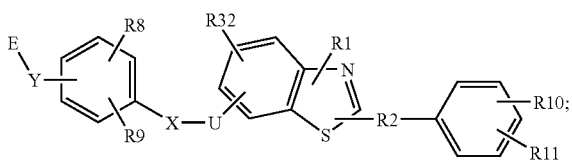

wherein the E, Y, R8, R9, X, U, R1, R32, R2, R10, and R11 are as defined above. It can be preferred that the compound of this invention is of the Structural Formula IV:

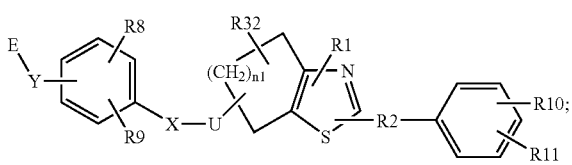

wherein E, Y, R8, R9, X, U, R1, R32, R2, R10, and R11 are as defined herein above; n1 is 1 to 5. It is preferred that n1 is 1 to 2.

It can be preferred that the compound of this invention is of the Structural Formula V:

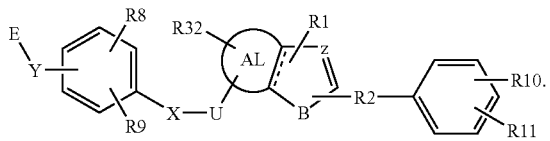

In one embodiment, the present invention also relates to pharmaceutical compositions comprising at least one compound of the present invention, or a pharmaceutically acceptable salt, solvate, hydrate, or stereioisomer thereof, and a pharmaceutically acceptable carrier.

In another embodiment, the present invention relates to a method of selectively modulating a PPAR delta receptor by contacting the receptor with at least one compound represented by Structural Formula I, or a pharmaceutically acceptable salt, solvate, hydrate, or stereioisomer thereof.

In another embodiment, the present invention relates to a method of modulating one or more of the PPAR alpha, beta, gamma, and/or delta receptors.

In a further embodiment, the present invention relates to a method of making a compound represented by Structural Formula I.

The compounds of the present invention are believed to be effective in treating and preventing Metabolic Syndrome, Type II diabetes, hyperglycemia, hyperlipidemia, obesity, coagaulopathy, hypertension, atherosclerosis, and other disorders related to Metabolic Syndrome and cardiovascular diseases. Further, compounds of this invention can be useful for lowering fibrinogen, increasing HDL levels, treating renal disease, controlling desirable weight, treating demyelinating diseases, treating certain viral infections, and treating liver disease. In addition, the compounds can be associated with fewer clinical side effects than compounds currently used to treat such conditions.

DETAILED DESCRIPTION OF THE INVENTION

The terms used to describe the instant invention have the following meanings.

As used herein, the term "aliphatic linker" or "aliphatic groups" is a non-aromatic, consisting solely of carbon and hydrogen and may optionally contain one or more units of unsaturation, e.g., double and/or triple bonds (also refer herein as "alkenyl" and "alkynyl"). An aliphatic or aliphatic group may be straight chained, branched (also refer herein as "alkyl") or cyclic (also refer herein as "cycloalkyl). When straight chained or branched, an aliphatic group typically contains between about 1 and about 10 carbon atoms, more typically between about 1 and about 6 carbon atoms. When cyclic, an aliphatic typically contains between about 3 and about 10 carbon atoms, more typically between about 3 and about 7 carbon atoms. Aliphatics are preferably $C_1$-$C_{10}$ straight chained or branched alkyl groups (i.e. completely saturated aliphatic groups), more preferably $C_1$-$C_6$ straight chained or branched alkyl groups. Examples include, but are not limited to methyl, ethyl, propyl, n-propyl, iso-propyl, n-butyl, sec-butyl, and tert-butyl. Additional examples include, but are not limited to, cyclopropyl, cyclopentyl, cyclohexyl, cyclopentyl, cyclohexylyl and the like. It may be preferred that one carbon of the aliphatic linker is replaced with a N, O, or S. It may be preferred that the aliphatic linker is substituted with from one to four substituents each independently selected from R30. It may be preferred that aliphatic linker is substituted with from two to three substituents each independently selected from R30.

The term "alkyl," unless otherwise indicated, refers to those alkyl groups of a designated number of carbon atoms of either a straight or branched saturated configuration. As used herein, "$C_0$ alkyl" means that there is no carbon and therefore represents a bond. Examples of "alkyl", include, but are not limited to, methyl, ethyl, n-propyl, isopropyl, n-butyl, isobutyl, sec-butyl and tert-butyl, pentyl, hexyl, isopentyl and the like. Alkyl as defined above may be optionally substituted with a designated number of substituents as set forth in the embodiment recited above. As used herein, the term "alkyloxo" means an alkyl group of the designated number of carbon atoms with a "=O" substituent.

The term "alkenyl" or "alkylenyl" means hydrocarbon chain of a specified number of carbon atoms of either a straight or branched configuration and having at least one carbon-carbon double bond, which may occur at any point along the chain, such as ethenyl, propenyl, butenyl, pentenyl, vinyl, alkyl, 2-butenyl and the like. Alkenyl as defined above may be optionally substituted with designated number of substituents as set forth in the embodiment recited above.

The term "alkynyl" means hydrocarbon chain of a specified number of carbon atoms of either a straight or branched configuration and having at least one carbon-carbon triple bond, which may occur at any point along the chain. Example of alkynyl is acetylene. Alkynyl as defined above may be optionally substituted with designated number of substituents as set forth in the embodiment recited above.

The term "heteroalkyl" refers to a means hydrocarbon chain of a specified number of carbon atoms wherein at least one carbon is replaced by a heteroatom selected from the group consisting of O, N and S.

The term "cycloalkyl" refers to a saturated or partially saturated carbocycle containing one or more rings of from 3 to 12 carbon atoms, typically 3 to 7 carbon atoms. Examples of cycloalkyl includes, but are not limited to cyclopropyl, cyclobutyl, cyclopentyl, cyclohexyl and cycloheptyl, and the like. "Cycloalkyaryl" means that an aryl is fused with a cycloalkyl, and "Cycloalkylaryl-alkyl" means that the cycloalkylaryl is linked to the parent molecule through the alkyl. Cycloalkyl as defined above may be optionally substituted with a designated number of substituents as set forth in the embodiment recited above.

The term "halo" refers to fluoro, chloro, bromo and iodo.

The term "haloalkyl" is a $C_1$-$C_6$ alkyl group, which is substituted with one or more halo atoms selected from F, Br, Cl and I. An example of a haloalkyl group is trifluoromethyl ($CF_3$).

The term "alkoxy" represents an alkyl group of indicated number of carbon atoms attached through an oxygen bridge, such as methoxy, ethoxy, propoxy, isopropoxy, butoxy, tert-butoxy, pentoxy, and the like. Alkoxy as defined above may be optionally substituted with a designated number of substituents as set forth in the embodiment recited above.

The term "haloalkyloxy" represents a $C_1$-$C_6$ haloalkyl group attached through an oxygen bridge, such as $OCF_3$. The "haloalkyloxy" as defined above may be optionally substituted with a designated number of substituents as set forth in the embodiment recited above.

The term "aryl", includes carbocyclic aromatic ring systems (e.g. phenyl), fused polycyclic aromatic ring systems (e.g. naphthyl and anthracenyl) and aromatic ring systems fused to carbocyclic non-aromatic ring systems (e.g., 1,2,3, 4-tetrahydronaphthyl). "Aryl" as defined above may be optionally substituted with a designated number of substituents as set forth in the embodiment recited above.

As used herein when "R8 and R9 optionally combine to form a five membered fused bicyclic with the phenyl to which R8 and R9 attach" means when R8 and R9 combine to form a five membered ring, the resulting fused bicyclic is a structure, for example, but not limited to, a compound of the formula X:

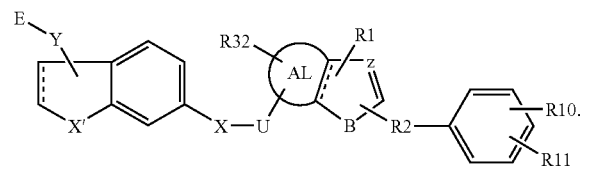

As shown by the above formula X, the variable X' is selected from the group consisting of S and O. The z,900 represents an optional double bond. The fused bicyclic may contain a heteroatom at any available position on the ring and the E-Y— group shall attach at any available position on the 5 membered fused ring.

As used herein, when AL is "a fused pyrimidyl", then the pyrimidyl is fused to the five membered ring to which AL is attached. The resulting structure is, for example, but not limited to, a compound of the formula:

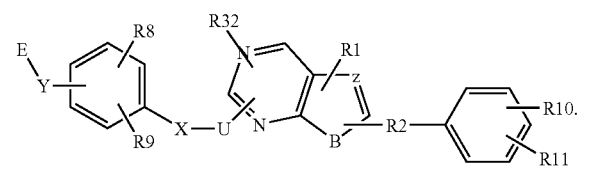

As used herein, when AL is "a fused pyridinyl", then the pyridinyl is fused to the five membered ring to which AL is attached. The resulting structure is, for example, but not limited to, a compound of the formula:

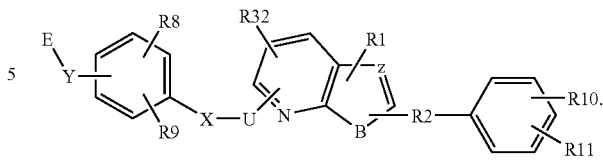

As used herein, the term "fused carbocyclic" means an optionally saturated $C_3$-$C_9$ ring system that is fused with the

group to form a 7 to 12 member bicyclic ring system. The fused ring system can optionally contain one or more double bonds. Such fused ring system is substituted with R1 and R32, as defined herein.

As used herein, the term "fused phenyl" means that the phenyl ring is fused with the

group to form a bicyclic group of the formula

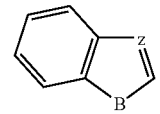

and wherein such group is substituted with R32 and R1, as defined herein.

The term "arylalkyl" refers to an aryl alkyl group which is linked to the parent molecule through the alkyl group, which may be further optionally substituted with a designated number of substituents as set forth in the embodiment recited above. When arylalkyl is aryl$C_0$alkyl, then the aryl group is bonded directly to the parent molecule. Likewise, arylheteroalkyl means an aryl group linked to the parent molecule through the heteroalkyl group.

The term "acyl" refers to alkylcarbonyl or aryl/heteroaryl carbonyl species.

The term "heteroaryl" group, as used herein, is an aromatic ring system having at least one heteroatom such as nitrogen, sulfur or oxygen and includes monocyclic, bicyclic or tricyclic aromatic ring of 5- to 14-carbon atoms containing one or more heteroatoms selected from the group consisting of O, N, and S. The "heteroaryl" as defined above may be optionally substituted with a designated Lumber of substituents as set forth in the embodiment recited above. Examples of heteroaryl are, but are not limited to, furanyl, indolyl, thienyl (also referred to herein as "thiophenyl") thiazolyl, imidazolyl, isoxazoyl, oxazoyl, pyrazoyl, pyrrolyl, pyrazinyl, pyridyl, pyrimidyl, pyrimidinyl and purinyl, cinnolinyl, benzofuranyl, benzothienyl, benzotriazolyl, benzoxazolyl, quinoline, isoxazolyl, isoquinoline and the like. The term "heteroarylalkyl" means that the heteroaryl group is linked to the parent molecule through the alkyl portion of the heteroarylalkyl.

The term "heterocycloalkyl" refers to a non-aromatic ring which contains one or more oxygen, nitrogen or sulfur and includes a monocyclic, bicyclic or tricyclic non-aromatic ring of 5 to 14 carbon atoms containing one or more heteroatoms selected from O, N or S. The "heterocycloalkyl" as defined above may be optionally substituted with a designated number of substituents as set forth in the embodiment recited above. Examples of heterocycloalkyl include, but are not limited to, morpholine, piperidine, piperazine, pyrrolidine, and thiomorpholine. As used herein, alkyl groups include straight chained and branched hydrocarbons, which are completely saturated.

As used herein, the phrase "selectively modulate" means a compound whose EC50 for the stated PPAR receptor is at least ten fold lower than its EC50 for the other PPAR receptor subtypes.

When a compound represented by Structural Formula I has more than one chiral substituent it may exist in diastereoisomeric forms. The diastereoisomeric pairs may be separated by methods known to those skilled in the art, for example chromatography or crystallization and the individual enantiomers within each pair may be separated using methods familiar to the skilled artisan. The present invention includes each diastereoisomer of compounds of Structural Formula I and mixtures thereof.

Certain compounds of Structural Formula I may exist in different stable conformational forms which may be separable. Torsional asymmetry due to restricted rotation about an asymmetric single bond, for example because of steric hindrance or ring strain, may permit separation of different conformers. The present invention includes each conformational isomer of compounds of Structural Formula I and mixtures thereof.

Certain compounds of Structural Formula I may exist in zwitterionic form and the present invention includes each zwitterionic form of compounds of Structural Formula I and mixtures thereof.

"Pharmaceutically-acceptable salt" refers to salts of the compounds of the Structural Formula I which are considered to be acceptable for clinical and/or veterinary use. Typical pharmaceutically-acceptable salts include those salts prepared by reaction of the compounds of the present invention with a mineral or organic acid or an organic or inorganic base. Such salts are known as acid additiona salts and base addition salts, respectively. It will be recognized that the particular counterion forming a part of any salt of this invention is not of a critical nature, so long as the salt as a whole is pharmaceutically-acceptable and as long as the counterion does not contribute undesired qualities to the salt as a whole. These salts may be prepared by methods known to the skilled artisan.

The term, "active ingredient" means the compounds generically described by Structural Formula I as well as the stereoisomers, salts, solvates, and hydrates, The term "pharmaceutically acceptable" means that the carrier, diluent, excipients and salt are pharmaceutically compatible with the other ingredients of the composition. Pharmaceutical compositions of the present invention are prepared by procedures known in the art using well known and readily available ingredients.

"Preventing" refers to reducing the likelihood that the recipient will incur or develop any of the pathological conditions described herein. The term "preventing" is particularly applicable to a patient that is susceptible to the particular pathological condition.

"Treating" refers to mediating a disease or condition and preventing, or mitigating, its further progression or ameliorate the symptoms associated with the disease or condition.

"Pharmaceutically-effective amount" means that amount of active ingredientit, that will elicit the biological or medical response of a tissue, system, or mammal. Such an amount can be administered prophylactically to a patient thought to be susceptible to development of a disease or condition. Such amount when administered prophylactically to a patient can also be effective to prevent or lessen the severity of the mediated condition. Such an amount is intended to include an amount which is sufficient to modulate a selected PPAR receptor or to prevent or mediate a disease or condition. Generally, the effective amount of a Compound of Formula I will be between 0.02 through 5000 mg per day. Preferably the effective amount is between 1 through 1,500 mg per day. Preferably the dosage is from 1 through 1,000 mg per day.

The desired dose may be presented in a single dose or as divided doses administered at appropriate intervals. It may be preferred that the dosages are administered at intervals which are less than daily. For example, but not limited to, every other day, weekly, biweekly, or monthly, as appropriate.

A "mammal" is an individual animal that is a member of the taxonomic class Mammalia. The class Mammalia includes humans, monkeys, chimpanzees, gorillas, cattle, swine, horses, sheep, dogs, cats, mice, and rats.

Administration to a human is most preferred. The compounds and compositions of the present invention are useful for the treatment and/or prophylaxis of cardiovascular disease, for raising serum HDL cholesterol levels, for lowering serum triglyceride levels and for lower serum LDL cholesterol levels. Elevated triglyceride and LDL levels, and low HDL levels, are risk factors for the development of heart disease, stroke, and circulatory system disorders and diseases.

Further, the compound and compositions of the present invention may reduce the incidence of undesired cardiac events in patients. The physician of ordinary skill will know how to identify humans who will benefit from administration of the compounds and compositions of the present invention.

The compounds and compositions of the present invention are also useful for treating and/or preventing obesity.

Further, these compounds and compositions are useful for the treatment and/or prophylaxis of non-insulin dependent diabetes mellitus (NIDDM) with reduced or no body weight gains by the patients. Furthermore, the compounds and compositions of the present invention are useful to treat or prevent acute or transient disorders in insulin sensitivity, such as sometimes occur following surgery, trauma, myocardial infarction, and the like.

The present invention further provides a method for the treatment and/or prophylaxis of hyperglycemia in a human or non-human mammal which comprises administering an effective amount of active ingredient, as defined herein, to a hyperglycemic human or non-human mammal in need thereof.

The invention also relates to the use of a compound of Formula I as described above, for the manufacture of a medicament for treating a PPAR receptor mediated condition.

A therapeutically effective amount of a compound of Structural Formula I can be used for the preparation of a medicament useful for treating Metabolic Syndrome, diabetes, treating obesity, lowering tryglyceride levels, lowering serum LDL levels, raising the plasma level of high density lipoprotein, and for treating, preventing or reducing the risk of developing atherosclerosis, and for preventing or reducing the risk of having a first or subsequent atherosclerotic disease event in mammals, particularly in humans. In general, a therapeutically effective amount of a compound of the present invention typically reduces serum triglyceride levels of a patient by about 20% or more, and increases serum HDL levels in a patient. Preferably, HDL levels will be increased by about 30% or more. In addition, a therapeutically effective amount of a compound, used to prevent or treat NIDDM, typically reduces serum glucose levels, or more specifically HbA1c, of a patient by about 0.7% or more.

When used herein Metabolic Syndrome includes pre-diabetic insulin resistance syndrome and the resulting complications thereof, insulin resistance, non-insulin dependent diabetes, dyslipidemia, hyperglycemia obesity, coagulopathy, hypertension and other complications associated with diabetes. The methods and treatments mentioned herein include the above and encompass the treatment and/or prophylaxis of any one of or any combination of the following: pre-diabetic insulin resistance syndrome, the resulting complications thereof, insulin resistance, Type II or non-insulin dependent diabetes, dyslipidemia, hyperglycemia, obesity and the complications associated with diabetes including cardiovascular disease, especially atherosclerosis.

In addition, the methods and treatments mentioned herein include the above and encompass the treatment and/or prophylaxis of any one of or any combination of the following inflammatory and autoimmune diseases: adult respiratory distress syndrome, rheumatoid arthritis, demyelinating disease, Chrohne's disease, asthma, systemic lupus erythematosus, psoriasis, and bursitis.

The compositions are formulated and administered in the same general manner as detailed herein. The compounds of the instant invention may be used effectively alone or in combination with one or more additional active agents depending on the desired target therapy. Combination therapy includes administration of a single pharmaceutical dosage composition which contains a compound of Structural Formula I, a stereoisomer, salt, solvate and/or hydrate thereof ("Active Ingredient") and one or more additional active agents, as well as administration of a compound of Active Ingredient and each active agent in its own separate pharmaceutical dosage formulation. For example, an Active Ingredient and an insulin secretogogue such as biguanides, thiazolidinediones, sulfonylureas, insulin, or α-glucosidose inhibitors can be administered to the patient together in a single oral dosage composition such as a tablet or capsule, or each agent administered in separate oral dosage formulations. Where separate dosage formulations are used, an Active Ingredient and one or more additional active agents can be administered at essentially the same time, i.e., concurrently, or at separately staggered times, i.e., sequentially; combination therapy is understood to include all these regimens.

An example of combination treatment or prevention of atherosclerosis may be wherein an Active Ingredient is administered in combination with one or more of the following active agents: antihyperlipidemic agents; plasma HDL-raising agents; antihypercholesterolemic agents, fibrates, vitamins, aspirin, and the like. As noted above, the Active Ingredient can be administered in combination with more than one additional active agent.

Another example of combination therapy can be seen in treating diabetes and related disorders wherein the Active Ingredient can be effectively used in combination with, for example, sulfonylureas, biguanides, thiazolidinediones, α-glucosidase inhibitors, other insulin secretogogues, insulin as well as the active agents discussed above for treating atherosclerosis.

The Active Ingredients of the present invention, have valuable pharmacological properties and can be used in pharmaceutical compositions containing a therapeutically effective amount of Active Ingredient of the present invention, in combination with one or more pharmaceutically acceptable excipients. Excipients are inert substances such as, without limitation carriers, diluents, fillers, flavoring agents, sweeteners, lubricants, solubilizers, suspending agents, wetting agents, binders, disintegrating agents, encapsulating material and other conventional adjuvants. Proper formulation is dependent upon the route of administration chosen. Pharmaceutical compositions typically contain from about 1 to about 99 weight percent of the Active Ingredient of the present invention.

Preferably, the pharmaceutical formulation is in unit dosage form. A "unit dosage form" is a physically discrete unit containing a unit dose, suitable for administration in human subjects or other mammals. For example, a unit dosage form can be a capsule or tablet, or a number of capsules or tablets. A "unit dose" is a predetermined quantity of the Active Ingredient of the present invention, calculated to produce the desired therapeutic effect, in association with one or more pharmaceutically-acceptable excipients. The quantity of active ingredient in a unit dose may be varied or adjusted from about 0.1 to about 1500 milligrams or more according to the particular treatment involved. It may be preferred that the unit dosage is from about 1 mg to about 1000 mg.

The dosage regimen utilizing the compounds of the present invention is selected by one of ordinary skill in the medical or veterinary arts, in view of a variety of factors, including, without limitation, the species, age, weight, sex, and medical condition of the recipient, the severity of the condition to be treated, the route of administration, the level of metabolic and excretory function of the recipient, the dosage form employed, the particular compound and salt thereof employed, and the like.

Advantageously, compositions containing the compound of Structural Formula I or the salts thereof may be provided in dosage unit form, preferably each dosage unit containing from about 1 to about 500 mg be administered although it will, of course, readily be understood that the amount of the compound or compounds of Structural Formula I actually to be administered will be determined by a physician, in the light of all the relevant circumstances.

Preferably, the compounds of the present invention are administered in a single daily dose, or the total daily dose may be administered in divided doses, two, three, or more times per day. Where delivery is via transdermal forms, of course, administration is continuous.

Suitable routes of administration of pharmaceutical compositions of the present invention include, for example, oral, eyedrop, rectal, transmucosal, topical, or intestinal administration; parenteral delivery (bolus or infusion), including intramuscular, subcutaneous, intramedullary injections, as well as intrathecal, direct intraventricular, intravenous, intraperitoneal, intranasal, or intraocular injections. The compounds of the invention can also be administered in a targeted drug delivery system, such as, for example, in a liposome coated with endothelial cell-specific antibody.

Solid form formulations include powders, tablets and capsules.

Sterile liquid formulations include suspensions, emulsions, syrups, and elixirs.

Pharmaceutical compositions of the present invention can be manufactured in a manner that is itself known, e.g., by means of conventional mixing, dissolving, granulating, dragee-making, levigating, emulsifying, encapsulating, entrapping, lyophilizing processes, and/or coupled with soluble polymers as targeted drug carriers.

The following pharmaceutical formulations 1 and 2 are illustrative only and are not intended to limit the scope of the invention in any way.

Formulation 1

Hard gelatin capsules are prepared using the following ingredients:

| | Quantity (mg/capsule) |
|---|---|
| Active Ingredient | 250 |
| Starch, dried | 200 |
| Magnesium stearate | 10 |
| Total | 460 mg |

Formulation 2

A tablet is prepared using the ingredients below:

| | Quantity (mg/tablet) |
|---|---|
| Active Ingredient | 250 |
| Cellulose, microcrystalline | 400 |
| Silicon dioxide, fumed | 10 |
| Stearic acid | 5 |
| Total | 665 mg |

The components are blended and compressed to form tablets each weighing 665 mg.

In yet another embodiment of the compounds of the present invention, the compound is radiolabelled, such as with carbon-14, or tritiated. Said radiolabelled or tritiated compounds are useful as reference standards for in vitro assays to identify new selective PPAR receptor agonists.

The compounds of the present invention can be useful for modulating insulin secretion and as research tools. Certain compounds and conditions within the scope of this invention are preferred. The following conditions, invention embodiments, and compound characteristics listed in tabular form may be independently combined to produce a variety of preferred compounds and process conditions. The following list of embodiments of this invention is not intended to limit the scope of this invention in any way.

Some preferred characteristics of compounds of formula I are:
- (a) R3 is methyl;
- (b) R4 is hydrogen;
- (c) R3 is $C_1$-$C_2$ alkyl;
- (d) R4 is $C_1$-$C_2$ alkyl;
- (e) R3 and R4 are each hydrogen;
- (f) R3 and R4 are each methyl;
- (g) A is carboxyl;
- (h) X is —O—;
- (i) X is —S—;
- (j) X is a bond;
- (k) U is CH;
- (l) U is $CH_2CH$;
- (m) R9 is methyl;
- (n) R9 is hydrogen;
- (o) R9 is $C_1$-$C_3$ alkyl;
- (p) R8 is methyl;
- (q) R8 and R9 are each hydrogen;
- (r) R8 and R9 combine to form a five membered fused ring;
- (s) R8 and R9 combine to form a five membered fused ring to form a compound of the formula IX:

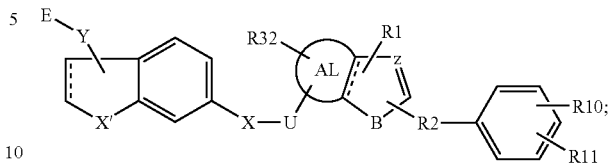

- (t) X' is O;
- (u) X' is S;
- (v) R10 is $CF_3$;
- (w) R10 is haloalkyl;
- (x) R10 is haloalkyloxy;
- (y) R11 is hydrogen
- (z) R10 and R11 are each hydrogen;
- (aa) R11 is haloalkyl;
- (bb) Z is N;
- (cc) Z and B are each N;
- (dd) Z is C and B is N;
- (ee) B is S;
- (ff) B is O;
- (gg) AL is unsaturated;
- (hh) AL is saturated;
- (ii) AL is aromatic;
- (jj) AL is a fused phenyl;
- (kk) AL is fused pyriminyl;
- (ll) AL is fused pyridinyl;
- (mm) AL is a fused $C_5$-$C_7$ cycloalkyl;
- (nn) ---- in the five membered ring each from a double bond at the designated position in Formula I;
- (oo) R1 is $C_1$-$C_4$ alkyl;
- (pp) R32 is hydrogen;
- (qq) R2 is a bond;
- (rr) R2 is $C_1$-$C_2$ alkyl;
- (ss) Y is O;
- (tt) Y is S;
- (uu) Y is C;
- (vv) E is C(R3)(R4)A;
- (ww) A is COOH;
- (xx) Aliphatic linker is saturated;
- (yy) Aliphatic linker is substituted with $C_1$-$C_3$ alkyl;
- (zz) Aliphatic linker is $C_1$-$C_3$ alkyl;
- (aaa) Aliphatic linker is $C_1$-$C_2$ alkyl;
- (bbb) Aliphatic linker is $C_1$-$C_3$ alkyl and one carbon is replaced with an —O—;
- (ccc) A compound of this invention of the Structural Formula VIII

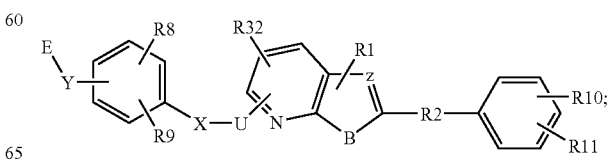

(ddd) A compound of this invention of the Structural Formula X:

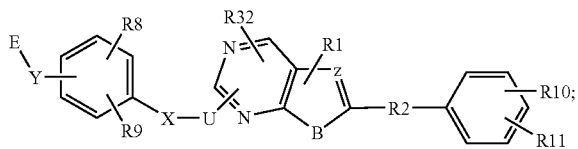

(eee) A compound of this invention of the Structural Formula II:

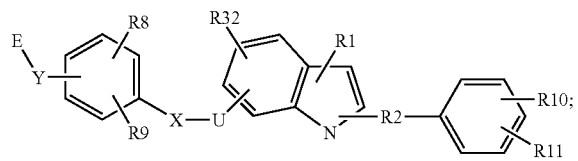

(fff) A compound of this invention of The Structural Formula III:

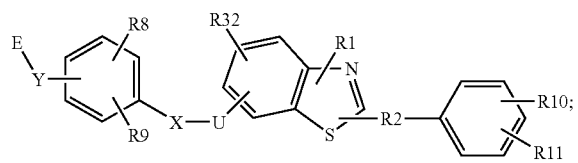

(ggg) A compound of this invention of the Structural Formula IV:

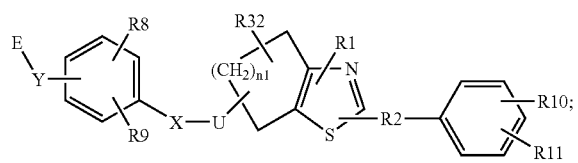

(hhh) A compound of this invention of the Structural Formula V:

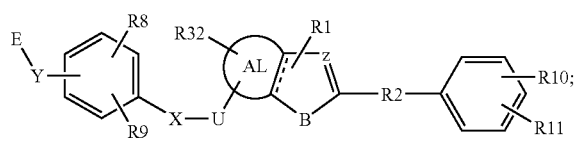

(iii) A compound of this invention of the Structural Formula VI:

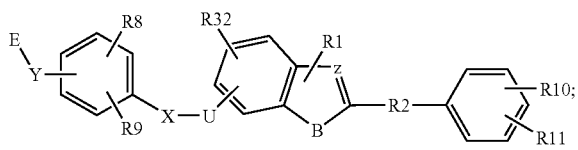

(jjj) A compound of this invention of the Structural Formula VII:

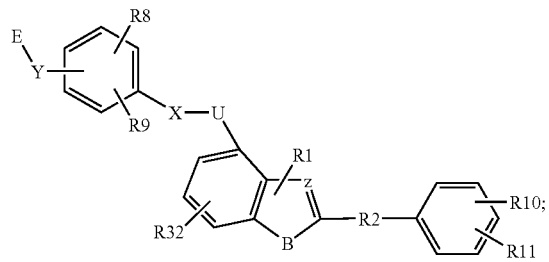

(kkk) Aryl is a phenyl group;
(lll) A compound of Formula I that selectively modulates a delta receptor;
(mmm) An Active Ingredient, as described herein, that is a PPAR coagaonist that modulates a gamma receptor and a delta receptor;
(nnn) An Active Ingredient, as described herein, for use in the treatment of cardiovascular disease;
(ooo) An Active Ingredient, as described herein, for use in the treatment of Metabolic Syndrome;
(ppp) An Active Ingredient for use in the control of obesity;
(qqq) An Active Ingredient for use in treating diabetes;
(rrr) An Active Ingredient that is a PPAR receptor agonist;
(sss) A compound of Formula I selected from the group consisting of Racemic-{2-Methyl-4-[2-(4-trifluoromethyl-phenyl)-5,6-dihydro-4H-cyclopentathiazol-4-ylmethylsulfanyl]-phenoxy}-acetic acid;
(R)-{2-Methyl-4-[2-(4-trifluoromethyl-phenyl)-5,6-dihydro-4H-cyclopentathiazol-4-ylmethylsulfanyl]-phenoxy}-acetic acid;
(S)-{2-Methyl-4-[2-(4-trifluoromethyl-phenyl)-5,6-dihydro-4H-cyclopentathiazol-4-ylmethylsulfanyl]-phenoxy}-acetic acid;
Racemic-3-{2-Methyl-4-[2-(4-trifluoromethyl-phenyl)-5,6-dihydro-4H-cyclopentathiazol-4-ylmethoxy]-phenyl}-propionic acid;
Racemic-3-{2-Methyl-4-[2-(4-trifluoromethyl-phenyl)-5,6-dihydro-4H-cyclopentathiazol-4-ylmethylsulfanyl]-phenyl}-propionic acid;
(R)-3-{2-Methyl-4-[2-(4-trifluoromethyl-phenyl)-5,6-dihydro-4H-cyclopentathiazol-4-ylmethylsulfanyl]-phenyl}-propionic acid;
(S)-3-{2-Methyl-4-[2-(4-trifluoromethyl-phenyl)-5,6-dihydro-4H-cyclopentathiazol-4-ylmethylsulfanyl]-phenyl}-propionic acid;
Racemic-{2-Methyl-4-[2-(4-trifluoromethyl-phenyl)-4,5,6,7-tetrahydro-benzothiazol-4-ylmethylsulfanyl]-phenoxy}-acetic acid;
(S)-{2-Methyl-4-[2-(4-trifluoromethyl-phenyl)-4,5,6,7-tetrahydro-benzothiazol-4-ylmethylsulfanyl]-phenoxy}-acetic acid;
(R)-{2-Methyl-4-[2-(4-trifluoromethyl-phenyl)-4,5,6,7-tetrahydro-benzothiazol-4-ylmethylsulfanyl]-phenoxy}-acetic acid;
{2-Methyl-4-[2-(4-trifluoromethyl-phenyl)-4,5,6,7-tetrahydro-benzothiazol-4-ylmethoxy]-phenoxy}-acetic acid;
Racemic-3-{2-Methyl-4-[2-(4-trifluoromethyl-phenyl)-4,5,6,7-tetrahydro-benzothiazol-4-ylmethylsulfanyl]-phenyl}-propionic acid;
(R)-3-{2-Methyl-4-[2-(4-trifluoromethyl-phenyl)-4,5,6,7-tetrahydro-benzothiazol-4-ylmethylsulfanyl]-phenyl}-propionic acid;

(S)-3-{2-Methyl-4-[2-(4-trifluoromethyl-phenyl)-4,5,6,7-tetrahydro-benzothiazol-4-ylmethylsulfanyl]-phenyl}-propionic acid;
{3-[2-(4-Trifluoromethyl-phenyl)-5,6-dihydro-4H-cyclopentathiazol-4-ylmethoxy]-phenyl}-acetic acid;
(S)-{3-[2-(4-Trifluoromethyl-phenyl)-5,6-dihydro-4H-cyclopentathiazol-4-ylmethoxy]-phenyl}-acetic acid;
(R)-{3-[2-(4-Trifluoromethyl-phenyl)-5,6-dihydro-4H-cyclopentathiazol-4-ylmethoxy]-phenyl}-acetic acid;
{2-Methyl-4-[7-methyl-2-(4-trifluoromethyl-phenyl)-4,5,6,7-tetrahydro-benzothiazol-4-ylmethylsulfanyl]-phenoxy}-acetic acid;
(S)-3-{2-Methyl-4-[2-(4-trifluoromethyl-phenyl)-4,5,6,7-tetrahydro-benzothiazol-4-ylmethoxy]-phenyl}-propionic acid;
(R)-3-{2-Methyl-4-[2-(4-trifluoromethyl-phenyl)-4,5,6,7-tetrahydro-benzothiazol-4-ylmethoxy]-phenyl}-propionic acid;
(R)-{3-[2-(4-Trifluoromethyl-phenyl)-4,5,6,7-tetrahydro-benzothiazol-4-ylmethoxy]-phenyl}-acetic acid;
(S)-{3-[2-(4-Trifluoromethyl-phenyl)-4,5,6,7-tetrahydro-benzothiazol-4-ylmethoxy]-phenyl}-acetic acid;
3-{2-Methyl-4-[2-(4-trifluoromethyl-phenyl)-5,6,7,8-tetrahydro-4H-cycloheptathiazol-4-ylmethylsulfanyl]-phenyl}-propionic acid;
{2-Methyl-4-[2-(4-trifluoromethyl-phenyl)-5,6,7,8-tetrahydro-4H-cycloheptathiazol-4-ylmethylsulfanyl]-phenoxy}-acetic acid;
(R)-{2-Methyl-4-[2-(4-trifluoromethyl-phenyl)-5,6,7,8-tetrahydro-4H-cycloheptathiazol-4-ylmethylsulfanyl]-phenoxy}-acetic acid;
(S)-{2-Methyl-4-[2-(4-trifluoromethyl-phenyl)-5,6,7,8-tetrahydro-4H-cycloheptathiazol-4-ylmethylsulfanyl]-phenoxy}-acetic acid;
3-{2-Methyl-4-[2-(4-trifluoromethyl-phenyl)-5,6,7,8-tetrahydro-4H-cycloheptathiazol-4-ylmethoxy]-phenyl}-propionic acid;
{3-[2-(4-Trifluoromethyl-phenyl)-5,6,7,8-tetrahydro-4H-cycloheptathiazol-4-ylmethoxy]-phenyl}-acetic acid;
(R)-3-{2-Methyl-4-[2-(4-trifluoromethyl-phenyl)-5,6,7,8-tetrahydro-4H-cycloheptathiazol-4-ylmethylsulfanyl]-phenyl}-propionic acid;
(S)-3-{2-Methyl-4-[2-(4-trifluoromethyl-phenyl)-5,6,7,8-tetrahydro-4H-cycloheptathiazol-4-ylmethylsulfanyl]-phenyl}-propionic acid;
{2-Methyl-4-[2-(4-trifluoromethyl-phenyl)-4,5,6,7,8,9-hexahydro-cyclooctathiazol-4-ylmethylsulfanyl]-phenoxy}-acetic acid;
{2-Methyl-4-[2-(4-trifluoromethyl-phenyl)-benzothiazol-4-ylmethylsulfanyl]-phenoxy}-acetic acid;
{2-Methyl-4-[2-(4-trifluoromethyl-phenyl)-benzothiazol-4-ylmethylsulfanyl]-phenoxy}-acetic acid ethyl ester;
3-{2-Methyl-4-[2-(4-trifluoromethyl-phenyl)-benzothiazol-4-ylmethylsulfanyl]-phenyl}-propionic acid;
{3-[2-(4-Trifluoromethyl-phenyl)-benzothiazol-4-ylmethoxy]-phenyl}-acetic acid;
3-{2-Methyl-4-[2-(4-trifluoromethyl-phenyl)-benzothiazol-4-ylmethoxy]-phenyl}-propionic acid;
(S)-2-Methoxy-3-{4-[2-(4-trifluoromethyl-phenyl)-benzothiazol-4-ylmethoxy]-phenyl)-propionic acid;
2-Methyl-2-(2-methyl-4-[2-(4-trifluoromethyl-phenyl)-benzothiazol-4-ylmethoxy]-phenoxy}-propionic acid;
Racemic-(2-methyl-4-{1-[2-(4-trifluoromethyl-phenyl)-benzothiazol-4-yl]-ethylsulfanyl}-phenoxy)-acetic acid; and
Racemic-3-(2-methyl-4-{1-[2-(4-trifluoromethyl-phenyl)-benzothiazol-4-yl]-ethylsulfanyl}-phenyl)-propionic acid;
(kkk) A compound of Formula I selected from the group consisting of {2-methyl-4-[2-(4-trifluoromethyl-phenyl)-benzothiazol-4-ylmethylsulfanyl]-phenoxy}-acetic acid and 3-{2-Methyl-4-[2-(4-trifluoromethyl-phenyl)-benzothiazol-4-ylmethylsulfanyl]-phenyl}-propionic acid; and (lll) A compound of this invention selected from

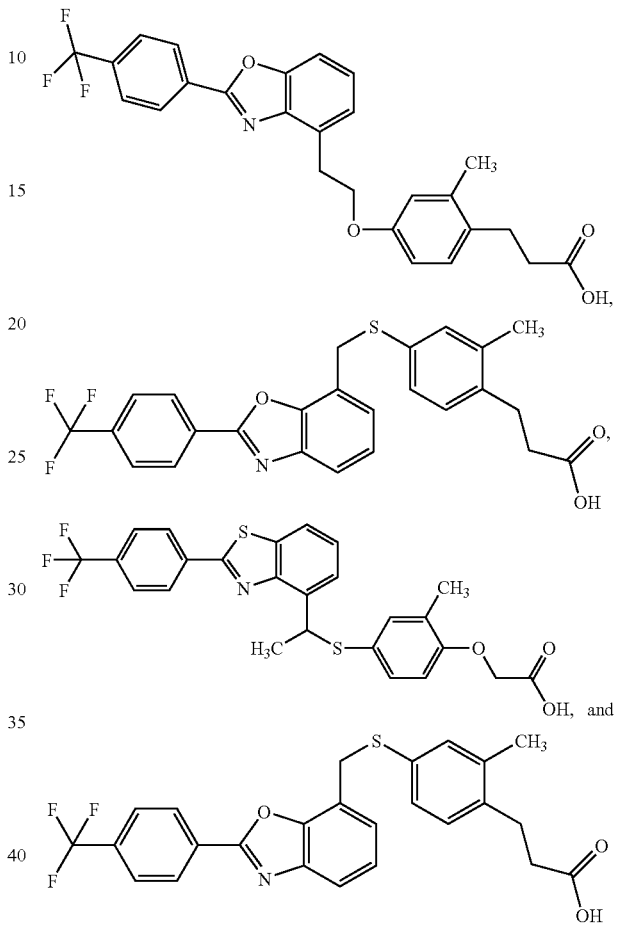

Synthesis

Compounds of the present invention have been formed as specifically described in the examples. Further, many compounds are prepared as more generally using a Mitsunobu protocol (O. Mitsunobu, 1981 Synthesis, p1) and other methods known to the skilled artisan. Alternative synthesis methods may also be effective and known to the skilled artisan.

For example, an intermediate like A is alkylated with an alkylating agent B in the presence of a base (e.g. K2CO3, Cs2CO3 etc.). Hydrolysis in the presence of aqueous NaOH or LiOH gave the acid product.

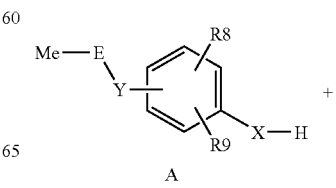

A

-continued

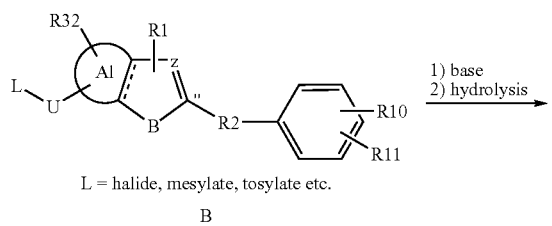

L = halide, mesylate, tosylate etc.

B

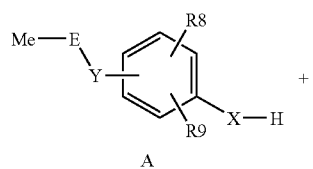

Alternatively, an intermediate like A is coupled with an alcohol C under Mitsunobu reaction condition (DEAD/PPh3, ADDP/PBu3 etc.). Hydrolysis in the presence of aqueous NaOH or LiOH gave the acid product:

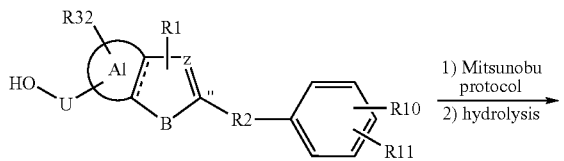

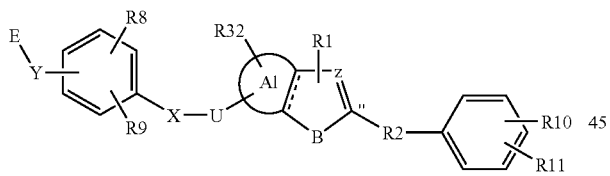

Thioether analogs could also be prepared by a ZnI2 mediated thioether formation reaction as shown below:

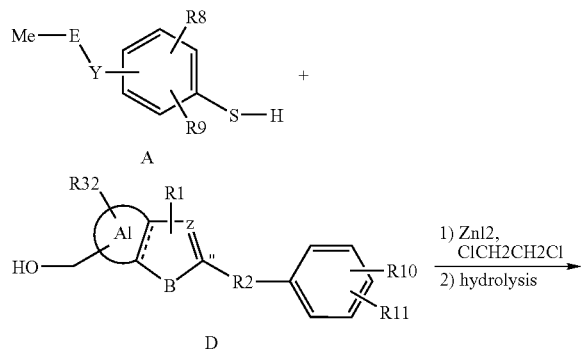

-continued

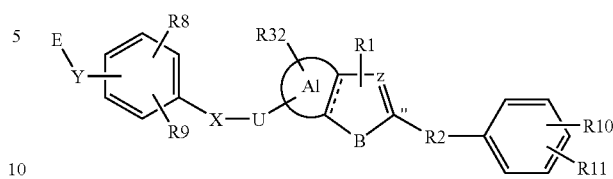

Intermediates B, C and D can be made in one of the following methods. Condensation α'-halo-β-ketoester with thioamide gave the thiazole compound:

Scheme 1

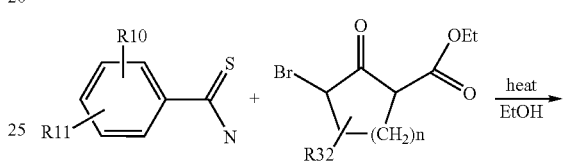

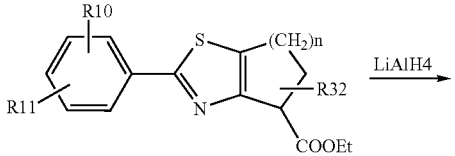

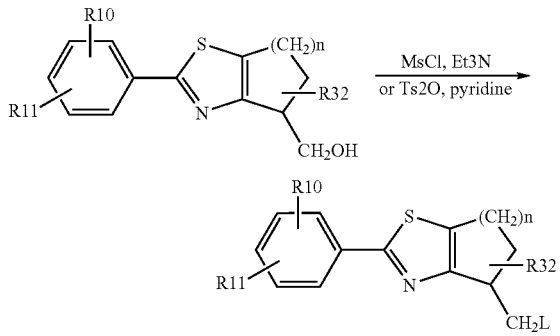

L = Cl, OTs

Alternatively, a convergent method was developed to make the variation at C2 position of the thiazole as shown in scheme 2:

Scheme 2

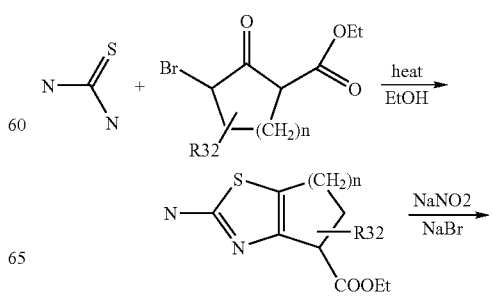

-continued

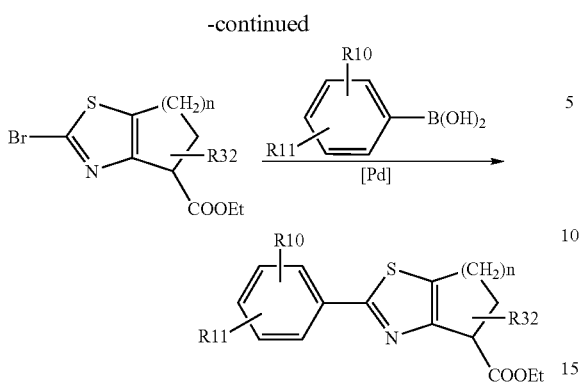

Benzothiazole analogs were made by DDQ oxidation reaction:

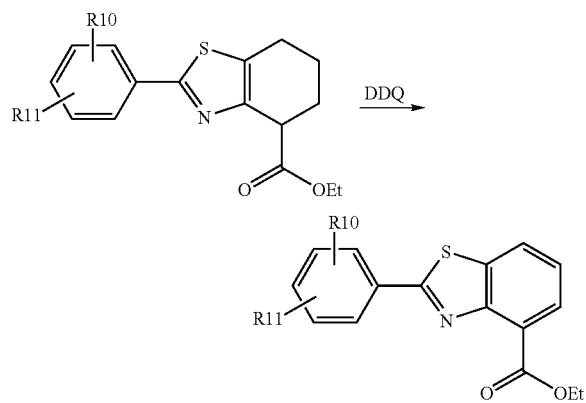

EXEMPLIFICATION

The Examples provided herein are illustrative of the invention claimed herein and are not intended to limit the scope of the claimed invention in any way.

Instrumental Analysis

Infrared spectra are recorded on a Perkin Elmer 781 spectrometer. $^1$H NMR spectra are recorded on a Varian 400 MHz spectrometer at ambient temperature. Data are reported as follows: chemical shift in ppm from internal standard tetramethylsilane on the δ scale, multiplicity (b=broad, s=singlet, d=doublet, t=triplet, q=quartet, qn=quintet and m=multiplet), integration, coupling constant (Hz) and assignment. $^{13}$C NMR are recorded on a Varian 400 MHz spectrometer at ambient temperature. Chemical shifts are reported in ppm from tetramethylsilane on the δ scale, with the solvent resonance employed as the internal standard (CDCl$_3$ at 77.0 ppm and DMSO-d$_6$ at 39.5 ppm). Combustion analyses are performed by Eli Lilly & Company Microanalytical Laboratory. High resolution mass spectra are obtained on VG ZAB 3F or VG 70 SE spectrometers. Analytical thin layer chromatography was performed on EM Reagent 0.25 mm silica gel 60-F plates. Visualization was accomplished with UV light.

Preparation 1

2-(4-Hydroxy-2-methyl-phenoxy)-2-methyl-propionic acid

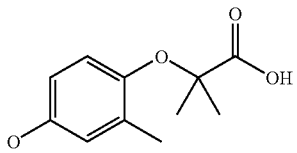

Step A 2-(4-Benzyloxy-2-formylphenoxy)-2-methyl propionic acid ethyl ester

5-Benzyloxy-2-hydroxy-benzaldehyde (Kappe, T.; Witoszynskyj, T. Arch. Pharm., 1975, 308 (5), 339-346) (2.28 g, 10.0 mmol), ethyl bromoisobutyrate (2.2 mL, 15 mmol), and cesium carbonate (3.26 g, 10.0 mmol) in dry DMF (25 mL) are heated at 80° C. for 18 h. The reaction mixture is cooled and partitioned between water (30 mL) and ether (75 mL). The organic layer is washed with brine (15 mL). The aqueous layers are back-extracted with ethyl acetate (30 mL), and the organic layer is washed with brine (20 mL). The combined organic layers are dried (Na$_2$SO$_4$) and concentrated to a brown oil. The crude product is purified by flash chromatography using hexanes:ethyl acetate (2.5:1) to give a pale yellow solid (3.04 g, 89%): mp 65° C.; $^1$H NMR (400 MHz, CDCl$_3$) δ 1.24 (t, 3H, J=7.1 Hz), 1.62 (s, 6H), 4.23 (q, 2H, J=7.1 Hz), 6.81 (d, 1H, J=8.8 Hz), 7.10 (dd, 1H, J=4.6, 9.0 Hz), 7.30-7.43 (m, 6H); MS (ES) m/e 343.1 [M+1].

Step B 2-(4-Hydroxy-2-methyl-phenoxy)-2-methyl-proionic acid ethyl ester 2-(4-Benzyloxy-2-formyl-phenoxy)-2-methyl-propionic acid ethyl ester (9.00 g, 26.3 mmol) in ethanol (250 mL) is treated with 5% Pd/C (1.25 g) and hydrogen (60 psi, rt, overnight). Additional 5% Pd/C (1.25 g) is added, and the reaction is continued for 6 h at 40° C. The mixture is filtered and concentrated to a tan oil (6.25 g). This oil contained 9 mol % of 2-(4-Hydroxy-2-hydroxymethyl-phenoxy)-2-methyl-propionic acid ethyl ester. $^1$H NMR (400 MHz, CDCl$_3$) δ 1.26 (t, 3H, J=7.3 Hz), 1.51 (s, 6H), 2.14 (s, 3H), 4.24 (q, 2H, J=7.3 Hz), 5.68 (brs, 1H), 6.47 (dd, 1H, J=3.4, 8.8 Hz), 6.59 (d, 1H, J=8.3 Hz), 6.60 (brs, 1H).

The following compound is prepared in a similar manner:

Preparation 2

2-(4-Hydroxy-2-methyl-phenoxy)-acetic acid ethyl ester

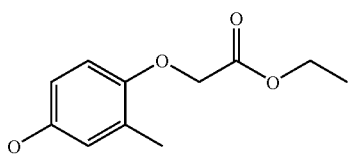

$^1$H NMR (400 MHz, CDCl3) δ 1.28 (t, 3H, J=7.1 Hz), 2.24 (s, 3H), 4.25 (q, 2H, J=7.1 Hz), 4.55 (s, 2H), 6.56 (dd, 1H, J=2.7, 8.5 Hz), 6.61 (d, 1H, J=8.3 Hz), 6.65 (d, 2H, J=2.9 Hz).

Preparation 3

(4-Hydroxy-2-propyl-phenoxy)-acetic acid ethyl ester

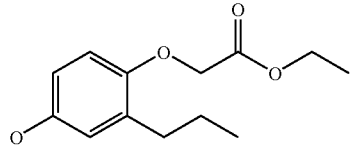

Step A

4-Benzyloxy-2-propylphenol

2-Allyl-4-benzyloxyphenol (WO 9728137 A1 19970807, Adams, A. D. et al.) (5.00 g, 20.8 mmol) in ethyl acetate (40 mL) is treated with 5% Pd/C (0.25 g) and hydrogen (1 atm) at ambient temperature for 18 h. The mixture is filtered and concentrated. The crude product is purified on a Bio age medium pressure chromatography system using a 40 L normal phase cartridge and eluted with 10% ethyl acetate in hexanes to give a tan solid (2.8 g, 56%). Rf=0.33 (25% EtOAc/Hexanes); $^1$H NMR (400 MHz, CDCl$_3$) δ 7.44-7.31 (m, 5H), 6.78 (s, 1H), 6.69 (d, J=1.5 Hz, 2H), 5.00 (s, 2H), 4.31 (s, 1H), 2.55 (t, J=7.6 Hz, 2H), 1.64 (q, J=7.5 Hz, 2H), 0.97 (t, J=7.3 Hz, 3H).

Step B (4-Benzyloxy-2-propylphenoxy)acetic acid ethyl ester

A solution of 4-benzyloxy-2-propylphenol (0.50 g, 1.94 mmol) in dry DMF (7 mL) is cooled in an ice bath and treated with NaH (0.15 g, 3.8 mmol, 60% oil dispersion). The ice bath is removed, ethyl bromoacetate (0.43 mL, 3.9 mmol) is added, and the mixture is placed in an oil bath (T=85° C.). After 18 h, the reaction mixture is cooled and concentrated in vacuo. The residue is diluted with EtOAc, washed with brine (2×), dried (Na$_2$SO$_4$), and concentrated. The crude product is purified by radial chromatography using 10% ethyl acetate in hexanes to give a tan solid (0.62 g, 97%). $^1$H NMR (400 MHz, CDCl$_3$) δ 7.44-7.31 (m, 5H), 6.82 (d, J=2.9 Hz, 1H), 6.72 (dd, J=8.8, 2.9 Hz, 1H), 6.66 (d, J=8.8 Hz, 1H), 5.00 (s, 2H), 4.57 (s, 2H), 4.25 (q, J=7.0 Hz, 2H), 2.63 (t, J=7.6 Hz, 2H), 1.64 (q, J=7.5 Hz, 2H), 1.29 (t, J=7.1 Hz, 3H), 0.95 (t, J=7.3 Hz, 3H); MS (FIA) m/e 329 (M+1).

Step C (4-Hydroxy-2-propylphenoxy)acetic acid ethyl ester

A solution of (4-benzyloxy-2-propylphenoxy)acetic acid ethyl ester (0.60 g, 1.83 mmol) in THF (15 mL) is treated with 5% Pd/C (75 mg) and hydrogen (60 psi) at ambient temperature for 24 h. The mixture is filtered and concentrated. The crude product is purified by radial chromatography using 15% ethyl acetate in hexanes to give a tan solid (0.25 g, 57%).
$^1$H NMR (400 MHz, CDCl$_3$) δ 6.66 (d, J=2.9 Hz, 1H), 6.62 (d, J=8.8 Hz, 1H), 6.57 (dd, J=8.8, 2.9 Hz, 1H), 4.56 (s, 1H), 4.40 (s, 1H), 4.25 (q, J=7.2 Hz, 2H), 2.61 (t, J=7.6 Hz, 2H), 1.63 (q, J=7.5 Hz, 2H), 1.29 (t, J=7.1 Hz, 3H), 0.95 (t, J=7.3 Hz, 3H); MS (FIA) m/e 239 (M+1).

Preparation 4

(3-Bromo-4-hydroxy-phenoxy)-acetic acid ethyl ester

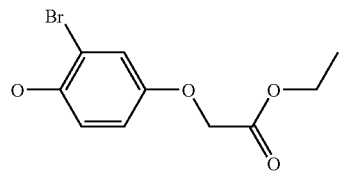

To a solution of (4-hydroxy-phenoxy)-acetic acid ethyl ester (0.59 g, 3 mmol) in acetic acid (1.5 mL) is added bromine (0.48 g, 9 mmol) in acetic acid (0.5 mL) at room temperature. After 5 min, solvent is evaporated and purified by column chromatography on silica gel giving the title compound (0.6 g).

Preparation 5

(4-Mercapto-phenoxy)-acetic acid ethyl ester

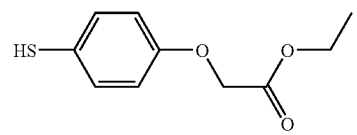

Step A (4-Chlorosulfonyl-phenoxy)-acetic acid ethyl ester

Phenoxy-acetic acid ethyl ester (9.1 mL) is added to chlorosulfonic acid (15 mL) at 0° C. dropwise. The reaction is stirred at 0° C. for 30 min, it is allowed to warm to room temperature. After 2 hrs, the reaction mixture is poured into ice, solid product is collected by filtration and dried under vacuum.

Step B (4-Mercapto-phenoxy)-acetic acid ethyl ester

To a mixture of (4-chlorosulfonyl)-phenoxy)-acetic acid ethyl ester (0.98 g, 3.5 mmol) and tin powder (2.1 g) in ethanol (4.4 mL) is added HCl in dioxane (1.0 M, 4.4 mL) under nitrogen. The mixture is heated to reflux for 2 hrs, it is poured into ice and methylene chloride and filtered. The layers are separated and extracted with methylene chloride, dried and concentrated. The crude product is used for next step without purification.

The following compounds are made in a similar manner:

Preparation 6

(4-Mercapto-2-propyl-phenoxy)-acetic acid ethyl ester

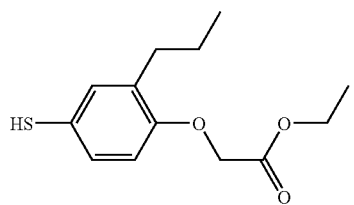

Preparation 7

(4-Mercapto-2-methyl-phenoxy)-acetic acid ethyl ester

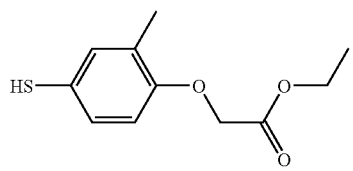

This compound can also be made by the following procedure: To a stirred suspension of Zn powder (10 μm, 78.16 g, 1.2 mol) and dichlorodimethyl silane (154.30 g, 145.02 mL, 1.2 mol) in 500 mL of dichloroethane is added a solution of (4-chlorosulfonyl-2-methyl-phenoxy)-acetic acid ethyl ester (100 g, 0.34 mol) and 1,3-dimethylimidazolidin-2-one (116.98 g, 112.05 mL, 1.02 mol) in 1 L of DCE. Addition is at a rate so as to maintain the internal temperature at ~52° C., cooling with chilled water as necessary. After addition is complete, the mixture is heated at 75° C. for 1 hour. It is then cooled to room temperature, filtered and concentrated iv. Add MTBE, washed twice with saturated LiCl solution concentrate iv again. Take up the residue in CH$_3$CN, wash with hexane (4×) and concentrate iv to yield a biphasic mixture. Let stand in a separatory funnel and separate layers, keeping the bottom layer for product. Filtration through a plug of silica gel (1 Kg, 25% EtOAc/hexane) and subsequent concentration yields 61 g (79%) of a clear, colorless oil.

NMR (DMSO-d$_6$) δ 7.1 (s, 1H), 7.05 (dd, 1H), 6.75 (d, 1H), 5.03 (s, 1H), 4.75 (s, 2H), 4.15 (q, 2H), 2.15 (s, 3H), 1.2 (t, 3H).

Preparation 8

3-(4-Hydroxy-2-methyl-phenyl)-propionic acid methyl ester

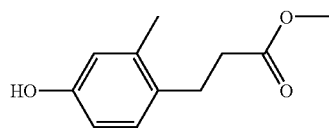

Step A

4-Bromo-3-methyl-Phenyl benzyl ester

To a solution of 4-Bromo-3-methyl-phenol (20.6 g, 0.0.11 mol) in DMF (100 mL) is added Cs2CO3 (54 g, 0.165 mol), followed by benzyl bromide (14.4 mL). After stirred at 60° C. for 40 h, the reaction mixture is diluted with ethyl acetate, filtered through celite. The filtrate is washed with water and brine, dried over sodium sulfate, concentration yields the title product (27 g).

Step B 3-(4-Benzyloxy-2-methyl-phenyl)-propionic acid methyl ester

To a solution of 4-bromo-3-methyl-phenyl benzyl ester (7.6 g, 27.4 mmol) in propronitrile (200 mL) is added methyl acrylate (10 mL) and diisopropylethyl amine (9.75 mL) the solution is degassed and filled with nitrogen for three times. To this mixture are added tri-o-tolyl-phosphane (3.36 g) and palladium acetate (1.25 g) under nitrogen, then heated at 110° C. overnight, cooled to room temperature filtered through celite. The solvent is evaporated, the residue is taken into ethyl acetate and washed with water and brine, dried over sodium sulfate. Concentration and column chromatography on silica gel eluted with hexanes and ethyl acetate yields the title compound (6.33 g).

Step C 3-(4-Hydroxy-2-methyl-phenyl)-propionic acid methyl ester

A mixture of 3-(4-Benzyloxy-2-methyl-phenyl)-propionic acid methyl ester (13.7 g, 48.5 mmol) and Pd/C (5%, 13.7 g) in MeOH (423 mL) is stirred under 60 psi of hydrogen for 24 hrs. Catalyst is filtered off, filtrate is concentrated giving the title compound (8.8 g, 93.5%).

Preparation 9

3-(4-Mercapto-2-methyl-phenyl)-propionic acid methyl ester

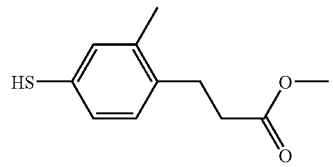

Step A 3-(4-Dimethylthiocarbamoyloxy-2-methyl-phenyl)-propionic acid methyl ester 3-(4-Hydroxy-2-methyl-phenyl)-propionic acid methyl ester (5.0 g, 25.75 mmol) is dissolved into dry dioxane (100 mL) and combined with 4-dimethylamino pyridine (0.500 g, 2.6 mmol), triethylamine (7.0 mL, 51.5 mmol), and dimethylaminothiocarbomoyl chloride (4.5 g, 32.17 mmol). The reaction is heated to reflux under nitrogen. The reaction is monitored by TLC until all of the phenol is consumed, 20 h. After cooling to room temperature, the reaction is diluted with ethyl acetate (200 mL). Water (75 mL) is added and the two layers are separated. The organic layer is washed with brine (75 mL)

then dried over anhydrous sodium sulfate. The solvent is removed and the residue is dried under vacuum.

Step B

3-(4-Dimethylcarbamoylsulfanyl-2-methyl-phenyl)-propionic acid methyl ester 3-(4-Dimethylthiocarbamoyloxy-2-methyl-phenyl)-propionic acid methyl ester, taken crude from the previous step, is diluted with 75 mL of tetradecane and heated to reflux under nitrogen. The reaction is monitored by TLC until all the conversion is complete, 20 h. The reaction is allowed to cool to room temperature, then the tetradecane is decanted away from the resulting oil. The residue is rinsed several times with hexanes. This oil is then purified using flash column chromatography, yielding 5.01 g, or 69% (2 steps) of the product.

Step C

3-(4-Mercapto-2-methyl-phenyl)-propionic acid methyl ester 3-(4-Dimethylcarbamoylsulfanyl-2-methyl-phenyl)-propionic acid methyl ester (5.01 g, 17.8 mmol) is diluted with methanol (30 mL) and to this is added sodium methoxide (1.7 mL of 4M in methanol, 7.23 mmol). The reaction is heated to reflux under nitrogen and monitored by TLC. After complete conversion, 20 h, the reaction is allowed to cool to room temperature. The reaction is neutralized with 1N HCl (7.23 mL) and diluted with ethyl acetate (150 mL). The two phases are separated and the organic layer is washed with water (75 mL), then brine (75 mL). The organic layer is then dried over anhydrous sodium sulfate, then concentrated to yield 4.43 g crude product that is used without further purification.

The following compounds were made in a similar manner starting from corresponding phenol analog

Preparation 10

(3-Chloro-4-mercapto-phenyl)-acetic acid methyl ester

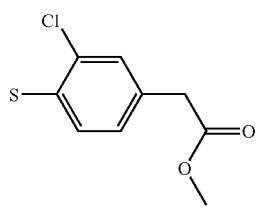

Preparation 11

3-(4-Mercapto-2-methyl-phenyl)-2,2-dimethyl-propionic acid methyl ester

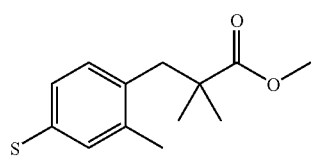

Preparation 12

(4-Hydroxy-2-methyl-phenyl)-acetic acid methyl ester

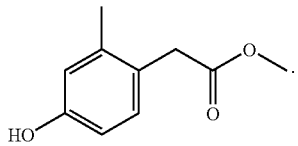

Step A

4-Methoxy-2-methylbenzoic acid (2.5 g, 15.04 mmol) is stirred in thionyl chloride (50 mL) at reflux 2 hr. The mixture is concentrated and diluted with toluene (10 mL) and concentrated. The resulting solid is dried under vacuum 18 hr. The resulting acid chloride is stirred in 20 mL ether at 0 deg C. A solution of diazomethane (39.6 mmol) in ether (150 mL) is added to the acid chloride solution and stirred 18 hr. The resulting diazoketone solution is concentrated. The residue is stirred in methanol (100 mL) and a solution of silver benzoate in triethylamine (1.0 g in 10 mL) is added and the reaction is heated to 60 deg C. and stirred 1 hr. The mixture is concentrated, diluted with 1.0 N aqueous hydrochloric acid (20 mL), extracted to three portions of ethyl acetate (50 mL each). The extracts are combined, washed with aqueous saturated sodium hydrogen carbonate, water, and brine (50 mL each), dried over anhydrous magnesium sulfate, filtered and concentrated. The residue is purified via silica gel chromatography eluting with 9:1 hexanes:ethyl acetate to afford 1.5 g (51%) of the homologated ester as a white solid.

Step B (4-Methoxy-2-methyl-phenyl)-acetic acid methyl ester (1.5 g, 7.72 mmol) is stirred in dichloromethane (50 mL) at 0 deg. C. Aluminum chloride (4.13 g, 31 mmol) is added followed by ethane thiol (2.9 mL, 38.6 mmol). The resulting mixture is stirred at room temperature for 2 hr. Water (50 mL) is added and the product is extracted into ethyl acetate (3×50 ml), the extracts are combined, dried over anhydrous magnesium sulfate, filtered, and concentrated to afford the title compound as a colorless oil, 1.4 g, 100%. MS M$^+$+1 181. The structure is confirmed by $^1$H NMR spectroscopy.

Preparation 13

(3-Hydroxy-phenyl)-acetic acid methyl ester

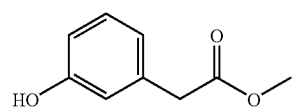

Step A

(3-Hydroxy-phenyl)-acetic acid methyl ester (3-Hydroxy-phenyl)-acetic acid (5.0 g, 32.86 mmol) is stirred in methanol (100 mL) and concentrated (98%) sulfuric acid (3.0 mL,) is added. The mixture is heated to reflux 18 hr. The reaction is cooled and concentrated. The residue is diluted with water (100 mL) and extracted with ethyl acetate (3×50 mL). The combined extracts are dried over anhydrous magnesium sulfate, filtered, and concentrated to yield the title compound as an orange oil, 5.46 g, 100%. MS M$^+$+1 167. The structure is confirmed by $^1$H NMR spectroscopy.

The following compounds are made in a similar manner:

Preparation 14

(3-Hydroxy-4-methoxy-phenyl)-acetic acid methyl ester

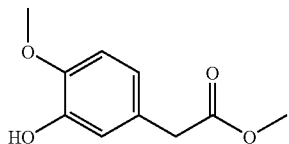

An orange oil. MS M$^+$+1 197. The structure is confirmed by $^1$H NMR spectroscopy.

Preparation 15

3-(3-Hydroxy-phenyl)-propionic acid methyl ester

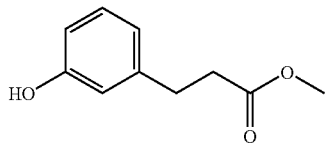

An orange oil. MS M$^+$+1 181. The structure is confirmed by $^1$H NMR spectroscopy.

Preparation 16

(3-Mercapto-phenyl)-acetic acid methyl ester

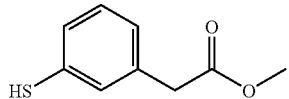

Step A (3-Dimethylthiocarbamoyloxy-phenyl)-acetic acid methyl ester

A mixture of (3-Hydroxy-phenyl)-acetic acid methyl ester (5.5 g, 33.1 mmol), N,N-dimethyl thiocarbamoyl chloride (5.11 g, 41.38 mmol), triethylamine (9.2 mL, 66.2 mmol), N,N-dimethylamino pyridine (0.4 g, 3.31 mmol) and dioxane (50 mL) is stirred at reflux 18 hr. The mixture is concentrated, partioned between 1M aqueous hydrochloric acid (200 mL) and ethyl acetate (3×75 mL). The combined organic extracts are dried over anhydrous magnesium sulfate, filtered, concentrated, and purified via silica chromatography eluting the product with dichloromethane to afford the title compound as a brown oil, 6.8 g, 81%. MS M$^+$+1 254. The structure is confirmed by $^1$H NMR spectroscopy.

Step B (3-Dimethylcarbamoylsulfanyl-phenyl)-acetic acid methyl ester (3-Dimethylthiocarbamoyloxy-phenyl)-acetic acid methyl ester (6.8 g, 26.84 mmol) is stirred in tetradecane (30 mL) at 255 deg C. for 8 hr. The mixture is cooled, the residue is purified by silica chromatography eluting the product with hexanes to 1:1 hexanes:ethyl acetate to afford the title compound as an orange oil, 4.9 g, 58%. MS M$^+$+254. The structure is confirmed by $^1$H NMR spectroscopy.

Step C (3-Mercapto-phenyl)-acetic acid methyl ester

A mixture of (3-dimethylcarbamoylsulfanyl-phenyl)-acetic acid methyl ester (2.0 g, 7.9 mmol), potassium hydroxide (1.4 g, 24 mmol) methanol (50 mL), and water (5 mL) is stirred at reflux 3 hr. The mixture is concentrated, and product partitioned between 1M aqueous hydrochloric acid (50 mL) and ethyl acetate (3×75 mL). The combined extracts are dried over anhydrous magnesium sulfate, filtered and concentrated. The residue is taken up in methanol (50 mL), 2 mL concentrated sulfuric acid is added, and the mixture refluxed 3 hr. The mixture is concentrated, and the residue purified by silica chromatography eluting with 7:3 hexanes:ethyl acetate to afford the title compound as a pale yellow oil, 1.0 g, 69%. MS M$^+$+1 183. The structure is confirmed by $^1$H NMR spectroscopy.

Preparation 17

3-(4-Iodomethyl-2-methyl-phenyl)-propionic acid methyl ester

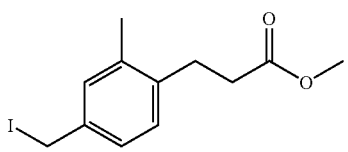

Step A 3-(4-Hydroxymethyl-2-methyl-phenyl)-acrylic acid methyl ester

A mixture of methyl-4-bromo-3-methylbenzoate (5.7 g, 24.88 mmol), lithium aluminum hydride (29 mL, 29 mmol, 1 M solution in tetrahydrofuran) and tetrahydrofuran (100 mL) is stirred in ice/water for 1 hr. The reaction is quenched with aqueous hydrochloric acid (50 mL, 1 M). The product is extracted into ethyl acetate (3×100 mL). The combined extracts are dried over anhydrous magnesium sulfate, filtered and concentrated. The crude product is taken up in propionitrile (100 mL). Methylacrylate (10 mL, 121.5 mmol), palladium acetate (1.12 g, 5 mmol), tri-o-tolylphosphine (3.0 g, 10 mmol), and N,N-diisopropyl ethylamine (8.7 mL, 50 mmol) are sequentially added and the resulting reaction mixture is heated to 110 deg C. 3 hr. The mixture is concentrated, and the residue diluted with aqueous hydrochloric acid (100 mL, 1M). The product is extracted with dichloromethane (2×100 mL) and ethyl acetate (100 mL). The combined extracts are dried over anhydrous magnesium sulfate, filtered, concentrated, and purified via silica chromatography eluting with 7:3 hexanes:ethyl acetate to 1:1 hexanes:ethyl acetate to afford the pure product as a yellow oil, 4.7 g, 91%. MS M$^+$+1 207. The structure is confirmed by $^1$H NMR spectroscopy.

Step B

3-(4-Hydroxymethyl-2-methyl-phenyl)-propionic acid methyl ester

A mixture of 3-(4-Hydroxymethyl-2-methyl-phenyl)-acrylic acid methyl ester (4.7 g, 22.8 mmol), Raney nickel (0.668 g) and tetrahydrofuran (618 mL) is shaken under 60 psig. Hydrogen 24 hr. The catalyst is filtered off, and the mixture is concentrated to afford the product as a pale yellow oil, 4.3 g, 91%. The structure is confirmed by $^1$H NMR spectroscopy.

Step C

3-(4-Iodomethyl-2-methyl-phenyl)-propionic acid methyl ester

A mixture of 3-(4-Hydroxymethyl-2-methyl-phenyl)-propionic acid methyl ester (0.62 g, 2.98 mmol), triphenyl phosphine (0.86 g, 3.27 mmol) and dichloromethane (10 mL) is stirred at room temperature. A solution of iodine (0.83 g, 3.27 mmol) in benzene (5 mL) is added and the black mixture is stirred at room temperature 2 hr. The brown mixture is diluted with 10% aqueous sodium hydrogen sulfite (5 mL) and the resulting clear mixture is washed with ethyl acetate (3×50 mL). The combined extracts are dried over anhydrous magnesium sulfate, filtered and concentrated. The residue is purified via silica chromatography eluting with 9:1 hexanes:ethyl acetate to afford the title compound as a crystalline ivory solid, 0.68 g, 72%. MS M$^+$+1 319. The structure is confirmed by $^1$H NMR spectroscopy.

Preparation 18

(4-Bromo-2-methyl-phenoxy)-acetic acid methyl ester

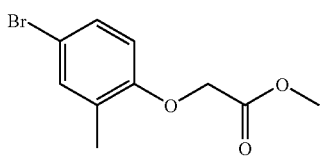

Step A

(4-Bromo-2-methyl-phenoxy)-acetic acid methyl ester

A mixture of 4-bromo-2-methylphenol (1.0 g, 5.35 mmol), sodium hydride (0.26 g, 6.42 mmol, 60% mineral oil), N,N-dimethylformamide (10 mL), and methyl-2-bromoacetate (0.56 mL, 5.88 mmol) is stirred at room temperature 18 hr. The mixture is diluted with water (50 mL) and the product extracted to ethyl acetate (3×50 mL). The combined extracts are dried over anhydrous magnesium sulfate, filtered, concentrated and purified via silica chromatography eluting with 8:2 hexanes:ethyl acetate to afford title compound as a colorless oil, 1.03 g, 74%. MS M$^+$−259. The structure is confirmed by $^1$H NMR spectroscopy.

Preparation 19

3-(4-Amino-2-methyl-phenyl)-propionic acid methyl ester

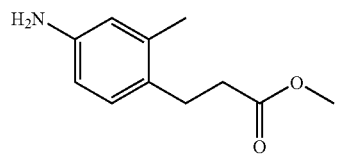

Step A

3-(2-Methyl-4-nitro-phenyl)-acrylic acid methyl ester

To a solution of 2-bromo-5-nitrotoluene (3.11 g, 14.39 mmol) in propionitrile (105 mL) is added DIPEA (5.1 mL, 29.28 mmol). The mixture is degassed three times. Methyl acrylate (5.2 mL, 57.74 mmol) is added and the mixture is degassed. Tri-o-tolylphosphine (1.77 g, 5.82 mmol) and Pd(OAc)$_2$ (0.64 g, 2.85 mmol) are added and the mixture is degassed a final two times followed by heating at 110° C. for 4 h. Upon cooling, the mixture is passed through Celite and the filtrate is concentrated. The residue is partitioned between Et$_2$O and 1N HCl. The organics are washed with saturated NaHCO$_3$ and brine, and dried with Na$_2$SO$_4$. The crude material is purified by flash chromatography to yield the title compound (2.90 g, 91%).

Step B

3-(4-Amino-2-methyl-phenyl)-propionic acid methyl ester

A mixture of 3-(2-Methyl-4-nitro-phenyl)-acrylic acid methyl, ester (1.47 g, 6.64 mmol) and 5% Pd/C (0.29 g) in MeOH (100 mL) is exposed to a hydrogen atmosphere (60 psi) for 12 h. The mixture is filtered through Celite and purified by flash chromatography to yield the title compound (0.99 g, 77%).

Preparation 20

3-(2-Methyl-4-methylaminomethyl-phenyl)-pro-ionic acid methyl ester TFA salt

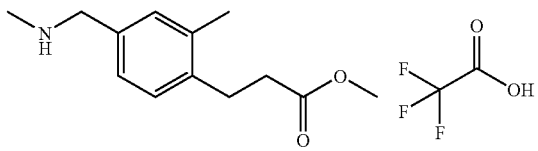

Step A

3-(4-Formyl-2-methyl-phenyl)-propionic acid methyl ester

A mixture of 3-(4-Hydroxymethyl-2-methyl-phenyl)-propionic acid methyl ester (0.49 g, 2.35 mmol) and MnO$_2$ (0.80 g, 9.20 mmol) in chloroform (5 mL) is stirred at RT for 4 days. The mixture is filtered through Celite; the Celite is washed with copious amounts of EtOAc. The filtrate is concentrated and purified by flash chromatography to yield the title compound (0.29 g, 60%).

Step B 3-(2-Methyl-4-methylaminomethyl-phenyl)-propionic acid methyl ester trifluoroacetic acid To a mixture of 3-(4-Formyl-2-methyl-phenyl)-propionic acid methyl ester (0.27 g, 1.31 mmol) and methylamine (2M in THF, 0.60 mL, 1.20 mmol) in anhydrous $CH_2Cl_2$ (10 mL) is added 4 Å molecular sieves followed by acetic acid (0.090 mL, 1.57 mmol). The mixture is stirred at RT for 1.5 h. Sodium triacetoxyborohydride (0.39 g, 1.85 mmol) is added, and the mixture is stirred overnight. The reaction is quenched with saturated $NaHCO_3$. The organics are washed with saturated $NaHCO_3$ and brine, and dried with $MgSO_4$. Upon concentration, the mixture is purified by reverse phase chromatography to yield the title compound (0.12 g, 45%).

Preparation 21

3-(4-Aminomethyl-2-methyl-phenyl)-propionic acid methyl ester

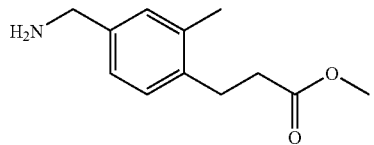

Step A 3-(4-Chloromethyl-2-methyl-phenyl)-propionic acid methyl ester

To a 0° C. solution of 3-(4-Hydroxymethyl-2-methyl-phenyl)-propionic acid methyl ester (1.02 g, 4.90 mmol) in anhydrous $CH_2Cl_2$ (15 mL) is added triethylamine (0.75 mL, 5.38 mmol) followed by thionyl chloride (0.40 mL, 5.48 mmol). The mixture is allowed to warm to RT overnight. Water is added, and the mixture is extracted with $CH_2Cl_2$. The organics are dried with $MgSO_4$ and concentrated. The crude material is purified by flash chromatography to yield the title compound (1.01 g, 91%).

Step B 3-(4-Azidomethyl-2-methyl-phenyl)-propionic acid methyl ester

To a solution of 3-(4-Chloromethyl-2-methyl-phenyl)-propionic acid methyl ester (0.52 g, 2.31 mmol) in DMF (7 mL) is added sodium azide (0.25 g, 3.84 mmol). The mixture is stirred overnight. Water is added, and the mixture is extracted with EtOAc. The organics are dried with $Na_2SO_4$ and concentrated to yield the title compound (0.49 g, 91%). The material is used without further purification.

Step C 3-(4-Aminomethyl-2-methyl-phenyl)-propionic acid methyl ester

A mixture of 3-(4-Azidomethyl-2-methyl-phenyl)-propionic acid methyl ester (0.20 g, 0.86 mmol) and 5% Pd/C (32 mg) in EtOH (50 mL) is exposed to a hydrogen atmosphere (60 psi) at RT overnight. Upon filtering the mixture through Celite, the filtrate is concentrated to yield the title compound (0.14 g, 78%). The material is used without further purification.

Preparation 22

4-(2-Methoxycarbonyl-ethyl)-3-methyl-benzoic acid

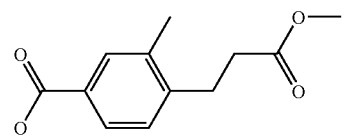

Step A

4-Bromo-3-methyl-benzoic acid benzyl ester

To a solution of 4-Bromo-3-methyl-benzoic acid benzyl (25.3 g, 0.118 mol) in DMF (200 mL) is added Cs2CO3 (76.6 g, 0.235 mol), followed by benzyl bromide (15.4 mL). After stirred at room temperature for 2 h, the reaction mixture is diluted with ethyl acetate, filtered through celite. The filtrate is washed with water and brine, dried over sodium sulfate, concentration yields the title product.

Step B 4-(2-methoxycarbonyl-vinyl)-3-methyl-benzoic acid benzyl ester

To a solution of 4-bromo-3-methyl-benzoic acid benzyl ester (36 g, 118 mmol) in propronitrile (1000 mL) is added methyl acrylate (43.3 mL) and diisopropylethyl amine (42 mL), the solution is degassed and filled with nitrogen for three times. To this mixture are added tri-o-tolyl-phosphane (14.5 g) and palladium acetate (5.34 g) under nitrogen, then heated at 110° C. overnight, cooled to room temperature filtered through celite. The solvent is evaporated, the residue is taken into ethyl acetate and washed with water and brine, dried over sodium sulfate. Concentration and column chromatography on silica gel eluted with hexanes and ethyl acetate yields the title compound (31 g, 84.7%).

Step C 4-(2-methoxycarbonyl-ethyl)-3-methyl-benzoic acid

A mixture of 4-(2-methoxycarbonyl-vinyl)-3-methyl-benzoic acid benzyl ester (11.6 g, 37.4 mmol) and Pd/C (5%, 1.5 g) in THF (300 mL) and methanol (100 mL) is stirred under 60 psi of hydrogen overnight. Catalyst is filtered off, filtrate is concentrated giving the title compound (8.3 g, 100%).

Preparation 23

2-(3-Hydroxy-phenyl)-2-methyl-propionic acid ethyl ester

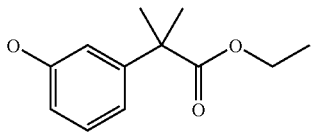

Step A 2-(3-Methoxy-phenyl)-propionic acid ethyl ester

To a solution of LDA (2M, 16.5 mL) in THF (10 mL) at −70° C. was added a solution of (3-methoxy-phenyl)-acetic acid methyl ester (5.4 g, 30 mmol) in THF (10 mL). After 40 minutes at −70° C., iodomethane (2.5 mL, 40 mmol) was added. The mixture was stirred at room temperature overnight. It was diluted with EtOAc, washed with 1N HCl. The organic layer was dried over Na2SO4 and concentrated to give the titled compound as an oil: 5.9 g (quant.)

Step B 2-(3-Methoxy-phenyl)-2-methyl-propionic acid ethyl ester

To a solution of LDA (2M, 11.4 mL) in THF (10 mL) at −70° C. was added a solution of 2-(3-methoxy-phenyl)-propionic acid ethyl ester (4 g, 20.6 mmol) in THF (10 mL). After 1 hour at −70° C., iodomethane (1.7 mL, 26.8 mmol) was added and the mixture was stirred at room temperature overnight. It was diluted with EtOAc and washed with 1N HCl. The organic was concentrated to give the titled compound as an oil: 4 g (93%).

Step C 2-(3-Hydroxy-phenyl)-2-methyl-propionic acid ethyl ester

To a solution of 2-(3-Methoxy-phenyl)-2-methyl-propionic acid ethyl ester (4 g, 19.2 mmol) in dichloromethane (20 mL) at 0° C. was added BBr3 (1M in dichloromethane, 50 mL). After 2 hours at ambient temperature, it was quenched with MeOH. Solvent was evaporated and the residue was partitioned between EtOAc and 1N HCl. The organic was concentrated and purified by column chromatography (0 to 30% EtOAc in hexanes) to give the titled compound as a solid: 2.6 g (70%).

ESMS−: 193 (M−1); 1H NMR is consistent with desired product.

Preparation 24

3-(4-Hydroxy-2-methyl-phenyl)-2,2-dimethyl-Propionic acid methyl ester

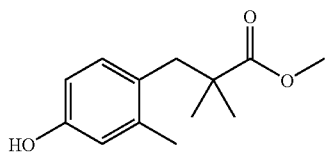

Step A

2-Methyl-4-anisaldehyde

A mixture of 2,3-dimethylanisole (50 g, 0.37 mol), $Cu^{2+}$ sulfate pentahydrate (90 g, 0.36 mol), and potassium peroxydisulfate (301 g, 1.11 mol) in acetonitrile/water (1:1, 2.6 L) was stirred vigorously and heated to reflux for 30 minutes. Thin layer chromatography (Hexane:EtOAc, 8:2) showed no starting material and one new spot. The reaction was cooled to room temperature and extracted with $CH_2Cl_2$ (4 L) and washed with water (2 L). The layers were separated and the aqueous layer was again extracted with $CH_2Cl_2$. The organic layers were combined and concentrated, 55 g obtained (~100%), product was taken on as is. $^1$H-NMR (DMSO-$d_6$): 10.05 (s, 1H), 7.78 (m, 1H), 6.95 (m, 1H), 6.88 (s, 1H), 3.84 (s, 3H), 2.6 (s, 3H).

Step B

4-Methoxy-2-methylbenzyl alcohol $NaBH_4$ (14.82 g, 0.39 mol) was added to a solution of 2-Methyl-4-anisaldehyde (55 g, 0.37 mol) in EtOH (800 mL). TLC shows multiple spots but a disappearance of starting material. The reaction was quenched with water (3 L), acidified with 5N HCl, and extracted with $Et_2O$. The organics were separated and concentrated. The crude product was purified by Biotage 75 L (Hexane:EtOAc, 9:1) to afford 17.35 g (30%). $^1$H-NMR (CDCl$_3$): 7.22 (m, 1H), 6.7 (m, 2H), 4.64 (s, 2H), 3.8 (s, 3H), 2.4 (s, 3H).

Step C

Acetic acid 4-methoxy-2-methyl-benzyl ester

A solution of 4-Methoxy-2-methylbenzyl alcohol (17.35 g, 0.114 mol) in $CH_2Cl_2$ (900 mL) was cooled 0° C. TEA (23.3 mL, 0.167 mol) and acetyl chloride (9.3 mL, 0.131 mol) were added. The reaction was allowed to stir for 1 h and was then quenched with 1N HCl, washed with aq. NaHCO$_3$, brine, dried (Na$_2$SO$_4$), and concentrated to an oil (22.14 g, ~100%). $^1$H-NMR (CDCl$_3$): 7.24 (m, 1H), 6.73 (m, 2H), 5.08 (s, 2H), 3.8 (s, 3H), 2.33 (s, 3H), 2.08 (s, 3H)

Step D 3-(4-Methoxy-2-methyl-phenyl)-2,2-dimethyl-propionic acid methyl ester Acetic acid 4-methoxy-2-methyl-benzyl ester (22.14 g, 0.114 mol) was dissolved in $CH_2Cl_2$ and treated with 1-methoxy-1trimethylsiloxy-2-methyl-1-propene (53.3 g, 0.306 mol) and Mg(ClO$_4$)$_2$ (2.58 g, 0.012 mol). The reaction was stirred overnight at room temperature. Upon completion the reaction was washed with water, brine, and dried with Na$_2$SO$_4$. The crude product was purified (Biotage 75M (Hexane:EtOAc, 9:1·8:2)) to obtain 18.7 g (70%). $^1$H-NMR (CDCl$_3$): 6.97 (d, 1H) 6.7 (m, 2H), 3.8 (s, 3H), 3.64 (s, 3H), 2.85 (s, 2H), 2.3 (s, 3H), 1.2 (s, 6H).

Step E 3-(4-Hydroxy-phenyl)-2,2-dimethyl-propionic acid methyl ester

BBr$_3$ (1M in CH$_2$Cl$_2$, 79 ml) was cooled to 0° C. and 3-(4-Methoxy-2-methyl-phenyl)-2,2-dimethyl-propionic acid methyl ester (9.35 g, 0.0395 mol) was added dropwise over 10 minutes. After stirring for 1 h at 0° C. the reaction was quenched with 1:1 MeOH:CH$_2$Cl$_2$. The organics were concentrated and the resulting oil was run through a plug of silica gel with Hexane:EtOAc (8:2). Fractions 1, 2 were concentrated and 7.5 g (85%) of the desired compound were isolated. $^1$H-NMR (CDCl$_3$): 6.87 (d, 1H), 6.6 (m, 2H), 4.9 (bs, 1H), 3.64 (s, 3H), 2.82 (s, 2H), 2.22 (s, 3H), 1.2 (s, 6H).

Preparation 25

2-(4-Hydroxy-henoxy)-2-methyl-propionic acid ethyl ester

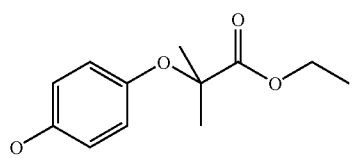

Preparation 26

2-(4-Hydroxy-phenylsulfanyl)-2-methyl-propionic acid ethyl ester

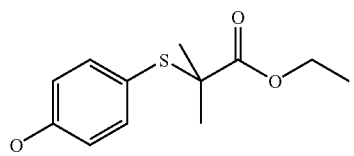

Preparation 27

4-hydroxy-2-ethyl-dihydro-ethyl cinnamate

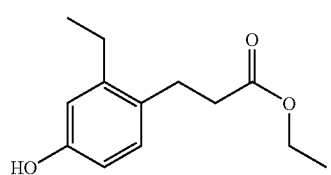

Step A 3-iodobenzyloxybenzene

Sodium hydride (mineral dispersion 60%) (1.36 g, 34.10 mmol) is added slowly to a solution of 3-iodophenol (5.0 g, 22.73 mmol) and TABI (0.84 g, 2.27 mmol) in THF (113 mL), and the mixture is stirred overnight. The crude is treated with water and extracted with EtOAc. The organic layers are combined, dried over sodium sulfate, filtered and concentrated under reduced pressure. Purification by flash chromatography, eluting with hexane:EtOAc 10:1 provides the title compound (7.00 g, 99%). Rf=0.77 (hexane:EtOAc 5:1). $^1$H NMR (200 MHz, CDCl$_3$): 5.03 (s, 2H), 6.93 (m, 1H), 7.02 (d, 1H, J=8.3 Hz), 7.27-7.34 (m, 7H)

Step B 3-ethylbenzyloxybenzene

Copper (I) chloride (0.016 g, 0.17 mmol), ethyl iodide (0.40 mL, 5.03 mmol) and diethyl zinc (1.0 M, THF) (4.61 mL, 4.61 mmol) are added successively to a solution of manganese bromide (0.054 g, 0.25 mmol) in 1,3-dimethyl-3,4,5,6-tetrahydro-2(1H)pyrimidinone (4.20 mL), and the mixture is stirred at for 4 h. A solution of 3-iodobenzyloxybenzene (1.3 g, 4.19 mmol) and dichloro(diphenylphosphinoferrocene)-Pd(II) (DCM complex) (0.14 g, 0.17 mmol) in THF (21 mL) is added, and the mixture is stirred under reflux for 2.5 h. The mixture is cooled to r.t. and HCl 1N is added. The mixture is extracted with EtOAc. The organic layers are combined, dried over sodium sulfate, filtered and concentrated under reduced pressure. Purification by flash chromatography, eluting with hexane:EtOAc 20:1 provides the title compound (0.81 g, 91%). Rf=0.82 (hexane:EtOAc 5:1).

$^1$H NMR (200 MHz, CDCl$_3$): 1.30 (t, 3H, J=7.8 Hz), 2.70 (q, 2H, J=7.5 Hz), 5.11 (s, 2H), 6.86-6.91 (m, 3H), 7.23-7.53 (m, 6H).

Step C 4-bromo-3-ethylbenzyloxybenzene

N-bromosuccinimide (0.75 g, 4.20 mmol) is added to a solution of 3-ethylbenzyloxybenzene (0.81 g, 3.82 mmol) in ACN (19 mL) and the mixture is stirred for an hour. The solvent is evaporated in vacuo and the resultant is purified by flash chromatography, eluting with hexane:EtOAc 20:1 to give the title compound (1.09 g, 98%). Rf=0.74 (hexane:EtOAc 5:1). $^1$H NMR (200 MHz, CDCl$_3$): 1.22 (t, 3H, J=7.5 Hz), 2.72 (q, 2H, J=7.5 Hz), 5.04 (s, 2H), 6.69 (dd, 1H, J=3.0, 8.6 Hz), 6.88 (d, 2H, J=3.0 Hz), 7.32-7.45 (m, 6H).

Step D 4-benzyloxy-2-ethyl-ethyl trans-cinnamate

A mixture of 4-bromo-3-ethylbenzyloxybenzene (0.95 g, 3.27 mmol), palladium acetate (0.073 g, 0.33 mmol), tri-o-tolylphosphine (0.20 g, 0.65 mmol), DIPEA (1.14 mL, 6.53 mmol) and ethyl acrylate (1.42 mL, 13.06 mmol) in propionitrile (49 mL) is stirred at 90° C. under nitrogen overnight. The solution is filtered through Celite and washed with EtOAc. The mixture is concentrated under reduced pressure. Purification by flash chromatography, eluting with hexane:EtOAc 10:1 provides the title compound (0.43 g, 43%). Rf=0.22 (hexane:EtOAc 20:1). $^1$H NMR (300 MHz, CDCl$_3$): 1.25 (t, 3H, J=7.7 Hz), 1.37 (t, 3H, J=7.1 Hz), 2.80 (q, 2H, J=7.7 Hz), 4.30 (q, 2H, J=7.3 Hz), 5.09 (s, 2H), 6.32 (d, 1H, J=15.7 Hz), 6.83-6.87 (m, 2H), 7.35-7.47 (m, 5H), 7.56 (d, 1H, J=8.5 Hz), 8.01 (d, 1H, J=15.9 Hz).

Step E

A solution of 4-benzyloxy-2-ethyl-ethyl trans-cinnamate (0.43 g, 1.39 mmol) and pd/C (10%) (0.074 g, 0.07 mmol) in methanol (14 mL) is stirred under 1 atm of hydrogen. After 4 h, the mixture is filtered through Celite and washed with methanol and concentrated under reduced pressure. Purification by flash chromatography, eluting with hexane:EtOAc 5:1 provides the title compound (0.29 g, 63%).

Rf: 0.17 (hexane:EtOAc 5:1). ¹H NMR (300 MHz, CDCl₃): 1.19 (t, 3H, J=7.5 Hz), 1.26 (t, 3H, J=7.3 Hz), 2.54-2.63 (m, 4H), 2.87-2.92 (m, 2H), 4.16 (q, 2H, J=7.1 Hz), 5.94 (s, 1H), 6.62 (dd, 1H, J=2.6, 8.3 Hz), 6.70 (d, 1H, J=2.6 Hz), 6.99 (d, 1H, J=8.3 Hz).

Preparation 28

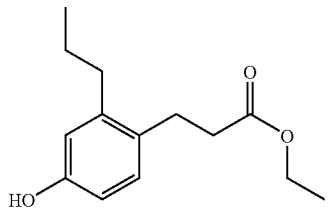

Step A 3-propylbenzyloxybenzene

Copper (I) chloride (0.016 g, 0.17 mmol), propyl iodide (0.49 mL, 5.03 mmol) and diethyl zinc (1.0M, THF) (4.61 mL, 4.61 mmol) is added successively to a solution of manganese bromide (0.054 g, 0.25 mmol) in 1,3-dimethyl-3,4,5,6-tetrahydro-2(1H)pyrimidinone (4.20 mL), and the mixture is stirred at r.t. for 4 h. A solution of 3-iodobenzyloxybenzene (Example 250, Step A) (1.3 g, 4.19 mmol) and dichloro-(diphenylphosphinoferrocene)palladium (II) (DCM complex) (0.14 g, 0.17 mmol) in THF (21 mL) is added, and the mixture is stirred under reflux for 2.5 h. The mixture is cooled to r.t. and 1N HCl is added. The mixture is extracted with EtOAc, and the organic layers are combined, dried over sodium sulfate, filtered and concentrated under reduced pressure. Purification by flash chromatography, eluting with hexane:EtOAc 20:1 provides the title compound together with 25% of 3-ethylbenzyloxybenzene (0.85 g, 81% overall). Rf=0.82 (hexane:EtOAc 5:1). ¹H NMR (200 MHz, CDCl₃): 1.13-1.20 (m, 3H), 1.81-1.92 (m, 2H), 2.74-2.85 (m, 2H), 5.22 (s, 2H), 7.00-7.03 (m, 3H), 7.37-7.61 (m, 6H).

Step B 4-bromo-3-propylbenzyloxybenzene

N-bromosuccinimide (0.66 g, 3.74 mmol) is added to a solution of 3-propylbenzyloxybenzene (0.85 g, 3.40 mmol) in ACN (17 mL), and the mixture is stirred for an hour. The solvent is evaporated in vacuo and purified by flash chromatography by eluting with hexane:EtOAc 20:1 to give the title compound together with 25% of 4-bromo-3-ethylbenzyloxybenzene (1.03 g, 99% overall). Rf=0.74 (hexane:EtOAc 5:1). ¹H NMR (200 MHz, CDCl₃): 1.00 (t, 3H, J=7.2 Hz), 1.65 (sext, 2H, J=7.2 Hz), 2.71 (q, 2H, J=7.5 Hz), 5.05 (s, 2H), 6.71 (dd, 1H, J=3.0, 8.6 Hz), 6.91 (d, 2H, J=3.0 Hz), 7.32-7.47 (m, 6H).

Step C 4-benzyloxy-propylbenzaldehyde n-BuLi (1.6 M in hexane) (7.03 mL, 11.25 mmol) is added to a solution of 4-bromo-3-propylbenzyloxybenzene (2.29 g, 7.50 mmol) in THF (30 mL) under nitrogen at −78° C., and the mixture is stirred for 30 minutes. N-Formylpiperidine (1.25 mL, 11.25 mmol) is added and stirred for 4 h. The mixture is allowed to gradually warm up to −40° C., and then water is added and extracted with EtOAc. The organic layers are combined, dried and filtered, and then the solvent is evaporated in vacuo. Purification by flash chromatography by eluting with hexane:EtOAc 10:1 provides the title compound together with 25% of 4-bromo-3-ethylbenzyloxybenzene (1.00 g, 52% overall). Rf=0.63 (hexane:EtOAc 5:1). ¹H NMR (300 MHz, CDCl₃): 1.26 (t, 3H, J=7.7 Hz), 1.65 (sext, 2H, J=7.2 Hz), 2.99 (q, 2H, J=7.7 Hz), 5.13 (s, 2H), 6.84-6.94 (m, 2H), 7.33-7.46 (m, 5H), 7.79 (d, 1H, J=8.2 Hz) 10.12 (s, 1H).

Step D 4-benzyloxy-2-propyl-ethyl trans-cinnamate

Method 1: A mixture of 4-bromo-3-ethylbenzyl-oxybenzene (0.56 g, 1.85 mmol), palladium acetate (0.042 g, 0.18 mmol), tri-o-tolylphosphine (0.11 g, 0.37 mmol), DIPEA (0.64 mL, 3.70 mmol) and ethyl acrylate (0.80 mL, 7.42 mmol) in propionitrile (28 mL) is stirred at 90° C. a under nitrogen overnight. The mixture is filtered through Celite, washed with EtOAc and concentrated under reduced pressure. Purification by flash chromatography by eluting with hexane:EtOAc 10:1 provides the title compound with a 25% of 4-benzyloxy-2-ethyl-ethyl trans-cinnamate (0.22 g, 37% overall).

Method 2: Triethylphosphono acetate (0.15 mL, 0.74 mmol) is added to a solution of 4-benzyloxy-proylbenzaldehyde (Step C) (0.16 g, 0.62 mmol) and potassium carbonate (0.26 g, 1.86 mmol) in ethanol (2.10 mL), and the mixture is stirred under reflux for 2.5 h. The mixture is cooled to r.t. and water is added. The mixture is extracted with EtOAc, and the organic layers are combined, dried and filtered. The solvent is evaporated in vacuo. Purification by flash chromatography by eluting with hexane:EtOAc 5:1 provides the title compound together with 25% of 4-benzyloxy-2-ethyl-ethyl trans-cinnamate (0.17 g, 86% overall). Rf=0.22 (hexane:EtOAc 20:1). ¹H NMR (300 MHz, CDCl₃): 0.99 (t, 3H, J=7.3 Hz), 1.25 (t, 3H, J=7.5 Hz), 1.58-1.69 (m, 2H), 2.75 (q, 2H, J=7.1 Hz), 4.29 (q, 2H, J=7.3 Hz), 5.10 (s, 2H), 6.31 (d, 1H, J=15.7 Hz), 6.85 (d, 2H, J=7.3 Hz), 7.35-7.47 (m, 5H), 7.56 (d, 1H, J=7.9 Hz), 8.00 (d, 1H, J=15.7 Hz)

Step E 4-hydroxy-2-propyl-dihydro-ethyl cinnamate

A solution of 4-benzyloxy-2-propyl-ethyl trans-cinnamate (0.44 g, 1.35 mmol) and pd/C (10%) (0.14 g, 0.14 mmol) in methanol (13 mL) is stirred under 1 atm of hydrogen. After 4 h, the mixture is filtered through Celite, washed with methanol, and concentrated under reduced pressure. Purification by flash chromatography by eluting with hexane:EtOAc 5:1 provides the title compound (0.17 g, 54%) with a 25% of 4-hydroxy-2-ethyl-dihydro-ethyl cinnamate. The mixture is separated by HPLC (reverse phase purification) under acidic conditions (ACN:TFA=99.95:0.05). Rf=0.17 (hexane: EtOAc 5:1). ¹H NMR (300 MHz, CDCl₃): 0.97 (t, 3H, J=7.5 Hz), 1.26 (t, 3H, J=7.1 Hz), 1.59 (sext, 2H, J=7.5 Hz), 2.55 (q, 4H, J=8.9 Hz), 2.89 (t, 2H, J=7.5 Hz), 4.16 (q, 2H, J=7.13 Hz), 5.72 (s, 1H), 6.71 (dd, 1H, J=3.0, 8.1 Hz), 6.67 (d, 1H, J=2.6 Hz), 6.99 (d, 1H, J=8.3 Hz

Preparation 29

Preparation of 4-(4-hydroxy-2-methylphenyl)-butyric acid ethyl ester

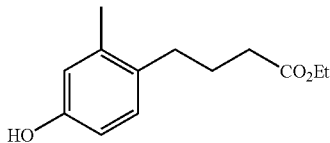

Step A 4-benzyloxy-2-methyl bromobenzene

To a solution of 15 g (80.2 mmol) of 4-bromo-3-methylphenol and 1.5 g (10% in weight) of tetrabutylammonium iodide in THF (100 ml) is added 60% NaH (2.88 gr, 120 mmol) at 0° C. After the mixture is stirred at 0° C. for 30 min, benzyl bromide (14.3 ml 120 mmol) is added drop wise. The reaction is stirred at r.t. overnight under argon atmosphere. Then the reaction is poured into ice-water and extracted with EtOAc (3×100 ml). The organic extracts are dried over $MgSO_4$ and concentrated. The title compound (16.5 g, 66%) is isolated by precipitation in hexane.

Step B 4-(4-benzyloxy-2-methyl-phenyl)-4-oxo-butyric acid

A solution of 4-benzyloxy-2-methyl bromobenzene (4 g, 14.4 mmol) in THF (25 ml) is added drop wise over a mixture of Mg (414 mg, 17.3 mmol), 1,2-dibromoethane (a few drops) and $I_2$ (a crystal) at 70° C. under argon atmosphere. After the addition is completed, the mixture is stirred at 70° C. for 3 hours. Grignard reagent is added over a solution of succinic anhydride (1.73 gr, 17.3 mmol) and $Fe(acac)_3$ (254 mg, 0.7 mmol) in 25 ml of THF over argon atmosphere and is stirred overnight at r.t. The reaction is quenched with sat $NH_4Cl$ and extracted with EtOAc (3×50 ml). The organic phase is basified with 2N NaOH, and the aqueous phase is washed with EtOAc (3×50 ml). The aqueous phase is acidified with 2N HCl and then extracted with EtOAc (3×50 ml), dried over $MgSO_4$ and concentrated to give 3.4 g (40%) of the title compound. The crude is used for the next step without further purification.

Step C 4-(4-benzyloxy-2-methylphenyl)-4-oxo-butyric acid ethyl ester

A solution of 4-(4-benzyloxy-2-methyl-phenyl)-4-oxo-butyric acid (1.6 g, 5.6 mmol) and $H_2SO_4$ (1 ml) in EtOH (50 ml) is stirred at 80° C. overnight. The solvent is evaporated, and water (100 ml) and sat. $NaHCO_3$ is added up to pH=9. The aqueous phase is extracted with EtOAc (3×50 ml) and the organics are dried over $MgSO_4$ and concentrated to give about 1.3 g (71%) of the title compound, which is used for the next step without further purification.

Step D 4-(4-hydroxy-2-methylphenyl)-butyric acid ethyl ester

A mixture of 4-(4-benzyloxy-2-methylphenyl)-4-oxo-butyric acid ethyl ester (1.2 g, 3.4 mmol), Pd/C (120 mg) 10% in 10 ml of AcOH is hydrogenated at 60 psi overnight. The mixture is filtered over celite, washed with EtOH and evaporated. Water (50 ml) and saturated $NaHCO_3$ are added until neutral pH is achieved. The aqueous phase is extracted with AcOEt (3×50 ml), and the organic phase is dried over $MgSO_4$ and concentrated. The crude is purificated using silica gel chromatography (hexane/EtOAc 6:1) to afford 700 mg (9%) of the title compound.

Preparation 30

Preparation of 4-hydroxy-2-fluoro-dihydro-ethyl cinnamate

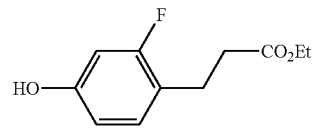

Step A 3-fluorobenzyloxyphenol

Benzyl bromide (2.9 mL, 24.08 mmol) is added to a suspension of 3-fluorophenol (3.0 g, 26.76 mmol) and $K_2CO_3$ (4.0 g, 28.94 mmol) in DMF (30 mL), and the mixture is stirred at r.t. for 5 h. It is acidified with diluted HCl (1M) and partitioned between EtOAc and $H_2O$. The organic layer is dried, filtered and concentrated, and the product is purified by flash chromatography on $SiO_2$ (3% EtOAc/hexanes) to afford 4.7 g of the title compound (87%, colorless oil).

Step B 4-bromo-3-fluorobenzyloxyphenol

NBS (2.11 g, 11.88 mmol) is added to a solution of 3-fluorobenzyl-oxyphenol (2.4 g, 11.88 mmol) in $CH_3CN$ (50 mL, HPLC grade). The mixture is stirred at r.t. overnight (c.a. 14 h) and extracted with EtOAc and $H_2O$. The organic layer is dried, filtered and concentrated, and the resulting crude residue is flash chromatographed on $SiO_2$ (5% EtOAc/hexanes) to afford 3.3 g of title compound (99%, white solid).

Step C 3-fluoro-4-ethylacrylate-benzyloxyphenol

Ethyl acrylate (6.73 mL, 74.73 mmol) is added to a solution of 4-bromo-3-fluorobenzyloxyphenol (3.5 g, 12.455 mmol), $Pd(OAc)_2$ (280 mg, 1.245 mmol), $P(o-tol)_3$ (758 mg, 2.49 mmol) and DIPEA (6.5 mL, 37.37 mmol) in EtCN (80 mL, HPLC grade). The mixture is warmed to 95° C. and stirred at that temperature for 1 h. It is allowed to reach r.t., filtered trough Celite and partitioned between EtOAc and $H_2O$. The organic layer is dried, filtered and concentrated, and the resulting crude is flash chromatographed on $SiO_2$ (2-3% EtOAc/hexanes) to afford 2.05 g of the Heck product (55%, white solid).

Step D

4-hydroxy-2-fluoro-dihydro-ethyl cinnamate

Palladium (120 mg, 10% on activated carbon, 0.112 mmol) is added to a solution of the fluorobenzyloxy compound of Step C (1.2 g, 4.0 mmol), and the mixture is stirred under H₂ atmosphere (H₂ balloon) overnight (c.a. 14 h). The mixture is filtered trough Celite, and the solvent is removed in a rotary evaporator. The crude residue is flash chromatographed on SiO₂ (10-20% EtOAc/hexanes) to afford 510 mg of the title compound (60%, colorless oil).

Preparation 31

4-hydroxy-2-chloro-dihydro-ethyl cinnamate

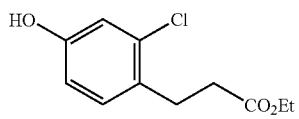

Step A

4-bromo-3-chlorobenzyloxyphenol

Benzyl bromide (0.83 mL, 6.95 mmol) is added to a suspension of 3-chloro-4-bromophenol (1.0 g, 4.82 mmol) and K₂CO₃ (960 mg, 6.95 mmol) in DMF (25 mL), and the mixture is stirred at r.t. for 3 h. It is acidified with diluted HCl (1M) and partitioned between Et₂O and H₂O. The organic layer is dried, filtered and concentrated, and the product is purified by flash chromatography on SiO₂ (1-2% EtOAc/hexanes) to afford 1.39 g of the title compound (97%, white solid).

Step B

3-chloro-4-ethylacrylate-benzyloxyphenol

Ethyl acrylate (5.0 mL, 55.5 mmol) is added to a solution of 4-bromo-3-chlorobenzyloxyphenol (2.7 g, 9.08 mmol), palladium acetate (215 mg, 0.96 mmol), P(o-tol)₃ (550 mg, 1.8 mmol) and Et₃N (3 mL, 21.5 mmol) in EtCN (100 mL, HPLC grade). The mixture is warmed to 95° C. and stirred at that temperature overnight (c.a. 16 h). It is allowed to reach r.t., filtered trough Celite and partitioned between EtOAc and H₂O. The organic layer is dried, filtered and concentrated, and the resulting crude is flash chromatographed on SiO₂ (5% EtOAc/hexanes) to afford 1.79 g of the Heck product (62%, white solid).

Step C

4-hydroxy-2-chloro-dihydro-ethyl cinnamate

Palladium (121 mg, 10% on activated carbon, 0.113 mmol) is added to a solution of the chlorobenzyloxyphenol (1.2 g, 3.79 mmol), and the mixture is stirred under H₂ atmosphere (H₂ balloon) overnight (c.a. 14 h). The mixture is filtered trough Celite, and the solvent is removed in a rotatory evaporator. The crude residue is flash chromatographed on SiO₂ (5-10% EtOAc/hexanes), and repurified by HPLC (normal phase) to afford 515 mg of the title compound (93%, colorless oil).

Preparation 32

Preparation of 4-hydroxy-2-ethyl-phenylsulfanyl-acetic acid ethyl ester

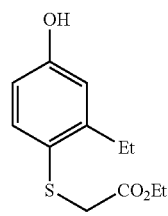

Step A

3-ethylbenzyloxyphenol

Benzyl bromide (4.92 mL, 41.36 mmol) is added to a suspension of 3-ethylphenol (5.055 g, 41.36 mmol) and K₂CO₃ (8.5 g, 61.5 mmol) in CH₃CN (50 mL, HPLC grade), and the mixture is stirred at r.t. for 5 h. The mixture is acidified with diluted HCl (1M) and partitioned between EtOAc and H₂O. The organic layer is dried, filtered and concentrated, and the product is purified by flash chromatography on SiO₂ (3% EtOAc/hexanes) to afford 8.3 g of 3-ethylbenzyloxyphenol (94%, colorless oil)

Step B

4-bromo-3-ethylbenzyloxyphenol

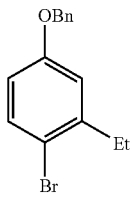

NBS (1.68 g, 9.438 mmol) is added to a solution of 3-ethylbenzyl-oxyphenol (2 g, 9.433 mmol) in CH₃CN (30 mL, HPLC grade). The mixture is stirred at r.t. overnight (c.a. 14 h) and extracted with EtOAc and H₂O. The organic layer is dried, filtered and concentrated, and the resulting crude residue is flash chromatographed on SiO₂ (2% EtOAc/hexanes) to afford 2.3 g of the bromide (84%, colorless oil).

Step C

4-benzyloxy-2-ethyl-phenylsulfanyl-acetic acid ethyl ester

Tert-BuLi (5.25 mL, 1.7 M solution, 8.94 mmol) is added to a −78° C. cooled solution of 4-bromo-3-ethylbenzyloxyphenol (1.3 g, 4.467 mmol) in THF (20 mL).

The mixture is stirred at low temperature for 30 min and allowed to reach r.t. Sulfur (150 mg, 4.68 mmol) is added in one portion, and the reaction is stirred at r.t. for 5 min. Ethylbromoacetate (2.5 mL, 22.33 mmol) is added, and the mixture is stirred at r.t. overnight (c.a. 14 h). It is quenched with NH₄Cl (sat) and extracted with EtOAc/H₂(The organic layer is dried, filtered and concentrated, and the crude residue is flash chromatographed on SiO₂ (2-4% EtOAc/hexanes) to afford 490 mg of the title compound (33%, colorless oil).

Step D 4-hydroxy-2-ethyl-phenylsulfanyl-acetic acid ethyl ester

TiCl₄ (1.3 mL, 1 M solution in CH₂Cl₂, 1.3 mmol) is added to a −78° C. cooled solution of the benzyloxyphenol (400 mg, 1.21 mmol) in CH₂Cl₂ (12 mL), and the mixture is allowed to reach 0° C., and then r.t. and stirred for 4 h. The reaction is quenched with H₂O and diluted with CH₂Cl₂. The organic layer is washed with brine, dried, filtered and concentrated. The crude residue is flash chromatographed on SiO₂ (5-10-15% EtOAc/hexanes) to afford 160 mg of the title compound (55%, colorless oil).

Preparation 33

Preparation of 4-hydroxy-2,6 dimethyl-dihydro-ethyl cinnamate

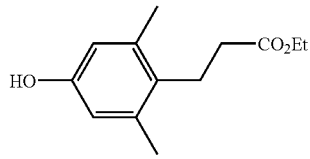

Step A 3,5-dimethyl-4-bromobenzyloxyphenol

Benzyl bromide (1.53 mL, 12.86 mmol) is added to a suspension of 3,5-dimethyl-4-bromophenol (2.6 g, 12.93 mmol) and K₂CO₃ (2.2 g, 14.47 mmol) in CH₃CN (30 mL, HPLC grade). The mixture is stirred at r.t. for 16 h. It is acidified with diluted HCl (1M) and partitioned between EtOAc and H₂O. The organic layer is dried, filtered and concentrated, and the product is purified by flash chromatography on SiO₂ (5% EtOAc/hexanes) to afford 3.66 g of the benzyloxyphenol (97%, white solid).

Step B 3,5-dimethyl-4-ethylacrylate-benzyloxyphenol

Ethyl acrylate (6 mL, 66.6 mmol) is added to a solution of 3,5-dimethyl-4-bromobenzyloxyphenol (3.6 g, 12.37 mmol), Pd(OAc)₂ (280 mg, 1.247 mmol), P(o-tol)₃ (750 mg, 2.464 mmol) and DIPEA (6 mL, 34.4 mmol) in EtCN (50 mL, HPLC grade). The mixture is warmed to 95° C. and stirred at that temperature for 36 h. It is allowed to reach r.t., filtered trough Celite and partitioned between EtOAc and H₂O. The organic layer is dried, filtered and concentrated, and the resulting crude is flash chromatographed on SiO₂ (2% EtOAc/hexanes) to afford 2.59 g of the Heck product (68%, white solid).

Step C 4-hydroxy-2,6 dimethyl-dihydro-ethyl cinnamate

Palladium (1 g, 10% on activated carbon, 0.94 mmol) is added to a solution of the benzyloxyphenol obtained in Step B (2.5 g, 8.012 mmol), and the mixture is stirred under H₂ atmosphere (H₂ balloon) overnight. The mixture is filtered trough Celite, and the solvent is removed. The crude residue is flash chromatographed on SiO₂ (10% EtOAc/hexanes) to afford 1.4 g of the title compound (79%, white solid).

Preparation 34

2-(4-Hydroxy-2-methyl-phenyl)-cyclopropanecarboxylic acid ethyl ester

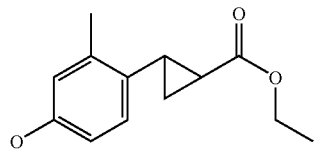

A solution of 2-(4-benzyloxy-2-methyl-phenyl)-cyclopropanecarboxylic acid ethyl ester (2.0 g, 6.75 mmol) in EtOAc (100 mL) is treated with 10% Palladium on carbon (0.5 g) and stirred under hydrogen (1 atm). The reaction stirred for 3 hours. The reaction is filtered through celite, and the filtrate is concentrated to afford 1.3 g (94%) of title compound. ¹H NMR (400 MHz, CDCl₃); MS (ES⁺) m/z mass calcd for C₂₀H₂₂O₃ 310, found 311 (M+1, 100%).

Preparation 35

(6-Hydroxy-benzo[b]thiophen-3-yl)-acetic acid ethyl ester

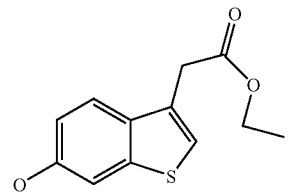

Step A 4-(3-Methoxy-phenylsulfanyl)-3-oxo-butyric acid ethyl ester

Ethyl 4-chloroacetoacetate (32.6 g, 0.188 mol), 3-methoxythiophenol (25.1 g, 0.179 mol) and DMF (700 mL) are combined and degassed by bubbling nitrogen through the stirred mixture for about 10 min, then potassium carbonate (50 g, 0.36 mol) is added to the stirred mixture in one batch. This mixture is stirred under nitrogen at room temperature for 2 h, the mixture is filtered to remove potassium carbonate, then diluted with ethyl acetate. The resulting solution is washed with water, then 5% aq. NaCl. The combined organics are washed with brine, dried over Na₂SO₄. Concentration yields the title compound as yellow liquid. This material is used without purification.

Step B (6-Methoxy-benzo[b]thiophen-3-yl)-acetic acid ethyl ester 4-(3-Methoxy-phenylsulfanyl)-3-oxo-butyric acid ethyl ester (10.0 g) is added to pre-cooled methanesulfonic acid (60 mL) at 0-5° C., then the reaction mixture is allowed to warm to room temperature. After 1 h, the mixture is diluted with ice water and extracted with ethyl acetate. The combined organics are washed with brine, dried over Na₂SO₄, concentrated. Chromatography on silica gel eluted with hexanes and ethyl acetate yields (6-methoxy-benzo[b]thiophen-3-yl)-acetic acid ethyl ester (4.8 g) and (4-methoxy-benzo[b]thiophen-3-yl)-acetic acid ethyl ester (0.8 g)

Step C (6-hydroxy-benzo[b]thiophen-3-yl)-acetic acid ethyl ester

To a solution of (6-Methoxy-benzo[b]thiophen-3-yl)-acetic acid ethyl ester (2.4 g, 9.6 mmol) in methylene chloride (60 mL) is added BBr3 (1.0 M, heptane, 29.4 mL, 29.4 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (2.2 g).

Preparation 36

(4-Hydroxy-benzo[b]thiophen-3-yl)-acetic acid ethyl ester

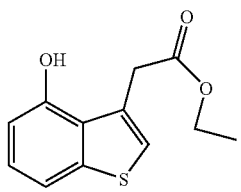

To a solution of (4-Methoxy-benzo[b]thiophen-3-yl)-acetic acid ethyl ester (0.7 g, 2.8 mmol) in methylene chloride (18 mL) is added BBr3 (1.0 M, heptane, 8.6 mL, 8.6 mmol) at −20~−30° C. The reaction mixture is allowed to warm to room temperature over 2 hrs, and TLC indicated clean conversion. The reaction is quenched by ice water, extracted with methylene chloride, dried over sodium sulfate, concentrated. Column chromatography on silica gel eluted with hexanes/ethyl acetate yields the title compound (0.4 g).

Preparation 37

(6-Hydroxy-benzofuran-3-yl)-acetic acid methyl ester

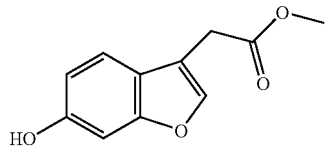

A mixture of 6-hydroxy-(2H)-benzofuran-3-one (5.1 g, 33.3 mmol), methyl (triphenylphosphoranylidene)acetate (25.0 g, 73 mmol), and xylenes (100 mL) is refluxed 6 hr. The reaction is concentrated and diluted with enough 1M aqueous hydrochloric acid to adjust pH to 2-3. The product is extracted into ethyl acetate (3×100 mL). The combined extracts are dried over anhydrous magnesium sulfate, filtered and concentrated. The residue is purified via silica chromatography eluting with 7:3 hexanes:ethyl acetate to afford the product as a orange oil, 1.3 g, 20%. MS M⁺+1 207. The structure is confirmed by ¹H NMR spectroscopy.

The following compound is made in a similar manner:

Preparation 38

2-(6-Hydroxy-benzofuran-3-yl)-propionic acid methyl ester

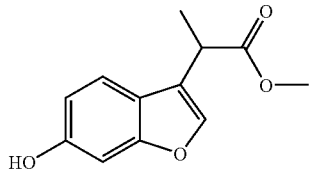

An orange oil. MS M⁺+1 221. The structure is confirmed by ¹H NMR spectroscopy.

Preparation 39

(6-Mercapto-benzo[b]thiophen-3-yl)-acetic acid ethyl ester

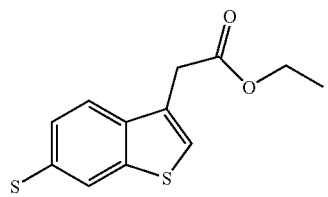

This compound was made from the corresponding phenol analog.

Preparation 40

[2-(4-Trifluoromethyl-phenyl)-4,5,6,7-tetrahydro-benzothiazol-4-yl]-methanol

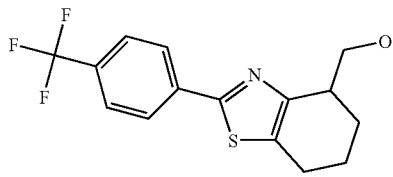

Step A

A solution of bromine (0.2056 mol, 32.85 g) in anhydrous dichloromethane (50 mL) is added dropwise over 2 h. to a solution of 2-oxo-cyclohexanecarboxylic acid ethyl ester (0.2056 mol, 35 g) in dichloromethane (200 mL) at 0° C.-5° C. After the addition, the mixture is allowed to stir 0.5 h. at 0° C., then the ice bath is removed and the mixture is allowed to stir at room temperature for 18 h. The reaction is monitored by TLC and HPLC until complete consumption of starting material, then ice water (200 mL) is added with stirring. The organic layer is collected and washed twice with ice water (200 mL), twice with 200 mL of 10% aqueous sodium thiosulfate, and 200 mL of brine. The filtered solution is dried over anhydrous sodium sulfate, then concentrated to a clear liquid, 0.189 mol, 47 g. 92% yield. *Actually a mix of methyl/ethyl ester due to impure starting ester (10% methyl ester)

Step B 4-trifluoromethyl-thiobenzamide (48.7 mmol, 10 g) is dissolved in denatured ethanol (200 mL) and 3-bromo-2-oxo-cyclohexanecarboxylic acid ethyl ester (12.4 g, 50 mmol) is added, then the reaction is heated under nitrogen to reflux. The reaction is monitored by TLC and HPLC to complete consumption of the thioamide, and then allowed to cool. The cooled reaction is concentrated and diluted with 250 mL ethyl acetate. The residue is washed with 100 mL saturated sodium bicarbonate followed by water and brine. The organic layer is dried over anhydrous sodium sulfate, then concentrated and purified by column chromatography. The fractions that contained pure product are concentrated to yield 5.06 g (30.6%) ester as a solid.

Step C THF (50 mL) solution of 2-(4-Trifluoromethyl-phenyl)-4,5,6,7-tetrahydro-benzothiazole-4-carboxylic acid ethyl ester (4.13 g, 11.6 mmol) is cooled to 0° C. and a 1M LiAlH$_4$ (11.6 mL, 11.6 mmol) is added slowly. The reaction is warmed to room temperature slowly, after stirring at room temperature for 2 h, tlc (15% EtOAc/hexane) showed that all the starting ester had been consumed. The reaction is cooled and carefully quenched with 2.4 mL water, 2.4 mL 5N NaOH and 7 mL water. The light tan solid is filter through celite and dried to give crude product (2.74 g, 8.74 mmol). The racemic alcohol [2-(4-Trifluoromethyl-phenyl)-4,5,6,7-tetrahydro-benzothiazol-4-yl]-methanol is resolved on a Chiralpak AD column (4.6×250 mm). Eluted with ethanol in heptane (9:1) and concentrated the fractions to provide pure enantiomer alcohols (isomer 1, 100% ee and isomer 2, 98.2% ee).

The following compounds are obtained in a substantially similar procedure:

Preparation 41

[2-(4-Trifluoromethyl-phenyl)-5,6-dihydro-4H-cyclopentathiazol-4-yl]-methanol

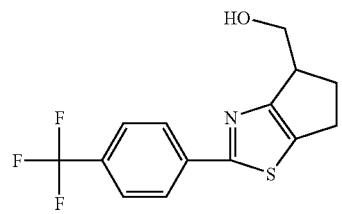

Preparation 42

[2-(4-Trifluoromethyl-phenyl)-5,6,7,8-tetrahydro-4H-cycloheptathiazol-4-yl]-methanol

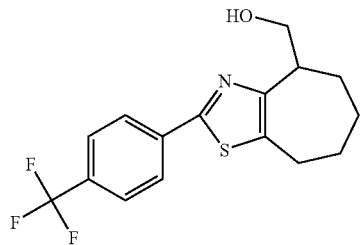

Preparation 43

[7-Methyl-2-(4-trifluoromethyl-phenyl)-4,5,6,7-tetrahydro-benzothiazol-4-yl]-methanol

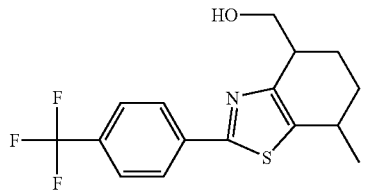

Preparation 44

[2-(4-Trifluoromethyl-phenyl)-4,5,6,7,8,9-hexahydro-cyclooctathiazol-4-yl]-methanol

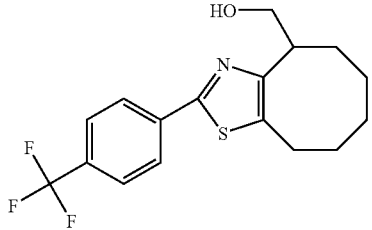

Preparation 45

3-Bromo-2-oxo-cyclohexanecarboxylic acid ethyl ester

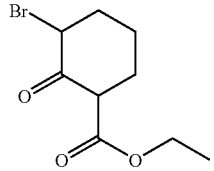

To a solution of 2-oxo-cyclohexanecarboxylic acid ethyl ester (30 g, 0.176 mol) in ether is added bromine (29.6 g, 0.185 mol) dropwise at room temperature, then stirred at room temperature for 2 h. The reaction mixture is quenched by water, and layers are separated. Organic layer is washed with Na2S2O4 and brine, dried over sodium sulfate. Concentration under vacuum gave the title compound, which is used for next step without further purification.

Preparation 46

2-Amino-4,5,6,7-tetrahydro-benzothiazole-4-carboxylic acid ethyl ester

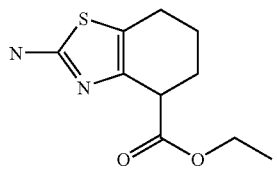

To a solution of thiourine (15 g, 0.197 mol) in ethanol (400 mL) is added 3-Bromo-2-oxo-cyclohexanecarboxylic acid ethyl ester (44.7 g, 0.179 mol) dropwise. After stirred at room temperature for 2 days, the reaction mixture is poured into ice, basified with 5N NaOH. Solid is formed when the mixture is basic. Filtration gave a solid product, dried under vacuum (37 g, 91.3% yield).

Preparation 47

2-Bromo-4,5,6,7-tetrahydro-benzothiazole-4-carboxylic acid ethyl ester

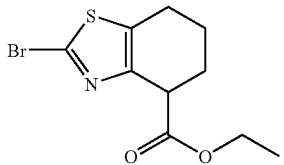

To a solution of CuSO4 11.6 g, 72.7 mmol) and sulfuric acid (139 mL) in water (324 mL) is added 2-Amino-4,5,6,7-tetrahydro-benzothiazole-4-carboxylic acid ethyl ester (11.3 g, 50 mmol) and a solution of sodium bromide (10.3 g, 100 mmol) in water (46 mL) at −10° C. Then a solution of sodium nitrite (6 g, 87 mmol) in water (46 mL) is added beneath the reaction mixture surface via a TFE tubing connected at the tip of the additional funnel. After addition, the reaction mixture is warmed to room temperature. The reaction mixture is extracted with ether, combined organic layers are washed with water and brine, dried over sodium sulfate. Column chromatography on silica gel gave the title compound (4.8 g, 33.1% yield).

Preparation 48

2-(4-Trifluoromethyl-phenyl)-4,5,6,7-tetrahydro-benzothiazole-4-carboxylic acid ethyl ester

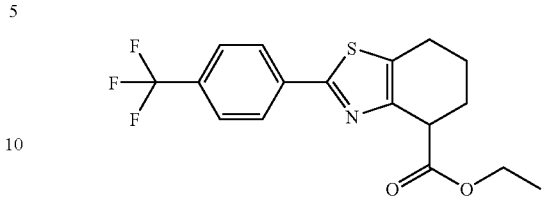

A mixture of 2-Bromo-4,5,6,7-tetrahydro-benzothiazole-4-carboxylic acid ethyl ester (3.5 g, 12.1 mmol) and 4-trifluoromethylphenyl boronic acid (2.52 g, 13.3 mmol) and CsF (6.44 g, 42.4 mmol) in dioxane (40 mL) is degassed and filled with nitrogen for three times, then PdCl2(dppf) (0.6 g, 0.7 mmol) is added under nitrogen. The reaction mixture is heated to reflux. After 40 hrs, the reaction mixture is cooled to room temperature, filtered through celite, concentrated and purified on silica gel (Hexane/ethyl acetate as eluent) giving 2.85 g of the title compound.

Preparation 49

[2-(4-Trifluoromethyl-phenyl)-4,5,6,7-tetrahydro-benzothiazol-4-yl]-methanol

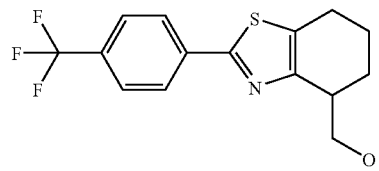

To a solution of 2-(4-Trifluoromethyl-phenyl)-4,5,6,7-tetrahydro-benzothiazole-4-carboxylic acid ethyl ester (5.27 g, 14.8 mmol) in THF (50 mL) is added LiAlH4 (1.0 M in THF, 16 mL, 16 mmol) at 0~5° C. After stirred for 4 hrs, quenched by water and NaOH (5.0 N, 1 mL), diluted with ether, filtered through celite. Concentration and column chromatography on silica gel gave the title compound (4.4 g, 94.9% yield).

Preparation 50

2-(4-Trifluoromethyl-phenyl)-benzothiazole-4-carboxylic acid ethyl ester

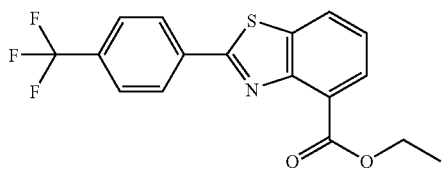

To a solution of 2-(4-trifluoromethyl-phenyl)-4,5,6,7-tetrahydro-benzothiazole-4-carboxylic acid ethyl ester (2.74 g, 7.71 mmol) in chlorobenzene (100 mL) is added DDQ (5.25 g, 23.1 mmol), then the mixture is refluxed for 3 hr, cooled to room temperature. The reaction mixture is loaded on 70 gram of SAX columns, which are pretreated with NaHCO3 aq, followed by water and methanol. The SAX column is eluted with acetone, concentration of the filtrate gave the title compound (2.70 g).

Preparation 51

[2-(4-Trifluoromethyl-phenyl)-benzothiazol-4-yl]-methanol

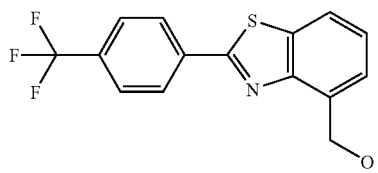

To a solution of 2-(4-trifluoromethyl-phenyl)-benzothiazole-4-carboxylic acid ethyl ester (2.8 g, 8.0 mmol) in THF (8 mL) is added LiAlH$_4$ (1.0 M in THF, 8 mL, 8 mmol) at 0~5° C. After stirred for 4 hrs, quenched by water and NaOH (15.0 N, 1 mL), diluted with ether, filtered through celite. Concentration and column chromatography on silica gel gave the title compound.

Preparation 52

Toluene-4-sulfonic acid 2-(4-trifluoromethyl-phenyl)-5,6-dihydro-4H-cyclopentathiazol-4-ylmethyl ester

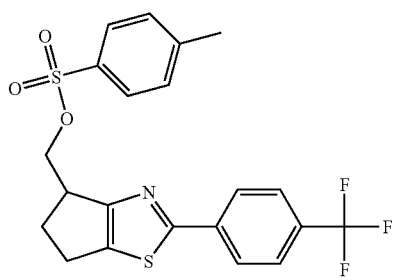

General Procedure for the Tosylate Formation:

To a solution of alcohol (9.60 mmol) in anhydrous dichloromethane (50 mL) is added 4-N,N-dimethylamino pyridine (0.500 g, 4.00 mmol), tosic anhydride (8.4 g, 24 mmol), and pyridine (3.4 mL, 42 mmol) at room temperature. The reaction is monitored by TLC, and upon complete consumption of the starting alcohol, the reaction is diluted with DCM and extracted against saturated sodium bicarbonate solution. The organic layer is washed with water and brine, then dried over anhydrous sodium sulfate and concentrated. The pure tosylate product is obtained after flash column chromatography.

The following compound is made in a similar manner:

Preparation 53

Toluene-4-sulfonic acid 2-(4-trifluoromethyl-phenyl)-4,5,6,7-tetrahydro-benzothiazol-4-ylmethyl ester

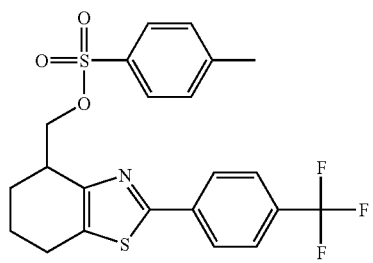

EXAMPLE 1

Racemic-{2-Methyl-4-[2-(4-trifluoromethyl-phenyl)-5,6-dihydro-4H-cyclopentathiazol-4-ylmethylsulfanyl]-phenoxy}-acetic acid

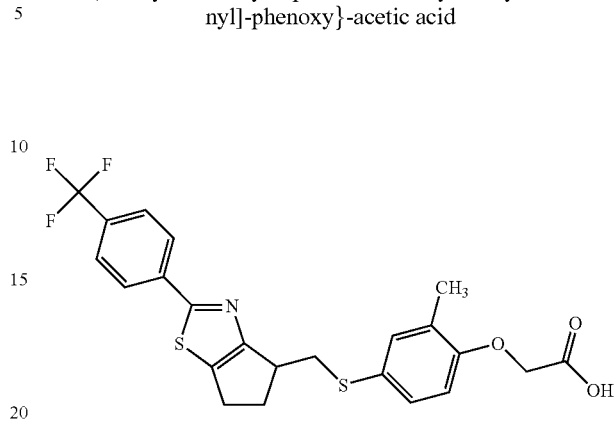

Step 1

(4-mercapto-2-methyl-phenoxy)-acetic acid methyl ester (109 mg, 0.500 mmol) is dissolved into anhydrous acetonitrile (ACN) (2 mL). Racemic-toluene-4-sulfonic acid 2-(4-trifluoromethyl-phenyl)-5,6-dihydro-4H-cyclopentathiazol-4-ylmethyl ester (206 mg, 0.495 mmol) is added to the reaction, followed by the addition of cesium carbonate (326 mg, 1.00 mmol). The reaction is allowed to stir under nitrogen at room temperature and monitored by TLC and HPLC. Upon complete consumption of the tosylate, the reaction is diluted with diethyl ether and quenched with 0.1N NaOH. The two phases are separated, then the organic layer washed with water and brine. The organic phase is dried over anhydrous sodium sulfate and concentrated under vacuum. The residue is further purified using either EtOAc/Hexanes(1:9) or Acetone/Hexanes(1:9) gradients on silica gel chromatography to yield {2-Methyl-4-[2-(4-trifluoromethyl-phenyl)-5,6-dihydro-4H-cyclopentathiazol-4-ylmethylsulfanyl]-phenoxy}-acetic acid ethyl ester (110 mg, 0.228 mmol) or 45%.

Step 2

{2-Methyl-4-[2-(4-trifluoromethyl-phenyl)-5,6-dihydro-4H-cyclopentathiazol-4-ylmethylsulfanyl]-phenoxy}-acetic acid ethyl ester (110 mg, 0.228 mmol) is dissolved in tetrahydrofuran (1 mL) and 1N LiOH (1 mL) is added. The mixture is heated to reflux until the conversion is complete. Upon complete conversion, the reaction is cooled to room temperature and 1N HCl (1 mL) is added. The mixture is diluted with diethyl ether and extracted with 1N HCl. The organic layer is washed with water and brine, then dried over anhydrous sodium sulfate. Concentration of the solvent reveals the pure {2-Methyl-4-[2-(4-trifluoromethyl-phenyl)-5,6-dihydro-4H-cyclopentathiazol-4-ylmethylsulfanyl]-phenoxy}-acetic acid (108 mg, 0.225 mmol) in near quantitative yield.

The following compounds are made in a substantially similar manner:

EXAMPLE 2

(R)-{2-Methyl-4-[2-(4-trifluoromethyl-phenyl)-5,6-dihydro-4H-cyclopentathiazol-4-ylmethylsulfanyl]-phenoxy}-acetic acid

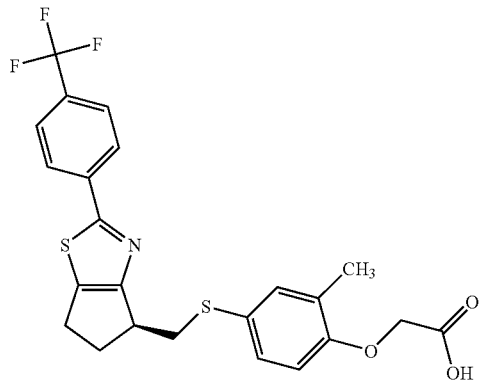

MS (ES): 480.44 (M$^+$+1).

EXAMPLE 3

(S)-{2-Methyl-4-[2-(4-trifluoromethyl-phenyl)-5,6-dihydro-4H-cyclopentathiazol-4-ylmethylsulfanyl]-phenoxy}-acetic acid

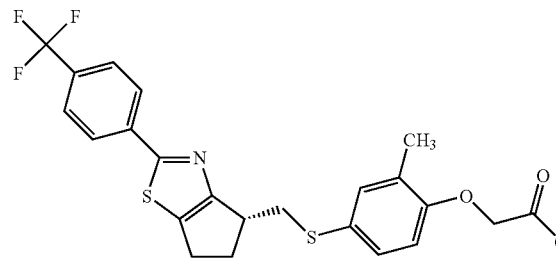

MS (ES): 480.44 (M$^+$+1).

EXAMPLE 4

Racemic-3-{2-Methyl-4-[2-(4-trifluoromethyl-phenyl)-5,6-dihydro-4H-cyclopentathiazol-4-yl-methoxy]-phenyl}-propionic acid

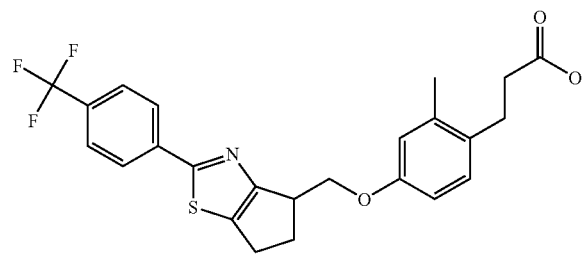

MS (ES): 484.2 (M$^+$+1).

EXAMPLE 5

Racemic-3-{2-Methyl-4-[2-(4-trifluoromethyl-phenyl)-5,6-dihydro-4H-cyclopentathiazol-4-ylmethylsulfanyl]-phenyl}-propionic acid

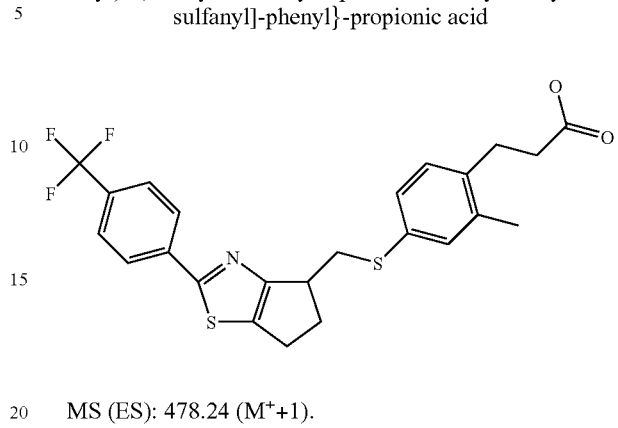

MS (ES): 478.24 (M$^+$+1).

EXAMPLE 6

(R)-3-{2-Methyl-4-[2-(4-trifluoromethyl-phenyl)-5,6-dihydro-4H-cyclopentathiazol-4-ylmethylsulfanyl]-phenyl}-propionic acid

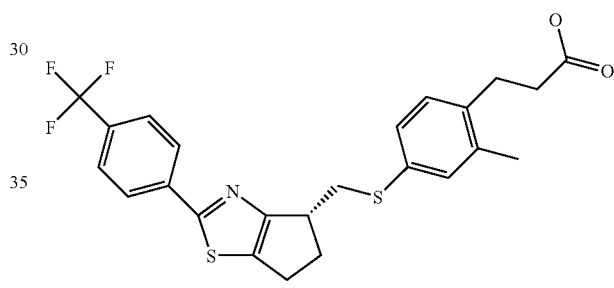

MS (ES): 478.15 (M$^+$+1).

EXAMPLE 7

(S)-3-{2-Methyl-4-[2-(4-trifluoromethyl-phenyl)-5,6-dihydro-4H-cyclopentathiazol-4-ylmethylsulfanyl]-phenyl}-propionic acid

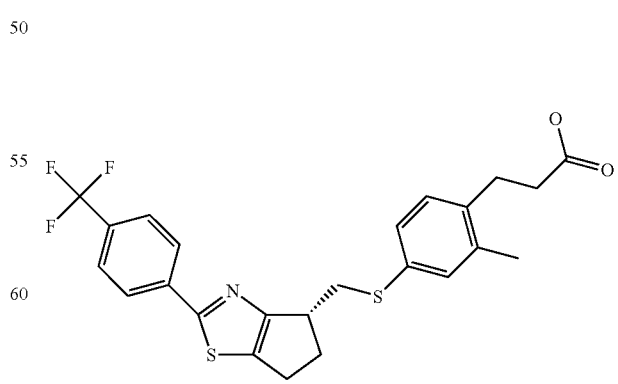

MS (ES): 478.15 (M$^+$+1).

EXAMPLE 8

Racemic-{2-Methyl-4-[2-(4-trifluoromethylphenyl)-4,5,6,7-tetrahydro-benzothiazol-4-ylmethylsulfanyl]-phenoxy}-acetic acid

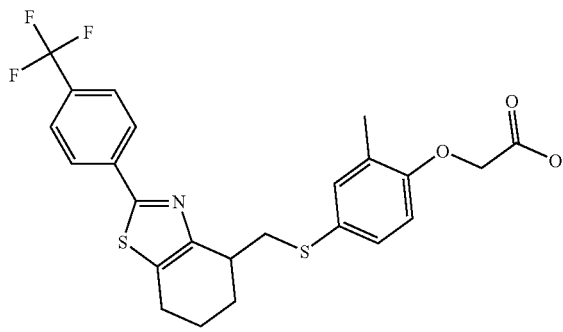

MS (ES): 494.2 (M$^+$+1).

EXAMPLE 9

(S)-{2-Methyl-4-[2-(4-trifluoromethyl-Phenyl)-4,5,6,7-tetrahydro-benzothiazol-4-ylmethylsulfanyl]-phenoxy}-acetic acid

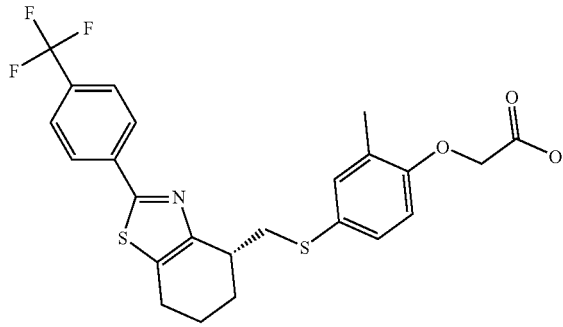

MS (ES): 494.0 (M$^+$+1).

EXAMPLE 10

(R)-{2-Methyl-4-[2-(4-trifluoromethyl-phenyl)-4,5,6,7-tetrahydro-benzothiazol-4-ylmethylsulfanyl] phenoxy}-acetic acid

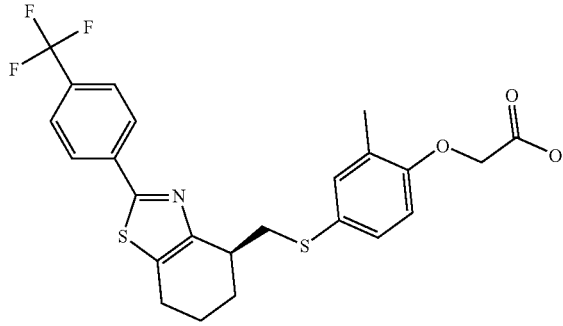

MS (ES): 494.0 (M$^+$+1).

EXAMPLE 11

{2-Methyl-4-[2-(4-trifluoromethyl-phenyl)-4,5,6,7-tetrahydro-benzothiazol-4-ylmethoxy]-phenoxy}-acetic acid

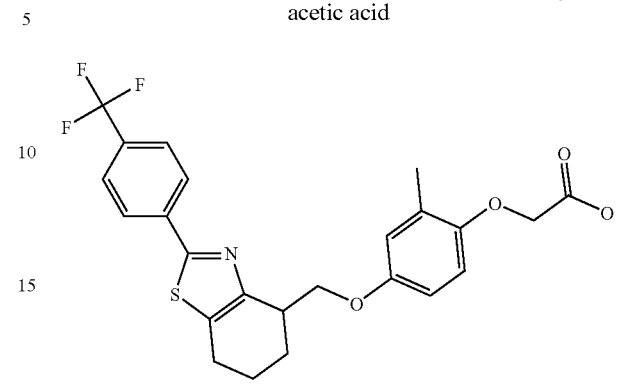

MS (ES): 478.2 (M$^+$+1).

EXAMPLE 12

Racemic-3-{2-Methyl-4-[2-(4-trifluoromethyl-phenyl)-4,5,6,7-tetrahydro-benzothiazol-4-ylmethylsulfanyl]-1-phenyl}-propionic acid

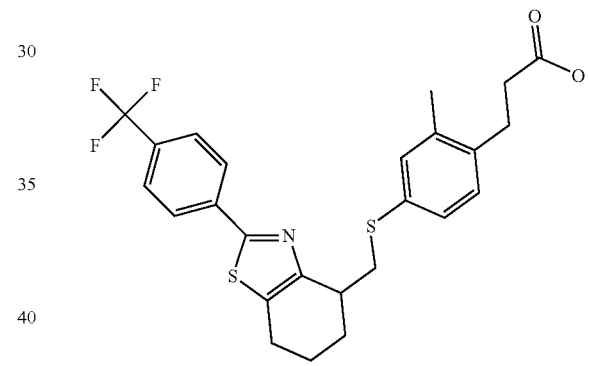

MS (ES): 492.25 (M$^+$+1).

EXAMPLE 13

(R)-3-{2-Methyl-4-[2-(4-trifluoromethyl-phenyl)-4,5,6,7-tetrahydro-benzothiazol-4-ylmethylsulfanyl]-phenyl}-propionic acid

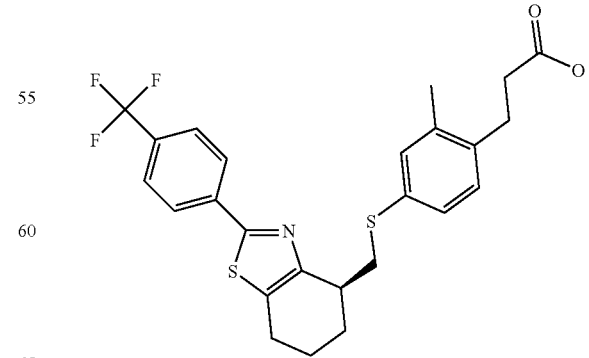

MS (ES): 492.13 (M$^+$+1).

EXAMPLE 14

(S)-3-{2-Methyl-4-[2-(4-trifluoromethyl-phenyl)-4,5,6,7-tetrahydro-benzothiazol-4-ylmethylsulfanyl]-phenyl}-propionic acid

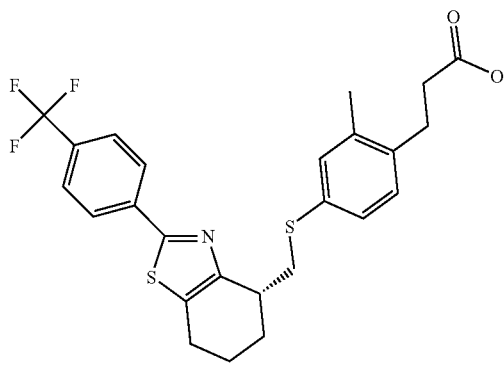

MS (ES): 492.14 (M⁺+1).

EXAMPLE 15

{3-[2-(4-Trifluoromethyl-phenyl)-5,6-dihydro-4H-cyclopentathiazol-4-ylmethoxy]-phenyl}-acetic acid

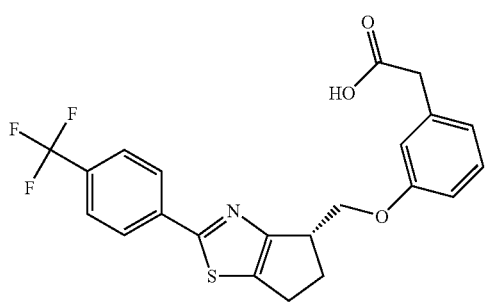

Step 1

[2-(4-Trifluoromethyl-phenyl)-5,6-dihydro-4H-cyclopentathiazol-4-yl]-methanol (299 mg, 1.0 mmol) is dissolved into anhydrous toluene (5 mL) and cooled in an ice bath to 0° C. with stirring under nitrogen. Tributyl phosphine (400 uL, 1.50 mmol) is added by syringe followed by 1-1'-azodicarbonyl-dipiperidine (405 mg, 1.50 mmol). Finally, (3-Hydroxy-phenyl)-acetic acid methyl ester (208 mg, 1.25 mmol) is then added. The reaction is allowed to stir under nitrogen at 0° C. for 1 hour, then room temperature and monitored by TLC and HPLC. Upon completion, the reaction is diluted with hexanes and allowed to stir vigorously for 10 min. The resulting white precipitate is then filtered away and the solution is concentrated under vacuum. The residue is further purified using either EtOAc/Hexanes(1:9) or Acetone/Hexanes(1:9) gradients on silica gel chromatography to yield {3-[2-(4-Trifluoromethyl-phenyl)-5,6-dihydro-4H-cyclopentathiazol-4-ylmethoxy]-phenyl}-acetic acid methyl ester (179 mg, 0.400 mmol) or 40%.

Step 2

{3-[2-(4-Trifluoromethyl-phenyl)-5,6-dihydro-4H-cyclopentathiazol-4-ylmethoxy]-phenyl}-acetic acidmethyl ester (179 mg, 0.400 mmol) is dissolved in tetrahydrofuran (1 mL) and 5N NaOH (1 mL) is added. The mixture is heated to reflux until the conversion is complete. Upon complete conversion, the reaction is cooled to room temperature and 5N HCl (1 mL) is added. The mixture is diluted with diethyl ether and extracted with 1N HCl. The organic layer is washed with water and brine, then dried over anhydrous sodium sulfate. Concentration of the solvent reveals the {3-[2-(4-Trifluoromethyl-phenyl)-5,6-dihydro-4H-cyclopentathiazol-4-ylmethoxy]-phenyl}-acetic acid (1158 mg, 0.3645 mmol)

The following compounds are made in a substantially similar manner:

EXAMPLE 16

(S)-{3-[2-(4-Trifluoromethyl-phenyl)-5,6-dihydro-4H-cyclopentathiazol-4-ylmethoxy]phenyl}-acetic acid

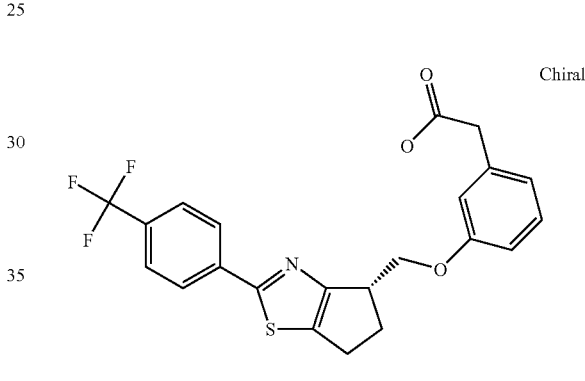

MS (ES): 434.06 (M+1).

EXAMPLE 17

(R)-{3-[2-(4-Trifluoromethyl-phenyl)-5,6-dihydro-4H-cyclopentathiazol-4-ylmethoxy]-phenyl}-acetic acid

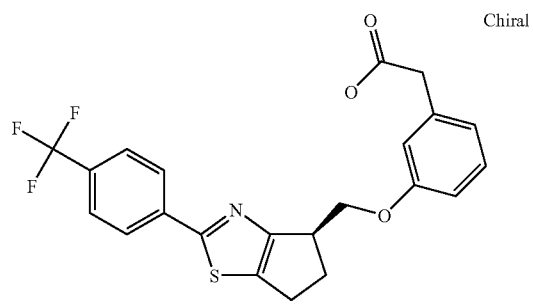

MS (ES): 434.06 (M⁺+1)

EXAMPLE 18

{2-Methyl-4-[7-methyl-2-(4-trifluoromethyl-phenyl)-4,5,6,7-tetrahydro-benzothiazol-4-ylmethylsulfanyl]-phenoxy}-acetic acid

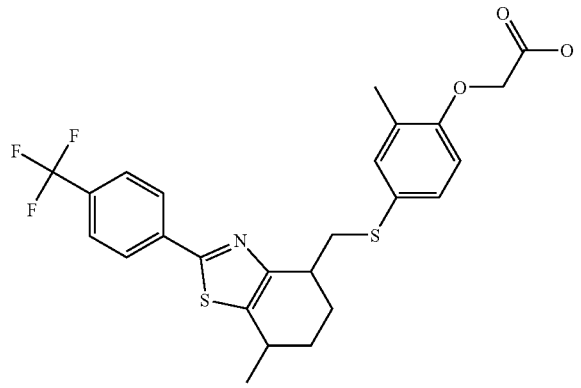

MS (ES): 508.15 (M⁺+1).

EXAMPLE 19

(S)-3-{2-Methyl-4-[2-(4-trifluoromethyl-phenyl)-4,5,6,7-tetrahydro-benzothiazol-4-ylmethoxy]-phenyl}-propionic acid

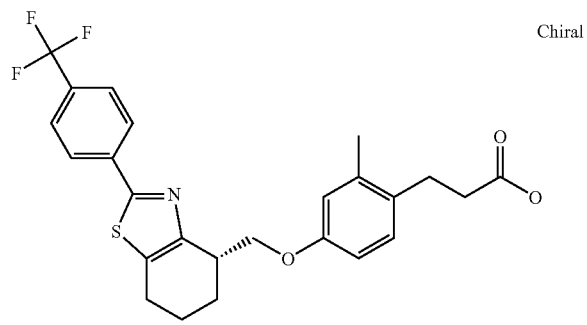

MS (ES): 476.08 (M⁺+1).

EXAMPLE 20

(R)-3-{2-Methyl-4-[2-(4-trifluoromethyl-Phenyl)-4,5,6,7-tetrahydro-benzothiazol-4-ylmethoxy]-phenyl}-propionic acid

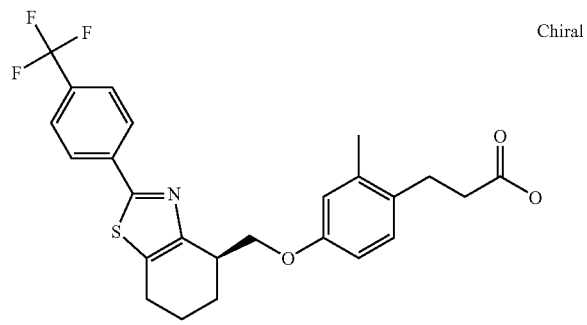

MS (ES): 476.07 (M⁺+1).

EXAMPLE 21

(R)-{3-[2-(4-Trifluoromethyl-phenyl)-4,5,6,7-tetrahydro-benzothiazol-4-ylmethoxy]-phenyl}-acetic acid

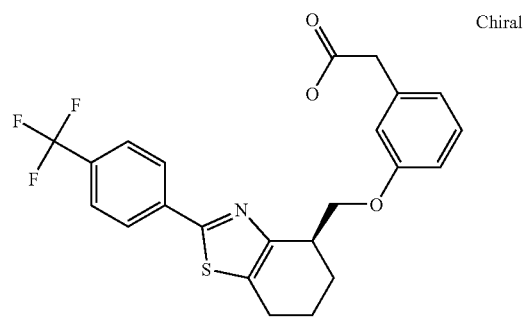

MS (ES): 448.07 (M⁺+1).

EXAMPLE 22

(S)-{3-[2-(4-Trifluoromethyl-phenyl)-4,5,6,7-tetrahydro-benzothiazol-4-ylmethoxy]-phenyl}-acetic acid

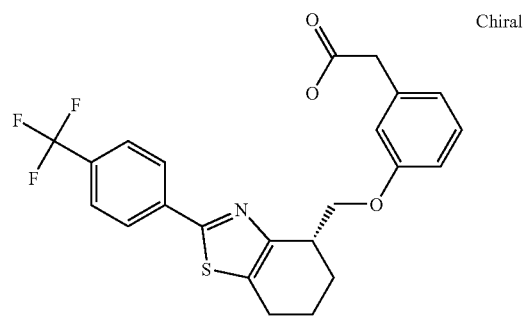

MS (ES): 448.07 (M⁺+1).

EXAMPLE 23

3-{2-Methyl-4-[2-(4-trifluoromethyl-phenyl)-5,6,7,8-tetrahydro-4H-cycloheptathiazol-4-ylmethylsulfanyl]-phenyl}-propionic acid

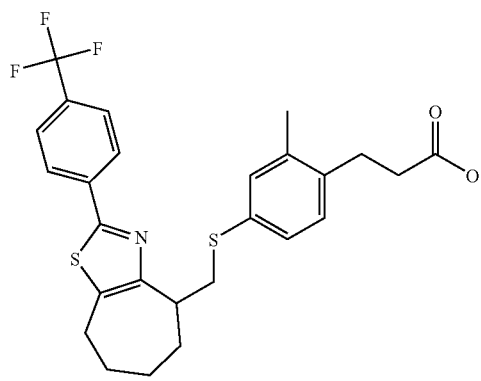

MS (ES): 506.13 (M⁺+1).

EXAMPLE 24

{2-Methyl-4-[2-(4-trifluoromethyl-phenyl)-5,6,7,8-tetrahydro-4H-cycloheptathiazol-4-ylmethylsulfanyl]-phenoxy}-acetic acid

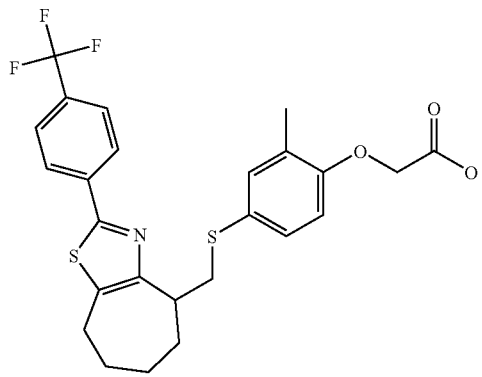

MS (ES): 508.09 (M$^+$+1)

EXAMPLE 25

(R)-{2-Methyl-4-[2-(4-trifluoromethyl-phenyl)-5,6,7,8-tetrahydro-4H-cycloheptathiazol-4-ylmethylsulfanyl]-phenoxy}-acetic acid

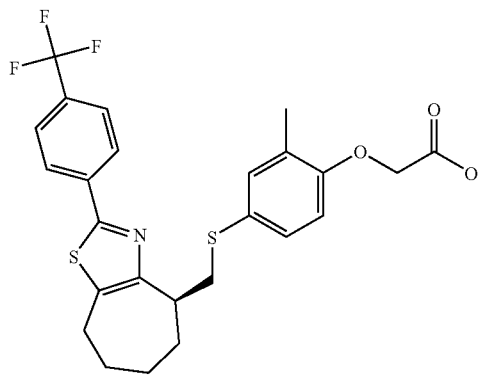

MS (ES): 508.1 (M$^+$+1).

EXAMPLE 26

(S)-{2-Methyl-4-[2-(4-trifluoromethyl-phenyl)-5,6,7,8-tetrahydro-4H-cycloheptathiazol-4-ylmethylsulfanyl]-phenoxy}-acetic acid

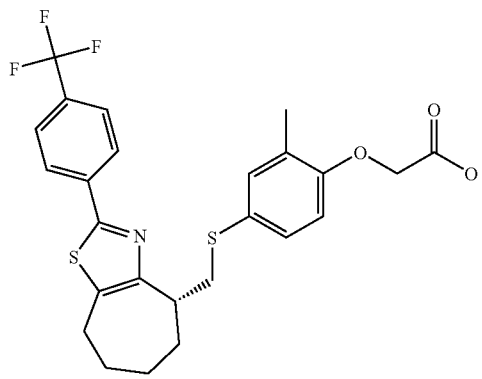

MS (ES): 508.1 (M$^+$+1).

EXAMPLE 27

3-{2-Methyl-4-[2-(4-trifluoromethyl-Phenyl)-5,6,7,8-tetrahydro-4H-cycloheptathiazol-4-ylmethoxy]-phenyl}-propionic acid

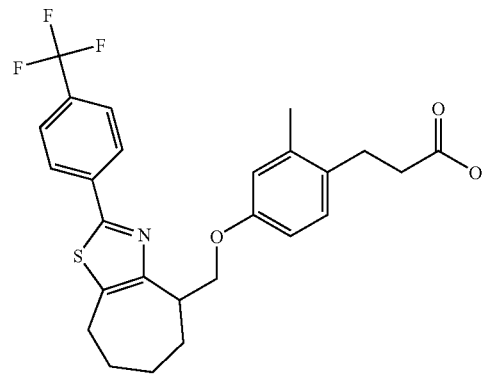

MS (ES): 490.15 (M$^+$+1)

EXAMPLE 28

{3-[2-(4-Trifluoromethyl-phenyl)-5,6,7,8-tetrahydro-4H-cycloheptathiazol-4-ylmethoxy]-phenyl}-acetic acid

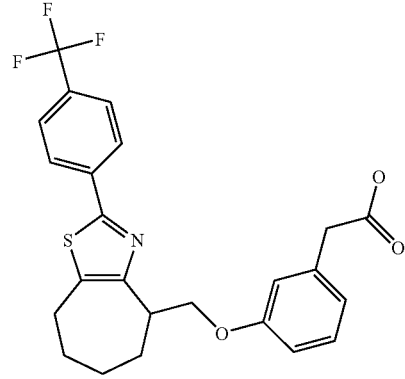

MS (ES): 462.07 (M$^+$+1).

EXAMPLE 29

(R)-3-{2-Methyl-4-[2-(4-trifluoromethyl-phenyl)-5,6,7,8-tetrahydro-4H-cycloheptathiazol-4-ylmethylsulfanyl]-phenyl}-propionic acid Chiral

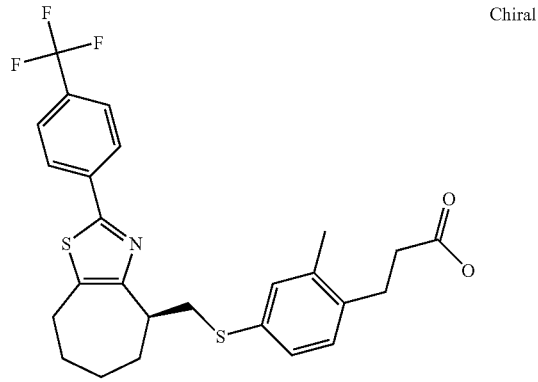

MS (ES): 506.01 (M$^+$+1).

EXAMPLE 30

(S)-3-{2-Methyl-4-[2-(4-trifluoromethyl-phenyl)-5,6,7,8-tetrahydro-4H-cycloheptathiazol-4-ylmethylsulfanyl]-phenyl}-propionic acid

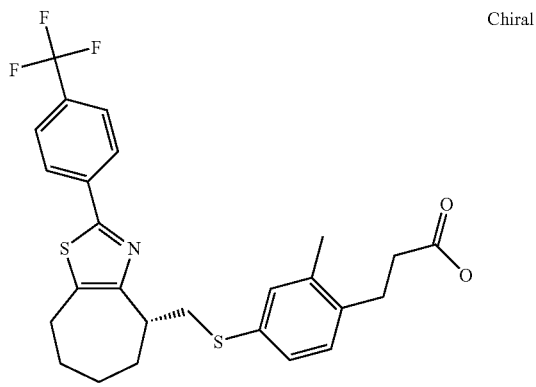

MS (ES): 506.01 (M⁺+1).

EXAMPLE 31

{2-Methyl-4-[2-(4-trifluoromethyl-phenyl)-4,5,6,7,8,9-hexahydro-cyclooctathiazol-4-ylmethylsulfanyl]-phenoxy}-acetic acid

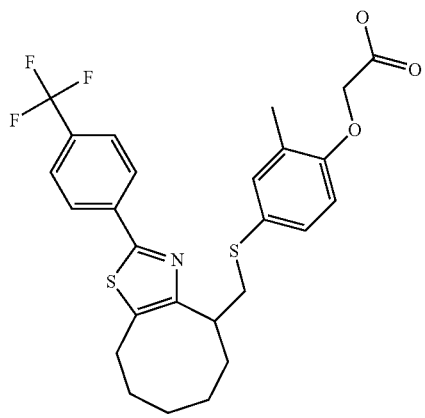

MS (ES): 594.11 (M⁺+1).

EXAMPLE 32

{2-Methyl-4-[2-(4-trifluoromethyl-phenyl)-benzothiazol-4-ylmethylsulfanyl]-phenoxy}-acetic acid

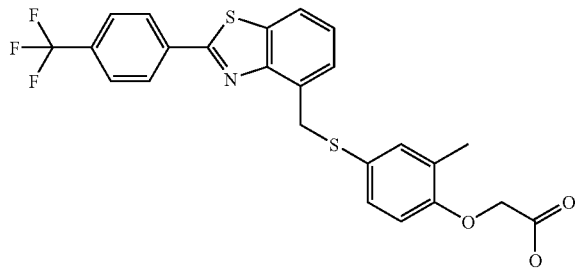

Step 1

{2-Methyl-4-[2-(4-trifluoromethyl-phenyl)-benzothiazol-4-ylmethylsulfanyl]-phenoxy}-acetic acid ethyl ester A solution of (4-mercapto-2-methyl-phenoxy)-acetic acid ethyl ester (113 mg, 0.5 mmol) and [2-(4-trifluoromethyl-phenyl)-benzothiazol-4-yl]-methanol (100 mg, 0.323 mmol) in toluene (3.0 mL) is degassed and filled with nitrogen for 3 times. Tributylphosphine (0.124 mL, 0.5 mmol) is added to the reaction mixture under nitrogen at 0° C., followed by addition of 1,1'-(azodicarbonyl)-dipiperidine (120 mg, 0.5 mmol). The reaction mixture is allowed to warm to room temperature and stirred overnight, the mixture is loaded on silica gel column. Chromatography gave the title compound (100 mg).

Step 2

{2-Methyl-4-[2-(4-trifluoromethyl-phenyl)-benzothiazol-4-ylmethylsulfanyl]-phenoxy}-acetic acid {2-Methyl-4-[2-(4-trifluoromethyl-phenyl)-benzothiazol-4-ylmethylsulfanyl]-phenoxy}-acetic acid ethyl ester from step A is taken into ethanol (1 mL) and treated with NaOH (5.0 N, 1 mL) for 2 hrs at 50° C. The reaction mixture is cooled to room temperature and acidified with 5 N HCl, extracted with ethyl ether, dried over sodium sulfate. Concentration yields the title compound. MS (ES): 490.1 (M⁺+1), the structure is also confirmed by proton NMR.

The following compounds are made in a similar manner:

EXAMPLE 33

3-{2-Methyl-4-[2-(4-trifluoromethyl-phenyl)-benzothiazol-4-ylmethylsulfanyl]-phenyl}-propionic acid

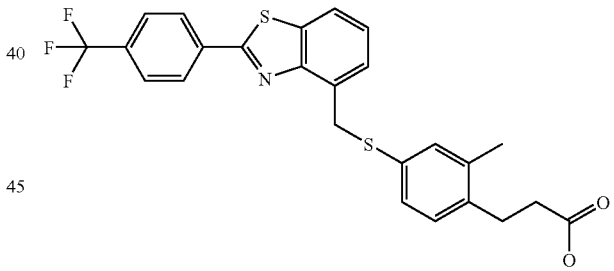

MS (ES): 488.1 (M⁺+1).

EXAMPLE 34

{3-[2-(4-Trifluoromethyl-phenyl)-benzothiazol-4-ylmethoxy]-phenyl}-acetic acid

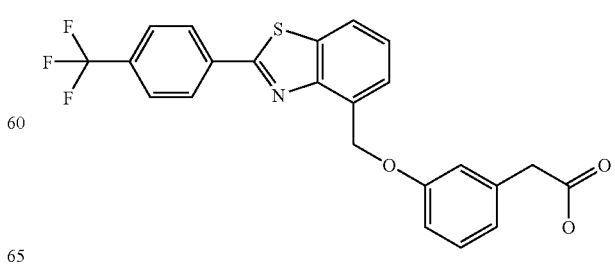

MS (ES): 444.1 (M⁺+1)

EXAMPLE 35

3-{2-Methyl-4-[2-(4-trifluoromethyl-phenyl)-benzothiazol-4-ylmethoxy]-phenyl}-propionic acid

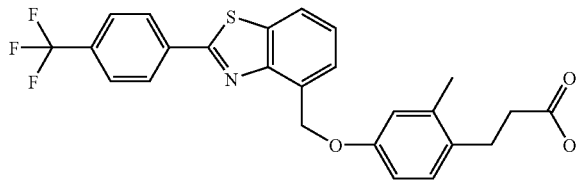

MS (ES): 472.1 (M$^+$+1).

EXAMPLE 36

(S)-2-Methoxy-3-{4-[2-(4-trifluoromethyl-phenyl)-benzothiazol-4-ylmethoxy]-phenyl}-propionic acid

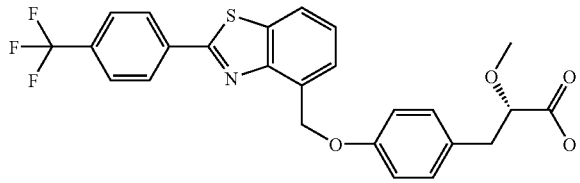

MS (ES): 472.1 (M$^+$+1).

EXAMPLE 37

2-Methyl-2-{2-methyl-4-[2-(4-trifluoromethyl-phenyl)-benzothiazol-4-ylmethoxy]-phenoxy}-propionic acid

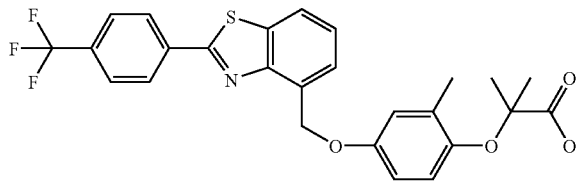

MS (ES): 502.2 (M$^+$+1).

EXAMPLE 38

Racemic-(2-methyl-4-{1-[2-(4-trifluoromethyl-phenyl)-benzothiazol-4-yl]-ethylsulfanyl}-phenoxy)-acetic acid

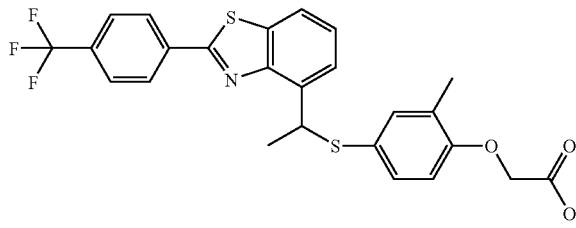

MS (ES): 504.3 (M$^+$+1).

EXAMPLE 39

Racemic-3-(2-methyl-4-{1-[2-(4-trifluoromethyl-phenyl)-benzothiazol-4-yl]-ethylsulfanyl}-phenyl)-propionic acid

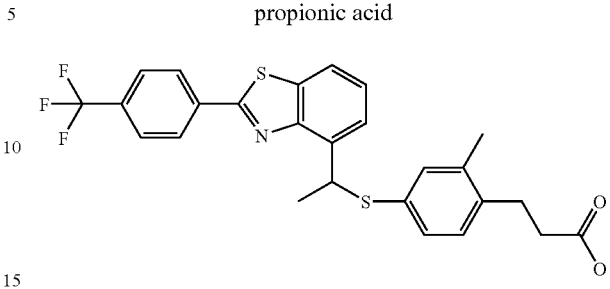

MS (ES): 502.9 (M$^+$+1).

Racemic methyl ester of example 38 and 39 can be resolved by ChiralPak AD column with heptane and isopropanol alcohol (4:1) as eluent, thus enantimerically pure compounds were obtained.

Examples 40-110 below are made using the following experimental procedures:

All non-aqueous reactions are performed under a dry atmosphere of nitrogen unless otherwise specified.

Commercial grade reagents and anhydrous solvents are used as received from vendors and no attempts are made to purify or dry these components further. Removal of solvents under reduced pressure is accomplished with a Buchi rotary evaporator at approximately 28 mm Hg pressure using a Teflon-lined KNF vacuum pump. Flash column chromatography is carried out using Kieselgel silica gel 60. Proton NMR spectra are obtained on a Bruker AC 300 MHz Nuclear Magnetic Resonance Spectrometer and are reported in ppm δ values, using tetramethylsilane as an internal reference. Melting points are obtained using an Electrothermal melting point apparatus and are uncorrected. API Mass spectroscopic analyses are performed on a Finnegan LCQ Duo Ion Trap or a PESciex API 150EX mass spectrometer, using electro spray ionization (ESI) or atmospheric pressure chemical ionization (APCI). HPLC analyses are conducted using a Waters Symmetry C18, 5 um, WAT046980, 3.9×150 mm column. The elution system consists of 90:10 (0.1% TFA in H$_2$O)/(0.1% TFA in CH$_3$CN) gradient elution to 10:90 (0.1% TFA in H$_2$O)/(0.1% TFA in CH$_3$CN) over 20 min, followed by 10:90 (0.1% TFA in H$_2$O)/(0.1% TFA in CH$_3$CN) isocratic elution for 10 min, followed by 90:10 (0.1% TFA in H$_2$O)/(0.1% TFA in CH$_3$CN) isocratic elution for 10 min. The flow rate is 1 mL/min. UV Detection is performed at 254 nm.

Examples 40-43 below are made employing the procedures of Scheme 3:

Scheme 3:

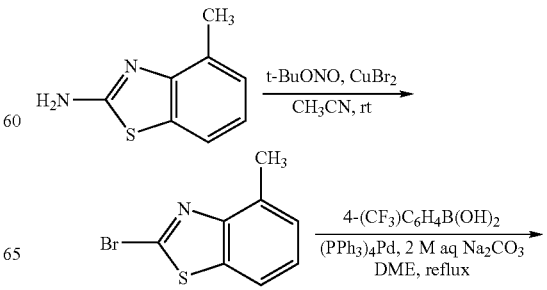

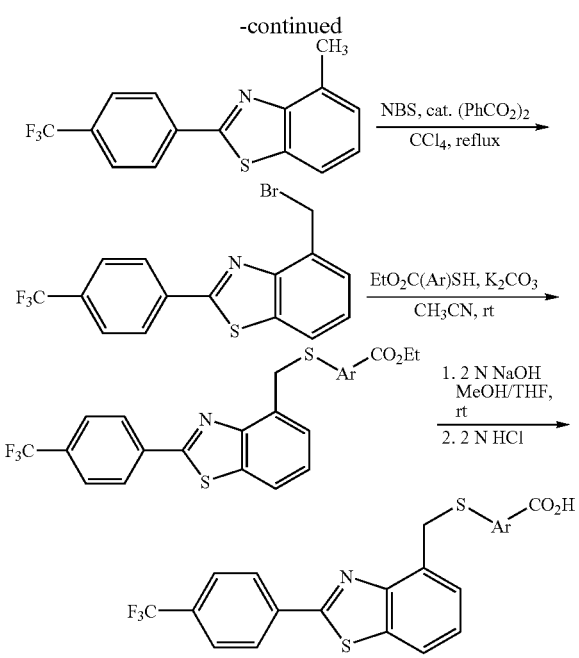

EXAMPLE 40

2-Ethyl-4-[2-(4-trifluoromethylphenyl)benzothiazol-4-ylmethylsulfanylphenoxyacetic Acid

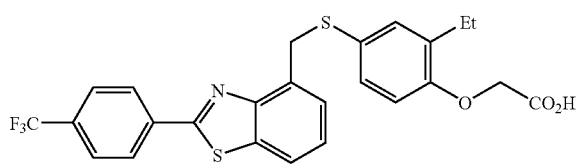

Step 1

2-Bromo-4-methylbenzothiazole

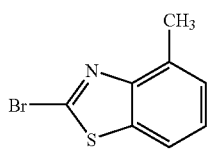

Add commercially available 2-amino-4-methyl-benzothiazole (10 g, 61 mmol) portionwise to a black solution of copper(II) bromide (16 g, 73 mmol) and tert-butyl nitrite (11.9 mL, 99 mmol) in acetonitrile (220 mL) at room temperature under nitrogen over the course of five min and stir the mixture for 30 min. Dilute the mixture with 1 N HCl (500 mL) and extract with ethyl acetate (3×500 mL). Wash the combined organic extracts with 1 N HCl (250 mL), dry over MgSO$_4$ and remove the solvents under reduced pressure. Purify the residue by filtration through a plug of silica gel, eluting with ethyl acetate (500 mL), and remove the solvents under reduced pressure to afford 2-bromo-4-methylbenzothiazole (Step 1) as a black solid (12.68 g, 91%): $^1$H NMR (CDCl$_3$) δ 2.70 (s, 1H), 7.20 (m, 2H), 7.60 (d, 1H); APCI mass spectrum m/z 228 [C$_8$H$_6$NSBr+H]$^+$.

Step 2

4-Methyl-2-(4-trifluoromethylphenyl)benzothiazole

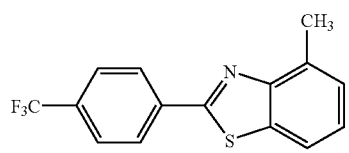

Add tetrakis(triphenylphosphine)palladium (0) (0.50 g, 0.43 mmol) to a degassed solution of 4-methyl-2-(4-trifluoromethylphenyl-benzothiazole (Step 1, 2.0 g, 8.7 mmol) in DME (30 mL) at room temperature under nitrogen, stir the mixture for 15 min and add a solution of 4-(trifluoromethyl)phenylboronic acid (2.3 g, 12.2 mmol) in ethanol (10 mL). Stir the mixture for 10 min, add 2 M aqueous sodium carbonate solution (40 mL) and heat the mixture at reflux for 22 h. Dilute the cooled mixture with brine (300 mL) and extract with chloroform (2×300 mL). Dry the combined organic extracts over MgSO$_4$, filter through a plug of celite and remove the solvents under reduced pressure. Purify the red residue by flash column chromatography on silica gel, eluting with hexanes/ethyl acetate (98:2), to afford 4-methyl-2-(4-trifluoromethylphenyl)benzothiazole (Step 2) as an off-white solid (2.0 g, 78%): $^1$H NMR (CDCl$_3$) δ 2.80 (s, 3H), 7.30 (m, 2H), 7.70 (m, 3H), 8.20 (d, 2H).

Step 3

4-Bromomethyl-2-(4-trifluoromethylphenyl)benzothiazole

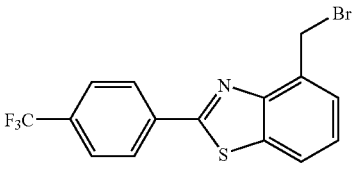

Add N-bromosuccinimide (0.61 g, 3.4 mmol) to a solution of 4-methyl-2-(4-trifluoromethylphenyl)benzothiazole (Step 2, 1.0 g, 3.4 mmol) in carbon tetrachloride (30 mL) at room temperature under nitrogen followed by benzoyl peroxide (100 mg, 0.4 mmol) and heat the mixture at reflux for 18 h. Add additional N-bromosuccinimide (100 mg, 0.5 mmol) and continue heating at reflux for an additional 3 h. Dilute the cooled mixture with chloroform (300 mL) and wash with water (200 mL). Back-extract the aqueous layer with chloroform (200 mL) and wash the combined organic extracts with 1 N NaOH (200 mL), dry over MgSO$_4$ and remove the solvents under reduced pressure. Purify the residue by flash, column chromatography on silica gel, eluting with hexanes/ethyl acetate (97:3) to afford 4-bromomethyl-2-(4-trifluoromethylphenyl)benzothiazole (Step 3) as a white solid (1.23 g, 97%): $^1$H NMR (CDCl$_3$) δ 5.10 (s, 2H), 7.40 (t, 1H), 7.60

(dd, 1H), 7.80 (d, 2H), 7.90 (dd, 1H), 8.30 (d, 2H); APCI mass spectrum m/z 373 [$C_{15}H_9NSF_3Br+H$]$^+$.

Step 4

Ethyl Ethyl-4-[2-(4-trifluoromethylphenyl)benzothiazol-4-ylmethylsulfanyl]phenoxyacetate

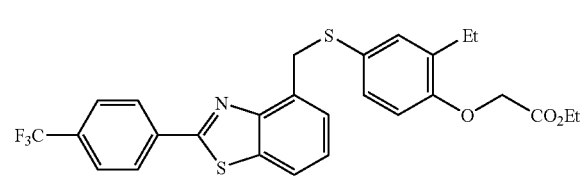

Add potassium carbonate (184 mg, 1.34 mmol) to a solution of 4-bromomethyl-2-(4-trifluoromethylphenyl)benzothiazole (Step 3, 200 mg, 0.537 mmol) and ethyl (2-ethyl-4-mercaptophenoxy)acetate (200 mg, 0.833 mmol) in acetonitrile (3 mL) at room temperature under nitrogen, stir for 18 h, dilute the mixture with water (120 mL) and extract with methylene chloride (2×100 mL). Dry the combined organic extracts over MgSO$_4$, remove the solvents under reduced pressure and purify the residue by flash column chromatography on silica gel, eluting with hexanes/ethyl acetate (97:3), to afford ethyl ethyl-4-[2-(4-trifluoromethylphenyl) benzothiazol-4-ylmethylsulfanyl]phenoxyacetate (Step 4) as a white solid (130 mg, 50%): $^1$H NMR (CDCl$_3$) δ 1.10 (t, 3H), 1.30 (t, 3H), 2.60 (q, 2H), 4.20 (q, 2H), 4.60 (s, 2H), 4.70 (s, 2H), 6.60 (d, 1H), 7.10 (m, 2H), 7.30 (m, 2H), 7.70 (d, 2H), 7.80 (m, 1H), 8.10 (d, 2H).

2-Ethyl-4-[2-(4-trifluoromethylphenyl)benzothiazol-4-ylmethylsulfanylphenoxyacetic Acid

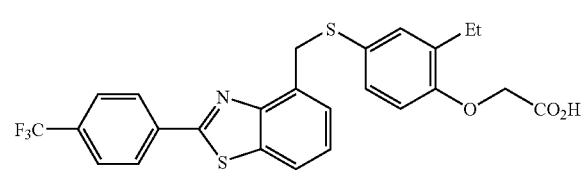

Add a solution of sodium hydroxide (100 mg, 2.4 mmol) in water (1.5 mL) to a solution of ethyl ethyl-4-[2-(4-trifluoromethylphenyl)benzothiazol-4-ylmethylsulfanyl]phenoxyacetate (Step 4, 130 mg, 0.24 mmol) in THF (2 mL) and ethanol (2 mL) at room temperature under nitrogen and stir the mixture for 2.5 h. Remove the solvents under reduced pressure, suspend the residue in 1 N NaOH (50 mL) and acidify to pH I with 2 N HCl. Collect the solids by vacuum filtration and wash with water (15 mL) to afford 2-ethyl-4-[2-(4-trifluoromethylphenyl)benzothiazol-4-ylmethylsulfanyl]phenoxyacetic acid (1) as a white solid (100 mg, 82%): mp 89-92° C.; $^1$H NMR (CDCl$_3$) δ 1.10 (t, 3H), 2.50 (q, 2H), 4.60 (s, 2H), 4.70 (s, 2H), 6.60 (d, 1H), 7.10 (m, 2H), 7.30 (m, 2H), 7.70 (d, 2H), 7.80 (m, 1H), 8.20 (d, 2H); APCI MS m/z 502 [$C_{25}H_{20}F_3NO_3S_2$–H]$^-$. HPLC analysis (retention time=15.8 min) shows one peak, with a total purity of 97.9% (area percent).

The following compounds are made in a substantially similar manner:

EXAMPLE 41

3-[2-(4-Trifluoromethylphenyl)benzothiazol-4-ylmethylsulfanyl-phenylacetic Acid

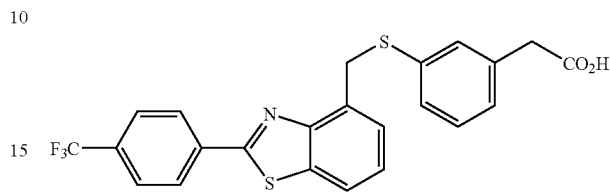

mp 140-143° C.; $^1$H NMR (CDCl$_3$) δ 3.50 (s, 2H), 4.70 (s, 2H), 7.10 (d, 1H), 7.20 (t, 1H), 7.30 (m, 2H), 7.40 (d, 1H), 7.70 (m, 3H), 8.2 (d, 2H); APCI MS m/z 458 [$C_{23}H_{16}F_3NO_2S_2$–H]$^-$. HPLC analysis (retention time=14.0 min) shows one peak, with a total purity of 95.8% (area percent).

EXAMPLE 42

6-[2-(4-Trifluoromethylphenyl)benzothiazol-4-ylmethoxy]benzo[b]thiophen-3-ylacetic Acid

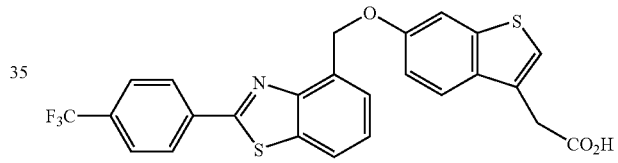

mp 185-190° C.; $^1$H NMR (DMSO-d$_6$) δ 3.80 (s, 2H), 3.70 (s, 2H), 7.20 (d, 1H), 7.50 (t, 1H), 7.70 (m, 3H), 8.00 (d, 2H), 8.20 (d, 1H), 8.40 (m, 3H); APCI MS m/z 498 [$C_{25}H_{16}F_3NO_3S_2$–H]$^-$. HPLC analysis (retention time=15.0 min) shows one peak, with a total purity of 96.0% (area percent).

EXAMPLE 43

6-[2-(4-Trifluoromethylphenyl)benzothiazol-4-ylmethylsulfanyl]benzo[b]thiophen-3-yl}acetic Acid

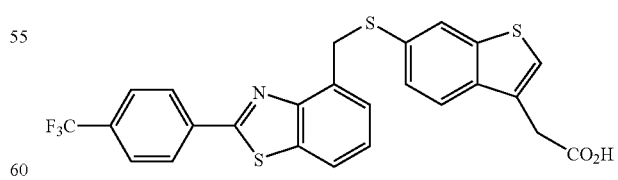

mp 168-170° C.; $^1$H NMR (DMSO-d$_6$) δ 3.76 (s, 2H), 4.83 (s, 2H), 7.30-7.55 (m, 4H), 7.66 (d, 1H), 7.92 (d, 2H), 8.05 (s, 1H), 8.08 (s, 1H), 8.25 (d, 2H), 12.41 (s, 1H); APCI MS m/z 514 [$C_{25}H_{16}F_3NO_2S_3$–H]$^-$. HPLC analysis (retention time=15.48 min) shows one peak, with a total purity of 98.5% (area percent).

Examples 44-47 below are made employing the procedures of Scheme 4:

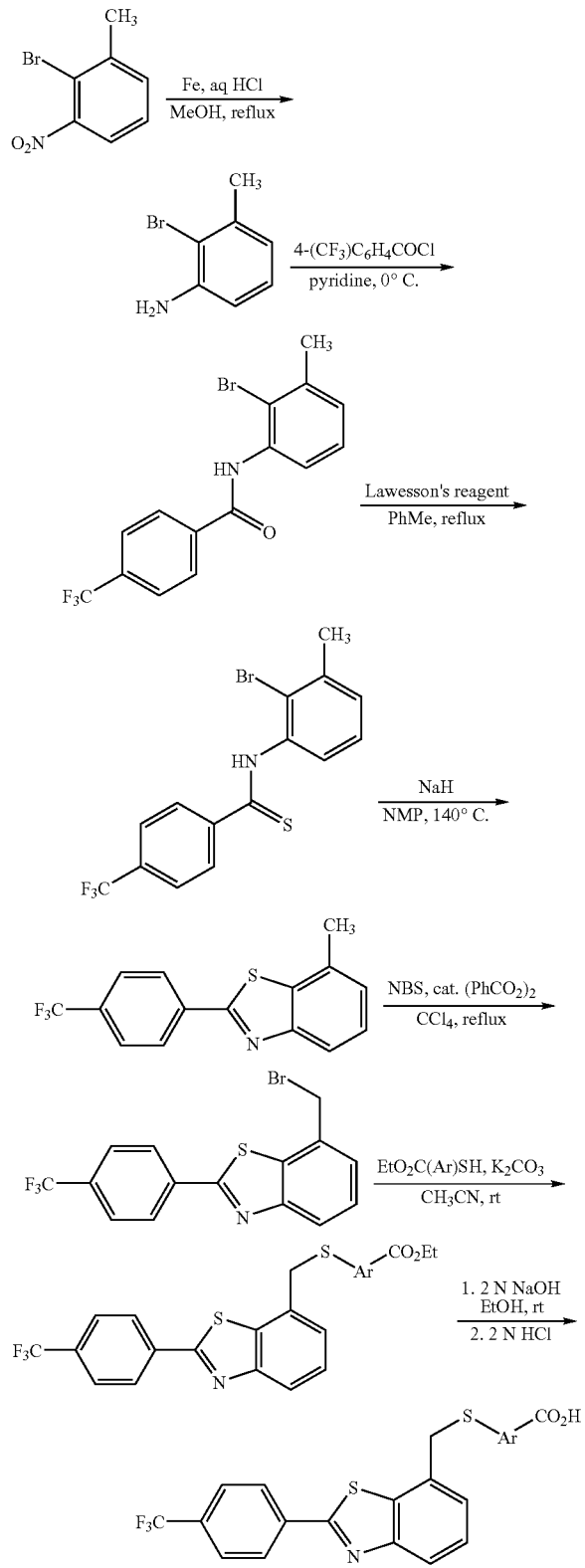

EXAMPLE 44

2-Methyl-4-[2-(4-trifluoromethylphenyl)benzothiazol-7-ylmethylsulfanyl]phenoxyacetic Acid

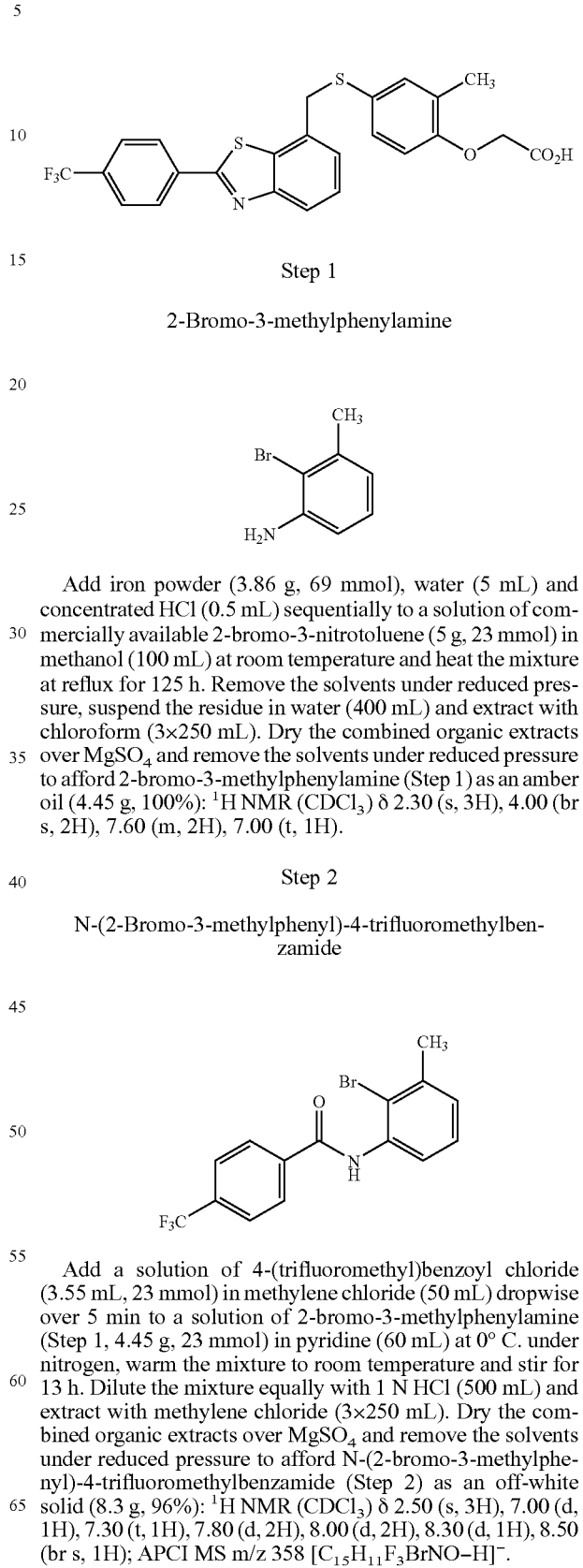

Step 1

2-Bromo-3-methylphenylamine

Add iron powder (3.86 g, 69 mmol), water (5 mL) and concentrated HCl (0.5 mL) sequentially to a solution of commercially available 2-bromo-3-nitrotoluene (5 g, 23 mmol) in methanol (100 mL) at room temperature and heat the mixture at reflux for 125 h. Remove the solvents under reduced pressure, suspend the residue in water (400 mL) and extract with chloroform (3×250 mL). Dry the combined organic extracts over $MgSO_4$ and remove the solvents under reduced pressure to afford 2-bromo-3-methylphenylamine (Step 1) as an amber oil (4.45 g, 100%): $^1$H NMR ($CDCl_3$) δ 2.30 (s, 3H), 4.00 (br s, 2H), 7.60 (m, 2H), 7.00 (t, 1H).

Step 2

N-(2-Bromo-3-methylphenyl)-4-trifluoromethylbenzamide

Add a solution of 4-(trifluoromethyl)benzoyl chloride (3.55 mL, 23 mmol) in methylene chloride (50 mL) dropwise over 5 min to a solution of 2-bromo-3-methylphenylamine (Step 1, 4.45 g, 23 mmol) in pyridine (60 mL) at 0° C. under nitrogen, warm the mixture to room temperature and stir for 13 h. Dilute the mixture equally with 1 N HCl (500 mL) and extract with methylene chloride (3×250 mL). Dry the combined organic extracts over $MgSO_4$ and remove the solvents under reduced pressure to afford N-(2-bromo-3-methylphenyl)-4-trifluoromethylbenzamide (Step 2) as an off-white solid (8.3 g, 96%): $^1$H NMR ($CDCl_3$) δ 2.50 (s, 3H), 7.00 (d, 1H), 7.30 (t, 1H), 7.80 (d, 2H), 8.00 (d, 2H), 8.30 (d, 1H), 8.50 (br s, 1H); APCI MS m/z 358 $[C_{15}H_{11}F_3BrNO-H]^-$.

Step 3

N-(2-Bromo-3-methylphenyl)-4-trifluoromethylthiobenzamide

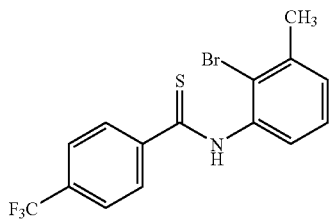

Heat a mixture of Lawesson's reagent (2.25 g, 5.5 mmol) and N-(2-bromo-3-methylphenyl)-4-trifluoromethylbenzamide (Step 2, 2 g, 5.5 mmol) in toluene (20 mL) at reflux under nitrogen for 20 h, and dilute the cooled mixture with 1 N HCl (250 mL). Extract the mixture with ethyl acetate (500 mL), wash with water (250 mL), dry over MgSO$_4$ and remove the solvents under reduced pressure. Purify the residue by flash column chromatography on silica gel, eluting with hexanes/ethyl acetate (97:3), to afford N-(2-bromo-3-methylphenyl)-4-trifluoromethylthiobenzamide (Step 3) as a yellow solid (1.89 g, 87%): $^1$H NMR (CDCl$_3$) δ 2.50 (s, 3H), 7.20 (m, 3H), 7.70 (d, 2H), 7.90 (m, 2H), 9.30 (br s, 1H); APCI MS m/z 375 [C$_{15}$H$_{11}$F$_3$BrNS–H]$^-$.

Step 4

7-Methyl-2-(4-trifluoromethylphenyl)benzothiazole

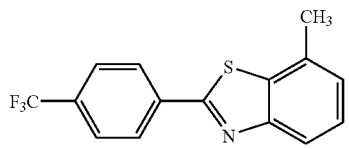

Add sodium hydride (100 mg, 4.1 mmol, 60% dispersion in mineral oil) portionwise to a solution of N-(2-bromo-3-methylphenyl)-4-trifluoromethylthiobenzamide (Step 3, 1 g, 2.6 mmol) in N-methylpyrrolidinone (5 mL) at room temperature under nitrogen, and heat the mixture at 140° C. for 1 h. Dilute the cooled mixture with water (400 mL) and extract with ethyl acetate (3×300 mL). Dry the combined organic extracts over MgSO$_4$ and remove the solvents under reduced pressure to afford 7-methyl-2-(4-trifluoromethylphenyl)benzothiazole (Step 4) as a brown solid (780 mg, 100%): $^1$H NMR (CDCl$_3$) δ 2.60 (s, 3H), 7.20 (d, 1H), 7.40 (t, 1H), 7.80 (d, 2H), 8.00 (d, 1H), 8.20 (d, 2H); APCI MS m/z 294 [C$_{15}$H$_{10}$F$_3$NS+H]$^+$.

Step 5

7-Bromomethyl-2-(4-trifluoromethylphenyl)benzothiazole

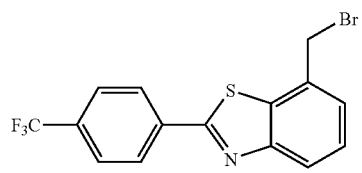

Add N-bromosuccinimide (2.54 g, 14.2 mmol) to a solution of 7-methyl-2-(4-trifluoromethylphenyl)benzothiazole (Step 4, 4.18 mg, 14.2 mmol) in carbon tetrachloride (75 mL) at room temperature under nitrogen, followed by benzoyl peroxide (200 mg, 0.8 mmol). Heat the mixture at reflux for 23 h, add additional N-bromosuccinimide (120 mg, 0.67 mmol) and stir the reaction mixture at reflux for an additional 3 h. Dilute the cooled mixture with water (400 mL) and extract with chloroform (3×300 mL). Dry the combined organic extracts over MgSO$_4$, remove the solvents under reduced pressure and purify the residue by flash column chromatography on silica gel, eluting with hexanes/ethyl acetate (98:2), to afford 7-bromomethyl-2-(4-trifluoromethylphenyl)benzothiazole (Step 5) as an off-white solid (3.15 g, 59%): $^1$H NMR (CDCl$_3$) δ 4.80 (s, 2H), 7.50 (m, 2H), 7.80 (d, 2H), 8.10 (d, 1H), 8.30 (d, 2H).

Step 6

Ethyl 2-Methyl-4-[2-(4-trifluoromethylphenyl)benzothiazol-7-ylmethylsulfanylphenoxyacetate

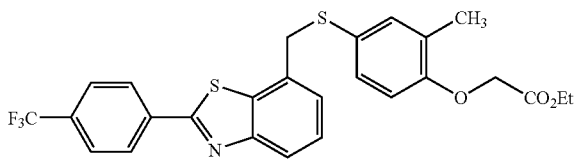

Add potassium carbonate (230 mg, 1.67 mmol) to a solution of 7-bromomethyl-2-(4-trifluoromethylphenyl)benzothiazole (250 mg, 0.67 mmol) and ethyl 4-mercapto-2-methylphenoxyacetate (151 mg, 0.67 mmol) in acetonitrile (4 mL) and carbon tetrachloride (2 mL) at room temperature under nitrogen and stir for 16 h. Dilute the mixture with water (200 mL) and extract with chloroform (2×150 mL). Dry the combined organic extracts over MgSO$_4$, remove the solvents under reduced pressure and purify the residue by flash column chromatography on silica gel, eluting with hexanes/ethyl acetate (95:5), to afford ethyl 2-methyl-4-[2-(4-trifluoromethylphenyl)benzothiazol-7-ylmethylsulfanyl]phenoxyacetate (Step 6) as a white solid (160 mg, 47%): $^1$H NMR (CDCl$_3$) δ 1.30 (t, 3H), 2.20 (s, 3H), 4.20 (m, 5H), 4.50 (s, 2H), 6.60 (d, 1H), 7.10 (m, 3H), 7.40 (t, 1H), 7.70 (d, 2H), 8.00 (d, 1H), 8.3 (d, 2H).

2-Methyl-4-[2-(4-trifluoromethylphenyl)benzothiazol-7-ylmethylsulfanyl]phenoxyacetic Acid

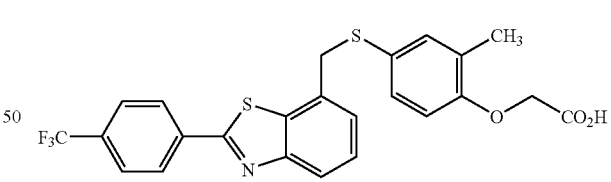

Add a solution of sodium hydroxide (140 mg) in water (3 mL) to a solution of ethyl 2-methyl-4-[2-(4-trifluoromethylphenyl)benzothiazol-7-ylmethylsulfanyl]phenoxyacetate (Step 6, 160 mg, 0.31 mmol) in diethyl ether (8 mL) and ethanol (8 mL) at room temperature under nitrogen and stir for 30 min. Dilute the mixture with water (10 mL), remove the solvents were removed under reduced pressure and acidify to pH 1 with 2 N HCl. Collect the solids by vacuum filtration and wash with water (10 mL) to afford 2-methyl-4-[2-(4-trifluoromethylphenyl)benzothiazol-7-ylmethylsulfanyl]phenoxyacetic acid (Example 44) as a white solid (140 mg, 92%): mp 193-196° C.; $^1$H NMR (DMSO-d$_6$) δ 2.00 (s, 3H), 4.10 (s, 2H), 4.30 (s, 2H), 6.70 (d, 1H), 7.10 (m, 2H), 7.40 (d, 1H), 7.50 (t, 1H), 7.90 (d, 1H), 8.00 (d, 1H), 8.30 (d, 2H); APCI MS m/z 488 [C$_{24}$H$_{18}$F$_3$NO$_3$S$_2$–H]$^-$. HPLC analysis (retention time=14.1 min) shows one peak, with a total purity of 98.9% (area percent).

The following compounds are made in a substantially similar manner:

EXAMPLE 45

2-Ethyl-4-[2-(4-trifluoromethylphenyl)benzothiazol-7-ylmethylsulfanyl]phenoxyacetic Acid

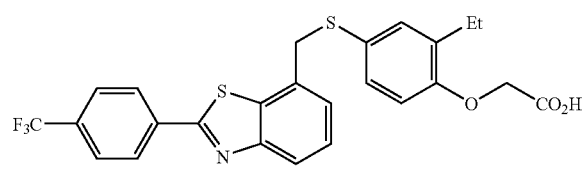

mp 160-164° C.; $^1$H NMR (CDCl$_3$) δ 0.90 (t, 3H), 2.40 q, 2H), 4.10 (s, 2H), 4.20 (s, 2H), 6.30 (d, 1H), 7.00 (m, 3), 7.20 (m, 1H), 7.60 (d, 2H), 7.80 (d, 1H), 8.10 (d, 2H); APCI MS m/z 504 [C$_{25}$H$_{20}$F$_3$NO$_3$S$_2$+H]$^+$. HPLC analysis (retention time=14.9 min) shows one peak, with a total purity of >99% (area percent).

EXAMPLE 46

3-{2-Methyl-4-[2-(4-trifluoromethylphenyl)benzothiazol-7-ylmethylsulfanyl]phenyl}propionic Acid

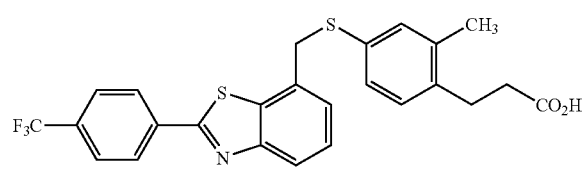

mp 136-139° C.; $^1$H NMR (CDCl$_3$) δ 2.20 (s, 3H), 2.50 (t, 2H), 2.90 (t, 2H), 4.30 (s, 2H), 7.00 (m, 3H), 7.20 (d, 1H), 7.40 (t, 1H), 7.70 (d, 2H), 8.00 (d, 1H), 8.20 (d, 2H); APCI MS m/z 486 [C$_{25}$H$_{20}$F$_3$NO$_2$S$_2$–H]$^-$. HPLC analysis (retention time=14.7 min) shows one peak, with a total purity of 98.3% (area percent).

EXAMPLE 47

6-[2-(4-Trifluoromethylphenyl)benzothiazol-7-ylmethylsulfanyl]benzo[b]thiophen-3-ylacetic Acid

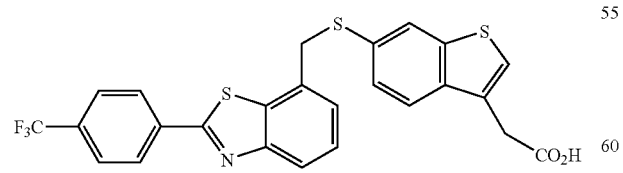

mp 201-204° C.; $^1$H NMR (DMSO-d$_6$) δ 3.70 (s, 2H), 4.60 (s, 2H), 7.40 (m, 4H), 7.70 (d, 1H), 7.90 (d, 2H), 8.00 (d, 1H), 8.30 (d, 2H); APCI MS m/z 514 [C$_{25}$H$_{16}$F$_3$NO$_2$S$_3$–H]$^-$. HPLC analysis (retention time=14.6 min) shows one peak, with a total purity of 97.6% (area percent).

Examples 48-50 below are made employing the procedures of Scheme 5:

Scheme 5:

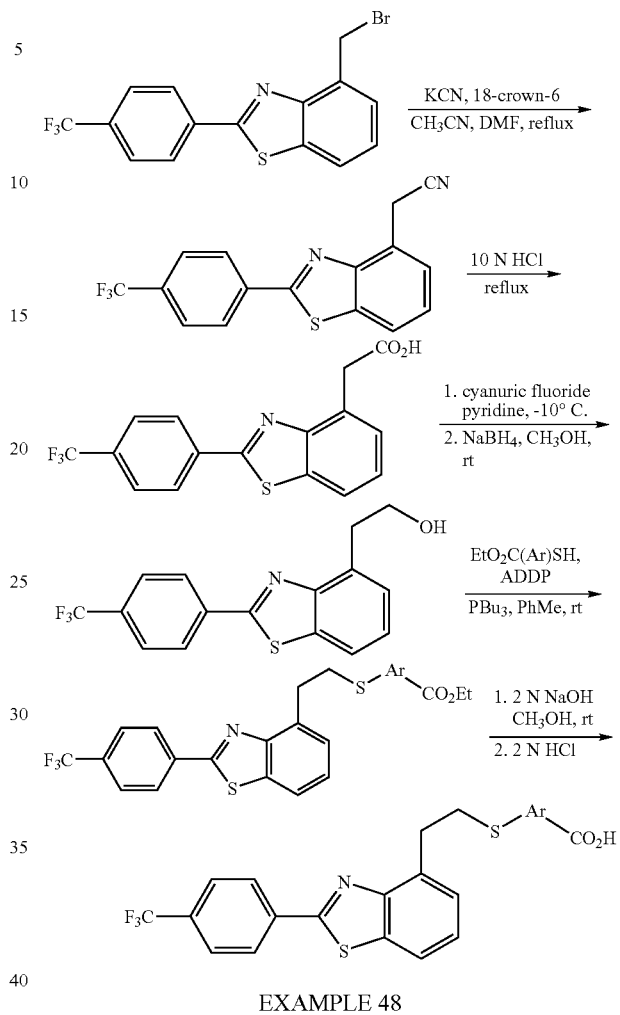

EXAMPLE 48

2-Methyl-4-{2-[2-(4-trifluoromethylphenyl)benzothiazol-4-yl]ethylsulfanyl]phenoxyacetic Acid

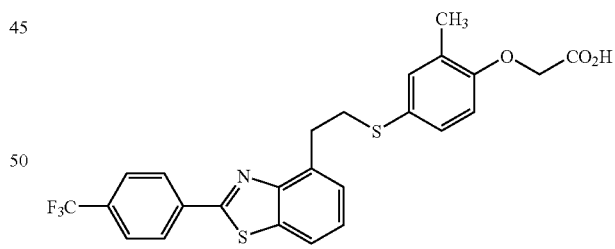

Step 1

[2-(4-Trifluoromethylphenyl)-1H-inden-4-yl]acetonitrile

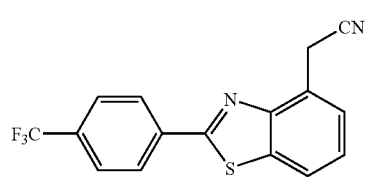

Add potassium cyanide (550 mg, 8.2 mmol) to a solution of 4-bromomethyl-2-(4-trifluoromethylphenyl)benzothiazole (Example 44, Step 5, 1.5 g, 4 mmol) and 18-crown-6 (160 mg, 0.5 mmol) in acetonitrile (20 mL) and DMF (5 mL) at room temperature under nitrogen and stir the mixture for 15 h. Add additional potassium cyanide (0.50 g, 7.6 mmol) and heat the mixture at reflux for 7 h. Cool the mixture and remove the solid potassium cyanide by filtration. Dilute the filtrate with methylene chloride (400 mL) and wash with water (2×300 mL). Dry the organic layer over MgSO$_4$, remove the solvents under reduced pressure and purify the residue by flash column chromatography on silica gel, eluting with hexanes/ethyl acetate (96:4), to afford [2-(4-trifluoromethylphenyl)-1H-inden-4-yl]acetonitrile (Step 1) as a white solid (600 mg, 46%): $^1$H NMR (CDCl$_3$) δ 4.30 (s, 2H), 7.50 (t, 1H), 7.60 (d, 1H), 7.70 (d, 2H), 7.80 (d, 1H), 8.10 (d, 2H).

Step 2

[2-(4-Trifluoromethylphenyl)benzothiazol-4-yl]acetic Acid

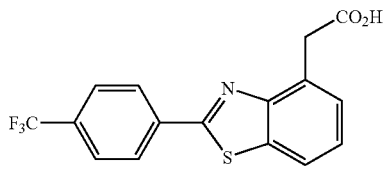

Heat a suspension of [2-(4-trifluoromethylphenyl)-1H-inden-4-yl]acetonitrile (Step 1, 600 mg, 1.8 mmol) in 10 N HCl (50 mL) at reflux for 3 h, dilute the cooled mixture with water (200 mL) and extract with chloroform (2×300 mL). Dry the combined organic extracts over MgSO$_4$ and remove the solvents were removed under reduced pressure to afford [2-(4-trifluoromethylphenyl)benzothiazol-4-yl]acetic acid (Step 2) as an off-white solid (600 mg, 97%): $^1$H NMR (CDCl$_3$) δ 4.20 (s, 2H), 7.40 (d, 1H), 7.50 (m, 1H), 7.80 (d, 2H), 7.90 (d, 1H), 8.10 (d, 2H).

Step 3

2-[2-(4-Trifluoromethylphenyl)benzothiazol-4-yl]ethanol

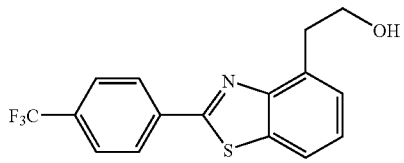

Add cyanuric fluoride (0.35 mL, 3.9 mmol) to a solution of [2-(4-trifluoromethylphenyl)benzothiazol-4-yl]acetic acid (Step 2, 600 mg, 1.75 mmol) in methylene chloride (4 mL) and pyridine (1 mL) at −10° C. under nitrogen and stir the mixture for 1 h. Dilute the mixture with water (200 mL) and extract with methylene chloride (2×200 mL). Dry the combined organic extracts over MgSO$_4$ and remove the solvents under reduced pressure. Dissolve the residue in methylene chloride (2 mL) at room temperature under nitrogen and treat with sodium borohydride (160 mg, 3.9 mmol). Add methanol (3 mL) dropwise, stir the mixture for 20 min, and neutralize the mixture with 1 NH$_2$SO$_4$ and remove the solvents under reduced pressure. Dilute the residue with ethyl acetate (200 mL) and wash with water (150 mL). Back-extract the aqueous layer with ethyl acetate (100 mL), dry the combined organic extracts over MgSO$_4$ and remove the solvents under reduced pressure to afford 2-[2-(4-trifluoromethylphenyl)benzothiazol-4-yl]ethanol (Step 3) as a white solid (600 mg, >99%): $^1$H NMR (CDCl$_3$) δ 3.40 (t, 2H), 4.10 (m, 2H), 7.30 (m, 2H), 7.70 (d, 2H), 7.90 (d, 1H), 8.20 (d, 2H).

Step 4

Ethyl 2-Methyl-4-{2-[2-(4-trifluoromethylphenyl)benzothiazol-4-yl]ethylsulfanyl}phenoxyacetate

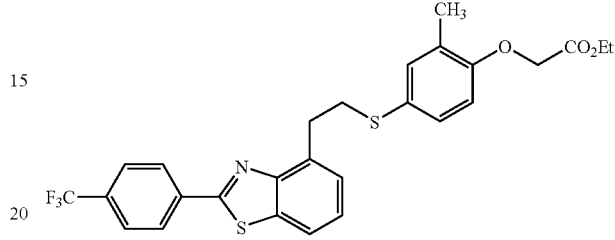

Add tri-n-butylphosphine (0.20 mL, 0.84 mmol) and 1,1'-(azodicarbonyl)dipiperidine (ADDP, 202 mg, 0.84 mmol) to a solution of 2-[2-(4-trifluoromethylphenyl)benzothiazol-4-yl]ethanol (Step 3, 170 mg, 0.53 mmol) and ethyl 4-mercapto-2-methylphenoxyacetate (190 mg, 0.84 mmol) in toluene (5 mL) at room temperature under nitrogen and stir the mixture for 16 h. Dilute the mixture with water (150 mL) and extract with chloroform (3×100 mL). Dry the combined organic extracts over MgSO$_4$ remove the solvents were removed under reduced pressure and purify the residue by flash column chromatography on silica gel, eluting with hexanes/ethyl acetate (97:3), to afford ethyl 2-methyl-4-{2-[2-(4-trifluoromethylphenyl)benzothiazol-4-yl]ethylsulfanyl}phenoxyacetate (Step 4) as a white solid (100 mg, 35%): $^1$H NMR (CDCl$_3$) δ 1.20 (t, 3H), 2.20 (s, 3H), 3.30 (m, 2H), 3.40 (m, 2H), 4.20 (q, 2H), 4.60 (s, 2H), 6.60 (do 1H), 7.20 (m, 4H), 7.70 (m, 3H), 8.10 (d, 2H).

2-Methyl-4-{2-[2-(4-trifluoromethylphenyl)benzothiazol-4-yl]ethylsulfanyl}phenoxyacetic Acid

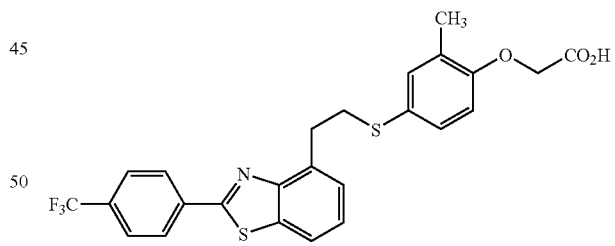

Add a solution of sodium hydroxide (100 mg) in water (1.5 mL) to a solution of ethyl 2-methyl-4-{2-[2-(4-trifluoromethylphenyl)benzothiazol-4-yl]ethylsulfanyl}phenoxyacetate (Step 4, 100 mg, 0.18 mmol) in methanol (4 mL) and diethyl ether (5 mL) at room temperature under nitrogen and stir the mixture for 2 h. Dilute the mixture with water (30 mL) and remove the solvents under reduced pressure. Dilute the residue with water (30 mL), acidify to pH 1 with 1 N HCl and cool to 0° C. Collect the solids by vacuum filtration and wash with water (15 mL) and hexanes (15 mL) to afford 2-methyl-4-{2-[2-(4-trifluoromethylphenyl)benzothiazol-4-yl]ethylsulfanyl}phenoxyacetic acid (Example 48) as a white solid (80 mg, 84%): mp 97-100° C.; $^1$H NMR (DMSO-d$_6$) δ 2.10 (s, 3H), 3.30 (m, 2H), 3.40 (m, 2H), 4.50 (s, 2H), 6.70 (d, 1H), 7.20 (m, 2H), 7.40 (m, 2H), 7.80 (d, 2H), 8.00 (m, 1H), 8.20 (d, 2H); APCI MS m/z 502 $[C_{25}H_{20}F_3NO_3S_2-H]^-$. HPLC analysis (retention time=16.2 min) shows one peak, with a total purity of 99.0% (area percent).

The following compounds are made in a substantially similar manner:

EXAMPLE 49

3-(2-Methyl-4-{2-[2-(4-trifluoromethylphenyl)benzothiazol-4-yl]ethylsulfanyl}phenyl)propionic Acid

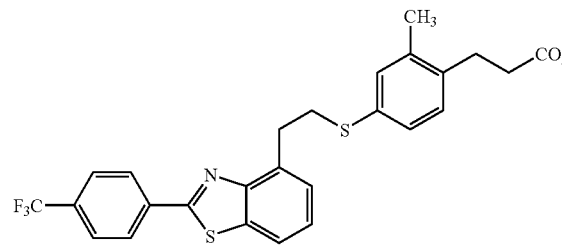

mp 118-120° C.; $^1$H NMR (CDCl$_3$) δ 2.20 (s, 3H), 2.60 (t, 2H), 2.90 (t, 2H), 3.50 (m, 4H), 7.10 (d, 1H), 7.20 (m, 2H), 7.30 (m, 2H), 7.70 (m, 3H), 8.20 (d, 2H); APCI MS m/z 500 $[C_{26}H_{22}F_3NO_2S_2-H]^-$. HPLC analysis (retention time=17.0 min) shows one peak, with a total purity of 98.8% (area percent).

EXAMPLE 50

2-Ethyl-4-{2-[2-(4-trifluoromethylphenyl)benzothiazol-4-yl]ethylsulfanyl}phenoxyacetic Acid

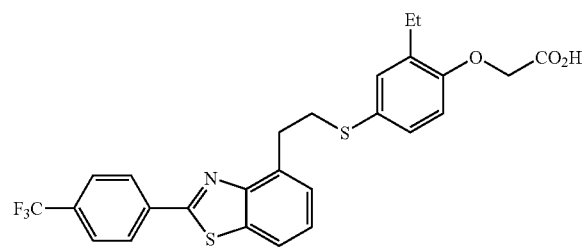

mp 84-86° C.; $^1$H NMR (DMSO-d$_6$) δ 1.10 (t, 3H), 2.60 (q, 2H), 3.30 (m, 4H), 4.70 (s, 2H), 6.80 (d, 1H), 7.20 (s, 1H), 7.30 (d, 1H), 7.40 (d, 2H), 7.90 (d, 2H), 8.10 (m, 1H), 8.20 (d, 2H); APCI MS m/z 516 $[C_{26}H_{22}F_3NO_3S_2-H]^-$. HPLC analysis (retention time=17.2 min) shows one peak, with a total purity of 99.0% (area percent).

Examples 51-55 below are made employing the procedures of Scheme 6:

Scheme 6:

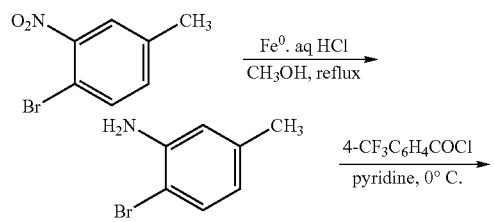

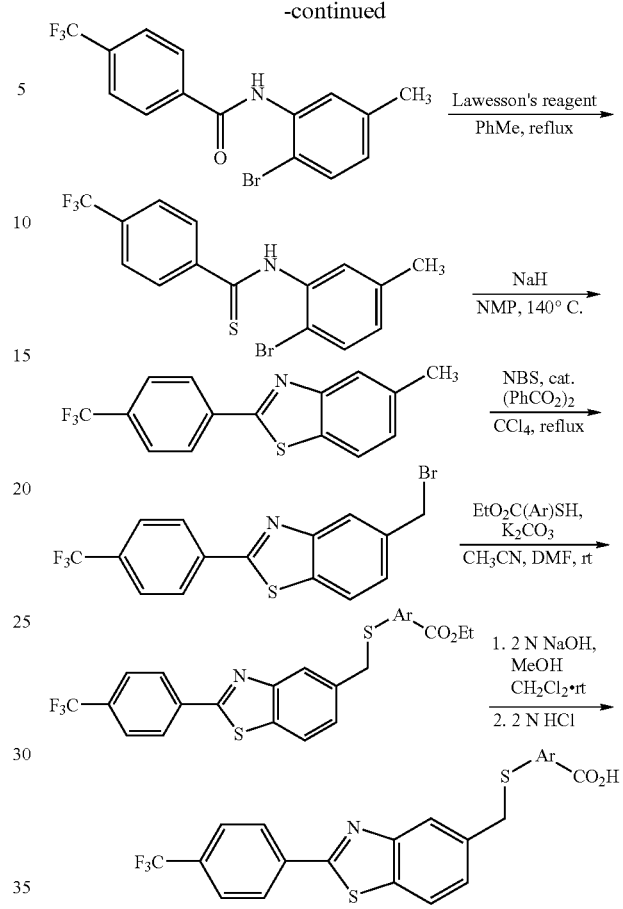

EXAMPLE 51

2-Methyl-4-[2-(4-trifluoromethylphenyl)benzothiazol-5-ylmethylsulfanyl]phenoxyacetic Acid

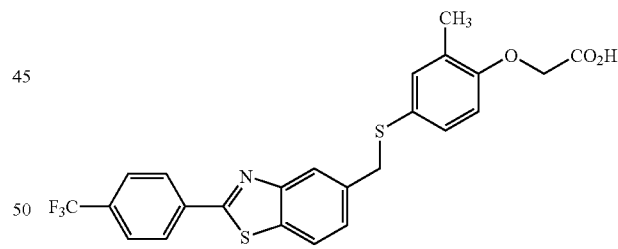

Step 1

2-Bromo-5-methylphenylamine

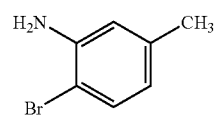

Add iron powder (7.75 g, 138 mmol), concentrated HCl (1 mL) and water (10 mL) to a solution of commercially available 4-bromo-3-nitrotoluene (10 g, 46 mmol) in methanol (200 mL) at room temperature under nitrogen and heat the mixture at reflux for 168 h. Remove the solvents under reduced pressure, suspend the residue in 0.1 N NaOH (350 mL) and extract with chloroform (3×300 mL). Dry the combined organic extracts over MgSO₄ and remove the solvents under reduced pressure to afford to afford 2-bromo-5-methylphenylamine (Step 1) as an amber oil (5.87 g, 68%): $^1$H NMR (CDCl₃) δ 2.20 (s, 3H), 4.00 (br s, 2H), 6.40 (d, 1H), 6.60 (s, 1H), 7.20 (d, 1H).

Step 2

N-(2-Bromo-5-methylphenyl)-4-trifluoromethylbenzamide

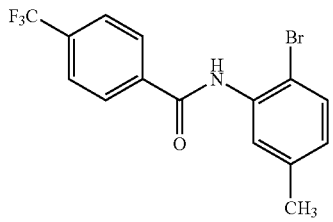

Add a solution of 4-(trifluoromethyl)benzoyl chloride (4.68 g, 31.5 mmol) in methylene chloride (30 mL) dropwise over the course of 30 min to a solution of 2-bromo-5-methylphenylamine (Step 1, 5.87 g, 31.5 mmol) in pyridine (50 mL) at 0° C. under nitrogen, warm the mixture to room temperature and stir for 18 h. Dilute the mixture with 1 N HCl (400 mL) and extract with chloroform (2×350 mL). Wash the combined organic extracts with water (300 mL), dry over MgSO₄ and remove the solvents under reduced pressure to afford N-(2-bromo-5-methylphenyl)-4-trifluoromethylbenzamide (Step 2) as a white solid (10.9 g, 96%): $^1$H NMR (CDCl₃) δ 2.30 (s, 3H), 6.80 (d, 1H), 7.40 (d, 1H), 7.80 (d, 2H), 8.00 (d, 2H), 8.30 (s, 1H), 8.40 (br s, 1H).

Step 3

N-(2-Bromo-5-methylphenyl)-4-trifluoromethylthiobenzamide

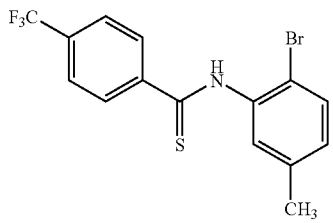

Heat a suspension of N-(2-bromo-5-methylphenyl)-4-trifluoromethylbenzamide (Step 2, 6 g, 16.7 mmol) and Lawesson's reagent (6.77 g, 16.7 mmol) in toluene (60 mL) at reflux under nitrogen for 18 h. Dilute the cooled mixture with water (400 mL) and extract with chloroform (3×250 mL). Dry the combined organic extracts over MgSO₄, remove the solvents were removed under reduced pressure and purify the residue by flash column chromatography on silica gel, eluting with hexanes/ethyl acetate (95:5), to afford N-(2-bromo-5-methylphenyl)-4-trifluoromethylthiobenzamide as a yellow solid (5 g, 80%): $^1$H NMR (CDCl₃) δ 2.40 (s, 3H), 7.00 (d, 1H), 7.40 (d, 1H), 7.70 (d, 2H), 8.00 (m, 2H), 8.40 (br s, 1H), 9.30 (s, 1H).

Step 4

5-Methyl-2-(4-trifluoromethylphenyl)benzothiazole

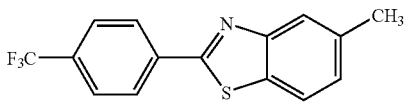

Add sodium hydride (360 mg, 60% dispersion in mineral oil) to a solution of N-(2-bromo-5-methylphenyl)-4-trifluoromethylthiobenzamide (Step 3, 5 g, 13.3 mmol) in N-methyl-2-pyrrolidinone (NMP, 30 mL) at room temperature under nitrogen and heat the mixture at 130° C. for 2.5 h. Dilute the cooled mixture was diluted with brine (400 mL) and extract with chloroform (2×350 mL). Dry the combined organic extracts over MgSO₄ and remove the solvents under reduced pressure. Dissolve the residue in acetonitrile (20 mL), precipitate with water (200 mL) and collect the solids by vacuum filtration and washed with water to afford 5-methyl-2-(4-trifluoromethylphenyl)benzothiazole (Step 4) as an off-white solid (3.42 g, 89%): $^1$H NMR (CDCl₃) δ 2.50 (s, 3H), 7.20 (m, 1H), 7.70 (d, 2H), 7.80 (m, 1H), 7.90 (s, 1H), 8.20 (d, 2H).

Step 5

5-Bromomethyl-2-(4-trifluoromethylphenyl)benzothiazole

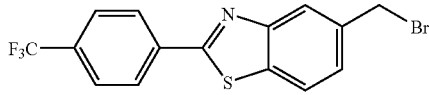

Add N-bromosuccinimide (2.1 g, 11.6 mmol) and benzoyl peroxide (20 mg, 0.1 mmol) to a suspension of 5-methyl-2-(4-trifluoromethylphenyl)benzothiazole (Step 4, 3.42 g, 11.6 mmol) in carbon tetrachloride (50 mL) at room temperature under nitrogen was and heat the mixture at reflux for 6 h. Add additional N-bromosuccinimide (400 mg, 2.2 mmol) and continue heating at reflux for 18 h. Dilute the cooled mixture with water (700 mL) and extract with methylene chloride (3×250 mL). Dry the combined organic extracts over MgSO₄, remove the solvents under reduced pressure and purify the residue by flash column chromatography on silica gel, eluting with hexanes/ethyl acetate (98:2), to afford 5-bromomethyl-2-(4-trifluoromethylphenyl)benzothiazole (Step 5) as a white solid (3.14 g, 76%): $^1$H NMR (CDCl₃) δ 4.70 (s, 2H), 7.50 (d, 1H), 7.80 (d, 2H), 7.90 (d, 1H), 8.10 (s, 1H), 8.20 (d, 2H).

Step 6

Ethyl 2-Methyl-4-[2-(4-trifluoromethylphenyl)benzothiazol-5-ylmethylsulfanyl]phenoxyacetate

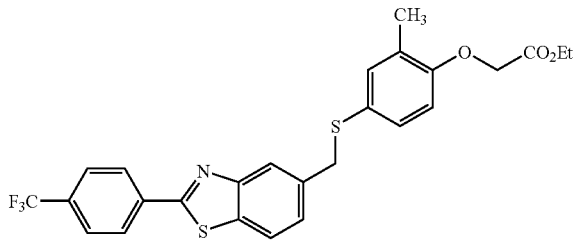

Stir a mixture of 5-bromomethyl-2-(4-trifluoromethylphenyl)benzothiazole (Step 5, 300 mg, 0.8 mmol), ethyl 4-mercapto-2-methylphenoxyacetate (250 mg, 1 mmol) and potassium carbonate (300 mg, 2.2 mmol) in DMF (3 mL) and acetonitrile (3 mL) at room temperature under nitrogen for 18 h, dilute with water (300 mL) and extract with ethyl acetate (4×250 mL). Dry the combined organic extracts over MgSO$_4$, filter through a plug of silica gel and remove the solvents under reduced pressure. Purify the residue by flash column chromatography on silica gel, eluting with hexanes/ethyl acetate (96:4), to afford ethyl 2-methyl-4-[2-(4-trifluoromethylphenyl)benzothiazol-5-ylmethylsulfanyl]phenoxyacetate (Step 6) as a white solid (160 mg, 38%): $^1$H NMR (CDCl$_3$) δ 1.20 (t, 3H), 2.20 (s, 3H), 4.10 (s, 2H), 4.20 (q, 2H), 4.60 (s, 2H), 6.60 (d, 1H), 7.10 (d, 1H), 7.20 (s, 1H), 7.30 (d, 1H), 7.70 (d, 2H), 7.80 (d, 1H), 7.90 (s, 1H), 8.20 (d, 2H).

2-Methyl-4-[2-(4-trifluoromethylphenyl)benzothiazol-5-ylmethylsulfanyl]phenoxyacetic Acid

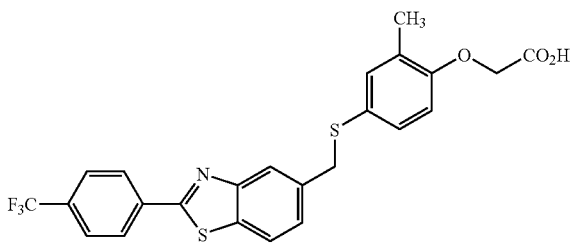

Add a solution of sodium hydroxide (200 mg, 5 mmol) in water (2 mL) to a solution of ethyl 2-methyl-4-[2-(4-trifluoromethylphenyl)benzothiazol-5-ylmethylsulfanyl]phenoxyacetate (Step 6, 160 mg, 0.3 mmol) in methylene chloride (5 mL) and methanol (5 mL) at room temperature and stir the mixture for 1.5 h. Remove the solvents under reduced pressure, suspend the residue in water (15 mL) and adjust to pH 1 with 1 N HCl. Collect the solids by vacuum filtration and wash with water (10 mL) and hexanes (10 mL) to afford 2-methyl-4-[2-(4-trifluoromethylphenyl)benzothiazol-5-ylmethylsulfanylphenoxyacetic acid (Example 51) as a white solid (110 mg, 75%): mp 138-140° C.; $^1$H NMR (CDCl$_3$) δ 2.10 (s, 3H), 4.10 (s, 2H), 4.50 (s, 2H), 6.60 (d, 1H), 7.10 (d, 1H), 7.20 (s, 1H), 7.30 (d, 1H), 7.70 (d, 2H), 7.80 (d, 1H), 7.90 (s, 1H), 8.20 (d, 2H); APCI MS m/z 488 [C$_{24}$H$_{18}$F$_3$NO$_3$S$_2$–H]$^-$. HPLC analysis (retention time=14.1 min) showed one peak, with a total purity of 98.9% (area percent).

The following compounds are made in a substantially similar manner:

EXAMPLE 52

3-{2-Methyl-4-[2-(4-trifluoromethylphenyl)benzothiazol-5-ylmethylsulfanyl]phenyl}propionic Acid

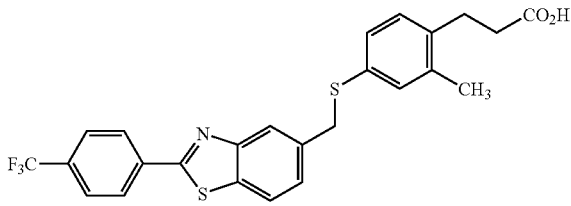

mp 141-143° C.; $^1$H NMR (CDCl$_3$) δ 2.20 (s, 3H), 2.60 (t, 2H), 3.00 (t, 2H), 4.00 (s, 2H), 6.90 (d, 1H), 7.00 (d, 1H), 7.10 (s, 1H), 7.20 (s, 1H), 7.30 (d, 1H), 7.70 (d, 2H), 7.80 (d, 1H), 8.20 (d, 2H); APCI MS m/z 486 [C$_{25}$H$_{20}$F$_3$NO$_2$S$_2$–H]$^-$.

HPLC analysis (retention time=14.8 min) showed one peak, with a total purity of 98.6% (area percent).

EXAMPLE 53

2-Ethyl-4-[2-(4-trifluoromethylphenyl)benzothiazol-5-ylmethylsulfanyl]phenoxyacetic Acid

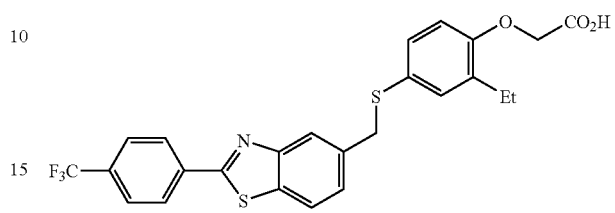

mp 140-142° C.; $^1$H NMR (CDCl$_3$) δ 1.10 (t, 3H), 2.60 (q, 2H), 4.00 (s, 2H), 4.60 (s, 2H), 6.50 (d, 1H), 7.10 (d, 1H), 7.20 (s, 1H), 7.30 (d, 1H), 7.60 (s, 1H), 7.70 (d, 2H), 7.80 (d, 1H), 8.10 (d, 2H); APCI MS m/z 502 [C$_{25}$H$_{20}$F$_3$NO$_3$S$_2$–H]$^-$. HPLC analysis (retention time=15.1 min) shows one peak, with a total purity of 98.6% (area percent).

EXAMPLE 54

3-{2-Methyl-4-[2-(4-trifluoromethylphenyl)benzothiazol-5-ylmethoxy]phenyl}propionic Acid

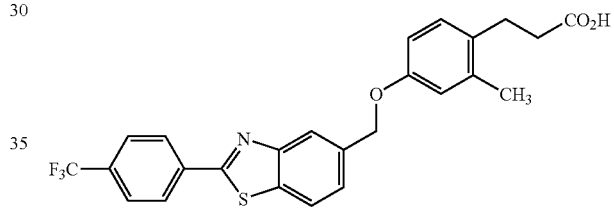

mp 174-176° C.; $^1$H NMR (CDCl$_3$) δ 2.20 (s, 3H), 2.50 (t, 2H), 2.90 (t, 2H), 5.20 (s, 2H), 6.70 (d, 1H), 6.80 (s, 1H), 7.10 (d, 1H), 7.60 (d, 1H), 7.80 (d, 2H), 8.00 (d, 1H), 8.15 (s, 1H), 8.20 (d, 2H); APCI MS m/z 470 [C$_{25}$H$_{20}$F$_3$NO$_3$S–H]$^-$. HPLC analysis (retention time=13.9 min) shows one peak, with a total purity of 99.0% (area percent).

EXAMPLE 55

3-{2-Ethyl-4-[2-(4-trifluoromethylphenyl)benzothiazol-5-ylmethoxy]phenyl}propionic Acid

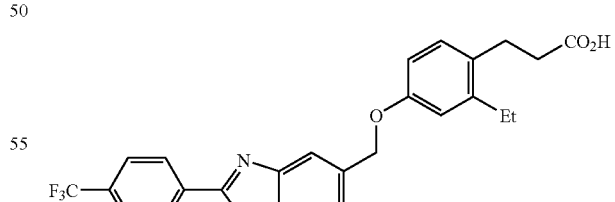

mp 188-190° C.; $^1$H NMR (CDCl$_3$) δ 1.20 (t, 3H), 2.60 (m, 4H), 2.90 (t, 2H), 5.10 (s, 2H), 6.70 (d, 1H), 6.80 (s, 1H), 7.00 (d, 1H), 7.40 (d, 1H), 7.70 (d, 2H), 7.90 (d, 1H), 8.20 (d, 2H), 8.25 (s, 1H); APCI MS m/z 484 [C$_{26}$H$_{22}$F$_3$NO$_3$S–H]$^-$. HPLC analysis (retention time=14.6 min) shows one peak, with a total purity of 98.8% (area percent).

Example 56 below is made employing the procedures of Scheme 7:

Scheme 7:

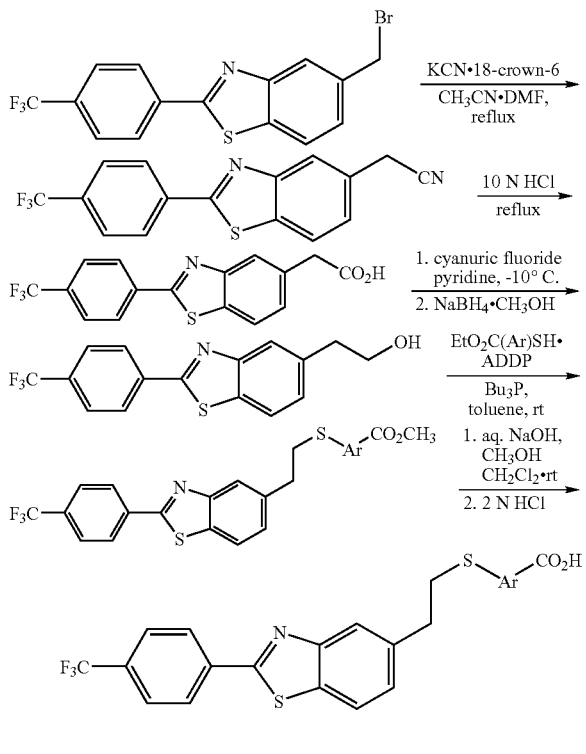

EXAMPLE 56

3-(2-Methyl-4-{2-[2-(4-trifluoromethylphenyl)benzothiazol-5-yl]ethylsulfanyl}phenyl)propionic Acid

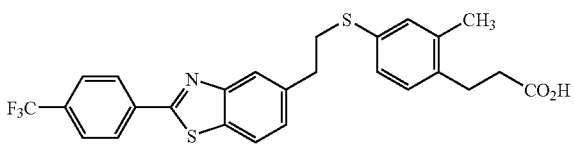

Step 1

[2-(4-Trifluoromethylphenyl)benzothiazol-5-yl]acetonitrile

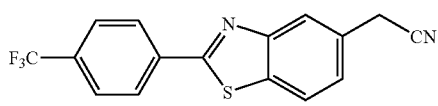

Add 18-crown-6 (70 mg, 0.24 mmol) and potassium cyanide (670 mg, 10.3 mmol) to a solution of 5-bromomethyl-2-(4-trifluoromethylphenyl)benzothiazole (Example 51, Step 5, 950 mg, 2.5 mmol) in acetonitrile (10 mL) and DMF (10 mL) at room temperature under nitrogen and heat the mixture to reflux. Stir for 20 h, cool the reaction mixture to room temperature and remove the excess of potassium cyanide by vacuum filtration. Wash the filtrate with 0.1 N NaOH (300 mL) and back-extract the aqueous layer with methylene chloride (200 mL). Dry the combined organic extracts over MgSO₄, remove the solvents under reduced pressure and purify the residue by flash column chromatography on silica gel, eluting with hexanes/ethyl acetate (9:1), to afford [2-(4-trifluoromethylphenyl)benzothiazol-5-yl]acetonitrile (Step 1) as a white solid (200 mg, 25%): $^1$H NMR (CDCl$_3$) δ 3.90 (s, 2H), 7.40 (d, 1H), 7.80 (d, 2H), 7.90 (d, 1H), 8.10 (s, 1H), 8.20 (d, 2H).

Step 2

[2-(4-Trifluoromethylphenyl)benzothiazol-5-yl]acetic Acid

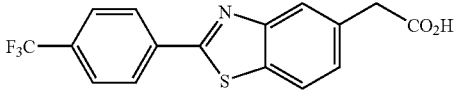

Heat a suspension of [2-(4-trifluoromethylphenyl)benzothiazol-5-yl]acetonitrile (Step 1, 200 mg, 0.62 mmol) in 10 N HCl (40 mL) at reflux for 3 h, cool the mixture to room temperature and dilute the mixture with saturated aqueous NaHCO$_3$ solution (100 mL) and water (300 mL). Extract with methylene chloride (3×150 mL), dry the combined organic extracts over MgSO$_4$ and remove the solvents under reduced pressure to afford [2-(4-trifluoromethylphenyl)benzothiazol-5-yl]acetic acid (Step 2) as a white solid (180 mg, 85%): $^1$H NMR (CDCl$_3$) δ 3.80 (s, 2H), 7.30 (d, 1H), 7.70 (d, 2H), 7.90 (d, 1H), 8.00 (s, 1H), 8.20 (d, 2H).

Step 3

2-[2-(4-Trifluoromethylphenyl)benzothiazol-5-yl]ethanol

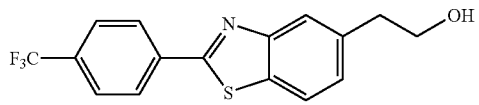

Add cyanuric fluoride (0.15 mL, 1.8 mmol) dropwise to a solution of [2-(4-trifluoromethylphenyl)benzothiazol-5-yl]acetic acid (Step 2, 180 mg, 0.52 mmol) in methylene chloride (4 mL) and pyridine (0.25 mL) at −20° C. under nitrogen and stir for 1 h. Dilute the mixture with water (150 mL) and extract with methylene chloride (3×100 mL). Dry the combined organic extracts over MgSO$_4$ and remove the solvents under reduced pressure. Dilute the resulting residue with methylene chloride (4 mL) and treat with NaBH$_4$ (90 mg, 2.2 mmol) and methanol (2 mL). Stir the mixture at room temperature for 20 min, dilute with water (150 mL) and extract with methylene chloride (4×100 mL). Dry the combined organic extracts over MgSO$_4$ and remove the solvents under reduced pressure to afford 2-[2-(4-trifluoromethylphenyl)benzothiazol-5-yl]ethanol (Step 3) as a white solid (130 mg, 76%): $^1$H NMR (CDCl$_3$) δ 3.00 (t, 2H), 4.00 (m, 2H), 7.30 (d, 1H), 7.70 (d, 2H), 7.80 (d, 1H), 8.00 (s, 1H), 8.20 (d, 2H).

Step 4

Methyl 3-(2-Methyl-4-{2-[2-(4-trifluoromethylphenyl)benzothiazol-5-yl]ethylsulfanyl}phenyl)propionate

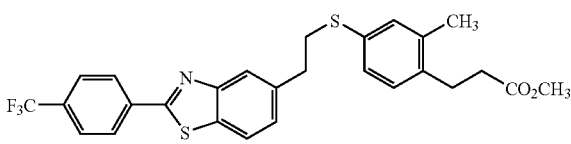

Add tri-n-butylphosphine (0.168 mL, 0.68 mmol) and 1,1'-(azodicarbonyl)dipiperidine (ADDP, 160 mg, 0.67 mmol) to a solution of 2-[2-(4-trifluoromethylphenyl)benzothiazol-5-yl]ethanol (130 mg, 0.4 mmol) and methyl 3-(4-mercapto-2-methylphenyl)propionate (136 mg, 0.65 mmol) in toluene (4 mL) at room temperature under nitrogen and stir the mixture for 18 h. Dilute the reaction mixture with water (150 mL) and extract with chloroform (2×150 mL). Dry the combined organic layers over MgSO$_4$, remove the solvents were removed under reduced pressure and purify the residue by flash column chromatography on silica gel, eluting with hexanes/ethyl acetate (95:5), to afford methyl 3-(2-methyl-4-{2-[2-(4-trifluoromethylphenyl)benzothiazol-5-yl]ethylsulfanyl}phenyl)propionate (Step 4) as a white solid (50 mg, 25%).

3-(2-Methyl-4-{2-[2-(4-trifluoromethylphenyl)benzothiazol-5-yl]ethylsulfanyl}phenyl)propionic Acid

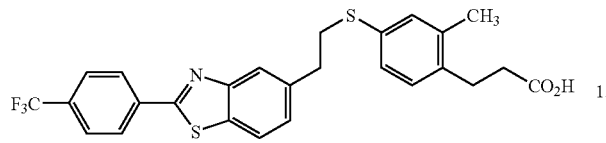

Add a solution of sodium hydroxide (120 mg, 3 mmol) in water (2 mL) to a solution of methyl 3-(2-methyl-4-{2-[2-(4-trifluoromethylphenyl)benzothiazol-5-yl]ethylsulfanyl}phenyl)propionate (Step 4, 50 mg, 0.097 mmol) in methylene chloride (3 mL) and methanol (3 mL) at room temperature and stir the mixture for 1 h. Dilute the reaction mixture with water (5 mL) and remove the organic solvents under reduced pressure. Dilute the resulting residue with water (10 mL) and acidify to pH 1 with 2 N HCl. Collect the resulting white solids by vacuum filtration and wash with water (10 mL) and hexanes (10 mL) to afford 3-(2-methyl-4-{2-[2-(4-trifluoromethylphenyl)benzothiazol-5-yl]ethylsulfanyl}phenyl)propionic acid (Example 56) as a white solid (52 mg, >99%): mp 108-110° C.; $^1$H NMR (CDCl$_3$) δ 2.60 (t, 2H), 3.00 (t, 2H), 3.10 (t, 2H), 3.20 (t, 2H), 7.00 (d, 1H), 7.10 (m, 2H), 7.20 (m, 1H), 7.70 (d, 2H), 7.80 (m, 2H), 8.20 (d, 2H); APCI MS m/z 500 [C$_{26}$H$_{22}$F$_3$NO$_2$S$_2$–H]$^-$. HPLC analysis (retention time=xxx min) shows one peak, with a total purity of 97.6% (area percent).

Example 57-61 below is made employing the procedures of Scheme 8:

Scheme 8:

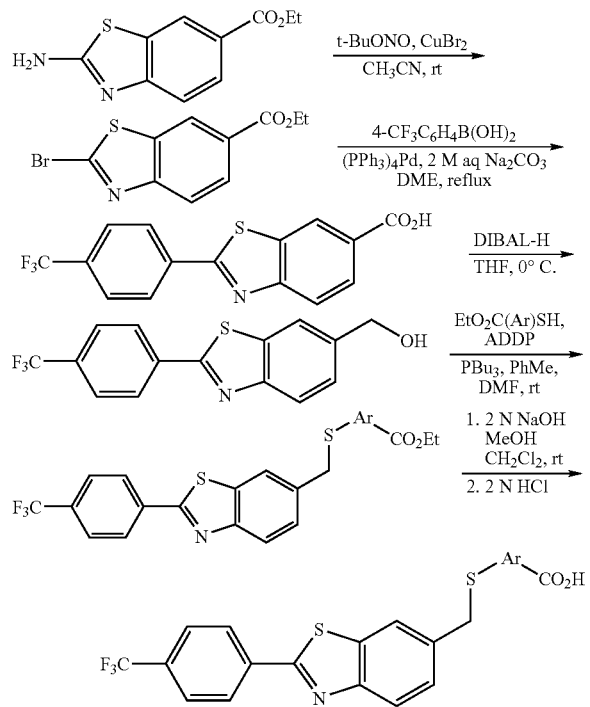

EXAMPLE 57

2-Methyl-4-[2-(4-trifluoromethylphenyl)benzothiazol-6-ylmethylsulfanyl]phenoxyacetic Acid

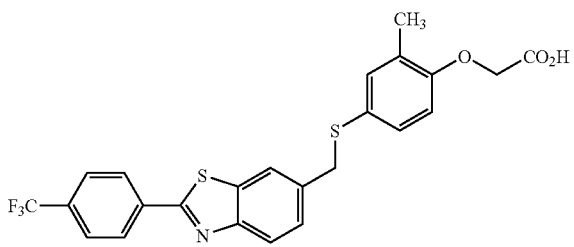

Step 1

Ethyl 2-Bromobenzothiazole-6-carboxylate

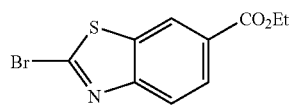

Add a solution of commercially available ethyl 2-aminobenzothiazole-6-carboxylate (10 g, 45 mmol) in acetonitrile (40 mL) to a solution of copper(II) bromide (12 g, 54 mmol) and tert-butyl nitrite (9 mL, 75 mmol) in acetonitrile (100 mL) at room temperature under nitrogen and stir for 45 min. Dilute the mixture with 1 N HCl (300 mL) and extract with methylene chloride (3×300 mL). Wash the combined organic extracts with water (300 mL), dry over MgSO$_4$, filter though a plug of silica gel and remove the solvents under reduced pressure to afford ethyl 2-bromobenzothiazole-6-carboxylate (Step 1) as an off-white solid (11.5 g, 89%): $^1$H NMR (CDCl$_3$) δ 1.40 (t, 3H), 4.40 (q, 2H), 8.00 (d, 1H), 8.20 (d, 1H), 8.60 (s, 1H).

Step 2

Ethyl 2-(4-Trifluoromethylphenyl)benzothiazole-6-carboxylate

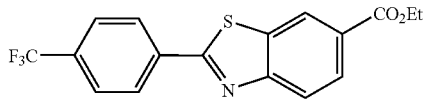

Heat a degassed solution of ethyl 2-bromobenzothiazole-6-carboxylate (Step 1, 7.75 g, 27.1 mmol), tetrakis(triphenylphosphine)palladium (0) (1.7 g, 1.5 mmol), 4-(trifluoromethyl)phenylboronic acid (6.2 g, 32.6 mmol) and 2 M aqueous sodium carbonate solution (120 mL) in DME (90 mL) at reflux under nitrogen for 19 h. Dilute the cooled mixture with 1 N NaOH (1.2 L) and extract with methylene chloride (2×500 mL). Dry the combined organic extracts over MgSO$_4$, remove the solvents under reduced pressure and purify the residue by flash column chromatography on silica gel, eluting with hexanes/ethyl acetate (98:2), to afford ethyl 2-(4-trifluoromethylphenyl)benzothiazole-6-carboxylate as a white solid (2.62 g, 27%): $^1$H NMR (CDCl$_3$) δ 1.40 (t, 3H), 4.40 (q, 2H), 7.80 (d, 2H), 8.10 (d, 1H), 8.20 (m, 3H), 8.60 (s, 1H).

Step 3

[2-(4-Trifluoromethylphenyl)benzothiazol-6-yl]methanol

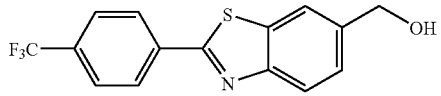

Add a solution of DIBAL-H (7.8 mL, 7.8 mmol, 1 M solution in hexanes) to a solution of ethyl (4-trifluoromethylphenyl)benzothiazole-6-carboxylate (1 g, 2.8 mmol) in THF (25 mL) at 0° C. under nitrogen, warmed the mixture to room temperature and stir for 15 h. Add additional DIBAL-H (1.5 mL, 1.5 mmol, 1 M in hexanes) and stir the mixture for 3 h. Treat the mixture with methanol (9 mL) and 2 N HCl (5 mL), stir for 2 h, dilute the mixture with 50% brine (300 mL) and extract with ethyl acetate (2×300 mL). Dry the combined organic extracts over MgSO$_4$ and remove the solvents under reduced pressure to afford [2-(4-trifluoromethylphenyl)benzothiazol-6-yl]methanol as a white solid (970 mg, >99%): $^1$H NMR (CDCl$_3$) δ 1.80 (t, 1H), 4.80 (d, 2H), 7.40 (d, 1H), 7.70 (d, 2H), 8.00 (s, 1H), 3.10 (d, 1H), 8.20 (d, 2H); APCI MS m/z 310 [C$_{15}$H$_{10}$F$_3$NOS$_2$+H]$^+$.

Step 4

Ethyl 2-Methyl-4-[2-(4-trifluoromethylphenyl)benzothiazol-6-ylmethylsulfanyl]phenoxyacetate

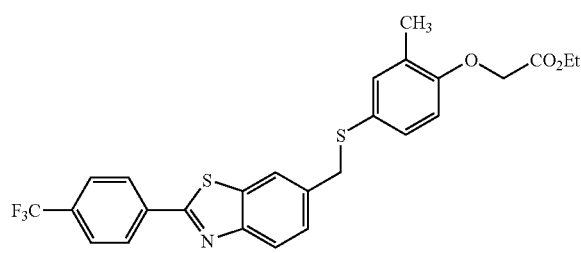

Add tri-n-butylphosphine (0.330 mL, 1.3 mmol) and 1,1'-(azodicarbonyl)dipiperidine (ADDP, 312 mg, 1.3 mmol) to a solution of [2-(4-trifluoromethylphenyl)benzothiazol-6-yl]methanol (Step 3, 250 mg, 0.8 mmol) and ethyl 4-mercapto-2-methylphenoxyacetate (300 mg, 1.35 mmol) in toluene (4 mL) and DMF (2 mL) at room temperature under nitrogen and stir for 18 h. Dilute the mixture with water (250 mL) and extract with chloroform (2×200 mL) and ethyl acetate (100 mL). Dry the combined organic extracts over MgSO$_4$, remove the solvents under reduced pressure and purify the residue by flash column chromatography on silica gel, eluting with hexanes/ethyl acetate (96:4), to afford ethyl 2-methyl-4-[2-(4-trifluoromethylphenyl)benzothiazol-6-ylmethylsulfanyl]phenoxyacetate (Step 4) as a white solid (300 mg, 72%): $^1$H NMR (CDCl$_3$) δ 1.30 (t, 3H), 2.20 (s, 3H), 4.10 (s, 2H), 4.20 (q, 2H), 4.60 (s, 2H), 6.60 (d, 1H), 7.00 (d, 1H), 7.20 (s, 1H), 7.50 (d, 1H), 7.65 (s, 1H), 7.70 (d, 2H), 8.00 (d, 1H), 8.20 (d, 2H).

2-Methyl-4-[2-(4-trifluoromethylphenyl)benzothiazol-6-ylmethylsulfanyl]phenoxyacetic Acid

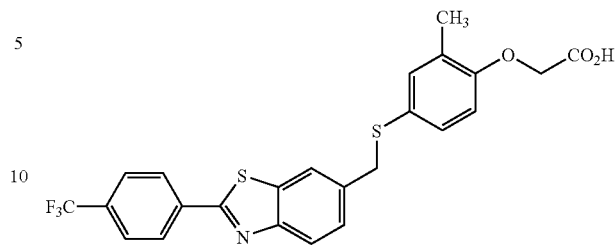

Add a solution of sodium hydroxide (280 mg, 7 mmol) in water (2-mL) to a solution of ethyl 2-methyl-4-[2-(4-trifluoromethylphenyl)benzothiazol-6-ylmethylsulfanyl]phenoxyacetate (Step 4, 300 mg, 0.6 mmol) in methylene chloride (5 mL) and methanol (5 mL) at room temperature was added and stir the mixture for 3 h. Dilute the mixture with water (10 mL) and remove the solvents under reduced pressure. Add additional water (10 mL) and adjust to pH 1 with 1 N HCl. Collect the solids by vacuum filtration and wash with water (15 mL) and hexanes (20 mL) to afford 2-methyl-[2-(4-trifluoromethylphenyl)benzothiazol-6-ylmethylsulfanyl]phenoxyacetic acid (Example 57) as a white solid (190 mg, 64%): mp 176-177° C.; $^1$H NMR (CDCl$_3$) δ 2.20 (s, 3H), 4.10 (s, 2H), 4.60 (s, 2H), 6.60 (d, 1H), 7.10 (d, 1H), 7.20 (s, 1H), 7.40 (d, 1H), 7.70 (d, 2H), 7.75 (s, 1H), 8.00 (d, 1H), 8.20 (d, 2H); APCI MS m/z 488 [C$_{24}$H$_{18}$F$_3$NO$_3$S$_2$–H]$^-$. HPLC analysis (retention time=14.2 min) shows one peak, with a total purity of >99% (area percent).

The following compounds are made in a substantially similar manner:

EXAMPLE 58

3-{2-Methyl-4-[2-(4-trifluoromethylphenyl)benzothiazol-6-ylmethylsulfanyl]phenyl}propionic Acid

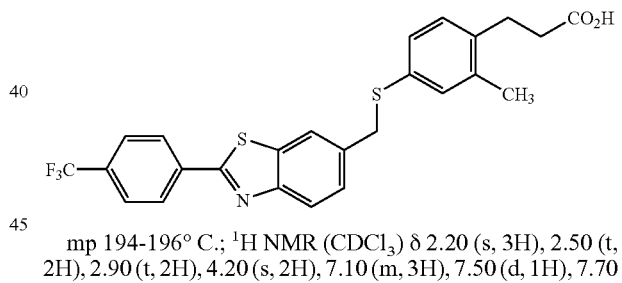

mp 194-196° C.; $^1$H NMR (CDCl$_3$) δ 2.20 (s, 3H), 2.50 (t, 2H), 2.90 (t, 2H), 4.20 (s, 2H), 7.10 (m, 3H), 7.50 (d, 1H), 7.70 (d, 2H), 7.80 (s, 1H), 8.00 (d, 1H), 8.20 (d, 2H); APCI MS m/z 486 [C$_{25}$H$_{20}$F$_3$NO$_2$S$_2$–H]$^-$. HPLC analysis (retention time 14.8 min) shows one peak, with a total purity of >99% (area percent).

EXAMPLE 59

2-Ethyl-4-[2-(4-trifluoromethylphenyl)benzothiazol-6-ylmethylsulfanyl]phenoxyacetic Acid

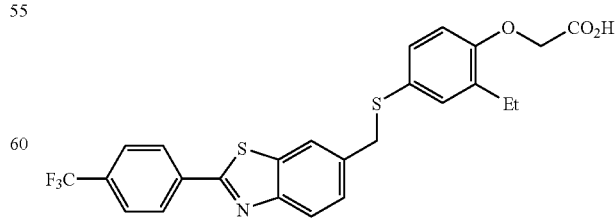

mp 144-147° C.; $^1$H NMR (CDCl$_3$) δ 1.10 (t, 3H), 2.60 (q, 2H), 4.10 (s, 2H), 4.60 (s, 2H), 6.60 (d, 1H), 7.10 (m, 2H), 7.30 (d, 1H), 7.70 (s, 1H), 7.80 (d, 2H), 8.00 (d, 1H), 8.20 (d, 2H); APCI MS m/z 502 [C$_{25}$H$_{20}$F$_3$NO$_3$S$_2$–H]$^-$. HPLC analy-

EXAMPLE 60

3-{2-Methyl-4-[2-(4-trifluoromethylphenyl)benzothiazol-6-ylmethoxy]phenyl}propionic Acid

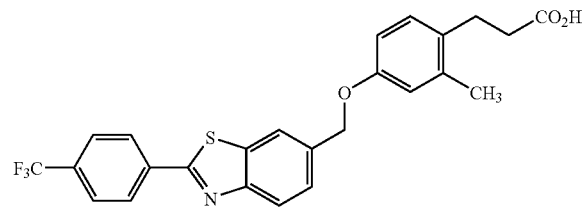

mp 198-200° C.; $^1$H NMR (CDCl$_3$) δ 2.30 (s, 3H), 2.50 (t, 2H), 2.90 (t, 2H), 5.20 (s, 2H), 6.70 (d, 1H), 6.80 (s, 1H), 7.10 (d, 1H), 7.60 (d, 1H), 7.80 (d, 2H), 8.10 (m, 2H), 8.20 (d, 2H); APCI MS m/z 470 [C$_{25}$H$_{20}$F$_3$NO$_3$S−H]$^-$. HPLC analysis (retention time=14.4 min) shows one peak, with a total purity of >99% (area percent).

EXAMPLE 61

3-{2-Ethyl-4-[2-(4-trifluoromethylphenyl)benzothiazol-6-ylmethoxy]phenyl}propionic Acid

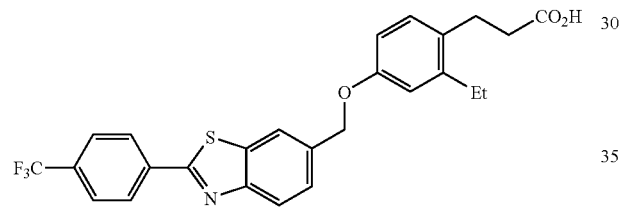

mp 203-205° C.; $^1$H NMR (CDCl$_3$) δ 1.20 (t, 3H), 2.50 (t, 2H), 2.60 (q, 2H), 2.90 (t, 2H), 5.20 (s, 2H), 6.70 (d, 1H), 6.80 (s, 1H), 7.10 (d, 1H), 7.60 (d, 1H), 7.70 (d, 2H), 8.00 (s, 1H), 8.10 (d, 1H), 8.20 (d, 2H); APCI MS m/z 484 [C$_{26}$H$_{22}$F$_3$NO$_3$S−H]$^-$. HPLC analysis (retention time=15.1 min) shows one peak, with a total purity of 99.0% (area percent).

Examples 62-63 below are made employing the procedures of Scheme 9:

Scheme 9:

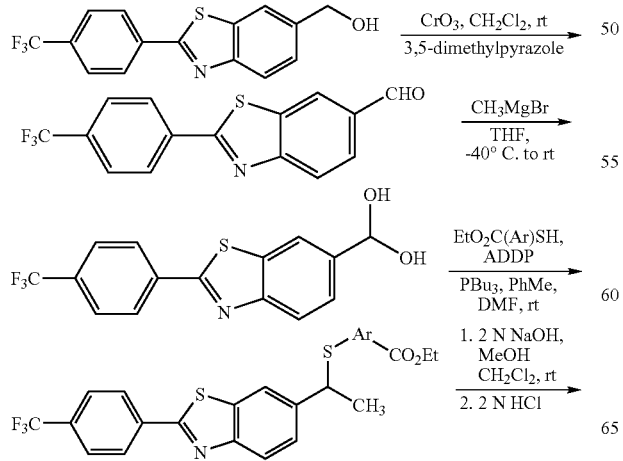

EXAMPLE 62

(+/−)-2-Methyl-4-{1-[2-(4-trifluoromethylphenyl)benzothiazol-6-yl]ethylsulfanyl}phenoxyacetic Acid

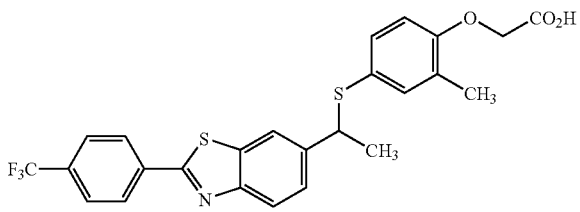

Step 1

2-(4-Trifluoromethylphenyl)benzothiazole-6-carbaldehyde

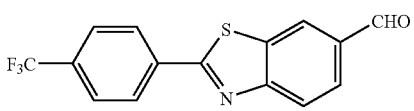

Add 3,5-dimethylpyrazole (340 mg, 3.4 mmol) to a suspension of CrO$_3$ (350 mg, 3.5 mmol) in methylene chloride (15 mL) at room temperature, after which the CrO$_3$ slowly dissolves. Add 2-(4-trifluoromethylphenyl)benzothiazol-6-ylmethanol (Example 57, Step 3, 400 mg, 1.3 mmol) followed by DMF (3 mL) and stir the mixture for 1 h. Remove the solids by vacuum filtration through a plug of silica gel, eluting with hexanes/ethyl acetate (4:1) and remove the solvents under reduced pressure to afford 2-(4-trifluoromethylphenyl)benzothiazole-6-carbaldehyde (Step 1) as a white solid (350 mg, 87%): $^1$H NMR (CDCl$_3$) δ 7.80 (d, 2H), 8.00 (d, 1H), 8.20 (m, 3H), 8.50 (s, 1H), 10.10 (s, 1H).

Step 2

(+/−)-1-[2-(4-Trifluoromethylphenyl)benzothiazol-6-yl]ethanol

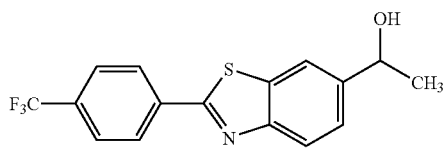

Add methylmagnesium bromide (0.5 mL, 1.5 mmol, 3 M in diethyl ether) dropwise to a solution of 2-(4-trifluoromethylphenyl)benzothiazole-6-carbaldehyde (350 mg, 1.14 mmol) in THF (8 mL) at −40° C. under nitrogen, warm the mixture to room temperature and stir for 20 min. Cool the mixture to −30° C. and treat with methylmagnesium bromide (0.2 mL, 0.6 mmol, 3 M in diethyl ether) and warm the mixture slowly to room temperature. Stir the mixture for 1 h, dilute the mixture with saturated ammonium chloride solution (150 mL) and water (100 mL) and extract with methylene chloride (3×100 mL). Dry the combined organic extracts over MgSO$_4$ and remove the solvents under reduced pressure to afford 1-[2-(4-trifluoromethylphenyl)benzothiazol-6-yl]ethanol (Step 2), as a white solid (450 mg, >99%): $^1$H NMR (CDCl$_3$) δ 1.60 (d, 3H), 2.00 (s, 1H), 5.10 (q, 1H), 7.50 (d, 1H), 7.80 (d, 2H), 8.00 (s, 1H), 8.10 (d, 1H), 8.20 (d, 2H).

Step 3

(+/−)-Ethyl 2-Methyl-4-{1-[2-(4-trifluoromethylphenyl)benzothiazol-6-yl]ethylsulfanyl}phenoxyacetate

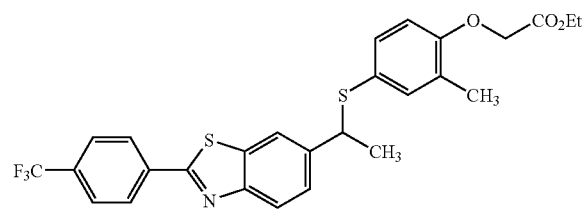

Add tri-n-butylphosphine (0.2 mL, 0.79 mmol) dropwise to a solution of 1-[2-(4-trifluoromethylphenyl)benzothiazol-6-yl]ethanol (Step 2, 160 mg, 0.49 mmol) and ethyl 4-mercapto-2-methylphenoxyacetate (179 mg, 0.79 mmol) in toluene (6 mL) at 0° C. under nitrogen, followed by 1,1'-(azodicarbonyl)dipiperidine (ADDP, 190 mg, 0.79 mmol). Warm the reaction mixture to room temperature and stir for 15.5 h. Dilute the mixture with water (200 mL) and extracted with chloroform (3×150 mL). Dry the combined organic layers over MgSO$_4$ and remove the solvents under reduced pressure. Purify the residue by flash column chromatography on silica gel, eluting with hexanes/ethyl acetate (95:5), to afford ethyl 2-methyl-4-{1-[2-(4-trifluoromethylphenyl)benzothiazol-6-yl]ethylsulfanyl}phenoxyacetate (Step 3) as a white solid (180 mg, 69%): $^1$H NMR (CDCl$_3$) δ 1.20 (t, 3H), 1.70 (d, 3H), 2.20 (s, 3H), 4.20 (q, 2H), 4.30 (q, 1H), 4.60 (s, 2H), 6.50 (1H), 7.00 (dd, 1H), 7.10 (d, 1H), 7.40 (d, 1H), 7.70 (m, 3H), 8.00 (d, 1H), 8.20 (d, 2H).

(+/−)-2-Methyl-4-{1-[2-(4-trifluoromethylphenyl)benzothiazol-6-yl]ethylsulfanyl}phenoxyacetic Acid

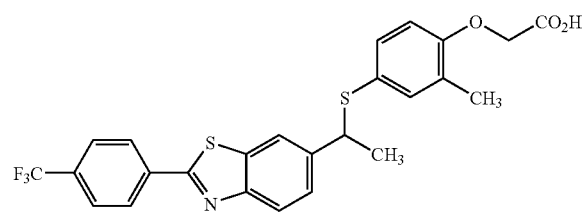

Add a solution of sodium hydroxide (200 mg, 4.2 mmol) in water (3 mL) to a solution of ethyl 2-methyl-4-{1-[2-(4-trifluoromethylphenyl)benzothiazol-6-yl]ethylsulfanyl}phenoxyacetate (Step 3, 180 mg, 0.33 mmol) in methylene chloride (5 mL) at room temperature followed by methanol (5 mL). Stir the mixture for 1.5 h, dilute with water (10 mL) and remove the organic solvents under reduced pressure. Further dilute the residue with water (10 mL) and acidify to pH 1 with 1 N HCl. Cool the resulting mixture to 0° C., collect the white solids and wash with water (10 mL) and hexanes (10 mL) to afford 2-methyl-4-{1-[2-(4-trifluoromethylphenyl)benzothiazol-6-yl]ethylsulfanyl}phenoxyacetic acid (Example 62) as a white solid (40 mg, 26%): mp 170-173° C.; $^1$H NMR (CDCl$_3$) δ 11.70 (d, 3H), 2.10 (s, 3H), 4.30 (q, 1H), 4.60 (s, 2H), 6.50 (d, 1H), 7.10 (m, 2H), 7.50 (m, 1H), 7.70 (m, 3H), 8.00 (d, 1H), 8.20 (d, 2H); APCI MS m/z 504 [C$_{25}$H$_{20}$F$_3$NO$_3$S$_2$+H]$^+$. HPLC analysis (retention time=14.9 min) shows one peak, with a total purity of 96.2% (area percent).

The following compounds are made in a substantially similar manner:

EXAMPLE 63

(+/−)-3-(2-Methyl-4-{1-[2-(4-trifluoromethylphenyl)benzothiazol-6-yl]ethylsulfanyl}phenyl)propionic Acid

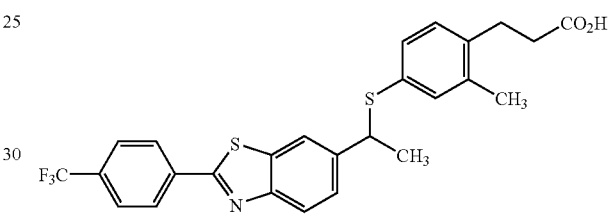

mp 159-161° C.; $^1$H NMR (CDCl$_3$) δ 1.70 (d, 3H), 2.20 (s, 3H), 2.40 (m, 2H), 2.90 (m, 2H), 4.40 (m, 1H), 7.10 (m, 3H), 7.50 (m, 1H), 7.80 (m, 3H), 8.00 (m, 1H), 8.20 (d, 2H); APCI MS m/z 500 [C$_{26}$H$_{22}$F$_3$NO$_2$S$_2$−H]$^-$. HPLC analysis (retention time=15.6 min) shows one peak, with a total purity of 97.5% (area percent).

Example 64 below is made employing the procedures of Scheme 10:

Scheme 10:

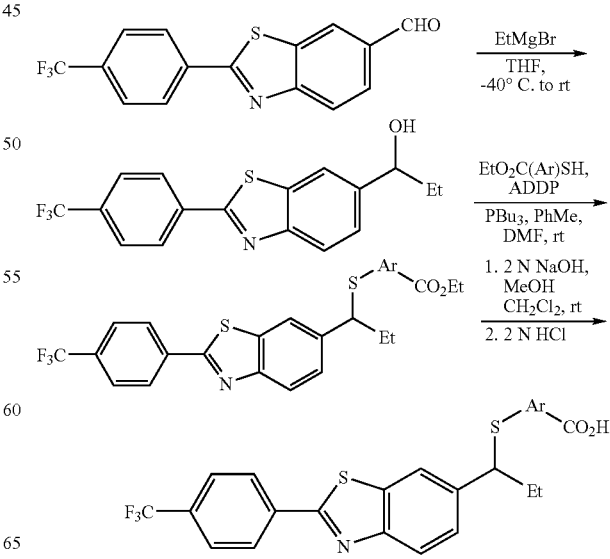

EXAMPLE 64

(+/−)-3-(2-Methyl-4-{1-[2-(4-trifluoromethylphenyl)benzothiazol-6-yl]propylsulfanyl}phenyl)propionic Acid

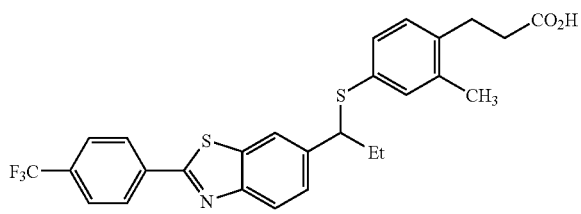

Step 1

1-[2-(4-Trifluoromethylphenyl)benzothiazol-6-yl]propan-1-ol

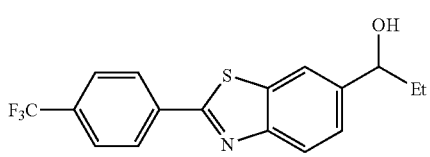

Add ethylmagnesium bromide (0.3 mL, 0.8 mmol, 3 M in diethyl ether) dropwise to a solution of 2-(4-trifluoromethylphenyl)benzothiazole-6-carbaldehyde (Example 63, Step 1, 179 mg, 0.5 mmol) in diethyl ether (20 mL) at −5° C. under nitrogen, warm the mixture to room temperature and stir for 30 min. Add additional ethylmagnesium bromide (0.3 mL, 0.8 mmol, 3 M in diethyl ether), stir for 30 min and dilute the mixture with water (100 mL). Extract with ethyl acetate (2×100 mL), dry the combined organic extracts over MgSO₄ and remove the solvents under reduced pressure to afford 1-[2-(4-trifluoromethylphenyl)benzothiazol-6-yl]propan-1-ol (Step 1), as a white solid, which was used in the next step without purification (180 mg, >99%).

Step 2

Methyl 3-(2-Methyl-4-{1-[2-(4-trifluoromethylphenyl)benzothiazol-6-yl]propylsulfanyl}phenyl)propionate

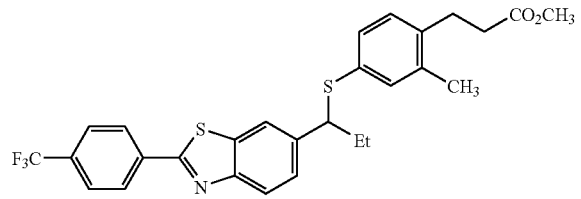

Add tri-n-butylphosphine (0.20 mL, 0.75 mmol) to a solution of 1-[2-(4-trifluoromethylphenyl)benzothiazol-6-yl]propan-1-ol (Step 1, 160 mg, 0.47 mmol), methyl 3-(4-mercapto-2-methylphenyl)propionate (160 mg, 0.76 mmol) and 1,1'-(azodicarbonyl)dipiperidine (ADDP, 190 mg, 0.79 mmol) in toluene (4 mL) and DMF (0.5 mL) at 0° C. under nitrogen and warm the mixture to room temperature. Stir the mixture 22 h, dilute with water (150 mL) and extract with methylene chloride (2×200 mL). Dry the combined organic extracts over MgSO₄, remove the solvents were reduced pressure and purify the residue by flash column chromatography on silica gel, eluting with hexanes/ethyl acetate (97:3), to afford methyl 3-(2-methyl-4-{1-[2-(4-trifluoromethylphenyl)benzothiazol-6-yl]propylsulfanyl}phenyl)propionate (Step 2) as a white solid (100 mg, 44%): $^1$H NMR (CDCl$_3$) δ 1.00 (t, 3H), 2.00 (dq, 2H), 2.20 (s, 3H), 2.50 (t, 2H), 2.80 (t, 2H), 31.60 (s, 3H), 4.10 (t, 1H), 7.00 (m, 3H), 7.40 (d, 1H), 7.70 (m, 3H), 8.00 (d, 1H), 8.20 (d, 2H).

(+/−)-3-(2-Methyl-4-{1-[2-(4-trifluoromethylphenyl)benzothiazol-6-yl]propylsulfanyl}phenyl)propionic Acid

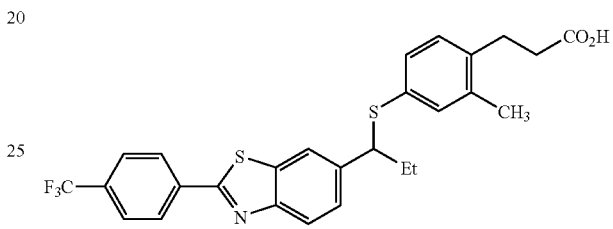

Add a solution of sodium hydroxide (150 mg, 3.75 mmol) in water (2.5 mL) to a solution of methyl 3-(2-methyl-4-{1-[2-(4-trifluoromethylphenyl)benzothiazol-6-yl]propylsulfanyl}phenyl)propionate (Step 2, 120 mg, 0.24 mmol) in methylene chloride (5 mL) and methanol (5 mL) at room temperature under nitrogen and stir for 2.5 h. Dilute the reaction mixture with water (15 mL) and remove the solvents under reduced pressure. Dilute the residue with water (15 mL) and acidify to pH 2 with 2 N HCl. Cool the residue to 0° C., collect the solids by vacuum filtration and wash with water (20 mL) and hexanes (30 mL) to afford 3-(2-methyl-4-{1-[2-(4-trifluoromethylphenyl)benzothiazol-6-yl]propylsulfanyl}phenyl)propionic acid (1) as a white solid (57 mg, 46%): mp 105-108° C.; $^1$H NMR (CDCl$_3$) δ 1.00 (t, 3H), 2.00 (dq, 2H), 2.20 (s, 3H), 2.50 (t, 2H), 2.80 (t, 2H), 4.10 (t, 1H), 7.00 (m, 3H), 7.40 (d, 1H), 7.70 (m, 3H), 8.00 (d, 1H), 8.20 (d, 2H); APCI MS m/z 514 [C$_{27}$H$_{24}$F$_3$NO$_2$S$_2$−H]$^-$. HPLC analysis (retention time=16.5 min) showed one peak, with a total purity of 98.7% (area percent).

Examples 65-67 below are made employing the procedures of Scheme 11:

Scheme 11:

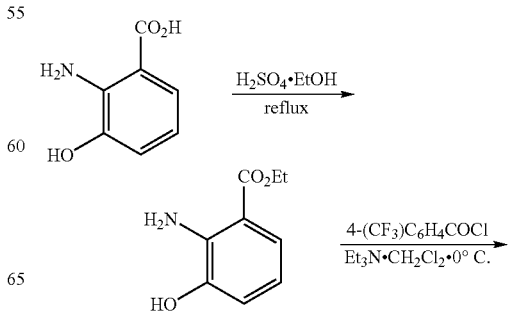

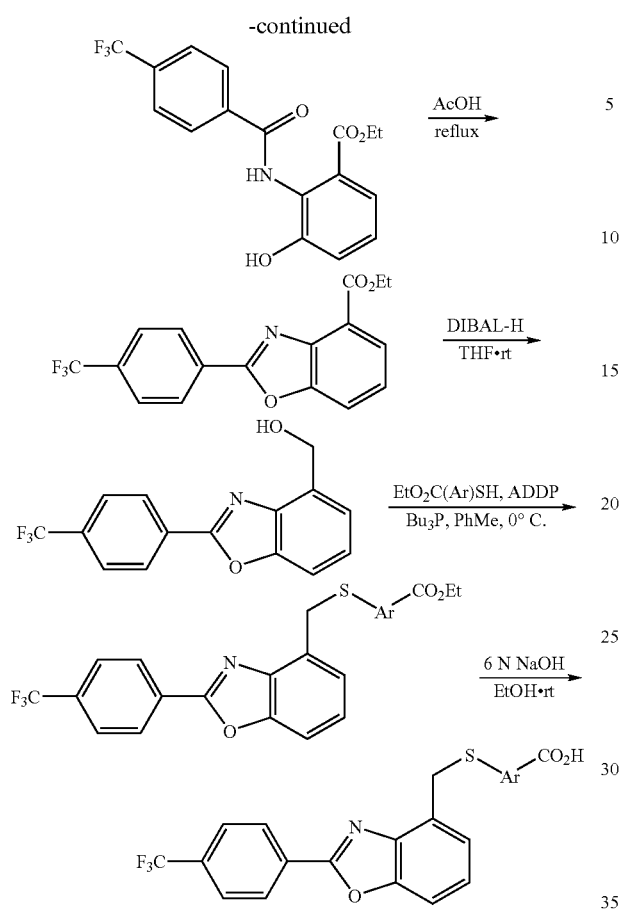

EXAMPLE 65

2-Methyl-4-[2-(4-trifluoromethylphenyl)benzooxazol-4-ylmethylsulfanyl]-phenoxyacetic Acid

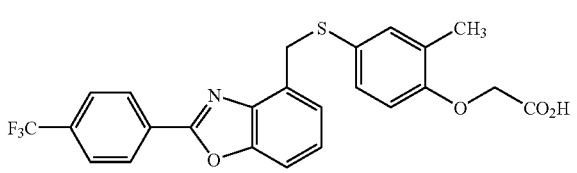

Step 1

Ethyl 2-Amino-3-hydroxybenzoate

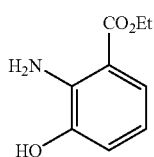

Add concentrated sulfuric acid (5 mL) to a suspension of commercially available 3-hydroxyanthranilic acid (5.10 g, 33.3 mmol) in ethanol (110 mL) and heat the mixture at reflux for 60 h. Dilute the cooled mixture with ethyl acetate (500 mL) and extract with 10% aqueous potassium carbonate solution (2×200 mL). Back-extract the combined aqueous layers with ethyl acetate (2×100 mL), dry the combined organic layers over $Na_2SO_4$ and remove the solvent under reduced pressure to provide ethyl 2-amino-3-hydroxybenzoate (Step 1, 5.13 g, 85%) as a dark brown solid, which is used in the next step without further purification: $^1$H NMR (CDCl$_3$) δ 1.38 (t, J=7.1 Hz, 3H), 4.33 (q, J=7.1 Hz, 2H), 5.31 (br s, 3H), 6.50 (t, J=7.9 Hz, 1H), 6.81 (dd, J=1.2, 7.6 Hz, 1H), 7.51 (dd, J=1.2, 8.2 Hz, 1H).

Step 2

Ethyl 3-Hydroxy-2-(4-trifluoromethylbenzoylamino)benzoate

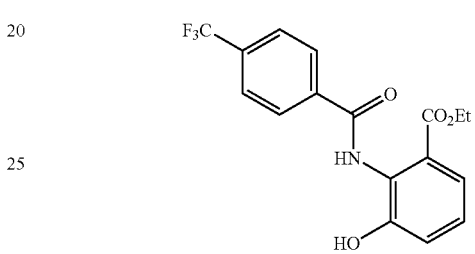

Add 4-trifluoromethylbenzoyl chloride (2.1 mL, 13.9 mmol) dropwise to a solution of ethyl 2-amino-3-hydroxybenzoate (Step 1, 2.29 g, 12.6 mmol) and triethylamine (2 mL, 13.9 mmol) in methylene chloride (50 mL) at 0° C. under nitrogen, warm the mixture to room temperature and stir for 12 h. Dilute the mixture with methylene chloride (50 mL), wash with saturated aqueous NaHCO$_3$ solution (50 mL) and dry over $Na_2SO_4$. Remove the solvent under reduced pressure to provide a mixture of ethyl 3-hydroxy-2-(4-trifluoromethylbenzoylamino)benzoate (Step 2) and the diacylated product, which is used in the next step as a mixture without further purification: $^1$H NMR (CDCl$_3$) δ 1.40 (t, J=7.1 Hz, 3H), 4.36 (q, J=7.1 Hz, 2H), 5.83 (br s, 2H), 6.71 (t, J=8.0 Hz, 1H), 7.26-7.28 (m, 1H), 7.79-7.87 (m, 3H), 8.35 (d, J=8.1 Hz, 2H).

Step 3

Ethyl 2-(4-Trifluoromethylphenyl)benzooxazole-4-carboxylate

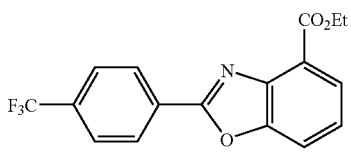

Heat a solution of ethyl 3-hydroxy-2-(4-trifluoromethylbenzoylamino)benzoate (Step 2, 4.28 g, 12.1 mmol) in acetic acid (125 mL) at reflux under nitrogen for 2.5 h and then pour the cooled mixture into ice water (500 mL). Filter the suspension through Celite®, rinse the solids with cold water (4×50 mL) and then ethyl acetate (500 mL). Dry the organic layer over $Na_2SO_4$ and remove the solvent under reduced pressure. Triturate the residue with diethyl ether and remove the solids by filtration, washing with cold diethyl ether (50 mL). Collect the precipitate in the filtrate and wash with cold diethyl ether (50 mL) to provide an initial crop of the desired product. Remove the filtrate solvent under reduced pressure and purify the residue by flash column chromatography on silica gel, eluting with hexanes/ethyl acetate (19:1), and combine with the first crystallization crop to provide ethyl 2-(4-trifluoromethylphenyl)benzooxazole-4-carboxylate as a light yellow solid (2.13 g, 56% over two steps): $^1$H NMR (CDCl$_3$) δ 1.50 (t, J=7.1 Hz, 3H), 4.53 (q, J=7.1 Hz, 2H), 7.46 (t, J=8.0 Hz, 1H), 7.79-7.82 (m, 3H), 8.05 (dd, J=1.0, 7.8 Hz, 1H), 8.47 (d, J=8.1 Hz, 2H); ESI MS m/z 336 [C$_{17}$H$_{12}$F$_3$NO$_3$+H]$^+$.

Step 4

[2-(4-Trifluoromethylphenyl)benzooxazol-4-yl]methanol

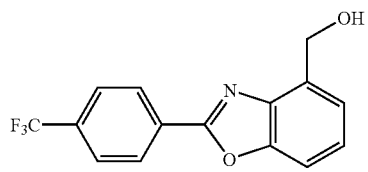

Add a solution of DIBAL-H (1.33 mL, 1.33 mmol, 1 M solution in hexanes) dropwise to a solution of ethyl 2-(4-trifluoromethylphenyl)benzooxazole-4-carboxylate (Step 3, 0.223 g, 0.665 mmol) in THF (5 mL) at 0° C. under nitrogen, and slowly warm the mixture to room temperature, to stir for a total of 12 h. Cool the mixture to 0° C. and charge with an additional amount of DIBAL-H (0.33 mL, 0.333 mmol, 1.0 M solution in hexanes). After 1 h, add a third portion of DIBAL-H (0.33 mL, 0.333 mmol, 1 M solution in hexanes) and stir the reaction for 40 min. Treat the mixture with methanol (2 mL) followed by 2 N HCl (5 mL), stir for 4 h, and add ethyl acetate (50 mL). Collect the organic extract and extract the aqueous layer with ethyl acetate (25 mL). Dry the combined organic extracts over Na$_2$SO$_4$ and remove the solvents under reduced pressure to provide [2-(4-trifluoromethylphenyl)benzooxazol-4-yl]methanol (Step 4) as an amber oil, which is used in the next step without further purification (0.188 g, 96%): $^1$H NMR (CDCl$_3$) δ 5.14 (s, 2H), 7.39 (t, J=7.6 Hz, 1H), 7.55 (d, J=7.8 Hz, 1H), 7.80 (d, J=8.2 Hz, 2H), 8.13 (d, J=8.1 Hz, 1H), 8.39 (d, J=8.1 Hz, 2H).

Step 5

Ethyl 2-Methyl-4-[2-(4-trifluoromethylphenyl)benzooxazol-4-ylmethylsulfanyl]-phenoxyacetate

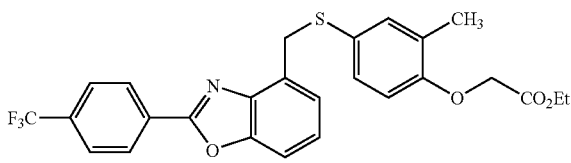

Add tri-n-butylphosphine (73 μL, 0.292 mmol) and 1,1'-(azodicarbonyl)dipiperidine (ADDP, 74 mg, 0.292 mmol) to a degassed mixture of [2-(4-trifluoromethylphenyl)benzooxazol-4-yl]methanol (Step 4, 57 mg, 0.194 mmol) and ethyl 4-mercapto-2-methylphenoxyacetate (66 mg, 0.292 mmol) in toluene (4 mL) at 0° C. under nitrogen and stir the mixture for 2 h. Dilute the mixture with ethyl acetate (50 mL), wash with 2 N HCl (25 mL) and brine (25 mL), dry over Na$_2$SO$_4$ and remove the solvents under reduced pressure. Triturate the residue with diethyl ether and remove the solids by filtration. Removed the filtrate solvent under reduced pressure and purify the residue by flash column chromatography on silica gel, eluting with hexanes/ethyl acetate (9:1), to afford ethyl 2-methyl-4-[2-(4-trifluoromethylphenyl)benzooxazol-4-ylmethylsulfanyl]-phenoxyacetate (Step 5) as an off-white solid (39 mg, 40%): $^1$H NMR (CDCl$_3$) δ 1.28 (t, J=7.1 Hz, 3H), 2.20 (s, 3H), 4.24 (q, J=7.1 Hz, 2H), 4.45 (s, 2H), 4.54 (s, 2H), 6.55 (d, J=8.4 Hz, 1H), 7.12-7.32 (m, 4H), 7.46 (dd, J=1.0, 8.2 Hz, 1H), 7.78 (d, J=8.2 Hz, 2H), 8.36 (d, J=8.1 Hz, 2H); ESI MS m/z 502 [C$_{26}$H$_{22}$F$_3$NO$_4$S+H]$^+$.

2-Methyl-4-[2-(4-trifluoromethylphenyl)benzooxazol-4-ylmethylsulfanyl]-phenoxyacetic Acid

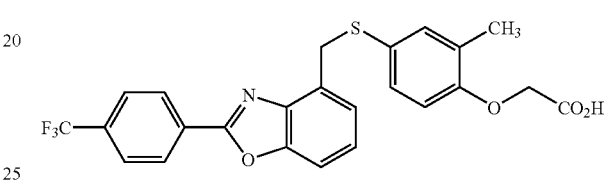

Heat a suspension of ethyl 2-methyl-4-[2-(4-trifluoromethylphenyl)benzooxazol-4-ylmethylsulfanyl]-phenoxyacetate (Step 5, 39 mg, 0.078 mmol) in ethanol (3 mL) and 6 N NaOH (1 mL) at 50° C. for 30 min. Adjust the cooled mixture to pH 1 with 2 N HCl and extract with diethyl ether (2×25 mL). Dry the combined organic extracts over Na$_2$SO$_4$ and remove the solvent under reduced pressure to provide 2-methyl-4-[2-(4-trifluoromethylphenyl)benzooxazol-4-ylmethylsulfanyl]-phenoxyacetic acid (Example 65) as an off-white solid (42 mg, >99%): mp 160-162° C. (dec); TLC R$_f$ (95:5:0.5 CHCl$_3$/MeOH/AcOH)=0.47; $^1$H NMR (CD$_3$OD) δ 2.11 (s, 3H), 4.38 (s, 2H), 4.51 (s, 2H), 6.62 (d, J=8.7 Hz, 1H), 7.07-7.09 (m, 2H), 7.17 (d, J=7.6 Hz, 1H), 7.28-7.34 (m, 1H), 7.52 (d, J=8.0 Hz, 1H), 7.87 (d, J=8.0 Hz, 2H), 8.36 (d, J=8.2 Hz, 2H); ESI MS m/z 474 [C$_{24}$H$_{18}$F$_3$NO$_4$S+H]$^+$. HPLC analysis (retention time=15.7 min) shows one peak, with a total purity of 97.9% (area percent).

The following compound is made in a substantially similar manner:

EXAMPLE 66

3-2-Methyl-4-[2-(4-trifluoromethylphenyl)benzooxazol-4-ylmethylsulfanyl]phenylpropionic Acid

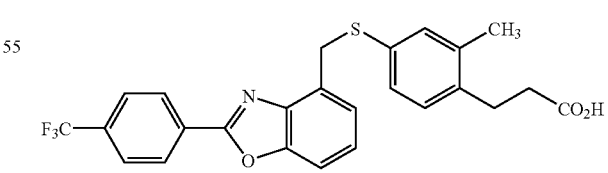

mp 181-183° C.; TLC R$_f$ (95:5:0.5 CHCl$_3$/MeOH/AcOH)=0.46; $^1$H NMR (CD$_3$OD) δ 2.19 (s, 3H), 2.38-2.43 (m, 2H), 2.75-2.80 (m, 2H), 4.48 (s, 2H), 6.98-7.01 (m, 1H), 7.07-7.10 (m, 2H), 7.26-7.28 (m, 1H), 7.31-7.37 (m, 1H), 7.55 (d, J=8.1 Hz, 1H), 7.89 (d, J=7.8 Hz, 2H), 8.42 (d, J=8.0 Hz, 2H); ESI MS m/z 472 [C$_{25}$H$_{20}$F$_3$NO$_3$S+H]$^+$. HPLC

EXAMPLE 67

2-Ethyl-4-[2-(4-trifluoromethylphenyl)benzooxazol-4-ylmethylsulfanyl]phenoxyacetic Acid

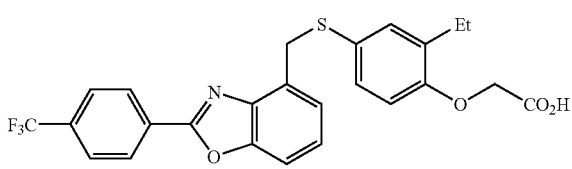

mp 127-128° C.; TLC $R_f$ (95:5:0.1 $CH_2Cl_2$/MeOH/AcOH)=0.29; $^1$H NMR (CD$_3$OD) δ 1.03 (t, J=7.5 Hz, 3H), 2.51 (q, J=17.5 Hz, 2H), 4.39 (s, 2H), 4.51 (s, 2H), 6.66 (d, J=8.5 Hz, 1H), 7.00 (s, 1H), 7.12-7.20 (m, 2H), 7.32 (t, J=7.7 Hz, 1H), 7.53 (d, J=8.1 Hz, 1H), 7.88 (d, J=8.5 Hz, 2H), 8.38 (d, J=8.3 Hz, 2H); ESI MS m/z 488 $[C_{25}H_{20}F_3NO_4S+H]^+$. HPLC analysis (retention time=16.8 min) shows one peak, with a total purity of >99% (area percent).

Examples 68-74 below are made employing the procedures substantially as described below.

EXAMPLE 68

2-Methyl-4-[2-(4-trifluoromethylphenyl)-benzooxazol-7-ylmethylsulfanyl]-phenoxyacetic Acid

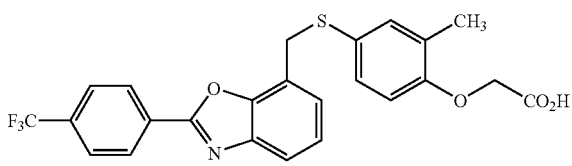

Step 1

Methyl 2-Hydroxy-3-nitrobenzoate

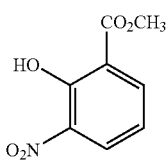

Add concentrated sulfuric acid (17 mL) dropwise to a suspension of commercially available 3-nitrosalicylic acid (17.0 g, 9.28 mmol) in methanol (200 mL) at room temperature under nitrogen and heat the mixture at reflux for 36 h. Remove the solvent under reduced pressure, neutralize the residue with saturated aqueous NaHCO$_3$ solution and extract with ethyl acetate (3×300 mL). Wash the organic extract with water (100 mL) and brine (100 mL), dry over MgSO$_4$ and remove the solvent under reduced pressure to afford methyl 2-hydroxy-3-nitrobenzoate (Step 1) as a yellow solid (18.1 g, >99%): $^1$H NMR (CDCl$_3$) δ 12.00 (s, 1H), 8.13-8.18 (m, 2H), 7.01 (t, J=8.1 Hz, 1H), 4.02 (s, 3H); ESI MS m/z 198 $[C_8H_7NO_5+H]^+$.

Step 2

Methyl 3-Amino-2-hydroxybenzoate

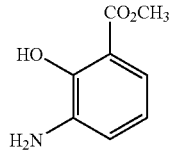

Shake a suspension of methyl 2-hydroxy-3-nitrobenzoate (Step 1, 18.1 g, 93 mmol) and 5% palladium on carbon (5 g) in methanol (200 mL) at room temperature under hydrogen (60 psi) in a Parr bottle for 49 h. Filter the mixture through a plug of Celite and remove the filtrate solvent under reduced pressure to afford methyl 3-amino-2-hydroxybenzoate (Step 2) as a yellow solid (15.6 g, >99%): $^1$H NMR (CDCl$_3$) δ 10.87 (s, 1H), 7.23 (dd, J=7.7 Hz, 2H), 6.87 (t, J=9.9 Hz, 1H), 3.95 (s, 3H), 3.80 (br s, 2H); ESI MS m/z 168 $[C_8H_9NO_3+H]^+$.

Step 3

Methyl 2-Hydroxy-3-(4-trifluoromethylbenzoylamino)benzoate

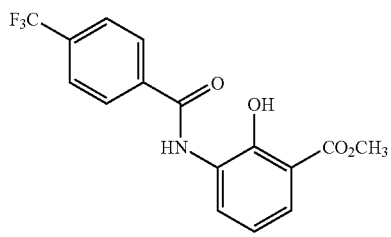

Add a solution of 4-(trifluoromethyl)benzoyl chloride (19.46 g, 93.3 mmol) in THF (60 mL) dropwise over 1 h to a solution of methyl 3-amino-2-hydroxybenzoate (Step 2, 15.6 g, 93.3 mmol) and triethylamine (13 mL) in THF (1.0 L)) at 0° C. under nitrogen, warm the mixture to room temperature and stir for 12 h. Remove the solvent under reduced pressure, dilute the residue with ethyl acetate (2 L), wash with 0.5 N HCl (3×500 mL), saturated aqueous NaHCO$_3$ solution (3×500 mL), water (100 mL), and brine (100 mL) and dry over MgSO$_4$. Remove the solvent under reduced pressure and purify the residue by flash column chromatography on silica gel, eluting with hexanes/ethyl acetate (4:1), to afford methyl 2-hydroxy-3-(4-trifluoromethylbenzoylamino)benzoate (Step 3) as a white solid (25.3 g, 80%): $^1$H NMR (CDCl$_3$) δ 11.41 (s, 1H), 8.72 (d, J=8.1 Hz, 1H), 8.61 (s, 1H), 8.03 (d, J=8.3 Hz, 2H), 7.77 (d, J=8.3 Hz, 2H), 7.61 (dd, J=8.5, 1.6 Hz, 1H), 6.97 (t, J=8.1 Hz, 1H), 3.99 (s, 3H); ESI MS m/z 340 $[C_{16}H_{12}F_3NO_4+H]^+$.

Step 4

Methyl 2-(4-Trifluoromethylphenyl)benzooxazole-7-carboxylate

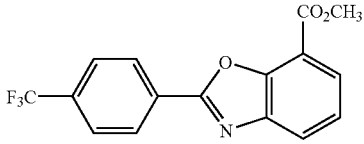

Heat a solution of methyl 2-hydroxy-3-(4-trifluoromethylbenzoylamino)benzoate (Step 3, 30.0 g, 88.4 mmol) and p-toluenesulfonic acid monohydrate (37 g, 194.5 mmol) in anhydrous toluene (400 mL) at reflux under nitrogen for 48 h. Remove the solvent under reduced pressure and purify the residue by flash column chromatography on silica gel, eluting with methylene chloride, to afford methyl 2-(4-trifluoromethylphenyl)benzooxazole-7-carboxylate (Step 4) as a white solid (18.46 g, 65%): $^1$H NMR (CDCl$_3$) δ 8.42 (d, J=8.2 Hz, 2H), 8.01 (q, J=7.7 Hz, 2H), 7.80 (d, J=8.2 Hz, 2H), 7.45 (t, J=7.9 Hz, 1H), 4.07 (s, 3H); ESI MS m/z 322 [C$_{16}$H$_{10}$F$_3$NO$_3$+H]$^+$.

Step 5

[2-(4-Trifluoromethyl-phenyl)benzooxazol-7-yl]methanol

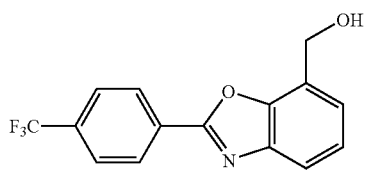

Add a solution of lithium aluminum hydride (56 mL, 56.3 mmol, 1 M solution in THF) dropwise to a solution of methyl 2-(4-trifluoromethylphenyl)benzooxazole-7-carboxylate (Step 4, 18 g, 56.3 mmol) in THF (250 mL) at 0° C. under nitrogen, warm the mixture to room temperature and stir for 3 h. Dilute the mixture with water (12 mL), 5 N NaOH (12 mL) and water (12 mL) and extract with ethyl acetate (5×50 mL). Wash the combined organic extracts with water (50 mL) and brine (50 mL), dry the mixture over MgSO$_4$ and remove the solvent under reduced pressure. Purify the residue by flash column chromatography on silica gel, eluting with hexanes/ethyl acetate (10:1), to afford [2-(4-trifluoromethyl-phenyl)benzooxazol-7-yl]methanol (Step 5) as a white solid (11.1 g, 67%): $^1$H NMR (CDCl$_3$) δ 8.2 (d, J=8.1 Hz, 2H), 7.78 (d, J=8.2 Hz, 2H), 7.72 (dd, J=7.7, 1.4 Hz, 1H), 7.35-7.44 (m, 2H), 5.07 (d, J=6.0 Hz, 2H), 2.15 (t, J=6.2 Hz, 1H); APCI MS m/z 294 [C$_{15}$H$_{10}$F$_3$NO$_2$+H]$^+$.

Step 6

Ethyl 2-Methyl-4-[2-(4-trifluoromethylphenyl)benzooxazol-7-ylmethylsulfanyl]phenoxyacetate

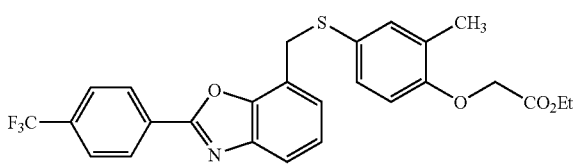

Add tri-n-butylphosphine (0.095 mL, 0.69 mmol) to a degassed solution of ethyl (4-mercapto-2-methylphenoxy)acetate (155 mg, 0.69 mmol) and [2-(4-trifluoromethylphenyl)benzooxazol-7-yl]methanol (Step 5, 130 mg, 0.44 mmol) in toluene (3 mL) at 0° C. under nitrogen, and then add 1,1'-(azodicarbonyl)dipiperidine (ADDP, 173 mg, 0.69 mmol). Warm the mixture to warm to room temperature, stir for 12 h and remove the solvent under reduced pressure. Purify the residue by flash column chromatography on silica gel, eluting with hexanes/ethyl acetate (9:1), to afford ethyl 2-methyl-4-[2-(4-trifluoromethylphenyl)benzooxazol-7-ylmethylsulfanyl]phenoxyacetate (Step 6) as a white solid (210 mg, 94%): $^1$H NMR (CDCl$_3$) δ 8.28 (d, J=8.3 Hz, 2H), 7.80 (d, J=8.3 Hz, 2H), 7.65, (dd, J=7.1 Hz, 1H), 7.05-7.40 (m, 4H), 6.50 (d, J=8.3 Hz, 1H), 4.45 (s, 2H), 4.30 (s, 2H), 4.19 (q, J=7.1 Hz, 2H), 2.26 (s, 3H), 1.29 (t, J=7.1 Hz, 3H); ESI MS m/z 502 [C$_{26}$H$_{22}$F$_3$NO$_4$S+H]$^+$.

2-Methyl-4-[2-(4-trifluoromethylphenyl)benzooxazol-7-ylmethylsulfanyl]phenoxyacetic Acid

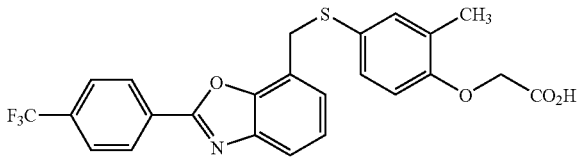

Add a solution of aqueous sodium hydroxide solution (1.0 mL, 5 N) to a solution of ethyl 2-methyl-4-[2-(4-trifluoromethylphenyl)benzooxazol-7-ylmethylsulfanyl]phenoxyacetate (Step 6, 130 mg, 0.26 mmol) in ethanol (1 mL) at room temperature under nitrogen and heat the mixture at 50° C. for 3 h. Dilute the cooled mixture with water (10 mL), wash with diethyl ether (3×10 mL) adjust to pH 5 with 6 N HCl and extract with ethyl acetate (3×20 mL). Dry the combined organic extracts over MgSO$_4$, remove the solvent under reduced pressure and recrystallized the residue from methylene chloride/methanol (1:1) to afford 2-methyl-4-[2-(4-trifluoromethylphenyl)benzooxazol-7-ylmethylsulfanyl]phenoxyacetic acid (Example 68) as a white solid (103 mg, 84%): mp: 180-182° C.; $^1$H NMR (DMSO-d$_6$) δ 12.95 (s, 1H), 8.27 (d, J=8.3 Hz, 2H), 7.98 (d, J=8.3 Hz, 2H), 7.71, (dd, J=7.2, 2.1 Hz, 1H), 7.31-7.38 (m, 2H), 7.07-7.17 (m, 2H), 6.69 (d, J=8.3 Hz, 1H), 4.48 (s, 2H), 4.41 (s, 2H), 2.00 (s, 3H); ESI MS m/z 474 [C$_{24}$H$_{18}$F$_3$NO$_4$S+H]$^+$. HPLC analysis (retention time=12.5 min) shows one peak, with a total purity of 98.8% (area percent).

The following compounds are made in a substantially similar manner:

EXAMPLE 69

3-{2-Methyl-4-[2-(4-trifluoromethylphenyl)benzooxazol-7-ylmethylsulfanyl]phenyl}propionic Acid

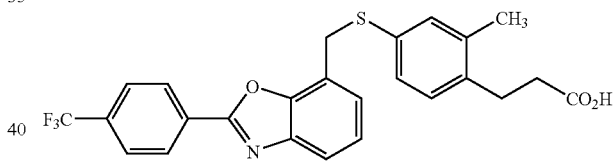

mp: 155-157° C.; $^1$H NMR (CDCl$_3$) δ 8.30 (d, J=8.4 Hz, 2H), 7.78 (d, J=8.4 Hz, 2H), 7.67 (dd, J=7.35, 1.3 Hz, 1H), 7.04-7.36 (m, 4H), 6.99 (d, J=8.8 Hz, 1H), 4.37 (s, 2H), 2.79 (t, J=7.8 Hz, 2H), 2.49 (t, J=7.8 Hz, 2H), 2.19 (s, 3H); ESI MS m/z 472 [C$_{25}$H$_{20}$F$_3$NO$_3$S+H]$^+$. HPLC analysis (retention time=12.8 min) shows one peak, with a total purity of >99% (area percent).

EXAMPLE 70

6-[2-(4-Trifluoromethylphenyl)benzooxazol-7-ylmethoxy]benzo[b]thiophen-3-ylacetic Acid

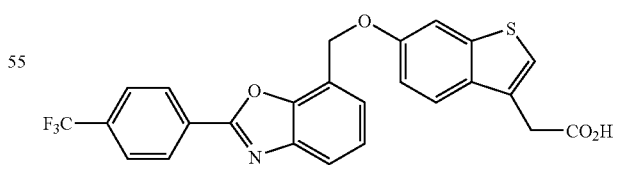

mp: 215-216° C.; $^1$H NMR (DMSO-d$_6$) (12.37 (s br, 1H), 8.41 (d, J=8.2 Hz, 2H), 7.98 (d, J=8.2 Hz, 2H), 7.86 (d, J=8.1 Hz, 1H), 7.79 (d, J=2.3 Hz, 1H), 7.70 (d, J=8.7 Hz, 1H), 7.62 (d, J=7.5 Hz, 1H), 7.48 (t, J=7.8 Hz, 1H), 7.39 (s, 1H), 7.18 (dd, J=8.7, 2.5 Hz, 1H), 5.58 (s, 2H), 3.79 (s, 2H); ESI MS m/z 484 [C$_{25}$H$_{16}$F$_3$NO$_4$S+H]$^+$. HPLC analysis (retention time=12.3 min) shows one peak, with a total purity of >99% (area percent).

EXAMPLE 71

6-[2-(4-Trifluoromethylphenyl)benzooxazol-7-ylm-ethylsulfanyl]benzo[b]thiophen-3-ylacetic Acid

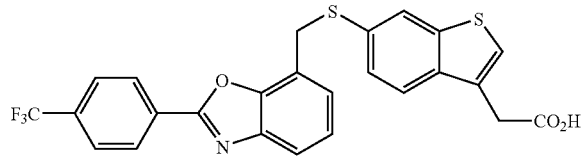

mp: 208-210° C.; $^1$H NMR (DMSO-d$_6$) δ 3.71 (s, 2H), 4.62 (s, 2H), 7.22-7.44 (m, 3H), 7.50 (s, 1H), 7.66 (d, 2H), 7.71 (dd, 1H), 7.92 (d, 2H), 8.03 (d, 1H), 8.22 (d, 2H), 12.42 (s, 1H); ESI MS m/z 500 [C$_{25}$H$_{16}$F$_3$NO$_3$S$_2$+H]$^+$. HPLC analysis (retention time=13.1 min) shows one peak, with a total purity of 97.4% (area percent).

EXAMPLE 72

2-Ethyl-4-[2-(4-trifluoromethylphenyl)benzooxazol-7-ylmethylsulfanyl]phenoxyacetic Acid

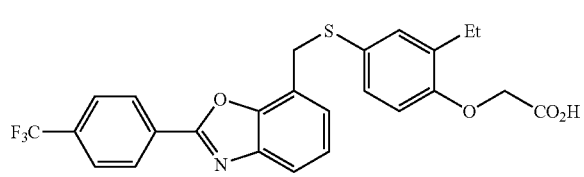

mp: 170-173° C.; $^1$H NMR (DMSO-d$_6$) δ 8.26 (d, J=8.3 Hz, 2H), 7.98 (d, J=8.3 Hz, 2H), 7.71 (dd, J=7.6, 1.6 Hz, 1H), 7.29-7.41 (m, 2H), 7.18 (dd, J=8.8, 2.3 Hz, 1H), 6.96 (d, J=2.0 Hz, 1H), 6.70 (d, J=8.8 Hz, 1H), 4.40 (s, 2H), 4.38 (s, 2H), 2.40 (q, J=7.6 Hz, 2H), 0.94 (t, J=7.6 Hz, 3H); ESI MS m/z 488 [C$_{25}$H$_{20}$F$_3$NO$_4$S+H]$^+$. HPLC analysis (retention time=13.1 min) shows one peak, with a total purity of >99% (area percent).

EXAMPLE 73

3-[2-(4-Trifluoromethylphenyl)benzooxazol-7-ylm-ethylsulfanyl]phenylacetic Acid

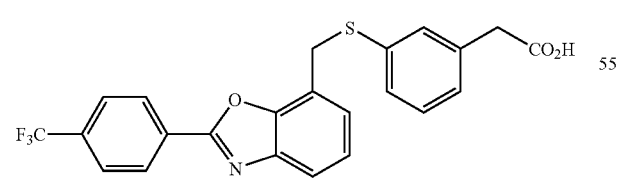

mp: 147-149° C.; $^1$H NMR (CD$_3$OD) δ 8.27 (d, J=8.2 Hz, 2H), 7.89 (d, J=8.2 Hz, 2H), 7.63 (m, 1H), 7.26-7.38 (m, 3H), 7.02-7.25 (m, 3H), 4.47 (s, 2H), 3.48 (s, 2H); ESI MS m/z 444 [C$_{23}$H$_{16}$F$_3$NO$_3$S+H]$^+$. HPLC analysis (retention time=12.0 min) shows one peak, with a total purity of 97.3% (area percent).

EXAMPLE 74

2-Methyl-4-[2-(4-trifluoromethylphenyl)benzoox-azol-7-ylmethylsulfanyl]phenoxyacetic Acid

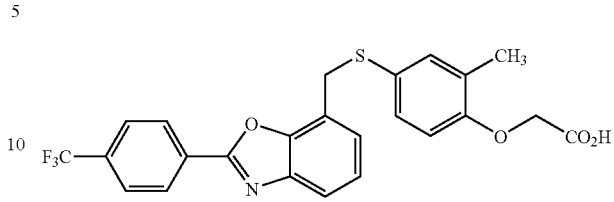

mp: 172-174° C.; $^1$H NMR (CD$_3$OD) δ 8.42 (d, J=8.3 Hz, 2H), 7.89 (d, J=8.3 Hz, 2H), 7.75 (d, J=7.7 Hz, 1H), 7.54 (d, J=7.4 Hz, 1H), 7.40-7.48 (m, 1H), 7.09 (d, J=8.3 Hz, 1H), 6.79-6.92 (m, 2H), 5.43 (s, 2H), 2.86 (t, J=7.7 Hz, 2H), 2.51 (t, J=7.7 Hz, 2H), 2.30 (s, 3H); APCI MS m/z 456 [C$_{25}$H$_{20}$F$_3$NO$_4$+H]$^+$. HPLC analysis (retention time=15.7 min) shows one peak, with a total purity of 95.5% (area percent).

Examples 75-78 below are made employing the procedures of Scheme 13:

Scheme 13:

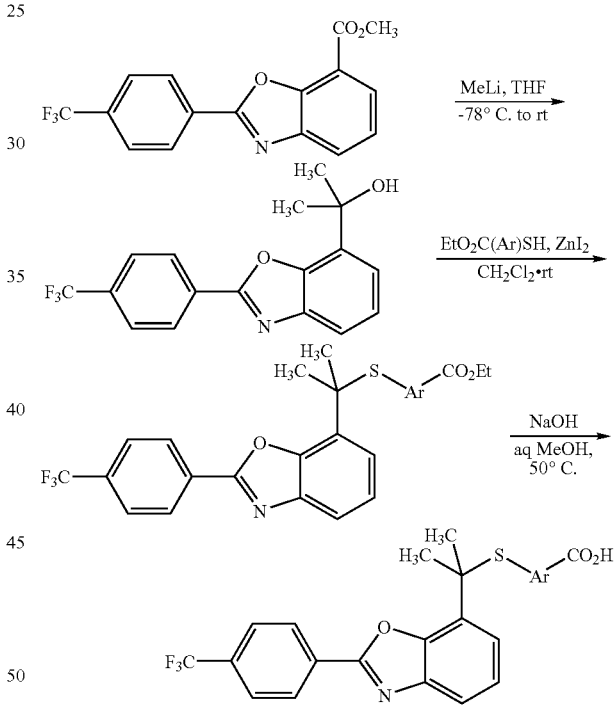

EXAMPLE 75

2-Methyl-4-{1-methyl-1-[2-(4-trifluoromethylphe-nyl)benzooxazol-7-yl]ethylsulfanyl}phenoxyacetic Acid

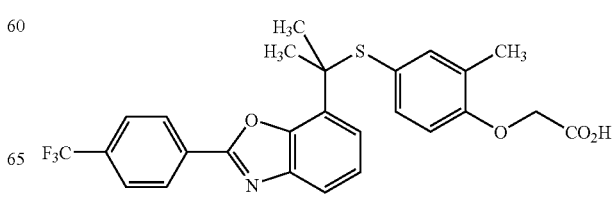

Steps 1 and 2

2-[2-(4-Trifluoromethylphenyl)benzooxazol-7-yl]propan-2-ol and 1-[2-(4-Trifluoromethylphenyl)benzooxazol-7-yl]ethanone

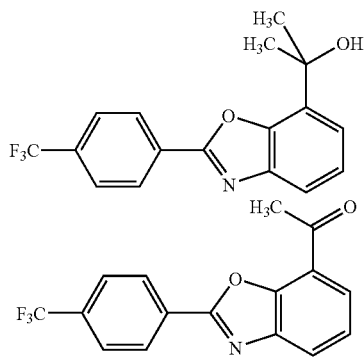

Add methyl lithium (50.4 mL, 70.6 mmol, 1.4 M solution in THF, 70.6 mmol) dropwise to a solution of methyl 2-(4-trifluoromethylphenyl)benzooxazole-7-carboxylate (Example 68, Step 4, 10.8 g, 33.6 mmol) in THF (120 mL) at −78° C. under nitrogen and stir the mixture for 2 h. Warm the mixture to room temperature, carefully dilute with saturated aqueous ammonium chloride (50 mL) and extract with ethyl acetate (3×200 mL). Wash the combined organic extract with water (100 mL) and brine (100 mL) and dry over $Na_2SO_4$. Remove the solvents under reduced pressure and purify by flash column chromatography on silica gel, eluting with ethyl acetate/hexanes (1:9), to afford 2-[2-(4-trifluoromethylphenyl)benzooxazol-7-yl]propan-2-ol (Step 1) as a white solid (4.2 g, 41%): $^1$H NMR (CDCl$_3$) δ 8.36 (d, J=8.2 Hz, 2H), 7.79 (d, J=8.2 Hz, 2H), 7.70 (dd, J=7.9, 1.1 Hz, 1H), 7.54 (dd, J=7.9, 1.1 Hz, 1H), 7.37 (t, J=7.8 Hz, 1H), 2.30 (s, 1H), 1.83 (s, 6H); ESI MS m/z 322 [$C_{17}H_{14}F_3NO_2$+H]$^+$. 1-[2-(4-Trifluoromethylphenyl)benzooxazol-7-yl]ethanone (Step 2) is also isolated as a white solid (4.0 g, 39%); $^1$H NMR (CDCl$_3$) δ 8.40 (d, J=8.3 Hz, 2H), 7.94-8.03 (m, 2H), 7.82 (d, J=8.3 Hz, 2H), 8.48 (t, J=7.8 Hz, 1H), 2.91 (s, 3H); ESI MS m/z 306 [$C_{16}H_{10}F_3NO_2$+H]$^+$.

Step 3

Ethyl 2-Methyl-4-{1-methyl-1-[2-(4-trifluoromethylphenyl)benzooxazol-7-yl]ethylsulfanyl}phenoxyacetate

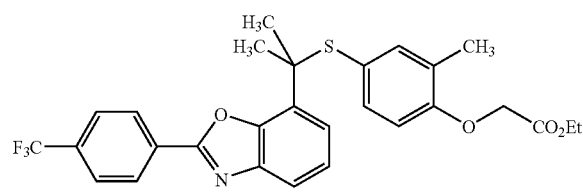

Add anhydrous zinc iodide (136 mg, 0.42 mmol) to a solution of 2-[2-(4-trifluoromethylphenyl)benzooxazol-7-yl]propan-2-ol (Step 1, 100 mg, 0.31 mmol) in anhydrous methylene chloride (4 mL) at room temperature under nitrogen, and then add ethyl 4-mercapto-2-methylphenoxyacetate (84.5 mg, 0.37 mmol). Stir the mixture for 1.5 h, dilute with water (10 mL) and extract with ethyl acetate (60 mL). Wash the organic extract with 0.5 N NaOH (2×20 mL), water (10 mL) and brine (10 mL), dry over $Na_2SO_4$ and remove the solvents under reduced pressure. Purify the residue by flash column chromatography on silica gel, eluting with methylene chloride/hexanes (1:1), to afford ethyl 2-methyl-4-{1-methyl-1-[2-(4-trifluoromethylphenyl)benzooxazol-7-yl]ethylsulfanyl}phenoxyacetate (Step 3) as a yellow oil (120 mg, 73%): $^1$H NMR (CDCl$_3$) δ 8.30 (d, J=8.3 Hz, 2H), 7.79 (d, J=8.3 Hz, 2H), 7.69 (d, J=7.7 Hz, 1H), 7.21-7.29 (m, 1H), 7.12 (d, J=7.4 Hz, 1H), 6.64-6.84 (m, 2H), 6.35 (d, J=8.5 Hz, 1H), 4.35 (s, 2H), 4.21 (q, J=7.1 Hz, 2H), 2.03 (s, 3H), 1.93 (s, 6H), 1.26 (t, J=7.1 Hz, 3H); ESI MS m/z 530 [$C_{28}H_{26}F_3NO_4S$+H]$^+$.

2-Methyl-4-{1-methyl-1-[2-(4-trifluoromethylphenyl)benzooxazol-7-yl]ethylsulfanyl}phenoxyacetic Acid

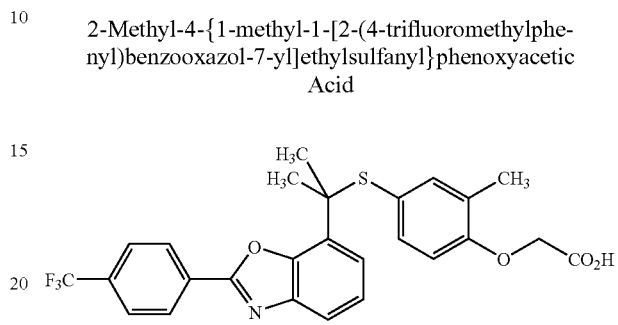

Heat a solution of ethyl 2-methyl-4-{1-methyl-1-[2-(4-trifluoromethylphenyl)benzooxazol-7-yl]ethylsulfanyl}phenoxyacetate (Step 3, 110 mg, 0.21 mmol) in methanol (3 mL) and a sodium hydroxide solution (2.5 mL, 2 N) at 50° C. for 3 h, and acidify the cooled mixture to pH 3 with 6 N HCl. Extract the mixture with ethyl acetate (3×10 mL), wash the combined organic extracts with water (5 mL) and brine (5 mL) and dry over $Na_2SO_4$. Remove the solvents under reduced pressure and purify the residue by flash column chromatography on silica gel, eluting with methanol/methylene chloride (1:9), to provide 2-methyl-4-{1-methyl-1-[2-(4-trifluoromethylphenyl)benzooxazol-7-yl]ethylsulfanyl}phenoxyacetic acid (Example 75) as a white solid (78 mg, 75%) as a white solid: mp: 131-133° C.; $^1$H NMR (CD$_3$OD) δ 8.16 (d, J=8.1 Hz, 2H), 7.79 (d, T=8.1 Hz, 2H), 7.54 (dd, J=7.7, 1.2 Hz, 1H), 7.09-7.26 (m, 2H), 6.67 (dd, J=8.7, 2.2 Hz, 1H), 6.44 (s, 1H), 6.33 (d, J=8.3 Hz, 1H), 4.06 (s, 2H), 1.83 (s, 6H); ESI MS m/z 502 [$C_{26}H_{22}F_3NO_4S$+H]$^+$. HPLC analysis (retention time=18.6 min) shows one peak, with a total purity of 97.8% (area percent).

The following compounds are made in a substantially similar manner:

EXAMPLE 76

3-(2-Methyl-4-{1-methyl-1-[2-(4-trifluoromethylphenyl)benzooxazol-7-yl]ethylsulfanyl}phenyl)propionic Acid

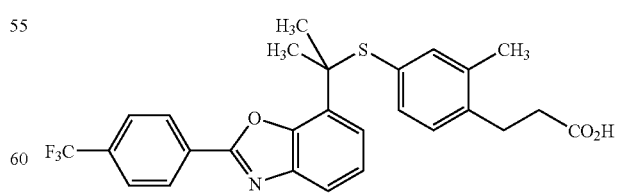

mp: 104-107° C.; $^1$H NMR (CD$_3$OD) δ 8.23 (d, J=8.2 Hz, 2H), 7.89 (d, J=8.2 Hz, 2H), 7.64 (dd, J=7.4, 2.0 Hz, 1H), 7.28-7.39 (m, 2H), 6.75-6.84 (m, 2H), 2.49 (t, J=7.9 Hz, 2H), 2.18 (t, J=7.9 Hz, 2H), 1.97 (s, 6H), 1.95 (s, 3H); ESI MS m/z

EXAMPLE 77

2-Ethyl-4-{1-methyl-1-[2-(4-trifluoromethylphenyl)benzooxazol-7-yl]ethylsulfanyl}phenoxyacetic Acid

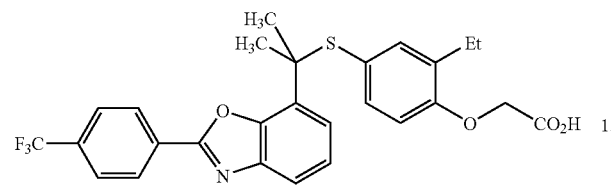

mp: 122-125° C.; $^1$H NMR (CD$_3$OD) δ 8.28 (d, J=8.3 Hz, 2H), 7.90 (d, J=8.3 Hz, 2H), 7.64 (dd, J=7.1 Hz, J=1.2 Hz, 1H), 7.18-7.36 (m, 2H), 6.91 (dd, J=8.3 Hz, J=2.2 Hz, 1H), 6.42-6.56 (m, 2H), 4.24 (s, 2H), 2.33 (q, J=7.4 Hz, 2H), 1.95 (s, 6H), 0.90 (t, J=7.4 Hz, 3H); APCI MS m/z 516 [C$_{27}$H$_{24}$F$_3$NO$_4$S+H]$^+$. HPLC analysis (retention time=20.5 min) shows one peak, with a total purity of 96.3% (area percent).

EXAMPLE 78

6-{1-Methyl-1-[2-(4-trifluoromethylphenyl)benzooxazol-7-yl]ethylsulfanyl}benzo[b]thiophen-3-ylacetic Acid

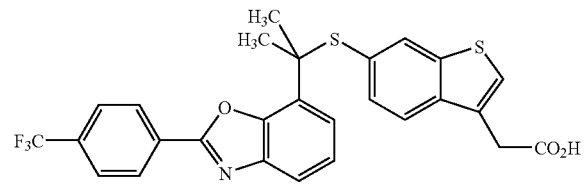

mp: 110-113° C.; $^1$H NMR (CD$_3$OD) δ 8.02 (d, J=8.2 Hz, 2H), 7.78 (d, J=8.2 Hz, 2H), 7.61-7.68 (m, 1H), 7.23-7.45 (m, 5H), 6.90 (dd, J=8.5 Hz, J=8.6 Hz, 1H), 3.47 (s, 2H), 2.00 (s, 6H); APCI MS m/z 528 [C$_{27}$H$_{20}$F$_3$NO$_3$S$_2$+H]$^+$. HPLC analysis (retention time=19.8 min) shows one peak, with a total purity of 96.1% (area percent).

Examples 79-84 below are made employing the procedures of Scheme 14:

Scheme 14:

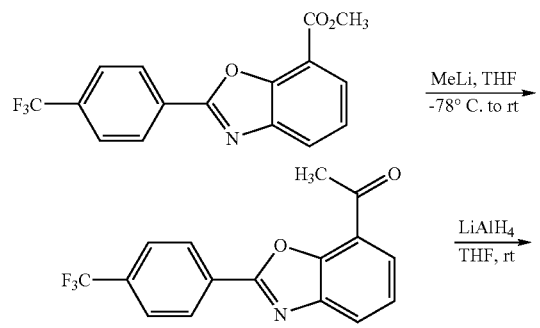

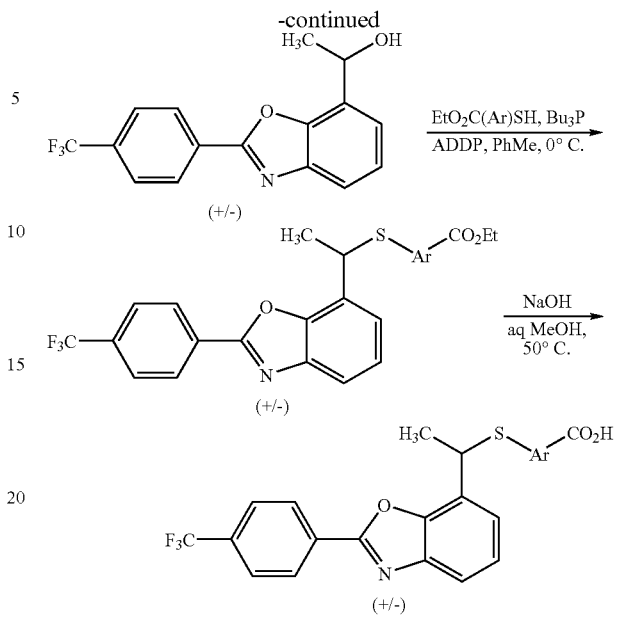

EXAMPLE 79

(+/−)-2-Methyl-4-{1-[2-(4-trifluoromethylphenyl)benzooxazol-7-yl]ethylsulfanyl}phenoxyacetic Acid

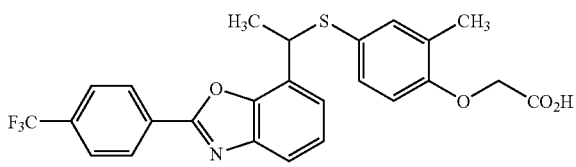

Step 1

(+/−) 1-[2-(4-Trifluoromethylphenyl)benzooxazol-7-yl]ethanol

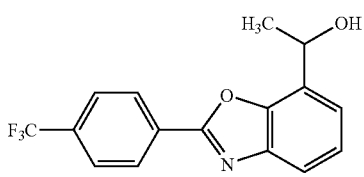

Add a solution of lithium aluminum hydride (30 mL, 30.0 mmol, 1 M in THF) to a solution of 1-[2-(4-trifluoromethylphenyl)benzooxazol-7-yl]ethanone (Example 75, Step 2, 4.0 g, 13.1 mmol) in THF (60 mL) at 0° C. under nitrogen and warm the mixture to room temperature, to stir for a total of 3 h. Dilute the mixture sequentially with water (5 mL), 5 N NaOH (6 mL) and water (12 mL) and extract the mixture with ethyl acetate (5×40 mL). Wash the combined organic extracts with water (30 mL) and brine (30 mL), dry over Na$_2$SO$_4$ and remove the solvents under reduced pressure. Purify the residue by flash column chromatography on silica gel, eluting with ethyl acetate/methylene chloride (1:9), to afford racemic 1-[2-(4-trifluoromethylphenyl)benzooxazol-7-yl]ethanol (Step 1) as a white solid (2.58 g, 64%): $^1$H NMR (CDCl$_3$) δ 8.33 (d, J=8.2 Hz, 2H), 7.76 (d, J=8.2 Hz, 2H), 7.66 (dd, J=7.9, 1.2 Hz, 1H), 7.43 (d, J=7.0 Hz, 1H), 7.33 (t, J=7.7 Hz, 1H), 5.40 (q, J=6.4 Hz, 1H), 2.57 (s, 1H), 1.71 (d, J=6.4 Hz, 3H); APCI MS m/z 308 [C$_{16}$H$_{12}$F$_3$NO$_2$+H]$^+$.

Step 2

(+/−) Ethyl 2-Methyl-4-{1-[2-(4-trifluoromethylphenyl)benzooxazol-7-yl]ethylsulfanyl}phenoxyacetate

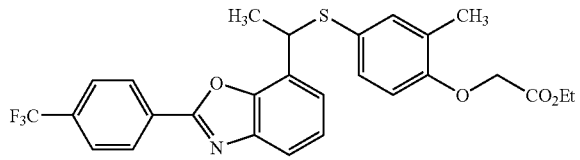

Add anhydrous zinc iodide (153 mg, 0.50 mmol) to a solution of (+/−)1-[2-(4-trifluoromethylphenyl)benzooxazol-7-yl]ethanol (Step 1, amount) in anhydrous methylene chloride (4 mL) at room temperature under nitrogen and then add ethyl 4-mercapto-2-methylphenoxyacetate (136 mg, 0.60 mmol). Stir the mixture for 48 h, dilute with water (5 mL) and remove the solvents under reduced pressure. Purify the residue by flash column chromatography on silica gel, eluting with ethyl acetate/hexanes (1:19) to afford racemic ethyl 2-methyl-4-{1-[2-(4-trifluoromethylphenyl)benzooxazol-7-yl]ethylsulfanyl}phenoxyacetate (Step 2) as a yellow oil (160 mg, 62%): $^1$H NMR (CDCl$_3$) δ 8.27 (d, J=8.2 Hz, 2H), 7.78 (d, J=8.2 Hz, 2H), 7.65 (dd, J=7.7, 1.1 Hz, 1H), 7.17-7.36 (m, 3H), 6.95-7.04 (m, 1H), 6.41 (d, J=8.7 Hz, 1H), 4.67 (q, J=7.1 Hz, 1H), 4.37 (s, 2H), 4.21 (q, J=7.2 Hz, 2H), 2.10 (s, 3H), 1.82 (d, J=7.1 Hz, 3H), 1.26 (t, J=7.2 Hz, 3H); APCI MS m/z 516 [C$_{27}$H$_{24}$F$_3$NO$_4$S+H]$^+$.

(+/−)-2-Methyl-4-{1-[2-(4-trifluoromethylphenyl)benzooxazol-7-yl]ethylsulfanyl}phenoxyacetic Acid

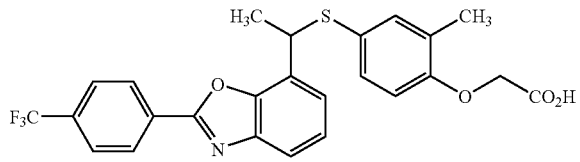

Heat a solution of ethyl 2-methyl-4-{1-[2-(4-trifluoromethylphenyl)benzooxazol-7-yl]ethylsulfanyl}phenoxyacetate (Step 2, 140 mg, 0.27 mmol) in methanol (4 mL) and sodium hydroxide solution (4 mL, 2 N) at 50° C. for 2 h, acidify the cooled mixture to pH 3 with 6 N HCl to pH 3 and extract with ethyl acetate (3×15 mL). Wash the combined organic extracts with water (6 mL) and brine (6 mL), dry over Na$_2$SO$_4$ and remove the solvents under reduced pressure. Purify the residue by flash column chromatography on silica gel, eluting with methanol/methylene chloride (1:19), to provide racemic 2-methyl-4-{1-[2-(4-trifluoromethylphenyl)benzooxazol-7-yl]ethylsulfanyl}phenoxyacetic acid (Example 79) as a white solid (107 mg, 81%): mp 134-138° C.; $^1$H NMR (CD$_3$OD) δ 8.21 (d, J=8.3 Hz, 2H), 7.85 (d, J=8.3 Hz, 2H), 7.57 (dd, J=7.2, 1.9 Hz, 1H), 7.26-7.39 (m, 2H), 6.96 (dd, J=8.5, 2.1 Hz, 1H), 6.83 (d, J=1.7 Hz, 1H), 6.47 (d, J=8.5 Hz, 1H), 4.69 (q, J=7.1 Hz, 1H), 4.21 (s, 2H), 1.97 (s, 3H), 1.79 (d, J=6.2 Hz, 3H); ESI MS m/z 488 [C$_{25}$H$_{20}$F$_3$NO$_4$S+H]$^+$. HPLC analysis (retention time=17.9 min) shows one peak, with a total purity of 96.3% (area percent).

The following compounds are made in a substantially similar manner:

EXAMPLE 80

(+/−)-3-(2-Methyl-4-{1-[2-(4-trifluoromethylphenyl)benzooxazol-7-yl]ethylsulfanyl}phenyl)propionic Acid

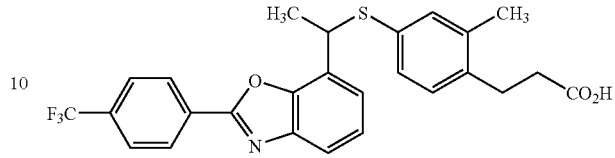

mp: 128-130° C.; $^1$H NMR (CD$_3$OD) δ 8.25 (d, J=8.3 Hz, 2H), 7.89 (d, J=8.3 Hz, 2H), 7.55-7.65 (m, 1H), 7.34-7.42 (m, 2H), 6.97 (d, J=8.2 Hz, 1H), 6.82-6.88 (m, 2H), 4.79 (m, 1H), 2.53 (t, J=7.6 Hz, 2H), 2.19 (t, J=7.6 Hz, 2H), 2.02 (s, 3H), 1.84 (d, J=7.0 Hz, 3H); ESI MS m/z 486 [C$_{26}$H$_{22}$F$_3$NO$_3$S+H]$^+$. HPLC analysis (retention time=18.2 min) shows one peak, with a total purity of 97.0% (area percent).

EXAMPLE 81

(+/−)-2-Ethyl-4-{1-[2-(4-trifluoromethylphenyl)benzooxazol-7-yl]ethylsulfanyl}phenoxyacetic Acid

mp: 172-175° C.; $^1$H NMR (CD$_3$OD) δ 8.26 (d, J=8.2 Hz, 2H), 7.88 (d, J=8.2 Hz, 2H), 7.60 (dd, J=7.3 Hz, J=1.5 Hz, 1H), 7.27-7.41 (m, 2H), 7.08 (dd, J=8.5 Hz, J=1.8 Hz, 1H), 6.76 (d, J=2.1 Hz, 1H), 6.54 (d, J=8.5 Hz, 1H), 4.72 (q, J=7.1 Hz, 1H), 4.22 (s, 2H), 2.39 (q, J=7.5 Hz, 2H), 1.82 (d, J=7.1 Hz, 3H), 0.94 (t, J=7.5 Hz, 3H); ESI MS m/z 502 [C$_{26}$H$_{22}$F$_3$NO$_4$S+H]$^+$. HPLC analysis (retention time=14.2 min) shows one peak, with a total purity of 98.9% (area percent).

EXAMPLE 82

(+/−)-6-{1-[2-(4-Trifluoromethylphenyl)benzooxazol-7-yl]ethylsulfanyl}benzo[b]thiophen-3-ylacetic Acid

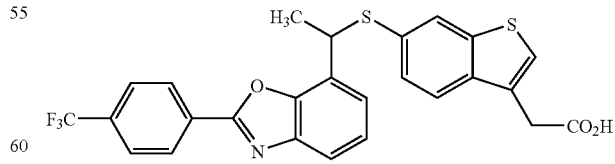

mp: 195-198° C.; $^1$H NMR (CD$_3$OD) δ 8.06 (d, J=8.2 Hz, 2H), 7.79 (d, J=8.2 Hz, 2H), 7.68 (d, J=1.3 Hz, 1H), 7.60 (dd, J=7.0 Hz, J=2.1 Hz, 1H), 7.33-7.50 (m, 3H), 7.28 (s, 1H), 7.17 (dd, J=8.5 Hz, J=1.6 Hz, 1H), 4.90 (m, 1H), 3.51 (s, 2H), 1.88 (d, J=7.2 Hz, 3H); API MS m/z 514 [C$_{26}$H$_{18}$F$_3$NO$_3$S$_2$+H]$^+$.

EXAMPLE 83

(+/−)-3-(2-Methyl-4-{1-[2-(4-trifluoromethylphenyl)benzooxazol-7-yl]ethoxy}phenyl)propionic Acid

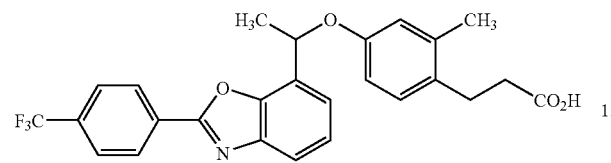

mp: 142-144° C.; $^1$H NMR (DMSO-$d_6$) δ 12.1 (br, s, 1H), 8.45 (d, J=8.1 Hz, 2H), 8.02 (d, J=8.1 Hz, 2H), 7.76 (d, J=7.7 Hz, 1H), 7.35-7.55 (m, 2H), 6.66-7.01 (m, 3H), 5.96 (q, J=6.2 Hz, 1H), 2.67 (t, J=7.7 Hz, 2H), 2.38 (t, J=7.7 Hz, 2H), 2.16 (s, 3H), 1.75 (d, J=6.2 Hz, 3H); ESI MS m/z 470 $[C_{26}H_{22}F_3NO_4+H]^+$. HPLC analysis (retention time=17.8 min) shows one peak, with a total purity of 96.5% (area percent).

EXAMPLE 84

(+/−)-3-(2-Ethyl-4-{1-[2-(4-trifluoromethylphenyl)benzooxazol-7-yl]ethoxy}phenyl)propionic Acid

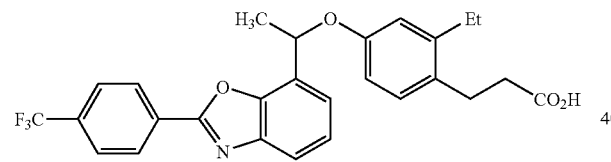

mp: 60-63° C.; $^1$H NMR (CD$_3$OD) δ 8.45 (d, J=8.2 Hz, 2H), 7.91 (d, J=8.2 Hz, 2H), 7.67 (d, J=7.9 Hz, 1H), 7.34-7.51 (m, 2H), 6.96 (d, J=8.5 Hz, 1H), 6.78 (d, J=2.6 Hz, 1H), 6.69 (dd, J=8.3 Hz, J=2.5 Hz, 1H), 5.90 (q, J=6.5 Hz, 1H), 2.79 (t, J=7.8 Hz, 2H), 2.53 (q, J=7.6 Hz, 2H), 2.43 (t, J=7.8 Hz, 2H), 1.81 (d, J=6.5 Hz, 3H), 1.06 (t, J=7.6 Hz, 3H); APCI MS m/z 484 $[C_{27}H_{24}F_3NO_4+H]^+$. HPLC analysis (retention time=18.8 min) shows one peak, with a total purity of 97.7% (area percent).

Examples 85-88 below are made employing the procedures of Scheme 15:

Scheme 15:

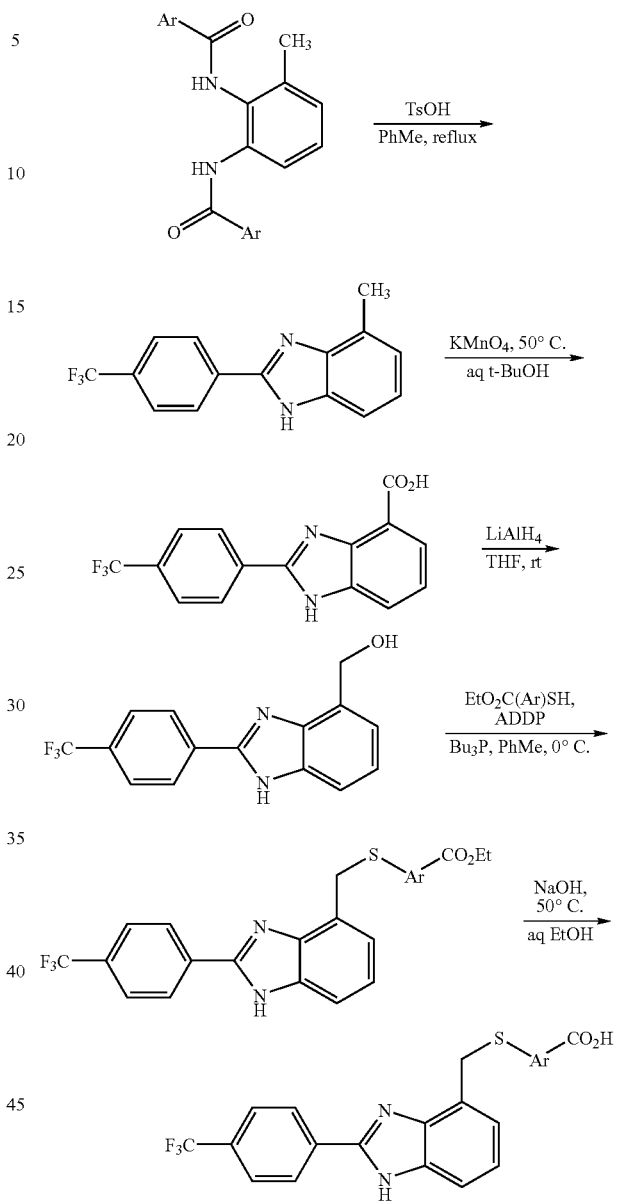

EXAMPLE 85

2-Methyl-4-[2-(4-trifluoromethylphenyl)-1H-benzoimidazol-4-ylmethylsulfanyl]phenoxyacetic Acid

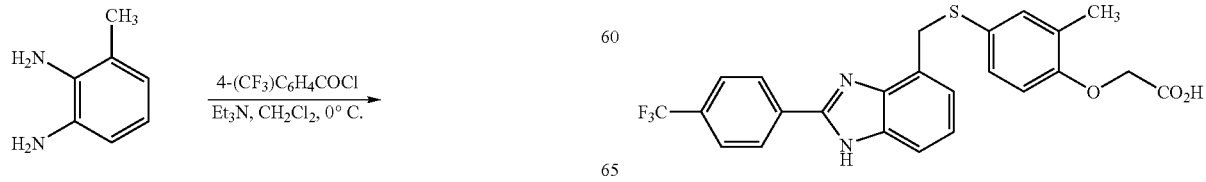

Step 1

N-(2-Trifluoromethylbenzoylamino-6-methylphenyl)-4-trifluoromethylbenzamide

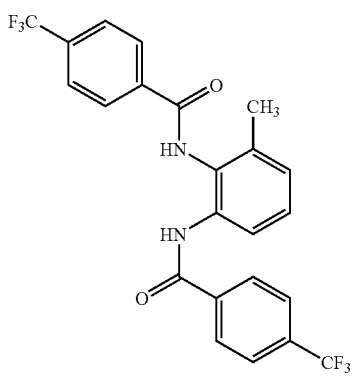

Add 4-(trifluoromethyl)benzoyl chloride (59.7 g, 286 mmol) dropwise to a mixture of commercially available 2,3-diaminotoluene (14.0 g, 114.6 mmol) and triethylamine (29 g, 286.5 mmol) in methylene chloride (1.2 L) at 0° C. under nitrogen, warm to warm to room temperature and stir for 12 h. Remove the solvent under reduced pressure and dilute the residue with ethyl acetate (1 L), wash with saturated aqueous NaHCO$_3$ solution (2×200 mL), 0.5 N HCl (2×200 mL), water (200 mL) and brine (200 mL) and dry over MgSO$_4$. Remove the under reduced pressure and purify the residue by flash column chromatography on silica gel, eluting with hexanes/ethyl acetate (4:1), to afford N-(2-trifluoromethylbenzoylamino-6-methylphenyl)-4-trifluoromethylbenzamide (Step 1) as a yellow solid (33.0 g, 62%): $^1$H NMR (CDCl$_3$) δ 9.32 (s, 1H), 9.08 (s, 1H), 8.06 (d, J=8.1 Hz, 2H), 7.90 (d, J=8.1 Hz, 2H), 7.77 (d, J=8.1 Hz, 2H), 7.69 (d, J=8.1 Hz, 2H), 7.09 (d, J=7.7 Hz, 1H), 6.84-6.96 (m, 2H), 2.34 (s, 3H); ESI MS m/z 467 [C$_{23}$H$_{16}$F$_6$N$_2$O$_2$+H]$^+$.

Step 2

4-Methyl-2-(4-trifluoromethylphenyl)-1H-benzoimidazole

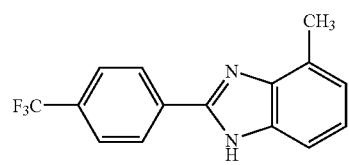

Heat a mixture of N-(2-trifluoromethylbenzoylamino-6-methylphenyl)-4-trifluoromethylbenzamide (Step 1, 24 g, 51.5 mmol) and p-toluenesulfonic acid monohydrate (19.6 g, 102.9 mmol) in o-xylene (300 mL) at reflux under nitrogen for 6 h. Dilute the cooled mixture with ethyl acetate (1.1 L), wash with 0.1 N NaOH (2×200 mL), water (2×100 mL) and brine (100 mL) and dry over Na$_2$SO$_4$. Remove the solvent under reduced pressure and purify the residue by flash column chromatography on silica gel, eluting with hexanes/ethyl acetate (19:1), to afford 4-methyl-2-(4-trifluoromethylphenyl)-1H-benzoimidazole (Step 2) as a white solid (11.0 g, 77%): $^1$H NMR (CDCl$_3$) δ 12.01 (br s, 1H), 8.13 (d, J=8.3 Hz, 2H), 7.51 (d, J=8.3 Hz, 2H), 7.44 (d, J=6.4 Hz, 1H), 7.12 (t, J=7.6 Hz, 1H), 7.07 (d, J=7.4 Hz, 1H), 2.57 (s, 3H); ESI MS m/z 277 [C$_{15}$H$_{11}$F$_3$N$_2$+H]$^+$.

Step 3

2 (4-Trifluoromethylphenyl)-1H-benzoimidazole-4-carboxylic Acid

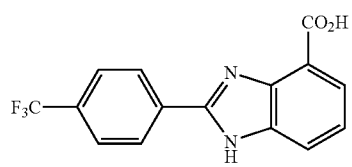

Add a solution of potassium permanganate (27.0 g, 171 mmol) in water (250 mL) in 10 mL portions over 2.5 h to a solution of 4-methyl-2-(4-trifluoromethyl-phenyl)-1H-benzoimidazole (Step 2, 8.0 g, 28.96 mmol) in tert-butanol (150 mL) at 50° C. under nitrogen, at a rate which maintains the reaction temperature between 50-55° C., and stir the mixture for 12 h. Collect the precipitate from the cooled solution by filtration, washing with warm water (2 L, 80° C.), and wash the filtrate with ethyl acetate (3×1 L). Acidify the aqueous layer to pH 2 with concentrated HCl and extract with ethyl acetate (3×250 mL). Dry the combined organic extracts over Na$_2$SO$_4$ and remove the solvent under reduced pressure to afford 2-(4-trifluoromethylphenyl)-1H-benzoimidazole-4-carboxylic acid (Step 3) as a white solid (6.1 g, 68%): $^1$H NMR (DMSO-d$_6$) δ 13.28 (br s, 1H), 12.65 (br s, 1H), 8.55 (d, J=7.5 Hz, 2H), 8.02-7.84 (m, 4H), 7.40-7.32 (m, 1H); ESI MS m/z 307 [C$_{15}$H$_9$F$_3$N$_2$O$_2$+H]$^+$.

Step 4

[2-(4-Trifluoromethylphenyl)-1H-benzoimidazol-4-yl]methanol

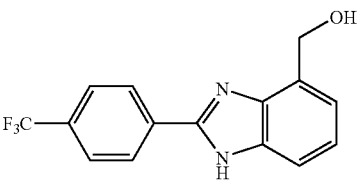

Add a solution of lithium aluminum hydride (40 ml, 40.0 mmol, 1 M solution in THF) dropwise to a solution of 2-(4-trifluoromethylphenyl)-1H-benzoimidazole-4-carboxylic acid (Step 3, 6.1 g, 19.9 mmol) in THF (120 mL) at 0° C. under nitrogen, warm the mixture to room temperature and stir for 2.5 h. Cool the reaction mixture to 0° C. and treat with water (2 mL), 15% NaOH (2 mL) and water (6 mL). Remove the solids by filtration and remove the filtrate solvent under reduced pressure. Purify the residue by flash column chromatography on silica gel, eluting with methylene chloride/ethyl acetate (3:2) to afford [2-(4-trifluoromethylphenyl)-1H-benzoimidazol-4-yl]methanol (Step 4) as a white solid (4.9 g, 84%): $^1$H NMR (CD$_3$OD) δ 8.30 (d, J=8.3 Hz, 2H), 7.84 (d, J=8.3 Hz, 2H), 7.57 (s, 1H), 7.22-7.37 (m, 2H), 5.04 (s, 2H); ESI MS m/z 293 $[C_{15}H_{11}F_3N_2O+H]^+$.

Step 5

Ethyl 2-Methyl-4-[2-(4-trifluoromethylphenyl)-3H-benzoimidazol-4-ylmethylsulfanyl]phenoxyacetate

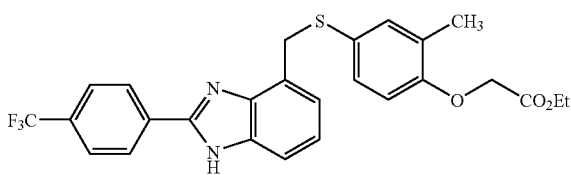

Add tri-n-butylphosphine (0.39 mL, 2.85 mmol) dropwise to a degassed solution of ethyl (4-mercapto-2-methylphenoxy)acetate (644.2 mg, 2.85 mmol) and [2-(4-trifluoromethyl-phenyl)-1H-benzoimidazol-4-yl]methanol (Step 4, 520 mg, 1.78 mmol) in THF (15 mL) at 0° C. under nitrogen, followed by 1,1'-(azodicarbonyl)dipiperidine (ADDP, 718 mg, 2.85 mmol). Warm the mixture to room temperature, stir for 12 h and remove the solvent under reduced pressure. Purify the residue by flash column chromatography on silica gel, eluting with methylene chloride, to afford ethyl 2-methyl-4-[2-(4-trifluoromethylphenyl)-3H-benzoimidazol-4-ylmethylsulfanyl]phenoxyacetate (Step 5) as a white solid (190 mg, 21%): $^1$H NMR (CDCl$_3$) δ 11.40 (br s, 1H), 8.15 (d, J=8.1 Hz, 2H), 7.59 (m, 3H), 7.14 (t, J=7.6 Hz, 1H), 6.70-7.09 (m, 3H), 6.45 (d, J=8.5 Hz, 1H), 4.57 (s, 2H), 4.28 (s, 2H), 4.27 (t, J=7.0 Hz, 2H), 2.09 (s, 3H), 1.30 (t, J=7.0 Hz, 3H); ESI MS m/z 501 $[C_{26}H_{23}F_3N_2O_3S+H]^+$.

2-methyl-4-[2-(4-trifluoromethylphenyl)-3H-benzoimidazol-4-ylmethylsulfanyl]phenoxyacetic Acid

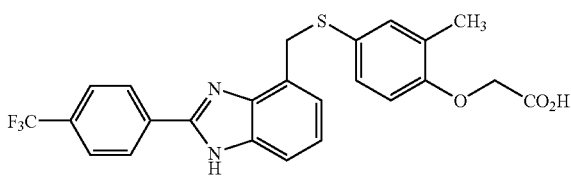

Add a solution of sodium hydroxide NaOH (1.5 mL, 5 N) to a solution of ethyl 2-methyl-4-[2-(4-trifluoromethylphenyl)-3H-benzoimidazol-4-ylmethylsulfanyl]phenoxyacetate (Step 5, 190 mg, 0.38 mmol) in ethanol (2 mL) at room temperature under nitrogen and heat the mixture at 50° C. for 3 h. Remove the solvent under reduced pressure, dilute the residue with water (15 mL) and wash with diethyl ether (2×15 mL). Acidify the aqueous solution to pH 6 with 6 N HCl and extract with ethyl acetate (3×30 mL). Combine the organic extracts, wash with water (10 mL) and brine (10 mL) and dry over MgSO$_4$. Remove the solvent under reduced pressure to afford 2-methyl-4-[2-(4-trifluoromethylphenyl)-3H-benzoimidazol-4-ylmethylsulfanyl]phenoxyacetic acid (Example 85) as a white solid (168 mg, 93%): mp: 238-240° C. (dec); $^1$H NMR (CD$_3$OD) δ 8.26 (d, J=8.2 Hz, 2H), 7.86 (d, J=8.2 Hz, 2H), 7.51 (dd, J=8.2, 0.9 Hz, 1H), 7.16 (t, J=8.2 1H), 6.96-7.10 (m, 3H), 6.62 (d, J=8.2 Hz, 1H), 4.53 (s, 2H), 4.38 (s, 2H), 2.10 (s, 3H); ESI MS m/z 473 $[C_{24}H_{19}F_3N_2O_3S+H]^+$. HPLC analysis (retention time=8.0 min) showed one peak, with a total purity of 97.4% (area percent).

The following compounds are made in a substantially similar manner:

EXAMPLE 86

3-{2-Methyl-4-[2-(4-trifluoromethylphenyl)-1H-benzoimidazol-4-ylmethylsulfanyl]phenyl}propionic Acid

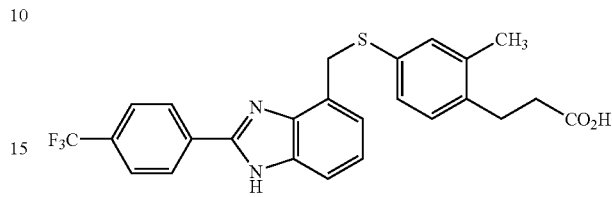

mp: 214-216° C.; $^1$H NMR (acetone-d$_6$) δ 8.45 (d, J=8.2 Hz, 2H), 7.90 (d, J=8.2 Hz, 2H), 7.52 (dd, J=7.0, 1.5 Hz, 1H), 7.06-7.26 (m, 5H), 4.61 (s, 2H), 2.84 (t, J=7.7 Hz, 2H), 2.52 (t, J=7.7 Hz, 2H), 2.25 (s, 3H); ESI MS m/z 471 $[C_{25}H_{21}F_3N_2O_2S+H]^+$. HPLC analysis (retention time=8.1 min) shows one peak, with a total purity of >99% (area percent).

EXAMPLE 87

2-Ethyl-4-[2-(4-trifluoromethylphenyl)-1H-benzoimidazol-4-ylmethylsulfanyl]phenoxyacetic Acid

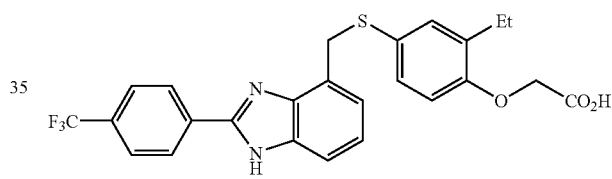

mp: 223° C. (dec); $^1$H NMR (acetone-d$_6$) δ 8.43 (d, J=8.4 Hz, 2H), 7.90 (d, J=8.4 Hz, 2H), 7.51 (d, J=7.9 Hz, 1H), 7.06-7.23 (m, 4H), 6.79 (d, J=8.5 Hz, 1H), 4.69 (s, 2H), 4.52 (s, 2H), 2.58 (q, J=7.5 Hz, 2H), 1.10 (t, J=7.5 Hz, 3H); ESI MS m/z 487 $[C_{25}H_{21}F_3N_2O_3S+H]^+$. HPLC analysis (retention time=8.2 min) shows one peak, with a total purity of 97.3% (area percent).

EXAMPLE 88

3-[2-(4-Trifluoromethylphenyl)-1H-benzoimidazol-4-ylmethylsulfanyl]phenylacetic Acid

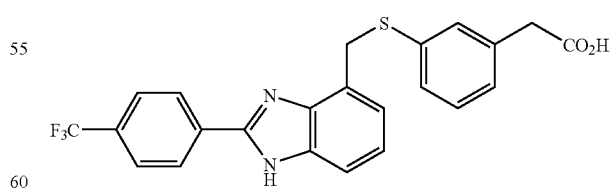

mp: 180-183° C.; $^1$H NMR (acetone-d$_6$) δ 8.47 (d, J=8.1 Hz, 2H), 7.87 (d, J=8.1 Hz, 2H), 7.52 (d, J=7.5 Hz, 1H), 7.42 (s, 1H), 7.06-7.33 (m, 5H), 4.66 (s, 2H), 3.59 (s, 2H); ESI MS m/z 443 $[C_{23}H_{17}F_3N_2O_2S+H]^+$. HPLC analysis (retention time=7.8 min) shows one peak, with a total purity of 95.8% (area percent).

Examples 89-92 below are made employing the procedures of Scheme 16:

Scheme 16:

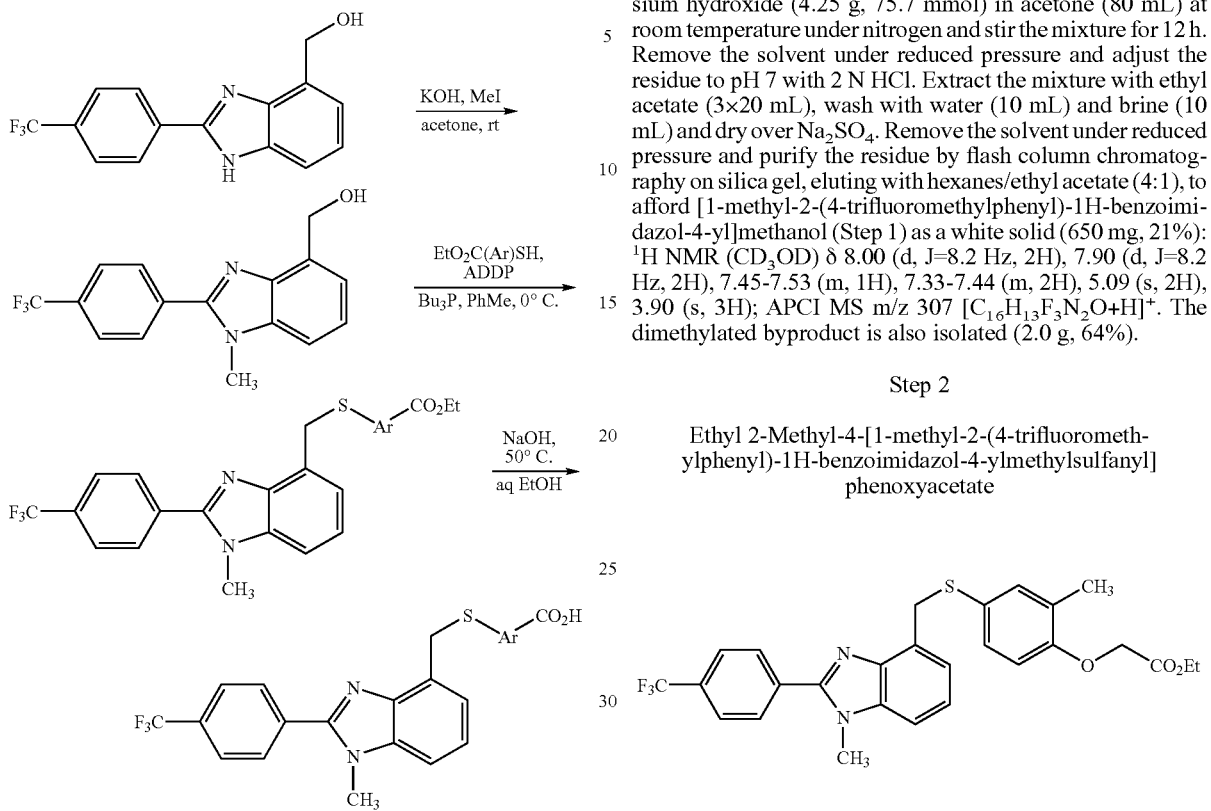

EXAMPLE 89

2-Methyl-4-[1-methyl-2-(4-trifluoromethylphenyl)-1H-benzoimidazol-4-ylmethylsulfanyl]phenoxyacetic Acid

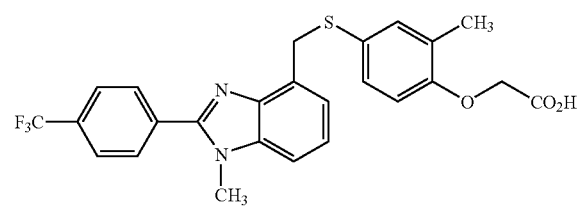

Step 1

[1-Methyl-2-(4-trifluoromethylphenyl)-1H-benzoimidazol-4-yl]methanol

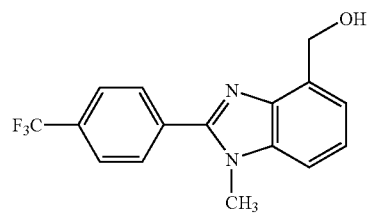

Add iodomethane (17.0 g, 120 mmol) to a solution of [2-(4-trifluoromethylphenyl)-1H-benzoimidazol-4-yl]methanol (Example 85, Step 4, 2.95 g, 10.1 mmol) and potassium hydroxide (4.25 g, 75.7 mmol) in acetone (80 mL) at room temperature under nitrogen and stir the mixture for 12 h. Remove the solvent under reduced pressure and adjust the residue to pH 7 with 2 N HCl. Extract the mixture with ethyl acetate (3×20 mL), wash with water (10 mL) and brine (10 mL) and dry over $Na_2SO_4$. Remove the solvent under reduced pressure and purify the residue by flash column chromatography on silica gel, eluting with hexanes/ethyl acetate (4:1), to afford [1-methyl-2-(4-trifluoromethylphenyl)-1H-benzoimidazol-4-yl]methanol (Step 1) as a white solid (650 mg, 21%): $^1$H NMR ($CD_3OD$) δ 8.00 (d, J=8.2 Hz, 2H), 7.90 (d, J=8.2 Hz, 2H), 7.45-7.53 (m, 1H), 7.33-7.44 (m, 2H), 5.09 (s, 2H), 3.90 (s, 3H); APCI MS m/z 307 $[C_{16}H_{13}F_3N_2O+H]^+$. The dimethylated byproduct is also isolated (2.0 g, 64%).

Step 2

Ethyl 2-Methyl-4-[1-methyl-2-(4-trifluoromethylphenyl)-1H-benzoimidazol-4-ylmethylsulfanyl]phenoxyacetate

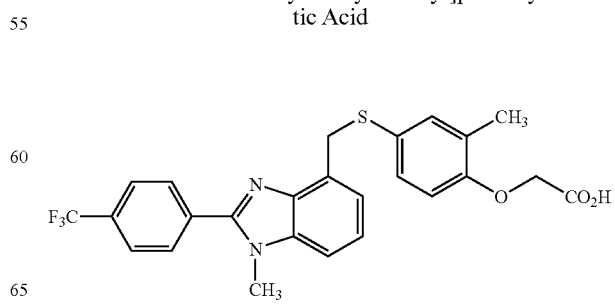

Add tri-n-butylphosphine (0.23 mL, 1.70 mmol) dropwise to a degassed solution of ethyl (4-mercapto-2-methylphenoxy)acetate (307 mg, 1.36 mmol) and [1-methyl-2-(4-trifluoromethylphenyl)-1H-benzoimidazol-4-yl]methanol (Step 1, 260 mg, 0.85 mmol) in THF (15 mL) at 0° C. under nitrogen, followed by 1,1'-(azodicarbonyl)dipiperidine (ADDP, 342 mg, 1.36 mmol). Warm the mixture to room temperature, stir for 12 h and remove the solvent under reduced pressure. Purify the residue by flash column chromatography on silica gel, eluting with hexanes/ethyl acetate (29:1), to afford ethyl 2-methyl-4-[1-methyl-2-(4-trifluoromethylphenyl)-1H-benzoimidazol-4-ylmethylsulfanyl]phenoxyacetate (Step 2) as a white solid (340 mg, 77%): $^1$H NMR ($CDCl_3$) δ 7.90 (d, J=8.4 Hz, 2H), 7.79 (d, J=8.4 Hz, 2H), 7.13-7.32 (m, 5H), 6.57 (d, J=8.3 Hz, 1H), 4.58 (s, 2H), 4.56 (s, 2H), 4.24 (q, J=7.2 Hz, 2H), 3.85 (s, 3H), 2.21 (s, 3H), 1.28 (t, J=7.2 Hz, 3H); ESI MS m/z 515 $[C_{27}H_{25}F_3N_2O_3S+H]^+$/

2-Methyl-4-[1-methyl-2-(4-trifluoromethylphenyl)-1H-benzoimidazol-4-ylmethylsulfanyl]phenoxyacetic Acid Add a solution of aqueous sodium hydroxide (8.0 mL, 2 N) to a solution of ethyl 2-methyl-4-[1-methyl-2-(4-trifluoromethylphenyl)-1H-benzoimidazol-4-ylmethylsulfanyl]phenoxyacetate (Step 2, 300 mg, 0.58 mmol) in ethanol (4 mL) at room temperature under nitrogen and heat the mixture at 50° C. for 3 h. Remove the solvent under reduced pressure, dissolve the residue in water (15 mL) and wash with diethyl ether (2×15 mL). Acidify the aqueous layer to pH 3 with 2 N HCl and extract with ethyl acetate (3×10 mL). Wash the combined organic extracts with water (10 mL) and brine (10 mL) and dry over $Na_2SO_4$. Remove the solvent under reduced pressure and recrystallized the residue from ethyl acetate/hexanes (1:4) to afford 2-methyl-4-[1-methyl-2-(4-trifluoromethylphenyl)-1H-benzoimidazol-4-ylmethylsulfanyl]phenoxyacetic acid (Example 89) as a white solid (250 mg, 88%): mp: 192-194° C.; $^1$H NMR ($CD_3OD$) δ 7.97 (d, J=8.3 Hz, 2H), 7.71 (d, J=8.3 Hz, 2H), 7.45 (d, J=8.3 Hz, 1H), 7.26 (t, J=7.7 Hz, 1H), 7.02-7.13 (m, 3H), 6.64 (d, J=8.1 Hz, 1H), 4.60 (s, 2H), 4.43 (s, 2H), 3.89 (s, 3H), 2.13 (s, 3H); ESI MS m/z 487 $[C_{25}H_{21}F_3N_2O_3S+H]^+$. HPLC analysis (retention time=8.2 min) shows one peak, with a total purity of >99% (area percent).

The following compounds are made in a substantially similar manner:

EXAMPLE 90

3-{2-Methyl-4-[1-methyl-2-(4-trifluoromethylphenyl)-1H-benzoimidazol-4-ylmethylsulfanyl]phenyl}propionic Acid

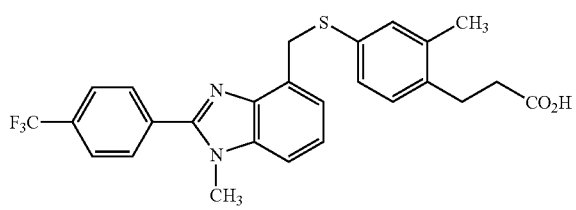

mp: 168-170° C.; $^1$H NMR ($CD_3OD$) δ 8.01 (d, J=8.5 Hz, 2H), 7.93 (d, J=8.5 Hz, 2H), 7.51 (d, J=8.1 Hz, 1H), 7.31 (t, J=7.8 Hz, 1H), 7.20 (d, J=7.4 Hz, 1H), 7.12 (m, 3H), 4.52 (s, 2H), 3.91 (s, 3H), 2.85 (t, J=7.9 Hz, 2H), 2.50 (t, J=7.9 Hz, 2H), 2.21 (s, 3H); APCI MS m/z 485 $[C_{26}H_{23}F_3N_2O_2S+H]^+$. HPLC analysis (retention time=8.2 min) shows one peak, with a total purity of 98.4% (area percent).

EXAMPLE 91

2-Ethyl-4-[1-methyl-2-(4-trifluoromethylphenyl)-1H-benzoimidazol-4-ylmethylsulfanyl]phenoxyacetic Acid

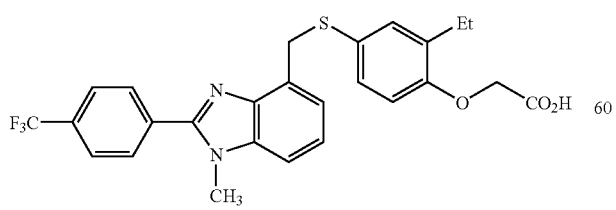

mp: 178-180° C.; $^1$H NMR ($CD_3OD$) δ 7.96 (d, J=8.4 Hz, 2H), 7.89 (d, J=8.4 Hz, 2H), 7.43 (d, J=8.5 Hz, 1H), 7.24 (t, J=7.5 Hz, 1H), 7.02-7.16 (m, 2H), 6.98 (d, J=2.3 Hz, 1H), 6.66 (d, J=8.5 Hz, 1H), 4.48 (s, 2H), 4.41 (s, 2H), 3.86 (s, 3H), 2.55 (q, J=7.3 Hz, 2H), 1.05 (t, J=7.3 Hz, 3H); ESI MS m/z 501 $[C_{26}H_{23}F_3N_2O_3S+H]^+$. HPLC analysis (retention time=8.3 min) shows one peak, with a total purity of >99% (area percent).

EXAMPLE 92

3-[1-Methyl-2-(4-trifluoromethylphenyl)-1H-benzoimidazol-4-ylmethylsulfanyl]phenylacetic Acid

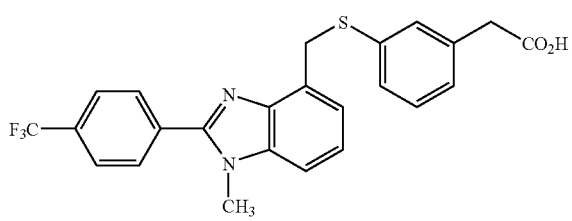

mp: 178-180° C.; $^1$H NMR ($CD_3OD$) δ 8.00 (d, J=8.2 Hz, 2H), 7.91 (d, J=8.2 Hz, 2H), 7.46 (dd, J=7.6, 1.5 Hz, 1H), 7.02-7.29 (m, 6H), 4.58 (s, 2H), 3.88 (s, 3H), 3.49 (s, 2H); ESI MS m/z 457 $[C_{24}H_{19}F_3N_2O_2S+H]^+$. HPLC analysis (retention time=8.0 min) shows one peak, with a total purity of >99% (area percent).

Examples 93-94 below are made employing the procedures of Scheme 17:

Scheme 17:

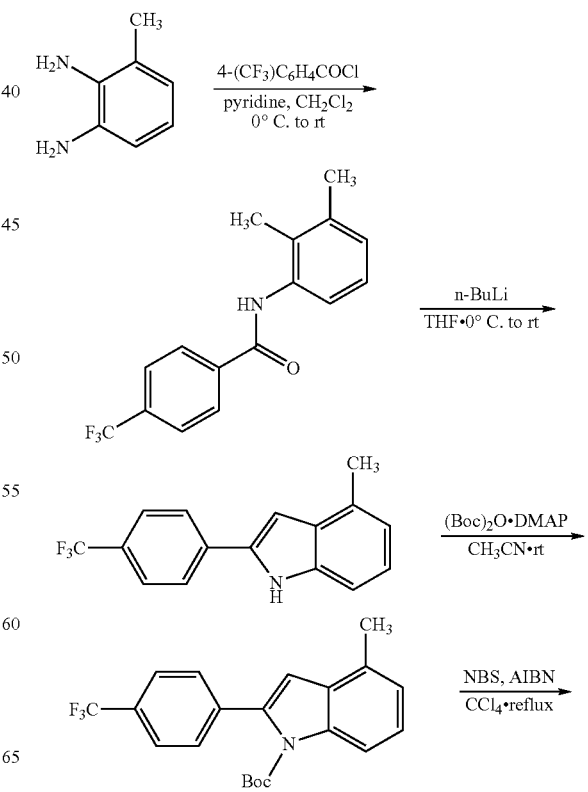

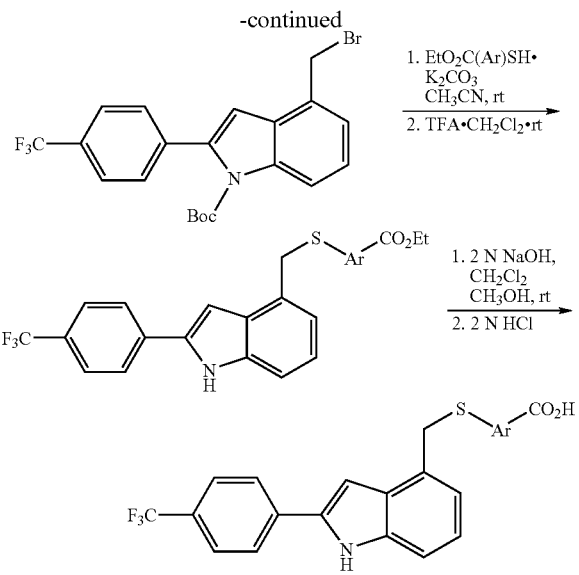

EXAMPLE 93

2-Methyl-4-[2-(4-trifluoromethylphenyl)-1H-indol-4-ylmethylsulfanyl]phenoxyacetic Acid

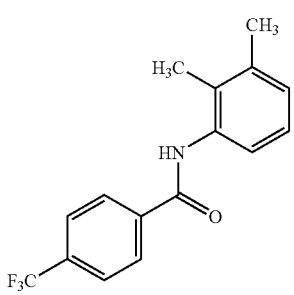

Step 1

N-(2,3-Dimethylphenyl)-4-trifluoromethylbenzamide

Add a solution of commercially available 4-(trifluoromethyl)phenylbenzoyl chloride (7 g, 33.6 mmol) in methylene chloride (35 mL) dropwise over the course of 20 minutes to a solution of commercially available 2,3-dimethylaniline (4 mL, 33.6 mmol) in pyridine (45 mL) at 0° C. under nitrogen, and slowly warm the mixture to room temperature. Stir for 22 h, dilute the reaction mixture with 1 N HCl (600 mL) and extract with chloroform (4×300 mL). Dry the combined organic layers over MgSO$_4$ and remove the solvents under reduced pressure to afford N-(2,3-dimethylphenyl)-4-trifluoromethylbenzamide (Step 1) as an off-white solid (9.21 g, 93%): $^1$H NMR (CDCl$_3$) δ 2.30 (s, 3H), 2.60 (s, 3H), 6.80 (m, 2H), 7.00 (t, 1H), 7.70 (d, 2H), 8.00 (d, 2H), 9.30 (s, 1H).

Step 2

4-Methyl-2-(4-trifluoromethylphenyl)-1H-indole

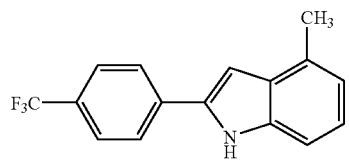

Add n-butyllithium (2.5 M in hexanes, 28 mL, 71.4 mmol) dropwise over 30 min to a suspension of N-(2,3-dimethylphenyl)-4-trifluoromethylbenzamide (Step 1, 4.2 g, 14.2 mmol) in THF (25 mL) at 0° C. under nitrogen, at which point the reagents dissolve. Warm the reaction mixture slowly to room temperature and stir for 16 h, dilute the mixture with 0.5 N HCl (200 mL) and stir for an additional 1 h. Extract the product with ethyl acetate (3×250 mL), dry the combined organic extracts over MgSO$_4$ and remove the solvents under reduced pressure. Purify the residue by flash column chromatography on silica gel, eluting with hexanes/ethyl acetate (95:5), to afford 4-methyl-2-(4-trifluoromethylphenyl)-1H-indole (Step 2) as an off-white solid (2.3 g, 59%): $^1$H NMR (CDCl$_3$) δ 1.60 (s, 3H), 7.00 (m, 2H), 7.20 (t, 1H), 7.30 (m, 2H), 7.70 (d, 2H), 7.80 (d, 2H), 8.30 (br s, 1H).

Step 3 tert-Butyl 4-Methyl-2-(4-trifluoromethylphenyl)indole-1-carboxylate

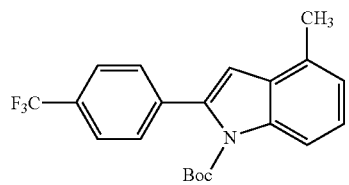

Add DMAP (18 mg, 0.15 mmol) and di-tert-butyl dicarbonate (719 mg, 3.3 mmol) to a solution of 4-methyl-2-(4-trifluoromethylphenyl)-1H-indole (Step 2, 2.3 g, 8.3 mmol) in acetonitrile (7 mL) at room temperature under nitrogen and stir for 21 h. Add additional di-tert-butyl dicarbonate (150 mg, 0.68 mmol), stir for an additional 7 h and remove the solvents under reduced pressure. Dissolve the residue in ethyl acetate (200 mL), wash with 1 N HCl (100 mL) and brine (100 mL) and dry over MgSO$_4$. Remove the solvents under reduced pressure to afford tert-butyl 4-methyl-2-(4-trifluoromethylphenyl)indole-1-carboxylate (Step 3) as an off-white solid (1.2 g, >99%): $^1$H NMR (CDCl$_3$) δ 1.30 (s, 9H), 2.50 (s, 3H), 6.60 (s, 1H), 7.10 (d, 1H), 7.30 (t, 1H) 7.60 (d, 2H), 7.80 (d, 2H), 8.00 (d, 1H).

Step 4 tert-Butyl 4-Bromomethyl-2-(4-trifluoromethylphenyl)indole-1-carboxylate

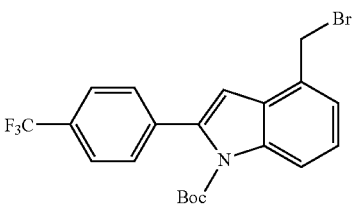

Add 2,2'-azobisisobutyronitrile (AIBN, 30 mg, 0.18 mmol) and N-bromosuccinimide (630 mg, 3.5 mmol) and to a solution of tert-butyl 4-methyl-2-(4-trifluoromethylphenyl) indole-1-carboxylate (Step 3, 1.2 g, 3.2 mmol) in carbon tetrachloride (15 mL) at reflux under nitrogen and stir for 30 min. Add additional 2,2'-azobisisobutyronitrile (30 mg, 0.18 mmol) stir for 30 min, and add additional 2,2'-azobisisobutyronitrile (30 mg, 0.18 mmol). Stir at reflux for 2 h, cool the reaction mixture to room temperature and remove the solids by vacuum filtration. Dilute the filtrate with water (150 mL) and extract with chloroform (2×250 mL). Dry the combined organic extracts over MgSO$_4$ and remove the solvents under reduced pressure to afford tert-butyl 4-bromomethyl-2-(4-trifluoromethylphenylindole-1-carboxylate (Step 4) as a yellow oil (1.4 g, 96%): $^1$H NMR (CDCl$_3$) δ 1.30 (s, 9H), 4.70 (s, 2H), 6.70 (s, 1H), 7.30 (m, 2H), 7.50 (d, 2H), 7.70 (d, 2H), 8.20 (d, 1H).

Step 5

Ethyl 2-Methyl-4-[2-(4-trifluoromethylphenyl)-1H-indol-4-ylmethylsulfanyl]phenoxyacetate

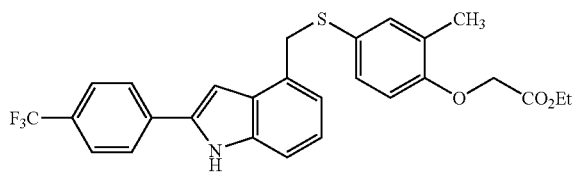

Add potassium carbonate (350 mg, 2.5 mmol) to a solution of tert-butyl 4-bromomethyl-2-(4-trifluoromethylphenyl)indole-1-carboxylate (Step 4, 450 mg, 1 mmol) and ethyl 4-mercapto-2-methylphenoxyacetate (271 mg, 1.2 mmol) in acetonitrile (7 mL) at room temperature under nitrogen and stir for 19 h. Dilute the reaction mixture with water (150 mL) and extract with chloroform (2×200 mL). Dry the combined organic layers over MgSO$_4$ and remove the solvents under reduced pressure. Dissolve the crude product in methylene chloride (8 mL), treat the solution with trifluoroacetic acid (4 mL) dropwise at room temperature and stir for 1.5 h. Dilute the mixture with saturated aqueous NaHCO$_3$ solution (100 mL) and water (100 mL) and extract with methylene chloride (3×100 mL). Dry the combined organic layers over MgSO$_4$, remove the solvents under reduced pressure and purify the residue by flash column chromatography on silica gel, eluting with hexanes/ethyl acetate (9:1), to afford ethyl 2-methyl L-4-[2-(4-trifluoromethylphenyl)-1H-indol-4-ylmethylsulfanyl]phenoxyacetate (Step 5) as a clear oil (200 mg, 40%): $^1$H NMR (CDCl$_3$) δ 1.30 (t, 3H), 2.20 (s, 3H), 4.20 (q, 2H), 4.30 (s, 2H), 4.50 (s, 2H), 6.60 (d, 1H), 7.00 (m, 2H), 7.10 (m, 3H), 7.30 (d, 1H), 7.70 (d, 2H), 7.80 (d, 2H), 8.40 (br s, 1H).

2-Methyl-4-[2-(4-trifluoromethylphenyl)-1H-indol-4-ylmethylsulfanyl]phenoxyacetic Acid

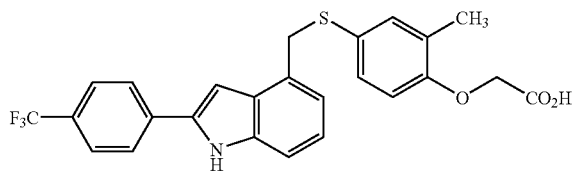

Add a solution of sodium hydroxide (180 mg, 4.2 mmol) in water (3 mL) to a solution of ethyl 2-methyl-4-[2-(4-trifluoromethylphenyl)-1H-indol-4-ylmethylsulfanyl]phenoxyacetate (Step 5, 200 mg, 0.4 mmol) in methylene chloride (5 mL) and methanol (5 mL) at room temperature under nitrogen and stir for 45 min. Dilute the reaction mixture with water (15 mL) and remove the organic solvents under reduced pressure. Acidify the reaction mixture to pH 1 with 1 N HCl, collect the resulting solids by vacuum filtration and wash with water (15 mL) and hexanes (10 mL) to afford 2-methyl-4-[2-(4-trifluoromethylphenyl)-1H-indol-4-ylmethylsulfanyl] phenoxyacetic acid (Example 93) as brown/green solids (89 mg, 47%): mp 85-88° C.; $^1$H NMR (CDCl$_3$) δ 2.20 (s, 3H), 4.30 (s, 2H), 4.60 (s, 2H), 6.60 (d, 1H), 6.90 (m, 2H), 7.10 (t, 1H), 7.20 (m, NH), 7.30 (d, 1H), 7.60 (d, 2H), 7.90 (d, 2H), 10.90 (br s, 1H); APCI MS m/z 470 [C$_{25}$H$_{20}$F$_3$NO$_3$S–H]$^-$. HPLC analysis (retention time=12.1 min) shows one peak, with a total purity of 97.4% (area percent).

The following compound is made in a substantially similar manner:

EXAMPLE 94

2-Ethyl-4-[2-(4-trifluoromethylphenyl)-1H-indol-4-ylmethylsulfanyl]phenoxyacetic Acid

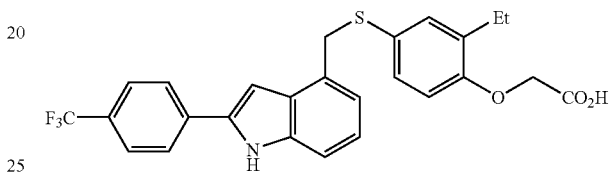

mp 174-176° C.; $^1$H NMR (CDCl$_3$) δ 1.10 (t, 3H), 2.60 (q, 2H), 4.30 (s, 2H), 4.50 (s, 2H), 6.60 (d, 1H), 6.90 (m, 2H), 7.10 (t, 1H), 7.20 (m, 2H), 7.30 (d, 1H), 7.60 (d, 2H), 7.80 (d, 2H); APCI MS m/z 484 [C$_{26}$H$_{22}$F$_3$NO$_3$S–H]$^-$. HPLC analysis (retention time=12.7 min) shows one peak, with a total purity of 98.0% (area percent).

Examples 95-99 below are made employing the procedures of Scheme 18:

Scheme 18:

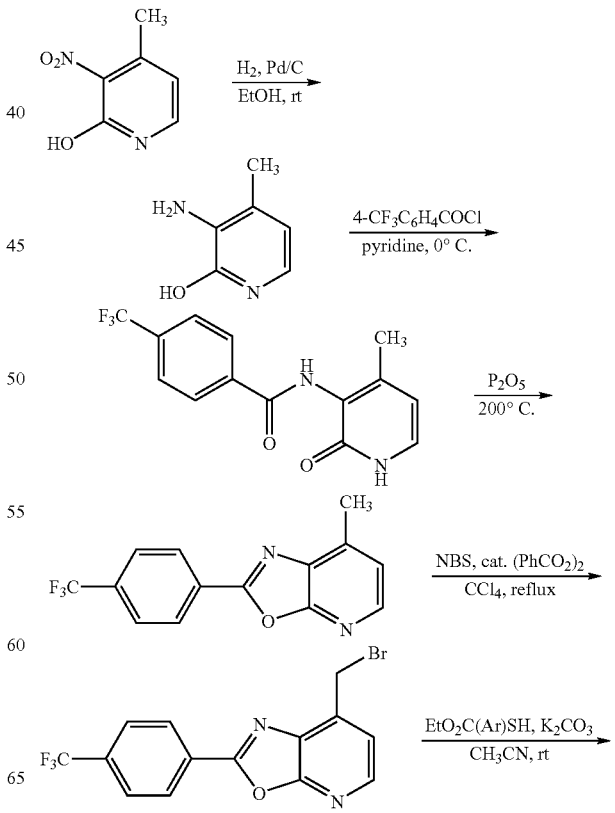

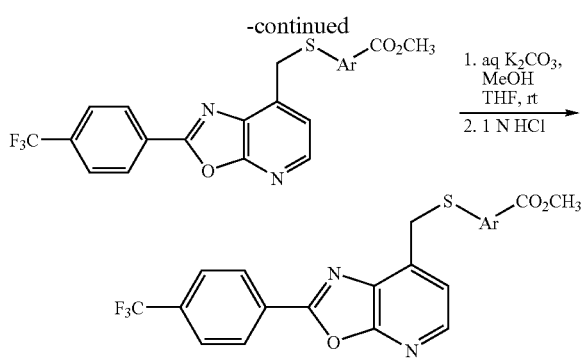

EXAMPLE 95

2-Methyl-4-[2-(4-trifluoromethylphenyl)oxazolo[5,4-b]pyridine-7-ylmethylsulfanyl]phenoxyacetic Acid

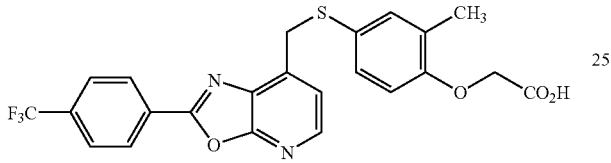

Step 1

3-Amino-4-methylpyridin-2-ol

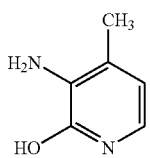

Shake a suspension of commercially available 2-hydroxy-4-methoxy-3-nitrophenol (5 g, 32.4 mmol) and 10% palladium on carbon (300 mg) in ethanol (170 mL) at room temperature under hydrogen (13 psi) in a Parr bottle for 18 h. Filter the mixture through a short plug of celite, eluting with ethanol, and remove the solvents under reduced pressure to afford 2-amino-4-methylpyridin-2-ol (Step 1) as an off-white solid (4.16 g, >99%): $^1$H NMR (CDCl$_3$) δ 2.00 (s, 3H), 4.00 (br s, 2H), 6.00 (d, 1H), 6.70 (d, 1H).

Step 2

N-(2-Hydroxy-4-methylpyridin-3-yl)-4-trifluoromethylbenzamide

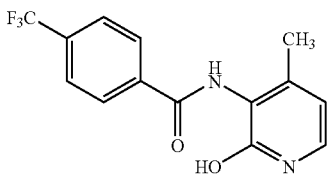

Add a solution of 4-(trifluoromethyl)benzoyl chloride (4.8 mL, 32 mmol) in methylene chloride (30 mL) dropwise to a solution of 2-amino-4-methylpyridin-2-ol (Step 1, 4 g, 32 mmol) in pyridine (60 mL) at 0° C. under nitrogen over the course of 10 min, warm to room temperature and stir for 16 h. Treat the mixture with 1 N HCl (200 mL), stir for 20 min, dilute with 1 N HCl (400 mL) and extract with chloroform/isopropanol (3:1, 3×600 mL). Combine the organic extracts, remove the solvents under reduced pressure and collect the solids by vacuum filtration to afford N-(2-hydroxy-4-methylpyridin-3-yl)-4-trifluoromethylbenzamide (Step 2) as a white solid (5.57 g, 58%): $^1$H NMR (CDCl$_3$) δ 2.00 (s, 3H), 6.10 (d, 1H), 7.20 (d, 1H), 7.90 (d, 2H), 8.20 (d, 2H), 9.70 (br s, 1H).

Step 3

7-Methyl-2-(4-trifluoromethylphenyl)oxazolo[5,4-b]pyridine

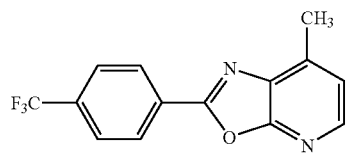

Heat a mixture of N-(2-hydroxy-4-methylpyridin-3-yl)-4-trifluoromethylbenzamide (Step 2, 6.5 g, 21.9 mmol) and phosphorous pentoxide (2.4 g, 17.5 mmol) at 200° C. under nitrogen for 45 min, and dilute the cooled mixture with water (40 mL). Collect the solids by vacuum filtration and wash with water (20 mL) to afford 7-methyl-2-(4-trifluoromethylphenyl)oxazolo[5,4-b]pyridine as an off-white solid (6.6 g, >99%): $^1$H NMR (DMSO-d$_6$) δ 2.70 (s, 3H), 7.40 (d, 1H), 8.00 (d, 2H), 8.30 (d, 1H), 8.40 (d, 2H); APCI MS m/z 279 [C$_{14}$H$_9$F$_3$N$_2$O+H]$^+$.

Step 4

7-Bromomethyl-2-(4-trifluoromethylphenyl)oxazolo[5,4-b]pyridine

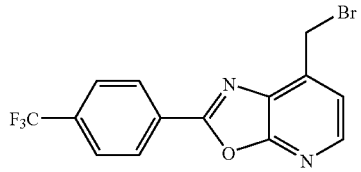

Add N-bromosuccinimide (4.5 g, 25.4 mmol) and benzoyl peroxide (200 mg, 0.8 mmol) to a solution of 7-methyl-2-(4-trifluoromethylphenyl)oxazolo[5,4-b]pyridine (Step 3, 6.73 g, 24.2 mmol) in carbon tetrachloride (200 mL) at room temperature under nitrogen and heat the mixture at reflux for 17 h. Dilute the cooled mixture with water (400 mL) and extract with chloroform (400 mL). Back-extract the aqueous phase with chloroform (400 mL) and wash the combined organic extracts with 1 N NaOH (300 mL), dry over MgSO$_4$ and Na$_2$SO$_4$ and remove the solvents under reduced pressure. Dissolve the crude product in carbon tetrachloride (200 mL), treat the mixture with N-bromosuccinimide (2 g, 11.2 mmol) and benzoyl peroxide (100 g, 0.4 mmol) and heat at reflux for 40 h. Dilute the cooled mixture with water (300 mL) and extract with methylene chloride (2×450 mL). Wash the combined organic extracts with dilute aqueous NaOH (300 mL), dry over MgSO$_4$ and remove the solvents under reduced pressure. Purify the residue by flash column chromatography on silica gel, eluting with hexanes/ethyl acetate (94:6), to afford 7-bromomethyl-2-(4-trifluoromethylphenyl)oxazolo[5,4-b]pyridine (Step 4) as a white solid (1.89 g, 22%): $^1$H NMR (CDCl$_3$) δ 4.90 (s, 2H), 7.40 (d, 1H), 7.80 (d, 2H), 8.40 (d, 1H), 8.50 (d, 2H).

Step 5

Ethyl 2-Methyl-4-[2-(4-trifluoromethylphenyl)oxazolo[5,4-b]pyridine-7-ylmethylsulfanyl]phenoxyacetate

Stir a mixture of 7-bromomethyl-2-(4-trifluoromethylphenyl)oxazolo[5,4-b]pyridine (Step 4, 250 mg, 0.70 mmol), ethyl 4-mercapto-2-methylphenoxyacetate (180 mg, 1 mmol) and potassium carbonate (241 mg) in acetonitrile (3 mL) at room temperature under nitrogen for 40 h. Dilute the mixture with water (100 mL) and extract with chloroform (3×100 mL). Dry the combined organic extracts over Na$_2$SO$_4$, remove the solvents under reduced pressure and purify the residue by flash column chromatography on silica gel, eluting with hexanes/ethyl acetate (92:8), to afford ethyl 2-methyl-4-[2-(4-trifluoromethylphenyl)oxazolo[5,4-b]pyridine-7-ylmethylsulfanyl]phenoxyacetate (Step 5) as a white solid (200 mg, 57%): $^1$H NMR (CDCl$_3$) δ 1.30 (t, 3H), 2.20 (s, 3H), 4.20 (q, 2H), 4.40 (s, 2H), 4.60 (s, 2H), 6.50 (d, 1H), 7.10 (d, 1H), 7.15 (d, 1H), 7.20 (m, 1H), 7.80 (d, 2H), 8.30 (d, 1H), 8.30 (d, 2H).

2-Methyl-4-[2-(4-trifluoromethylphenyl)oxazolo[5,4-b]pyridine-7-ylmethylsulfanyl]phenoxyacetic Acid

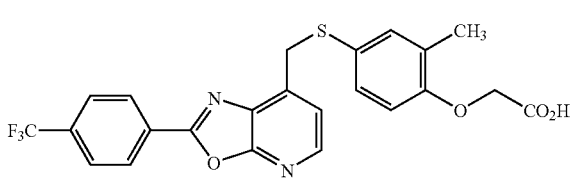

Add a solution of potassium carbonate (300 mg, 2.1 mmol) in water (10 mL) to a solution of ethyl 2-methyl-4-[2-(4-trifluoromethylphenyl)oxazolo[5,4-b]pyridine-7-ylmethylsulfanyl]phenoxyacetate (Step 5, 200 mg, 0.4 mmol) in ethanol (5 mL) and THF (12 mL) at room temperature and stir for 15 h. Add additional potassium carbonate (120 mg, 0.8 mmol) and stir for an additional 4 h. Remove the solvents under reduced pressure, dissolve the residue in water (50 mL) and adjust to pH 2 with 1 N HCl. Collect the solids by vacuum filtration, wash with water and triturate with ethyl acetate/diethyl ether (1:1) to afford 2-methyl-4-[2-(4-trifluoromethyl-phenyl)oxazolo[5,4-b]pyridine-7-ylmethylsulfanyl]phenoxyacetic acid as a white solid (35 mg, 18%); mp 154-157° C.; $^1$H NMR (CDCl$_3$) δ 2.20 (s, 3H), 4.40 (s, 2H), 4.60 (s, 2H), 6.50 (d, 1H), 7.10 (m, 3H), 7.80 (d, 2H), 8.20 (d, 1H), 8.40 (d, 2H); APCI MS m/z 473 [C$_{23}$H$_{17}$F$_3$N$_2$O$_4$S−H]$^-$. HPLC analysis (retention time=11.9 min) shows one peak, with a total purity of 95.4% (area percent).

The following compounds are made in a substantially similar manner:

EXAMPLE 96

3-{2-Methyl-4-[2-(4-trifluoromethylphenyl)oxazolo[5,4-b]pyridin-7-ylmethylsulfanyl]phenyl}propionic Acid

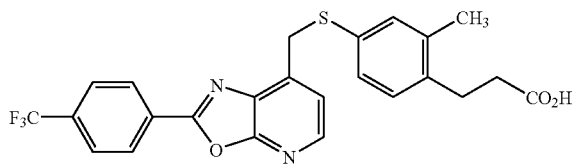

mp >260° C. (dec); $^1$H NMR (DMSO-d$_6$) δ 2.20 (m, 2H), 2.60 (s, 3H), 2.70 (m, 2H), 4.60 (s, 2H), 7.00 (m, 3H), 7.30 (m, 1H), 8.00 (m, 2H), 8.30 (m, 1H), 8.40 (m, 2H); APCI MS m/z 471 [C$_{24}$H$_{19}$F$_3$N$_2$O$_3$S−H]$^-$. HPLC analysis (retention time=12.2 min) shows one peak, with a total purity of >99% (area percent).

EXAMPLE 97

2-Ethyl-4-[2-(4-trifluoromethylphenyl)oxazolo[5,4-b]pyridin-7-ylmethylsulfanyl]phenoxyacetic Acid

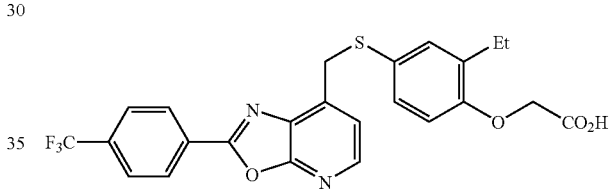

mp 59-62° C.; $^1$H NMR (CDCl$_3$) δ 1.10 (t, 3H), 2.60 (q, 2H), 4.30 (s, 2H), 4.60 (s, 2H), 6.50 (d, 1H), 7.10 (m, 3H), 7.70 (d, 2H), 8.30 (d, 1H), 8.40 (d, 2H); APCI MS m/z 487 [C$_{24}$H$_{19}$F$_3$N$_2$O$_4$S−H]$^-$. HPLC analysis (retention time=12.4 min) shows one peak, with a total purity of 98.6% (area percent).

EXAMPLE 98

6-[2-(4-Trifluoromethylphenyl)oxazolo[5,4-b]pyridine-7-ylmethylsulfanyl]benzo[b]thiophen-3-ylacetic Acid

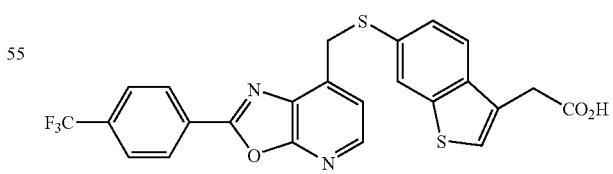

mp 203-205° C.; $^1$H NMR (DMSO-d$_6$) δ 3.74 (s, 2H), 4.66 (s, 2H), 7.35-7.47 (m, 2H), 7.51 (s, 1H), 7.67 (d, 1H), 7.98 (d, 2H), 8.05 (d, 1H), 8.32 (d, 2H), 8.34 (s, 1H); APCI MS m/z 499 [C$_{24}$H$_{15}$F$_3$N$_2$O$_3$S$_2$−H]$^-$. HPLC analysis (retention time=12.16 min) shows one peak, with a total purity of 98.9% (area percent).

EXAMPLE 99

3-[2-(4-Trifluoromethylphenyl)oxazolo[5,4-b]pyridin-7-ylmethylsulfanyl]phenylacetic Acid

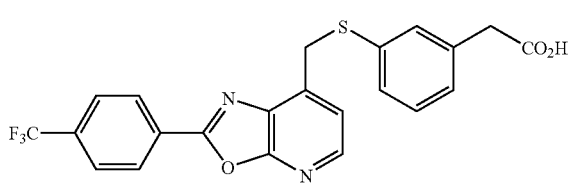

mp 164-166° C.; ¹H NMR (CDCl₃) δ 3.50 (s, 2H), 4.50 (s, 2H), 7.10 (d, 1H), 7.20 (m, 4H), 7.70 (d, 2H), 8.20 (d, 1H), 8.40 (d, 2H); APCI MS m/z 443 [$C_{22}H_{15}F_3N_2O_3S-H$]⁻. HPLC analysis (retention time=9.4 min) shows one peak, with a total purity of 95.7% (area percent).

Examples 100 below are made employing the procedures of Scheme 19:

Scheme 19:

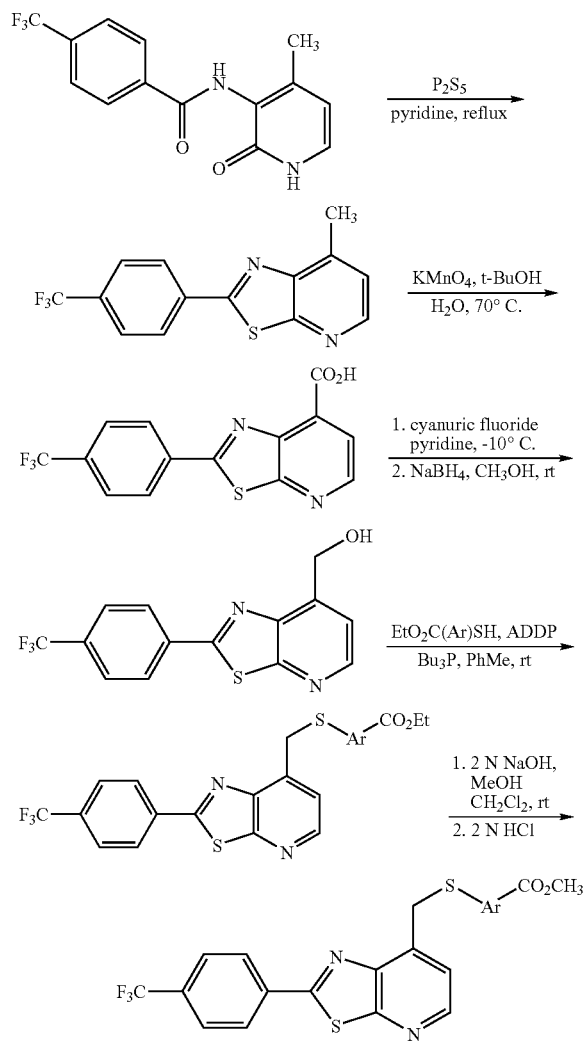

EXAMPLE 100

2-Methyl-4-[2-(4-trifluoromethylphenyl)thiazolo[5,4-b]pyridine-7-ylmethylsulfanyl]phenoxyacetic Acid

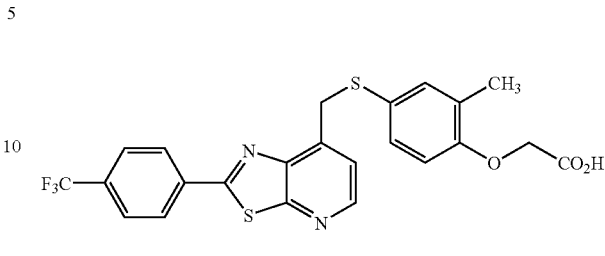

Step 1

7-Methyl-2-(4-trifluoromethyl-phenyl)-thiazolo[5,4-b]pyridine

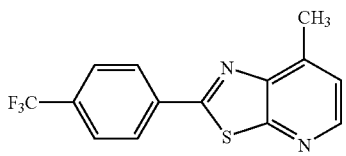

Heat a suspension of N-(2-hydroxy-4-methyl-pyridin-3-yl)-4-trifluoromethyl-benzamide (Step 2, 14.4 g, 48.6 mmol) and phosphorous pentasulfide (21.6 g, 48 mmol) in pyridine (150 mL) at reflux under nitrogen for 18 h, and dilute the cooled mixture with 1 N HCl (1.5 L). Extract the mixture with methylene chloride (4×400 mL) and wash the combined extracts with saturated sodium bicarbonate solution (400 mL). Back-extract the aqueous phase with methylene chloride (500 mL), dry the combined organic extracts over MgSO₄ and remove the solvents under reduced pressure to afford 7-methyl-2-(4-trifluoromethylphenyl)thiazolo[5,4-b]pyridine (Step 1) as an off-white solid (6.5 g, 46%): ¹H NMR (CDCl₃) δ 2.80 (s, 3H), 7.20 (d, 1H), 7.80 (d, 2H), 8.20 (d, 2H), 8.50 (d, 1H).

Step 2

2-(4-Trifluoromethylphenyl)thiazolo[5,4-b]pyridin-7-carboxylic Acid

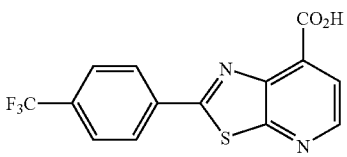

Add potassium permanganate (24 mg, 150 mmol) to a suspension of 7-methyl-2-(4-trifluoromethylphenyl)thiazolo[5,4-b]pyridine (Step 1, 8 g, 27.3 mmol) in tert-butyl alcohol (150 mL) and water (150 mL) at room temperature and heat the mixture at 65° C. for 18 h. Filter the cooled mixture through a short plug of silica gel, eluting with ethyl acetate, and extract the filtrate with water (4×400 mL). Adjust the combined aqueous layers to pH 3 and extract with methylene chloride (2×800 mL). Dry the combined organic extracts over MgSO₄ and remove the solvents under reduced pressure to afford 2-(4-trifluoromethylphenyl)thiazolo[5,4-b]pyridine-7-carboxylic acid (Step 2) as a white solid (3.8 g, 46%): ¹H NMR (CDCl₃) δ 7.80 (d, 2H), 8.20 (m, 3H), 8.90 (m, 1H).

Step 3

[2-(4-Trifluoromethylphenyl)thiazolo[5,4-b]pyridine-7-yl]methanol

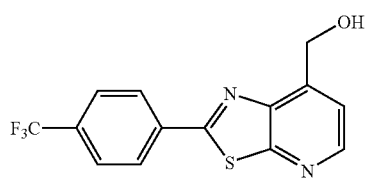

Add cyanuric fluoride (2.2 mL, 24 mmol) to a solution of 2-(4-trifluoromethylphenyl)thiazolo[5,4-b]pyridine-7-carboxylic acid (Step 2, 3.8 g, 11.7 mmol) in methylene chloride (45 mL) and pyridine (3.5 mL) at −10° C. under nitrogen and stir for 75 min. Dilute the mixture with cold water (200 mL) and extract with chloroform (2×150 mL). Dry the combined organic extracts over MgSO$_4$ and remove the solvents under reduced pressure. Dissolve the residue in methylene chloride (10 mL) at room temperature under nitrogen and treat with sodium borohydride (1 g, 24 mmol) and methanol (10 mL) dropwise over the course of 15 min. Stir the mixture for 10 min, neutralize the mixture with 1 N H$_2$SO$_4$ and remove the solvents under reduced pressure. Dilute the residue with methylene chloride (400 mL) and wash with water (300 mL). Back-extract the aqueous phase with methylene chloride (200 mL) and dry the combined organic extracts over MgSO$_4$. Remove the solvents under reduced pressure and purify the residue by flash column chromatography on silica gel, eluting with hexanes/ethyl acetate (7:3), to afford [2-(4-trifluoromethylphenyl)thiazolo[5,4-b]pyridine-7-yl]methanol (Step 3) as a white solid (1.67 g, 50%): $^1$H NMR (CDCl$_3$) δ 5.20 (s, 2H), 7.50 (d, 1H), 7.80 (d, 2H), 8.20 (d, 2H), 8.60 (d, 1H).

Step 4

Ethyl 2-Methyl-4-[2-(4-trifluoromethylphenyl)thiazolo[5,4-b]pyridine-7-ylmethylsulfanyl]phenoxyacetate

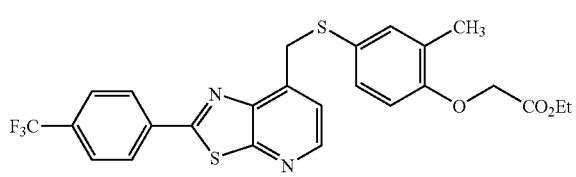

Add tri-n-butylphosphine (0.32 mL) and 1,1'-(azodicarbonyl)dipiperidine (ADDP, 310 mg, 1.3 mmol) to a solution of [2-(4-trifluoromethylphenyl)thiazolo[5,4-b]pyridine-7-yl]methanol (Step 3, 250 mg, 0.8 mmol) and ethyl 4-mercapto-2-methylphenoxyacetate (300 mg, 1.3 mmol) in toluene (9 mL) and DMF (1 mL) at room temperature under nitrogen, stir for 16 h. Dilute the mixture with water (200 mL) and extract with chloroform (3×150 mL). Dry the combined organic extracts over MgSO$_4$, remove the solvents under reduced pressure and purify the residue by flash column chromatography on silica gel, eluting with hexanes/ethyl acetate (92:8), to afford ethyl 2-methyl-4-[2-(4-trifluoromethylphenyl)thiazolo[5,4-b]pyridine-7-ylmethylsulfanyl]phenoxyacetate (Step 4) as a white solid (250 mg, 60%): $^1$H NMR (CDCl$_3$) δ 1.20 (t, 2H), 2.20 (s, 3H), 4.20 (q, 3H), 4.50 (s, 2H), 4.55 (s, 2H), 6.50 (d, 1H), 7.10 (m, 3H), 7.80 (d, 2H), 8.20 (d, 2H), 8.50 (d, 1H).

2-Methyl-4-[2-(4-trifluoromethylphenyl)thiazolo[5,4-b]pyridine-7-ylmethylsulfanyl]phenoxyacetic Acid

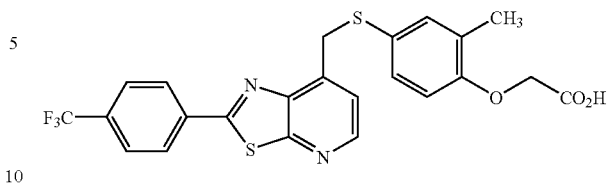

Add a solution of sodium hydroxide (200 mg) in water (2 mL) to a solution of ethyl 2-methyl-4-[2-(4-trifluoromethylphenyl)thiazolo[5,4-b]pyridine-7-ylmethylsulfanyl]phenoxyacetate (Step 4, 250 mg, 0.48 mmol) in methylene chloride (6 mL) and methanol (6 mL) at room temperature under nitrogen and stir the mixture for 45 min. Dilute the mixture with water (15 mL) and remove the solvents under reduced pressure. Dilute the residue with water (10 mL), adjust to pH 1 with 1 N HCl and cool the mixture to 0° C. Collect the solids by vacuum filtration and wash with water (15 mL) and hexanes (20 mL) to afford 2-methyl-4-[2-(4-trifluoromethylphenyl)thiazolo[5,4-b]pyridine-7-ylmethylsulfanyl]phenoxyacetic acid as a white solid (170 mg, 72%): mp 82-85° C.; $^1$H NMR (DMSO-d$_6$) δ 2.00 (s, 3H), 4.50 (s, 2H), 4.60 (s, 2H), 6.60 (d, 1H), 7.10 (m, 2H), 7.40 (d, 1H), 7.90 (d, 2H), 8.30 (d, 2H), 8.60 (d, 1H); APCI MS m/z 489 [C$_{23}$H$_{17}$F$_3$N$_2$O$_3$S$_2$–H]$^-$. HPLC analysis (retention time=13.1 min) shows one peak, with a total purity of 96.3% (area percent).

The following compounds are made in a substantially similar manner:

EXAMPLE 101

3-{2-Methyl-4-[2-(4-trifluoromethylphenyl)thiazolo[5,4-b]pyridin-7-ylmethylsulfanyl]phenyl}propionic Acid

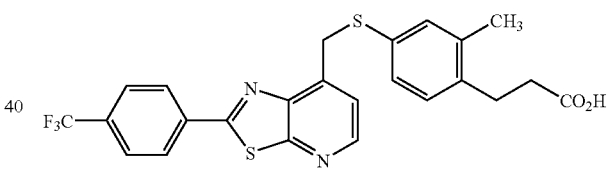

mp 65-70° C.; $^1$H NMR (DMSO-d$_6$) δ 2.10 (s, 3H), 2.30 (t, 2H), 2.60 (t, 2H), 4.70 (s, 2H), 7.00 (d, 1H), 7.10 (m, 2H), 7.50 (d, 1H), 8.00 (d, 2H), 8.30 (d, 2H), 8.60 (d, 1H); APCI MS m/z 487 [C$_{24}$H$_{19}$F$_3$N$_2$O$_2$S$_2$–H]$^-$. HPLC analysis (retention time=13.6 min) shows one peak, with a total purity of 97.8% (area percent).

EXAMPLE 102

2-Ethyl-4-[2-(4-trifluoromethylphenyl)thiazolo[5,4-b]pyridin-7-ylmethylsulfanyl]phenoxyacetic Acid

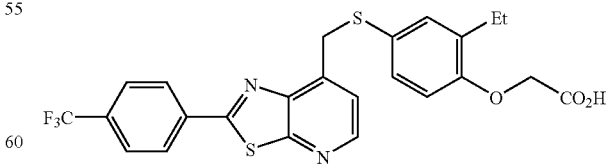

mp 176-178° C.; $^1$H NMR (DMSO-d$_6$) (1.00 (t, 3H), 2.40 (q, 2H), 4.60 (s, 2H), 4.70 (s, 2H), 6.70 (d, 1H), 7.00 (s, 1H), 7.10 (d, 1H), 7.40 (d, 1H), 7.90 (d, 2H), 8.30 (d, 2H), δ 160 (d, 1H); APCI MS m/z 503 [C$_{24}$H$_{19}$F$_3$N$_2$O$_3$S$_2$–H]$^-$. HPLC analysis (retention time=13.9 min) shows one peak, with a total purity of 96.7% (area percent).

Examples 103-107 below are made employing the procedures of Scheme 20:

Scheme 20:

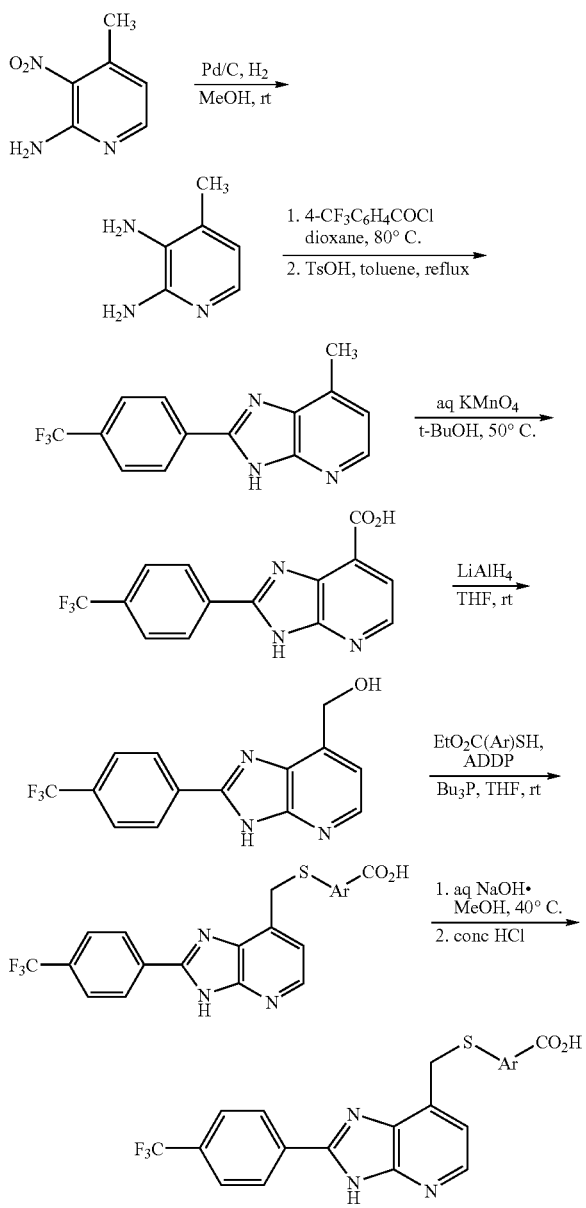

EXAMPLE 103

2-Methyl-4-[2-(4-trifluoromethylphenyl)-3H-imidazo[4,5-b]pyridin-7-ylmethylsulfanyl]phenoxyacetic Acid

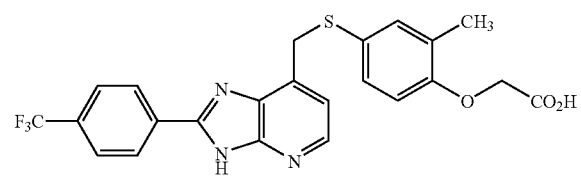

Step 1

4-Methylpyridine-2,3-diamine

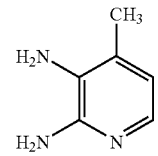

Shake a mixture of commercially available 4-methyl-3-nitro-pyridin-2-ylamine (5.00 g, 32.65 mmol) and 5% palladium on carbon (750 mg) in methanol (200 mL) at room temperature under hydrogen (20 psi) in a Parr bottle for 3.5 h. Filter the mixture through a plug of Celite, eluting with methanol (2×50 mL) and remove the filtrate solvent under reduced pressure to afford 4-methylpyridine-2,3-diamine (Step 1) as yellow solid, which is used in the next step without further purification (3.92 g, 97%): APCI MS m/z 124 $[C_6H_9N_3+H]^+$.

Step 2

7-Methyl-2-(4-trifluoromethylphenyl)-3H-imidazo[4,5-b]pyridine

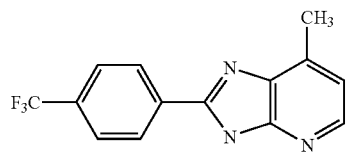

Add 4-(trifluoromethyl)benzoyl chloride (14.58 g, 69.91 mmol) to a solution of 4-methylpyridine-2,3-diamine (Step 1, 7.83 g, 63.58 mmol) in anhydrous dioxane (200 mL) at 0° C. under nitrogen, stir the mixture for 1 h, and heat at 80° C. for 4 h. Remove the solvent under reduced pressure, dissolve the residue in anhydrous toluene (200 mL) and treat with p-toluenesulfonic acid (42.33 g, 222.53 mmol). Heat the mixture at reflux for 36 h and remove the solvent under reduced pressure. Dilute the mixture with ethyl acetate (800 mL) and wash with saturated aqueous NaHCO$_3$. Back-extract the aqueous phase with ethyl acetate (2×400 mL), dry the combined organic extracts over Na$_2$SO$_4$ and remove the solvent under reduced pressure. Purify the residue by flash column chromatography on silica gel, eluting with ethyl acetate/hexanes (1:1), to provide 7-methyl-2-(4-trifluoromethylphenyl)-3H-imidazo[4,5-b]pyridine (Step 2) as white solid (7.05 g, 40%): $^1$H NMR (DMSO-d$_6$) δ 2.63 (s, 3H), 7.10 (m, 1H), 7.95 (d, 2H), 8.25 (d, 1H), 8.47 (d, 1H), 13.20 (bs, 0.3H), 13.65 (bs, 0.7H); APCI MS m/z 278 $[C_{14}H_{10}F_3N_3+H]^+$.

Step 3

2-(4-Trifluoromethylphenyl)-3H-imidazo[4,5-b]pyridine-7-carboxylic Acid

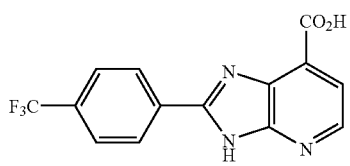

Add a solution of KMnO$_4$ (4.95 g, 31.3 mmol) in water (50 mL) portionwise over 30 min to a suspension of 7-methyl-2-

(4-trifluoromethylphenyl)-3H-imidazo[4,5-b]pyridine (Step 2, 1.66 g, 6.0 mmol) in tert-butanol (50 mL) at room temperature, and heat the mixture at 50° C. for 12 h. Treat the cooled mixture with 1 N HCl (100 mL), methanol (20 mL) and ethyl acetate (200 mL) and stir the mixture for 30 min. Filter the mixture through a short plug of celite, eluting with methanol/ethyl acetate (1:19) and collect the organic phase. Extract the aqueous phase with ethyl acetate (3×200 mL) and wash the combined organic extracts with brine (300 mL), dry over MgSO$_4$ and remove the solvents under reduced pressure to provide 2-(4-trifluoromethylphenyl)-3H-imidazo[4,5-b]pyridine-7-carboxylic acid (Step 3) as an off white solid (1.15 g, 62%): $^1$H NMR (DMSO-d$_6$) δ 7.70 (d, 1H), 7.96 (d, 2H), 8.55-8.70 (m, 3H).

Step 4

[2-(4-Trifluoromethylphenyl)-3H-imidazo[4,5-b]pyridine 7-yl]methanol

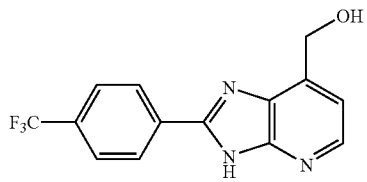

Add 2-(4-trifluoromethylphenyl)-3H-imidazo[4,5-b]pyridine-7-carboxylic acid (Step 3, 1.12 g, 3.65 mmol) portionwise over 15 min to a solution of lithium aluminum hydride (0.275 g, 7.25 mmol) in anhydrous THF (50 mL) at 0° C. under nitrogen, warm the mixture to room temperature and stir for 8 h. Cool the mixture to 0° C. and dilute with water (0.5 mL) and 10% aqueous NaOH solution (0.5 mL). Stir the mixture for 10 min, dilute with THF (200 mL) and remove the solids by vacuum filtration. Extract the solids with hot THF (2×150 mL), combine the THF extracts and remove the solvents under reduced pressure to provide [2-(4-Trifluoromethylphenyl)-3H-imidazo[4,5-b]pyridine 7-yl]methanol (1D) as a pale yellow solid (625 mg, 66%): $^1$H NMR (DMSO-d$_6$) δ 5.00 (bs, 2H), 5.49 (bs, 1H), 7.35 (d, 1H), 7.95 (d, 2H), 8.30-8.60 (m, 3H), 13.10 (bs, 0.3H), 13.76 (bs, 0.7H); APCI MS m/z 294 [C$_{14}$H$_{10}$F$_3$N$_3$O+H]$^+$.

Step 5

Ethyl 2-Methyl-4-[2-(4-trifluoromethylphenyl)-3H-imidazo[4,5-b]pyridin-7-ylmethylsulfanyl]phenoxyacetate

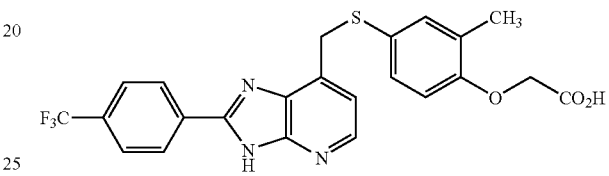

Add tri-n-butylphosphine (0.20 mL, 1.45 mmol) dropwise to a mixture of [2-(4-trifluoromethylphenyl)-3H-imidazo[4,5-b]pyridine 7-yl]methanol (Step 4, 176 mg, 0.600 mmol), ethyl 4-mercapto-2-methylphenoxyacetater (204 mg, 0.902 mmol) and 1,1'-(azodicarbonyl)dipiperidine (ADDP, 303 mg, 1.20 mmol) in anhydrous THF (6.0 mL) at 0° C. under nitrogen. Stir the mixture at 0° C. for 3 h, warm the mixture to room temperature and stir for 12 h. Dilute the mixture with methanol (50 mL), treat with silica gel (2 g) and remove the solvent under reduced pressure. Purify the supported residue by flash column chromatography on silica gel, eluting with ethyl acetate/hexanes (1:1), to provide ethyl 2-methyl-4-[2-(4-trifluoromethylphenyl)-3H-imidazo[4,5-b]pyridin-7-ylmethylsulfanyl]phenoxyacetate (Step 5) as a white solid (116 mg, 39%): $^1$H NMR (DMSO-d$_6$) δ 1.18 (t, 3H), 2.10 (s, 3H), 4.13 (q, 2H), 4.45 (s, 1H), 4.52 (s, 1H), 4.71 (s, 2H), 6.74 (d, 1H), 6.95-7.30 (m, 4H), 7.93-8.05 (m, 2H), 8.20 (m, 1H), 8.43 (d, 2H), 13.12 (s, 0.3H), 13.80 (s, 0.7H); APCI MS m/z 502 [C$_{25}$H$_{22}$F$_3$N$_3$O$_3$S+H]$^+$.

2-Methyl-4-[2-(4-trifluoromethylphenyl)-3H-imidazo[4,5-b]pyridin-7-ylmethylsulfanyl]phenoxyacetic Acid

Add a solution of 1 N sodium hydroxide (1.0 mL, 1.0 mmol) to a suspension of ethyl 2-methyl-4-[2-(4-trifluoromethylphenyl)-3H-imidazo[4,5-b]pyridine-7-ylmethylsulfanyl]phenoxyacetate (Step 5, 110 mg, 0.2:9 mmol) in methanol (4.0 mL) at room temperature under and heat the mixture at 40° C. for 2 h. Cool the mixture to 0° C., dilute with water (10 mL) and treated with 1 N HCl (1.0 mL, 1.0 mmol). Collect the solids and wash with water (5 mL) to provide 2-methyl-4-[2-(4-trifluoromethylphenyl)-3H-imidazo[4,5-b]pyridin-7-ylmethylsulfanyl]phenoxyacetic acid (Example 103) as a white solid (83 mg, 80%): mp 239-241° C.; $^1$H NMR (DMSO-d$_6$) δ 2.11 (s, 3H), 4.50 (s, 2H), 4.63 (s, 2H), 6.73 (d, 1H), 6.95-7.25 (m, 3H), 7.97 (d, 2H), 8.27 (d, 1H), 8.44 (d, 2H), 13.15 (bs, 1H); APCI MS m/z 472 [C$_{23}$H$_{18}$F$_3$N$_3$O$_3$S–H]$^-$. HPLC analysis (retention time=7.68 min) shows one peak, with a total purity of 95.2% (area percent).

The following compounds are made in a substantially similar manner:

EXAMPLE 104

3-{2-Methyl-4-[2-(4-trifluoromethylphenyl)-3H-imidazo[4,5-b]pyridin-7-ylmethylsulfanyl]phenyl}propionic Acid mp 180-182° C.; $^1$H NMR (DMSO-d$_6$) δ 2.18 (s, 3H), 2.41 (t, 2H), 2.71 (t, 2H), 4.59 (s, 2H), 7.05 (d, 1H), 7.13 (d, 1H), 7.20 (m, 2H), 7.97 (d, 2H), 8.29 (d, 1H), 8.47 (d, 2H); APCI MS m/z 470 [C$_{24}$H$_{20}$F$_3$N$_3$O$_2$S–H]$^-$. HPLC analysis (retention time=7.88 min) shows one peak, with a total purity of 96.8% (area percent).

EXAMPLE 105

2-Ethyl-4-[2-(4-trifluoromethylphenyl)-3H-imidazo[4,5-b]pyridin-7-ylmethylsulfanyl]phenoxyacetic Acid

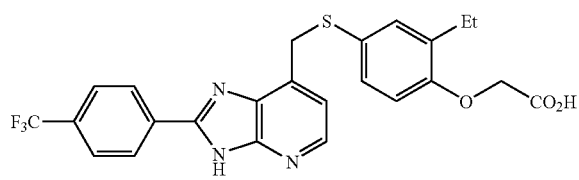

mp 188-190° C.; $^1$H NMR (DMSO-$d_6$) δ 1.00 (t, 3H), 2.49 (q, 2H), 4.51 (s, 2H), 4.61 (s, 2H), 6.75 (d, 1H), 6.95-7.20 (m, 3H), 7.98 (d, 2H), 8.29 (d, 1H), 8.44 (d, 2H), 12.97 (bs, 1H); APCI MS m/z 486 [$C_{24}H_{20}F_3N_3O_3S$–H]$^-$. HPLC analysis (retention time=7.96 min) shows one peak, with a total purity of 98.5% (area percent).

EXAMPLE 106

5-[2-(4-Trifluoromethylphenyl)-3H-imidazo[4,5-b]pyridin-7-ylmethylsulfanyl]benzo[b]thiophen-3-ylacetic Acid

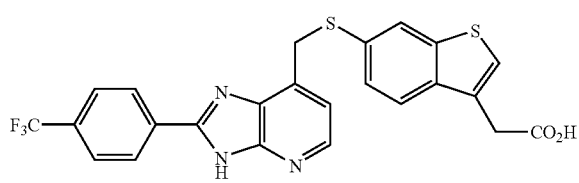

mp 248-250° C.; $^1$H NMR (DMSO-$d_6$) δ 4.71 (s, 2H), 7.21 (d, 1H), 7.41 (d, 1H), 7.52 (s, 1H), 7.68 (d, 1H), 7.96 (d, 2H), 8.10 (d, 1H), 8.28 (d, 1H), 8.46 (d, 2H); APCI MS m/z 498 [$C_{24}H_{16}F_3N_3O_2S_2$–H]$^-$. HPLC analysis (retention time=7.90 min) shows one peak, with a total purity of 97.0% (area percent).

EXAMPLE 107

{3-[2-(4-Trifluoromethylphenyl)-3H-imidazo[4,5-b]pyridin-7-ylmethylsulfanyl]phenylacetic Acid

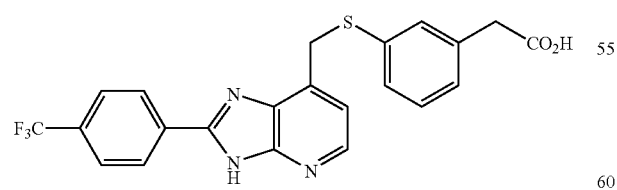

mp 213-215° C.; $^1$H NMR (DMSO-$d_6$) δ 3.51 (s, 2H), 4.60 (s, 1H), 4.65 (s, 1H), 7.04-7.45 (m, 5H), 7.98 (d, 2H), 8.37 (d, 1H), 8.47 (d, 2H), 12.35 (bs, 1H); APCI MS m/z 442 [$C_{22}H_{16}F_3N_3O_2S$–H]$^-$. HPLC analysis (retention time=7.71 min) shows one peak, with a total purity of 96.1% (area percent).

Examples 108-110 below are made employing the procedures of Scheme 21:

Scheme 21:

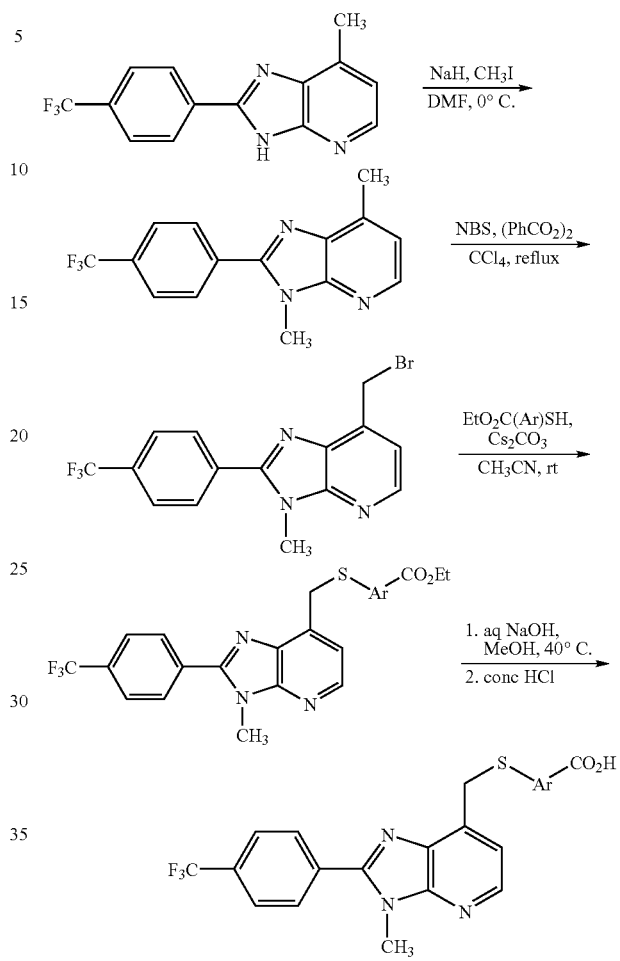

EXAMPLE 108

3-{2-Methyl-4-[3-methyl-2-(4-trifluoromethylphenyl)-3H-imidazo[4,5-b]pyridin-7-ylmethylsulfanyl]phenyl}propionic Acid

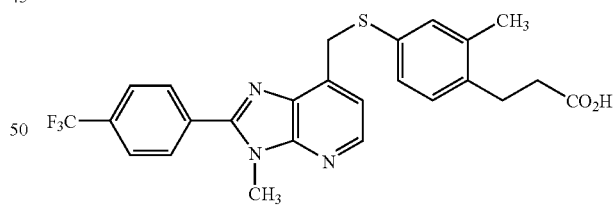

Step 1

3,7-Dimethyl-2-(4-trifluoromethylphenyl)-3H-imidazo[4,5-b]pyridine

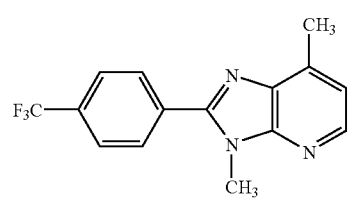

Add sodium hydride (0.572 g, 14.30 mmol, 60% dispersion in mineral oil) to a suspension of 7-methyl-2-(4-trifluoromethylphenyl)-3H-imidazo[4,5-b]pyridine (Example 103, Step 2, 3.05 g, 11.00 mmol) in anhydrous DMF (30 mL) at 0° C. under nitrogen, stir the mixture for 30 min and add iodomethane (1.75 g, 12.33 mmol). Stir the mixture for 4 h, warm to room temperature and stir for 6 h. Dilute the mixture with water (150 mL), extract with ethyl acetate (3×150 mL) and dry the combined organic extracts over $MgSO_4$. Remove the solvents under reduced pressure and purify the residue by flash column chromatography on silica gel, eluting with ethyl acetate/hexanes (6:4), to provide 3,7-dimethyl-2-(4-trifluoromethylphenyl)-3H-imidazo[4,5-b]pyridine (Step 1) as a white solid (765 mg, 24%): $^1$H NMR (DMSO-$d_6$) δ 2.63 (s, 3H), 3.95 (s, 3H), 7.18 (d, 1H), 7.96 (d, 2H), 8.18 (d, 2H), 8.30 (d, 1H).

Step 2

7-Bromomethyl-3-methyl-2-(4-trifluoromethylphenyl)-3H-imidazo[4,5-b]pyridine

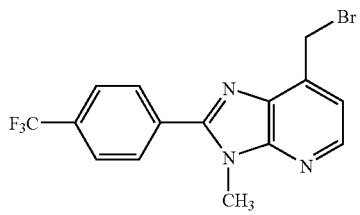

Heat a mixture of 3,7-dimethyl-2-(4-trifluoromethylphenyl)-3H-imidazo[4,5-b]pyridine (Step 1, 489 mg, 1.68 mmol), N-bromosuccinimide (301 mg, 1.69 mmol) and benzoyl peroxide (40 mg, 0.16 mmol) in carbon tetrachloride (200 mL) at reflux under nitrogen for 5 h. Treat the cooled mixture with silica gel (3 g) and remove the solvent under reduced pressure. Purify the residue on support by flash column chromatography on silica gel, eluting with ethyl acetate/hexanes (1:4), to provide 7-bromomethyl-3-methyl-2-(4-trifluoromethylphenyl)-3H-imidazo[4,5-b]pyridine (Step 2) as a white solid (307 mg, 49%): 8H NMR (DMSO-$d_6$) δ 3.98 (s, 3H), 5.03 (s, 2H), 7.44 (d, 1H), 7.99 (d, 2H), 8.20 (d, 2H), 8.43 (d, 1H); APCI MS m/z 370 $[C_{15}H_{11}BrF_3N_3]^+$.

Step 3

Methyl 3-{2-Methyl-4-[3-methyl-2-(4-trifluoromethylphenyl)-3H-imidazo[4,5-b]pyridine-7-ylmethylsulfanyl]phenyl}propionate

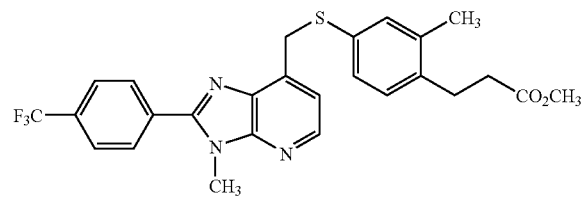

Stir a mixture of 7-bromomethyl-3-methyl-2-(4-trifluoromethylphenyl)-3H-imidazo[4,5-b]pyridine (Step 2, 92 mg, 0.249 mmol), methyl 4-mercapto-2-methylphenylpropionate (79 mg, 0.376 mmol) and cesium carbonate (163 mg, 0.50 mmol) in acetonitrile (7.0 mL) at room temperature under nitrogen for 8 h. Filter the mixture through a short plug of silica gel, eluting with ethyl acetate, and remove the filtrate solvent under reduced pressure. Purify the residue by flash column chromatography on silica gel, eluting with ethyl acetate/hexanes (1:3), to provide methyl 3-{2-methyl-4-[3-methyl-2-(4-trifluoromethylphenyl)-3H-imidazo[4,5-b]pyridine-7-ylmethylsulfanyl]phenyl}propionate (Step 3) as a viscous brown oil (85 mg, 68%): $^1$H NMR (CDCl$_3$) δ 2.23 (s, 3H), 2.53 (t, 2H), 2.87 (t, 2H), 3.67 (s, 3H), 3.98 (s, 3H), 4.58 (s, 2H), 7.00 (d, 1H), 7.10-7.25 (m, 3H), 7.83 (d, 2H), 7.97 (d, 2H), 8.33 (d, 1H); APCI MS m/z 500 $[C_{26}H_{24}F_3N_3O_2S]^+$.

3-{2-Methyl-4-[3-methyl-2-(4-trifluoromethylphenyl)-3H-imidazo[4,5-b]pyridin-7-ylmethylsulfanyl]phenyl}propionic Acid

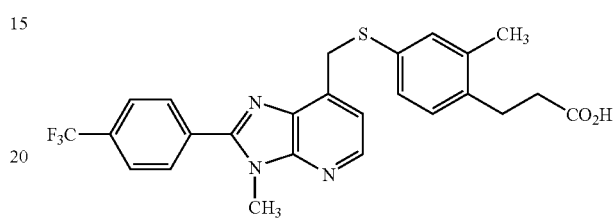

Add a solution of 1 N sodium hydroxide (1.00 mL, 1.00 mmol) to a solution of 3-{2-methyl-4-[3-methyl-2-(4-trifluoromethylphenyl)-3H-imidazo[4,5-b]pyridine-7-ylmethylsulfanyl]phenyl}propionate (Step 3, 80 mg, 0.160 mmol) in methanol (4.0 mL) at room temperature under nitrogen, and heat the mixture at 40° C. for 2.5 h. Cool the mixture to 0° C., dilute with water (5.0 mL) and treating with 1 N HCl (1.00 mL). Collect the solids by vacuum filtration and wash with water to provide 3-{2-methyl-4-[3-methyl-2-(4-trifluoromethylphenyl)-3H-imidazo[4,5-b]pyridin-7-ylmethylsulfanyl]phenyl}propionic acid (Example 108 as a white solid (67 mg, 87%): mp 89-91° C.; $^1$H NMR (DMSO-$d_6$) δ 2.18 (s, 3H), 2.42 (t, 2H), 2.73 (t, 2H), 3.96 (s, 3H), 4.59 (s, 2H), 7.05 (d, 1H), 7.13 (dd, 1H), 7.20 (s, 1H), 7.27 (d, 1H), 7.98 (d, 2H), 8.18 (d, 2H), 8.33 (d, 1H); APCI MS m/z 484 $[C_{25}H_{22}F_3N_3O_2S-H]^-$. HPLC analysis (retention time=9.51 min) shows one peak, with a total purity of 97.2 (area percent).

The following compounds are made in a substantially similar manner:

EXAMPLE 109

2-Ethyl-4-[3-methyl-2-(4-trifluoromethylphenyl)-3H-imidazo[4,5-b]pyridin-7-ylmethylsulfanyl]phenoxyacetic Acid

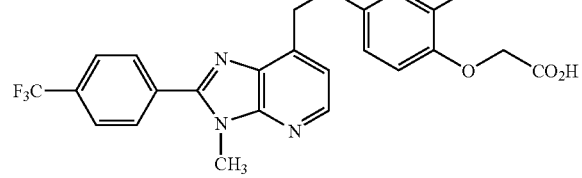

mp 118-120° C.; $^1$H NMR (DMSO-$d_6$) δ 1.00 (t, 3H), 2.50 (q, 2H), 3.94 (s, 3H), 4.49 (s, 2H), 4.64 (s, 2H), 6.75 (d, 1H), 7.11 (d, 1H), 7.15 (d, 1H), 7.18 (d, 1H), 7.97 (d, 2H), 8.14 (d, 2H), 8.32 (d, 1H); APCI ms m/z 500 $[C_{25}H_{22}F_3N_3O_3S-H]^-$. HPLC analysis (retention time=9.59 min) shows one peak, with a total purity of 96.6% (area percent).

EXAMPLE 110

{5-[3-Methyl-2-(4-trifluoromethylphenyl)-3H-imidazo[4,5-b]pyridin-7-ylmethylsulfanyl]benzo[b]thiophen-3-ylacetic Acid

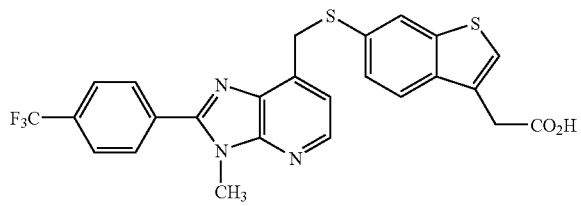

mp 85-87° C.; $^1$H NMR (DMSO-$d_6$) δ 3.79 (s, 2H), 3.94 (s, 3H), 4.69 (s, 2H), 7.29 (d, 1H), 7.40 (dd, 1H), 7.52 (s, 1H), 7.66 (d, 1H), 7.97 (d, 2H), 8.08 (d, 1H), 8.14 (d, 2H), 8.33 (d, 1H), 12.43 (s, 1H); APCI ms m/z 512 [$C_{25}H_{18}F_3N_3O_2S_2-$H]$^-$. HPLC analysis (retention time=9.55 min) shows one peak, with a total purity of 97.6% (area percent).

BIOLOGICAL ASSAYS

Binding and Cotransfection Studies

The in vitro potency of compounds in modulating PPARα receptors are determined by the procedures detailed below. DNA-dependent binding (ABCD binding) is carried out using SPA technology with PPAR receptors. Tritium-labeled PPARα agonists are used as radioligands for generating displacement curves and $IC_{50}$ values with compounds of the invention. Cotransfection assays are carried out in CV-1 cells. The reporter plasmid contained an acylCoA oxidase (AOX) PPRE and TK promoter upstream of the luciferase reporter cDNA. Appropriate PPARs are constitutively expressed using plasmids containing the CMV promoter. For PPARα, interference by endogenous PPARγ in CV-1 cells is an issue. In order to eliminate such interference, a GAL4 chimeric system is used in which the DNA binding domain of the transfected PPAR is replaced by that of GAL4, and the GAL4 response element is utilized in place of the AOX PPRE. Cotransfection efficacy is determined relative to PPARα agonist reference molecules. Efficacies are determined by computer fit to a concentration-response curve, or in some cases at a single high concentration of agonist (10 μM).

These studies are carried out to evaluate the ability of compounds of the invention to bind to and/or activate various nuclear transcription factors, particularly huPPARα ("hu" indicates "human"). These studies provide in vitro data concerning efficacy and selectivity of compounds of the invention. Furthermore, binding and cotransfection data for compounds of the invention are compared with corresponding data for marketed compounds that act on huPPARα.

The binding and cotransfection efficacy values for compounds of the invention which are especially useful for modulating a PPAR receptor, are ≦100 nM and ≧50%, respectively.

Evaluation of Triglyceride Reduction and HDL Cholesterol Elevation in HuapoAI Transgenic Mice Compounds of the present invention are studied for effects upon HDL and triglyceride levels in human apoAI mice. For each compound tested, seven to eight week old male mice, transgenic for human apoAI (C57BL/6-tgn(apoa1)1rub, Jackson Laboratory, Bar Harbor, Me.) are acclimated in individual cages for two weeks with standard chow diet (Purina 5001) and water provided ad libitum. After the acclimation, mice and chow are weighed and assigned to test groups (n=5) with randomization by body weight. Mice are dosed daily by oral gavage for 8 days using a 29 gauge, 1½ inch curved feeding needle (Popper & Sons). The vehicle for the controls, test compounds and the positive control (fenofibrate 100 mg/kg) is 1% carboxymethylcellulose (w/v) with 0.25% tween 80 (w/v). All mice are dosed daily between 6 and 8 a.m. with a dosing volume of 0.2 ml. Prior to termination, animals and diets are weighed and body weight change and food consumption are calculated. Three hours after last dose, mice are euthanized with CO2 and blood is removed (0.5-1.0 ml) by cardiac puncture. After sacrifice, the liver, heart, and epididymal fat pad are excised and weighed. Blood is permitted to clot and serum is separated from the blood by centrifugation.

Cholesterol and triglycerides are measured calorimetrically using commercially prepared reagents (for example, as available from Sigma #339-1000 and Roche #450061 for triglycerides and cholesterol, respectively). The procedures are modified from published work (McGowan M. W. et al., Clin Chem 29:538-542, 1983; Allain C. C. et al., Clin Chem 20:470-475, 1974. Commercially available standards for triglycerides and total cholesterol, respectively, commercial quality control plasma, and samples are measured in duplicate using 200 μl of reagent. An additional aliquot of sample, added to a well containing 200 μl water, provided a blank for each specimen. Plates are incubated at room temperature on a plate shaker and absorbance is read at 500 nm and 540 nm for total cholesterol and triglycerides, respectively. Values for the positive control are always within the expected range and the coefficient of variation for samples is below 10%. All samples from an experiment are assayed at the same time to minimize inter-assay variability.

Serum lipoproteins are separated and cholesterol quantitated by fast protein liquid chromatography (FPLC) coupled to an in line detection system. Samples are applied to a Superose 6 HR size exclusion column (Amersham Pharmacia Biotech) and eluted with phosphate buffered saline-EDTA at 0.5 ml/min. Cholesterol reagent (Roche Diagnostics Chol/HP 704036) at 0.16 ml/min mixed with the column effluent through a T-connection and the mixture passed through a 15 m×0.5 mm id knitted tubing reactor immersed in a 37 C water bath. The colored product produced in the presence of cholesterol is monitored in the flow strem at 505 nm and the analog voltage from the monitor is converted to a digital signal for collection and analysis. The change in voltage corresponding to change in cholesterol concentration is plotted vs time and the area under the curve corresponding to the elution of very low density lipoprotein (VLDL), low density lipoprotein (LDL) and high density lipoprotein (HDL) is calculated using Perkin Elmer Turbochrome software.

Triglyceride Serum Levels in Mice Dosed with a Compound of the Invention is Compared to Mice Receiving the Vehicle to identify compounds which could be particularly useful for lowering triglycerides. Generally, triglyceride decreases of greater than or equal to 30% (thirty percent) compared to control following a 30 mg/kg dose suggests a compound that can be especially useful for lowering triglyceride levels.

The percent increase of HDLc serum levels in mice receiving a compound of the invention is compared to mice receiving vehicle to identify compounds of the invention that could be particularly useful for elevating HDL levels. Generally, and increase of greater than or equal to 25% (twenty five percent) increase in HDLc level following a 30 mg/kg dose suggests a compound that can be especially useful for elevating HDLc levels.

It may be particularly desirable to select compounds of this invention that both lower triglyceride levels and increase HDLc levels. However, compounds that either lower triglyceride levels or increase HDLc levels may be desirable as well.

Evaluation of Glucose Levels in db/db Mice

The effects upon plasma glucose associated with administering various dose levels of different compounds of the present invention and the PPAR gamma agonist rosiglitazone (BRL49653) or the PPAR alpha agonist fenofibrate, and the control, to male db/db mice, are studied.

Five week old male diabetic (db/db) mice [for example, C57BlKs/j-m+/+Lepr(db), Jackson Laboratory, Bar Harbor, Me.] or lean littermates are housed 6 per cage with food and water available at all times. After an acclimation period of 2 weeks, animals are individually identified by ear notches, weighed, and bled via the tail vein for determination of initial glucose levels. Blood is collected (100 µl) from unfasted animals by wrapping each mouse in a towel, cutting the tip of the tail with a scalpel, and milking blood from the tail into a heparinized capillary tube. Sample is discharged into a heparinized microtainer with gel separator and retained on ice. Plasma is obtained after centrifugation at 4° C. and glucose measured immediately. Remaining plasma is frozen until the completion of the experiment, when glucose and triglycerides are assayed in all samples. Animals are grouped based on initial glucose levels and body weights. Beginning the following morning, mice are dosed daily by oral gavage for 7 days. Treatments are test compounds (30 mg/kg), a positive control agent (30 mg/kg) or vehicle [1% carboxymethylcellulose (w/v)/0.25% Tween80 (w/v); 0.3 ml/mouse]. On day 7, mice are weighed and bled (tail vein) 3 hours after dosing. Twenty-four hours after the $7^{th}$ dose (i.e., day 8), animals are bled again (tail vein). Samples obtained from conscious animals on days 0, 7 and 8 are assayed for glucose. After the 24-hour bleed, animals are weighed and dosed for the final time. Three hours after dosing on day 8, animals are anesthetized by inhalation of isoflurane and blood obtained via cardiac puncture (0.5-0.7 ml). Whole blood is transferred to serum separator tubes, chilled on ice and permitted to clot. Serum is obtained after centrifugation at 4° C. and frozen until analysis for compound levels. After sacrifice by cervical dislocation, the liver, heart and epididymal fat pads are excised and weighed.

Glucose is measured calorimetrically using commercially purchased reagents. According to the manufacturers, the procedures are modified from published work (McGowan, M. W., Artiss, J. D., Strandbergh, D. R. & Zak, B. Clin Chem, 20:470-5 (1974) and Keston, A. Specific calorimetric enzymatic analytical reagents for glucose. Abstract of papers 129th Meeting ACS, 31C (1956).); and depend on the release of a mole of hydrogen peroxide for each mole of analyte, coupled with a color reaction first described by Trinder (Trinder, P. Determination of glucose in blood using glucose oxidase with an alternative oxygen acceptor. Ann Clin Biochem, 6:24 (1969)). The absorbance of the dye produced is linearly related to the analyte in the sample. The assays are further modified in our laboratory for use in a 96 well format. The commercially available standard for glucose, commercially available quality control plasma, and samples (2 or 5 µl/well) are measured in duplicate using 200 R1 of reagent. An additional aliquot of sample, pipetted to a third well and diluted in 200 µl water, provided a blank for each specimen. Plates are incubated at room temperature for 18 minutes for glucose on a plate shaker (DPC Micormix 5) and absorbance read at 500 nm on a plate reader. Sample absorbances are compared to a standard curve (100-800 for glucose). Values for the quality control sample are always within the expected range and the coefficient of variation for samples is below 10%. All samples from an experiment are assayed at the same time to minimize inter-assay variability.

Evaluation of the Effects of Compounds of the Present Invention upon $A^y$ Mice Body Weight, Fat Mass, Glucose and Insulin Levels Female $A^y$ Mice Female $A^y$ mice are singly housed, maintained under standardized conditions (22° C., 12 h light:dark cycle), and provided free access to food and water throughout the duration of the study. At twenty weeks of age the mice are randomly assigned to vehicle control and treated groups based on body weight and body fat content as assessed by DEXA scanning (N=6). Mice are then dosed via oral gavage with either vehicle or a Compound of this invention (50 mg/kg) one hour after the initiation of the light cycle (for example, about 7 A.M.) for 18 days. Body weights are measured daily throughout the study. On day 14 mice are maintained in individual metabolic chambers for indirect calorimetry assessment of energy expenditure and fuel utilization. On day 18 mice are again subjected to DEXA scanning for post treatment measurement of body composition.

The results of p.o. dosing of compound for 18 days on body weight, fat mass, and lean mass are evaluated and suggest which compounds of this invention can be especially useful for maintaining desirable weight and/or promoting desired lean to fat mass.

Indirect calorimetry measurements revealing a significant reduction in respiratory quotient (RQ) in treated animals during the dark cycle [0.864±0.013 (Control) vs. 0.803±0.007 (Treated); p<0.001] is indicative of an increased utilization of fat during the animals' active (dark) cycle and can be used to selected especially desired compounds of this invention. Additionally, treated animals displaying significantly higher rates of energy expenditure than control animals suggest such compounds of this invention can be especially desired.

Male KK/$A^y$ Mice

Male KK/$A^y$ mice are singly housed, maintained under standardized conditions (22° C., 12 h light:dark cycle), and provided free access to food and water throughout the duration of the study. At twenty-two weeks of age the mice are randomly assigned to vehicle control and treated groups based on plasma glucose levels. Mice are then dosed via oral gavage with either vehicle or a Compound of this invention (30 mg/kg) one hour after the initiation of the light cycle (7 A.M.) for 14 days. Plasma glucose, triglyceride, and insulin levels are assessed on day 14.

The results of p.o. dosing of compound for 14 days on plasma glucose, triglycerides, and insulin are evaluated to identify compounds of this invention which may be especially desired.

Method to Elucidate the LDL-cholesterol Total-cholesterol and Triglyceride Lowering Effect Male Syrian hamsters (Harlan Sprague Dawley) weighing 80-120 g are placed on a high-fat cholesterol-rich diet for two to three weeks prior to use. Feed and water are provided ad libitum throughout the course of the experiment. Under these conditions, hamsters become hypercholesterolemic showing plasma cholesterol levels between 180-280 mg/dl. (Hamsters fed with normal chow have a total plasma cholesterol level between 100-150 mg/dl.) Hamsters with high plasma cholesterol (180 mg/dl and above) are randomized into treatment groups based on their total cholesterol level using the GroupOptimizeV211.xls program.

A Compound of this invention is dissolved in an aqueous vehicle (containing CMC with Tween 80) such that each hamster received once a day approx. 1 ml of the solution by garvage at doses 3 and 30 mg/kg body weight. Fenofibrate (Sigma Chemical, prepared as a suspension in the same vehicle) is given as a known alpha-agonist control at a dose of 200 mg/kg, and the blank control is vehicle alone. Dosing is performed daily in the early morning for 14 days.

Quantification of Plasma Lipids:

On the last day of the test, hamsters are bled (400 ul) from the suborbital sinus while under isoflurane anesthesia 2 h after dosing. Blood samples are collected into heparinized microfuge tubes chilled in ice bath. Plasma samples are separated from the blood cells by brief centrifugation. Total cholesterol and triglycerides are determined by means of enzymatic assays carried out automatically in the Monarch equipment (Instrumentation Laboratory) following the manufacturer's procedure. Plasma lipoproteins (VLDL, LDL and HDL) are resolved by injecting 25 ul of the pooled plasma samples into an FPLC system eluted with phosphate buffered saline at 0.5 ml/min through a Superose 6 HR 10/30 column (Pharmacia) maintained room temp. Detection and characterization of the isolated plasma lipids are accomplished by postcolumn incubation of the effluent with a Cholesterol/HP reagent (for example, Roche Lab System; infused at 0.12 ml/min) in a knitted reaction coil maintained at 37° C. The intensity of the color formed is proportional to the cholesterol concentration and is measured photometrically at 505 nm.

The effect of administration of a Compound of this invention for 14 days is studied for the percent reduction in LDL level with reference to the vehicle group. Especially desired compounds are markedly more potent than fenofibrate in LDL-lowering efficacy. Compounds of this invention that decrease LDL greater than or equal to 30% (thirty percent) compared to vehicle can be especially desired.

The total-cholesterol and triglyceride lowering effects of a Compound of this invention is also studied. The data for reduction in total cholesterol and triglyceride levels after treatment with a compound of this invention for 14 days is compared to the vehicle to suggest compounds that can be particularly desired. The known control fenofibrate did not show significant efficacy under the same experimental conditions.

Method to Elucidate the Fibrinogen-Lowering Effect of PPAR Modulators

Zucker Fatty Rat Model:

The life phase of the study on fibrinogen-lowering effect of compounds of this invention is part of the life phase procedures for the antidiabetic studies of the same compounds. On the last (14$^{th}$) day of the treatment period, with the animals placed under surgical anesthesia, ~3 ml of blood is collected, by cardiac puncture, into a syringe containing citrate buffer. The blood sample is chilled and centrifuged at 4° C. to isolate the plasma that is stored at −70° C. prior to fibrinogen assay.

Quantification of Rat Plasma Fibrinogen:

Rat plasma fibrinogen levels are quantified by using a commercial assay system consists of a coagulation instrument following the manufacturer's protocol. In essence, 100 ul of plasma is sampled from each specimen and a 1/20 dilution is prepared with buffer. The diluted plasma is incubated at 37° C. for 240 seconds. Fifty microliters of clotting reagent thrombin solution (provided by the instrument's manufacturer in a standard concentration) is then added. The instrument monitors the clotting time, a function of fibrinogen concentration quantified with reference to standard samples. Compounds that lower fibrinogen level greater than vehicle can be especially desired.

Cholesterol and triglyceride lowering effects of compounds of this invention are also studied in Zucker rats. Method to Elucidate the Anti-body Weight Gain and Anti-appetite Effects of Compounds of this invention Fourteen-Day Study in Zucker Fatty Rat[1] or ZDF Rat[2] Models:

Male Zucker Fatty rats, non-diabetic (Charles River Laboratories, Wilmington, Mass.) or male ZDF rats (Genetic Models, Inc, Indianapolis, Ind.) of comparable age and weight are acclimated for 1 week prior to treatment. Rats are on normal chow and water is provided ad libitum throughout the course of the experiment.

Compounds of this invention are dissolved in an aqueous vehicle such that each rat received once a day approximately 1 ml of the solution by garvage at doses 0.1, 0.3, 1 and 3 mg/kg body weight. Fenofibrate (Sigma Chemical, prepared as a suspension in the same vehicle) a known alpha-agonist given at doses of 300 mg/kg, as well as the vehicle are controls. Dosing is performed daily in the early morning for 14 days. Over the course of the experiment, body weight and food consumption are monitored.

Using this assay, compounds of this invention are identified to determine which can be associated with a significant weight reduction.

Method to Elucidate the Activation of the PPAR Delta Receptor in vivo

This method is particularly useful for measuring the in vivo PPARdelta receptor activation of compounds of this invention that are determined to possess significant in vitro activity for that receptor isoform over the PPAR gamma isoform.

Male PPARa null mice (129s4 Svjae-PPARa<tm1Gonz> mice; Jackson Laboratories) of 8-9 weeks of age are maintained on Purina 5001 chow with water ad libitum for at least one week prior to use. Feed and water are provided ad libitum throughout the course of the experiment. Using the GroupOptimizeV211.xls program, mice are randomized into treatment groups of five animals each based on their body weight.

Compounds of this invention are suspended in an aqueous vehicle of 1% (w/v) carboxymethylcellulose and 0.25% Tween 80 such that each mouse receives once a day approx. 0.2 ml of the solution by gavage at doses ranging from 0.2 to 20 mg/kg body weight. A control group of mice is included in each experiment whereby they are dosed in parallel with vehicle alone. Dosing is performed daily in the early morning for 7 days.

On the last day of dosing, mice are euthanized by CO2 asphyxiation 3 hours after the final dose. Blood samples are collected by heart draw into EDTA-containing microfuge tubes and chilled on ice. Liver samples are collected by necropsy and are flash-frozen in liquid nitrogen and stored at −80 degrees Celsius. For RNA isolation from liver, five to ten mg of frozen liver is placed in 700 μl of 1× Nucleic Acid Lysis Solution (Applied Biosystems Inc., Foster City, Calif.) and homogenized using a hand-held tissue macerator (Biospec Products Inc., Bartlesville, Okla.). The homogenate is filtered through an ABI Tissue pre-filter (Applied Biosystems Inc., Foster City, Calif.) and collected in a deep well plate on an ABI 6100 Nucleic Acid prep station (Applied Biosystems Inc., Foster City, Calif.). The filtered homogenate is then loaded onto an RNA isolation plate and the RNA Tissue-Filter-DNA method is run on the ABI 6100. The isolated RNA is eluted in 150 μl of RNase free water. For quality assessment, 9 μl of the isolated RNA solution is loaded onto a 1% TBE agarose gel, and the RNA is visualized by ethidium bromide fluorescence.

Complementary DNA (cDNA) is synthesized using the ABI High Capacity Archive Kit (Applied Biosystems Inc., Foster City, Calif.). Briefly, a 2× reverse transcriptase Master Mix is prepared according to the manufacturer's protocol for the appropriate number of samples (RT Buffer, dNTP, Random Primers, MultiScribe RT (50 U/μl), RNase free water). For each reaction, 50 μl of 2×RT Master Mix is added to 50 μl of isolated RNA in a PCR tube that is incubated in a thermocycler (25° C. for 10 minutes followed by 37° C. for 2 hours). The resultant cDNA preparation is diluted 1:100 in dH2O for analysis by real-time PCR. Also, a standard curve of cDNA is diluted 1:20, 1:100, 1:400, 1:2000, 1:10,000 for use in final quantitation.

A real-time PCR Master Mix for mouse Cyp4A1 gene expression is mixed to contain:
- 1× Taqman Universal PCR Master Mix (Applied Biosystems Inc., Foster City, Calif.)
- 6 micromolar final concentration Forward primer; Qiagen/Operon Technologies, Alameda, Calif.)
- 6 micromolar final concentration Reverse primer (Qiagen/Operon Technologies, Alameda, Calif.)
- 0.15 micromolar final concentration Probe (5' 6-FAM and 3' Tamra-Q; Qiagen/Operon Technologies, Alameda, Calif.)
- RNase free water to 10 microliters A real-time PCR Master Mix for the 18S ribosomal RNA control gene expression is mixed to contain
- 1× Taqman Universal PCR Master Mix (Applied Biosystems Inc., Foster City, Calif.)
- 0.34 micromolar Probe/Primer TaqMan® Ribosomal RNA Control Reagents #4308329 Applied Biosystems Inc., Foster City, Calif.)
- RNase free water to 10 microliters For the real-time PCR analysis, 6 ul of the respective Master Mix solution (either Cyp4A1 or 18S) and 4 ul either of diluted cDNA or of Standard Curve samples is added to individual wells of a 384-well plate (n=2 for Standards; n=4 for unknowns). Reactions are performed using the ABI 7900 HT standard universal RT-PCR cycling protocol. Data are analyzed using SDS 2.1 (Applied Biosystems Inc., Foster City, Calif.). Average quantity and standard deviation are calculated automatically for each individual sample, according to the standard curve values. Using Microsoft Excel 2000, mean values for each group of five individual mice is calculated. The mean value of each compound-treated group is divided by the mean value of the vehicle-treated group. The fold induction over the vehicle group is determined by assigning the vehicle group to the value of 1.0, and the fold change of the mean value for each group is expressed as fold-induction versus vehicle (1.0). Data are plotted using Jandel SigmaPlot 8.0.

MONKEY STUDIES

Efficacy Studies

Compounds of the invention may be examined in a dyslipidemic rhesus monkey model. After an oral dose-escalation study for 28 days in obese, non-diabetic rhesus monkeys a determination of HDL-c elevation is made with each dose and compared with pretreatment levels. LDL cholesterol is also determined with each dose. C-reactive protein levels are measured and compared to pretreatment levels.

Compound of Formula 1 may be shown to elevate plasma HDL-cholesterol levels in an African Green Monkey model in a manner similar to that described above in rhesus monkeys.

Two groups of monkeys are placed in a dose-escalating study that consists of one week of baseline measurements, 9 weeks of treatments (vehicle, Compound of Formula I), and four weeks of washout. During baseline, monkeys in all three groups are administered vehicle once daily for seven days. Test compound of Formula I, is administered in vehicle once daily for three weeks, then at a greater concentration (double the dose may be desired) once daily for three weeks, and then a still greater concentration (double the most recent dose may be desired) once daily for three weeks. At the completion of treatment, monkeys in both groups are administered vehicle once daily and monitored for an additional six weeks.

Animals are fasted overnight and then sedated for body weight measurements and blood collection at weeks 1 (vehicle), 2, 3, 4, 6, 7, 9, 10, 12, and 14 of the study.

Parameters to measured, for example:
Body weight
Total plasma cholesterol
HDL
LDL
Triglycerides
Insulin
Glucose
PK parameters at week 4, 7, and 10 (plasma drug concentration at last week of each dose)
ApoAI
ApoAII
ApoB
ApoCIII
Liver enzymes (SGPT, SGOT, OGT)
Complete blood count Additionally, other measures may be made, as appropriate, and consistent with the stated study design.

EQUIVALENTS

While this invention has been particularly shown and described with references to preferred embodiments thereof, it will be understood by those skilled in the art that various changes in form and details may be made therein without departing from the scope of the invention encompassed by the appended claims.

What is claimed is:

1. A compound of the structural Formula VIII:

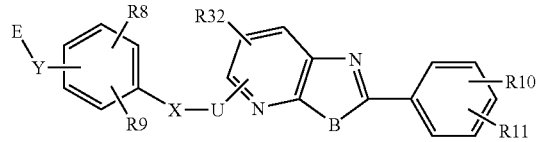

or a pharmaceutically acceptable salt thereof, wherein:
(a) R26, R27, R28 and R31 are each independently selected from the group consisting of hydrogen, hydroxy, cyano, nitro, halo, oxo, $C_1$-$C_6$ alkyl, $C_1$-$C_6$ alkyl-COOR12, $C_1$-$C_6$ alkoxy, $C_1$-$C_6$ haloalkyl, $C_1$-$C_6$ haloalkyloxy, $C_3$-$C_7$ cycloalkyl, aryloxy, aryl-$C_{0-4}$-alkyl, heteroaryl, heterocycloalkyl, C(O)R13, COOR14, OC(O)R15, OS(O)$_2$R16, N(R17)$_2$, NR18C(O)R19, NR20SO$_2$R21, SR22, S(O)R23, S(O)$_2$R24, and S(O)$_2$N(R25)$_2$; R12, R13, R14, R15, R16, R17, R18, R19, R20, R21, R22, R23, R24 and R25 are each independently selected from the group consisting of hydrogen, $C_1$-$C_6$ alkyl and aryl;
(b) X is selected from the group consisting of a O, S, S(O)$_2$ and N;
(c) U is an aliphatic linker of $C_1$-$C_3$ alkyl;
(d) Y is selected from the group consisting of C, O, S, NH, and a single bond;
(e) E is C(R3)(R4)A and wherein
 (i) A is selected from the group consisting of carboxyl, $C_1$-$C_6$ alkylnitrile, carboxamide, sulfonamide and acylsulfonamide; wherein sulfonamide, and acylsulfonamide are each optionally substituted with from one to two groups independently selected from $R^7$;

(ii) each $R^7$ is independently selected from the group consisting of hydrogen, $C_1$-$C_6$ haloalkyl, aryl $C_0$-$C_4$ alkyl and $C_1$-$C_6$ alkyl;

(iii) R3 is selected from the group consisting of hydrogen, and $C_1$-$C_5$ alkyl; and (iv) R4 is selected from the group consisting of H and $C_1$-$C_5$ alkyl, and wherein alkyl, alkoxy, aryloxy, cycloalkyl and aryl-alkyl are each optionally substituted with one to three substituents each independently selected from R26;

(f) B is selected from the group consisting of N, S and O;

(g) Z is selected from the group consisting of N and C;

(h) R8 is selected from the group consisting of hydrogen, $C_1$-$C_4$ alkyl, $C_1$-$C_4$ alkylenyl, and halo;

(i) R9 is selected from the group consisting of hydrogen, $C_1$-$C_4$ alkyl, $C_1$-$C_4$ alkylenyl, halo, aryl-$C_0$-$C_4$ alkyl and wherein aryl-$C_0$-$C_4$ alkyl is optionally substituted with from one to three independently selected from R27; R8 and R9 optionally combine to form a five membered fused bicyclic with the phenyl to which R8 and R9 attach, provided that when R8 and R9 form a fused ring, the group E-Y— is bonded at any available position on the five membered ring of such R8 and R9 fused bicyclic;

(j) R10, R11 are each independently selected from the group consisting of hydrogen, hydroxy, cyano, nitro, halo, oxo, $C_1$-$C_6$ alkyl, $C_0$-$C_6$ alkoxy, and $C_1$-$C_6$ haloalkyl;

(k) R30 is selected from the group consisting of $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl, and wherein $C_1$-$C_6$ alkyl, aryl-$C_{0-4}$-alkyl, aryl-$C_{1-4}$-heteroalkyl, heteroaryl-$C_{0-4}$-alkyl, and C3-C6 cycloalkylaryl-$C_{0-2}$-alkyl are each optionally substituted with from one to three substituents each independently selected from R31; and (l) R32 is selected from the group consisting of hydrogen, halo, $C_1$-$C_6$ alkyl, $C_1$-$C_6$ haloalkyl, and $C_1$-$C_6$ alkyloxo.

2. A compound as claimed by claim 1 wherein X is —O—.

3. A compound as claimed by claim 1 wherein X is —S.

4. A compound as claimed by claim 1 wherein Y is O.

5. A compound as claimed by claim 1 wherein Y is C.

6. A compound as claimed by claim 1 wherein Y is S.

7. A compound as claimed by claim 1 wherein B is O.

8. A compound as claimed by claim 1 wherein R10 is haloalkyl.

9. A compound as claimed by claim 8 wherein R10 is $CF_3$.

10. A compound as claimed by claim 1 wherein R8 is selected from the group consisting of $C_1$-$C_3$ alkyl and $C_1$-$C_4$ alkylenyl.

11. A compound as claimed by claim 1, wherein R8 and R9 are each independently selected from the group consisting of hydrogen and C1-$C_3$ alkyl.

12. A compound as claimed by claim 1 wherein R8 is $C_1$-$C_4$ alkylenyl.

13. A compound as claimed by claim 1 wherein R2, R3, and R4 are each independently selected from the group consisting of C1-C2 alkyl.

14. A compound as claimed by claim 1 wherein R3, and R4 are each independently selected from the group consisting of hydrogen and $C_1$-$C_2$ alkyl.

15. A compound as claimed by claim 1 wherein U is $C_1$-$C_3$ alkyl.

16. A compound as claimed by claim 15 wherein U is saturated.

17. A compound as claimed by claim 1 wherein X is S, Y is selected from the group consisting of C and O, and E is $CH_2COOH$.

18. A compound as claimed by claim 1, wherein B is S.

19. A compound as claimed by claim 1 wherein R32 is hydrogen, R8 is hydrogen and R9 is $C_1$-$C_4$ alkyl.

20. A compound as claimed by claim 1 selected from the group consisting of 2-Ethyl-4-[2-(4-trifluoromethylphenyl)-3H-imidazo[4,5-b]pyridin-7-ylmethylsulfanyl]phenoxyacetic Acid.

21. A compound as claimed by claim 1 that is in the R conformation.

22. A pharmaceutical composition, comprising as an active ingredient, at least one compound as claimed by claim 1 together with a pharmaceutically acceptable carrier or diluent.

23. A method of treating diabetes mellitus in a mammal, comprising the step of administering to the mammal in need thereof a therapeutically effective amount of at least one compound of claim 1.

24. A compound as claimed by claim 1 wherein the compound is radiolabeled.

\* \* \* \* \*